US006265183B1

(12) United States Patent
Dorner et al.

(10) Patent No.: US 6,265,183 B1
(45) Date of Patent: Jul. 24, 2001

(54) DIRECT MOLECULAR CLONING OF FOREIGN GENES INTO POXVIRUSES AND METHODS FOR THE PREPARATION OF RECOMBINANT PROTEINS

(75) Inventors: Friedrich Dorner, Vienna; Friedrich Scheiflinger, Orth/Donau; Falko Gunter Falkner, Mannsdorf; Michael Pfleiderer, Breitstetten, all of (AT)

(73) Assignee: Baxter Aktiengesellschaft, Vienna (AU)

(*) Notice: Subject to any disclaimer, the term of this patent is extended or adjusted under 35 U.S.C. 154(b) by 0 days.

(21) Appl. No.: 08/358,928

(22) Filed: Dec. 19, 1994

Related U.S. Application Data

(63) Continuation-in-part of application No. 07/914,738, filed on Jul. 20, 1992, now abandoned, which is a continuation-in-part of application No. 07/750,080, filed on Aug. 26, 1991, now Pat. No. 5,445,953.

(51) Int. Cl.[7] .......................... C12P 21/06; C12N 15/00; A61K 39/275

(52) U.S. Cl. ................. 435/69.1; 435/320.1; 424/232.1; 424/199.1; 424/208.1

(58) Field of Search ................................ 435/67.1, 70.1, 435/71.1, 172.3; 424/188.1, 208.1

(56) References Cited

U.S. PATENT DOCUMENTS

| | | | |
|---|---|---|---|
| 4,722,848 | 2/1988 | Paoletti et al. | 424/89 |
| 4,769,330 | 9/1988 | Paoletti et al. . | |
| 5,110,587 | 5/1992 | Paoletti et al. | 424/89 |
| 5,155,020 | 10/1992 | Paoletti | 435/69.1 |
| 5,174,993 | 12/1992 | Paoletti | 424/89 |

(List continued on next page.)

FOREIGN PATENT DOCUMENTS

| | | |
|---|---|---|
| WO92/05263 | 4/1992 | (WO) . |
| WO94/03595 | 2/1994 | (WO) . |
| WO95/27507 | 10/1995 | (WO) . |
| WO96/21727 | 7/1996 | (WO) . |
| WO96/39177 | 12/1996 | (WO) . |
| WO96/39491 | 12/1996 | (WO) . |
| WO96/40241 | 12/1996 | (WO) . |

OTHER PUBLICATIONS

Moss, B., in "Poxviridae and their replication", in Virology, Second Edition, Fields et al., eds., Raven Press Ltd., New York, 1990, pp. 2079–2081.

(List continued on next page.)

*Primary Examiner*—Donald E. Adams
*Assistant Examiner*—Jeffrey S. Parkin
(74) *Attorney, Agent, or Firm*—Foley & Lardner

(57) ABSTRACT

A method is disclosed for producing a modified eukaryotic cytoplasmic DNA virus by direct molecular cloning of a modified DNA molecule comprising a modified cytoplasmic DNA virus genome. The inventive method comprises the steps of (I) modifying under extracellular conditions a DNA molecule comprising a first cytoplasmic DNA virus genome to produce a modified DNA molecule comprising the modified cytoplasmic DNA virus genome; (II) introducing the modified DNA molecule into a first host cell which packages the modified DNA molecule into infectious virions; and (III) recovering from the host cell virions comprised of the modified viral genome. The host cell is infected with a helper virus which is expressed to package the modified viral genome into infectious virions. Examples of packaging a modified poxvirus genome by a helper poxvirus of the same or different genus are described. Also disclosed are novel poxvirus vectors for direct molecular cloning of open reading frames into a restriction enzyme cleavage site that is unique in the vector. In one model poxvirus vector, the open reading frame is transcribed by a promoter located in the vector DNA upstream of a multiple cloning site comprised of several unique cleavage sites.

17 Claims, 77 Drawing Sheets left arm (la) right arm (ra)
NotI vaccinia virus genomic DNA
cleave with NotI, dephosphorylate
la ra
NotI NotI
ligate
P1 gpt
NotI NotI
P1 gpt
NotI NotI 'a'-orientation
+
gpt P1
NotI NotI 'b'-orientation
-transfect into helper virus infected cells
in-vivo packaging of the modified viral genome
cell
selection for virus containing the gpt gene

U.S. PATENT DOCUMENTS

| | | | |
|---|---|---|---|
| 5,204,243 | 4/1993 | Paoletti | 435/69.1 |
| 5,225,336 | 7/1993 | Paoletti | 435/69.1 |
| 5,266,313 | 11/1993 | Esposito et al. . | |
| 5,338,683 | 8/1994 | Paoletti | 435/320 |
| 5,364,773 | 11/1994 | Paoletti et al. | 435/69.1 |
| 5,453,364 | 9/1995 | Paoletti | 435/69.3 |
| 5,494,807 | 2/1996 | Paoletti et al. | 435/69.3 |
| 5,505,941 | 4/1996 | Paoletti | 424/93 |
| 5,583,028 | 12/1996 | Paoletti et al. | 435/235.1 |

OTHER PUBLICATIONS

Coffin, J., in "Retroviridae and their replication" in Virology, Second Edition, Fields et al., eds., Raven Press Ltd., New York, 1990, pp. 1437–1440.
Barrett et al. Aids Research and Human Retroviruses 5(2): 159–171 (1989).
Boshart et al. Cell 41: 521–530 (1985).
Broyles et al. Journal of Biological Chemistry 263(22): 10754–10760 (1988).
Broyles et al. Journal of Biological Chemistry 263(22): 10761–10765 (1988).
Broyles et al. Journal of Virology 67(9) : 5677–5680 (1993).
Condit et al. Virology 128: 429–443 (1983).
Gunning et al. Proc. Natl. Acad. Sci. USA 84: 4831–4835 (1987).
Hunt et al. Proc. Natl. Acad. Sci. USA 82:6455–6459 (1985).
Isaacs et al. Virology 178: 626–630 (1990).
Kane et al. Jounal of Virology 67(5): 2689–2698 (1993).
Kriegler Gene Transfer and Expression, A Laboratory Manual, Stockton Press, pp. 47–56.
Mann et al. Cell 33: 153–159 (1983).
Taylor et al. Vaccine 6: 466–468 (1988).
Jindal et al. Journal of Virology 66(9): 5357–5362 (1992).
Fenner et al. The Orthopoxvirus, Chapter 12, pp. 353–377 (1988).
Falkner et al. Journal of Virology 64(6): 3108–3111 (1990).
Falkner et al. Journal of Virology 62(6): 1849–1854 (1988).
Gershon et al. Proc. Natl. Acad. Sci. USA 87: 4401–4405 (1990).
Graham et al. Virology 54: 536–539 (1973).
Wittek et al. Journal of Virology 49(2): 371–378 (1984).
Weir et al. Journal of Virology 56(2): 534–540 (1985).
Lai et al. Journal of Biological Chemistry 265(36): 22174–22180 (1990).
Zhang et al. Virology 187: 643–653 (1992).
Zhang et al. Journal of Virology 65(11): 6101–6110 (1991).
Yanisch–Perron et al. Gene 33: 103–119 (1985).
Towbin et al. Proc. Natl. Acad. Sci. USA 76(9): 4350–4354 (1979).
Perkus et al. Journal of Virology 63(9): 3829–3836 (1989).
Wang et al. Gene Therapy 2: 775–783 (1995).
Krougliak et al. Human Gene Therapy 6: 1575–1586 (1995).
Sutter et al. Journal of Virology 68(7): 4109–4116 (1994).
Fenner Fields Virology, Third Edition, pp. 2673–2707 (1996).
Panicali et al. J. of Virology 37: 1000–1010 (1981).
Goebel et al. Virology 179: 247–266 (1990).
Ghildyal et al. Archives of Virology 106: 85–92 (1989).
Schnitzlein et al. Virus Research 10: 65–76 (1988).
Fenner et al. Virology 11: 185–201 (1960).
Boyle et al. Research in Virology, 140: 483–491 (1989).
Bostock Vet Microbiol 23: 55–71 (1990).
Chakrabarti et al. Molecular and Cellular Biology 5(12): 3403–3409 (1985).
Spehner et al. J. of Virology 64(2): 527–533 (1990).
Boursnell et al. J. of General Virology 71: 621–628 (1990).
Burke et al. Genet. Anal. Tech. Appl. 7: 94–99 (1990).
Steinberg et al. Genet Anal. Tech. Appl. 7: 126–132 (1990).
Mackett et al. Proc. Natl. Acad. Sci. 79: 7415–7419 (1982).
Merchlinsky et al. Virology 190: 522–526 (1992).
Rixon et al. J. of General Virology 71: 2931–2939 (1990).
Langridge et al. J. Invert. Pathol. 42: 77–82 (1983).
Scheiflinger et al. Proc. Natl. Acad. Sci. 89: 9977–9981 (1992).
Altenburger et al. Archives of Virology 105: 15–27 (1989).
Baxby et al. "Vaccinia Virus," *Vaccinia Viruses as Vectors for Vaccine Antigens* Quinnan, Ed., Elsevier NY pp. 3–8 (1985).
Henderson et al. "Utilization of Vaccine in the Global Eradication of Smallpox," *Vaccinia Viruses as Vectors for Vaccine Antigens* Quinnan, Ed., Elsevier NYpp. 61–67 (1985).
Haber et al. "Innovative Approaches to Plasminogeen Activator Therapy," *Science* 243:51–56 (1989).
Weir et al. "Maping of the Vaccinia Virus Thymidine Kinase Gene by Marker Rescue and by Cell–Free Translation of Selected mRNA," *P.N.A.S.* 79:1210–1214 (1982).
Smith et al. "Construction and Characterization of an Infectious Vaccinia Virus Recombinant that Expresses the Influenza Hemagglutinin Gene and Induces Resistance to Influenza Virus Infection in Hamsters," *P.N.A.S.* 80:7155–7159 (1983).
Smith et al. "Infectious Vaccinia Virus Recombinants that Express Hepatitis B Surface Antigen," *Nature* 302:490–495 (1983).
Buller et al. "Decreased Virulence of Recombinant Vaccinia Virus Expression Vectors is Associated with a Thymidine KInase–Negative Phenotype," *Nature* 317:813–815 (1885).
Buller et al. "Deletion of the Vaccinia Virus Growth Factor Gene Reduces Virus Virulence," *Journal of Virology* 62:866–874 (1988).
Flexner et al. "Prevention of Vaccinia Virus Infection in Immunodeficient Mice by Vector–Directed IL–2 Expression," *Nature* 330:259–262 (1987).
Shida et al. "Effects and Virulence of Recombinant Vaccinia Viruses Derived from Attenuated Strains that Express the Human T–Cell Leukemia Virus ZType I Envelope Gene," *Journal of Virology* 62:4474–4480 (1988).
Kotwal et al. "Mapping and Isertional Mutagenesis of a Vaccinia Virus Gene Encoding a 13,800–Da Secreted Protein," *Virology* 171:579–587 (1989).
Child et al. "Insertional Inactivation of the Large Subunit of Ribonucleotide Reductase Encoded by Vaccinia Virus is Associated with Reduced Virulence in Vivo," *Virology* 174:625–629 (1990).
Taylor et al. *Virology* 6:497–(1988).
Moss et al. "Vaccinia Virus: A Tool for Research and Vaccine Development," *Science* 252:1662–1667 (1991).
Cooney et al. "Safety of an Immunological Response to a Recombinant Vaccinia Virus Vaccine Expressing HIV Envelope Glycoprotein," *Lancet* 337:567–572 (1991).
Moss, B., "Poxviridae: The Viruses and Their Replication", in *Virology,* Third Edition, Fields et al., eds., Lippincott–Raven Publishers, Philadelphia, 1996, pp. 2637 and 2639.
Fenner, F., "Poxviruses", in *Virology,* Third Edition, Fields et al., eds., Lippincott–Raven Publishers, Philadelphia, 1996, page 2699.
Fenner et al. *The Orthopoxviruses* pp. 29–60 (1989) (Academic Press, NY).
Altenburger et al. *Archives of Virology* 105:15–27 (1989).

Fig.1.1
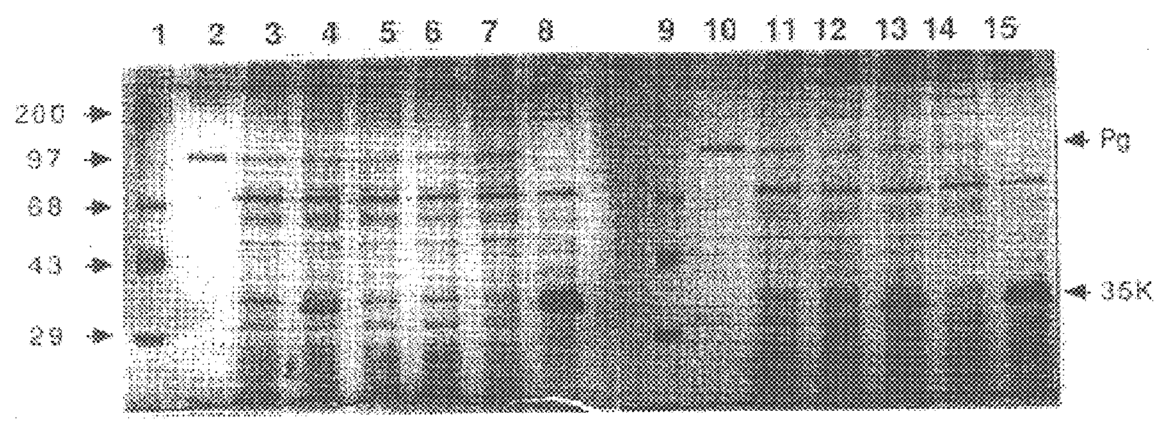

FIG. 1.2
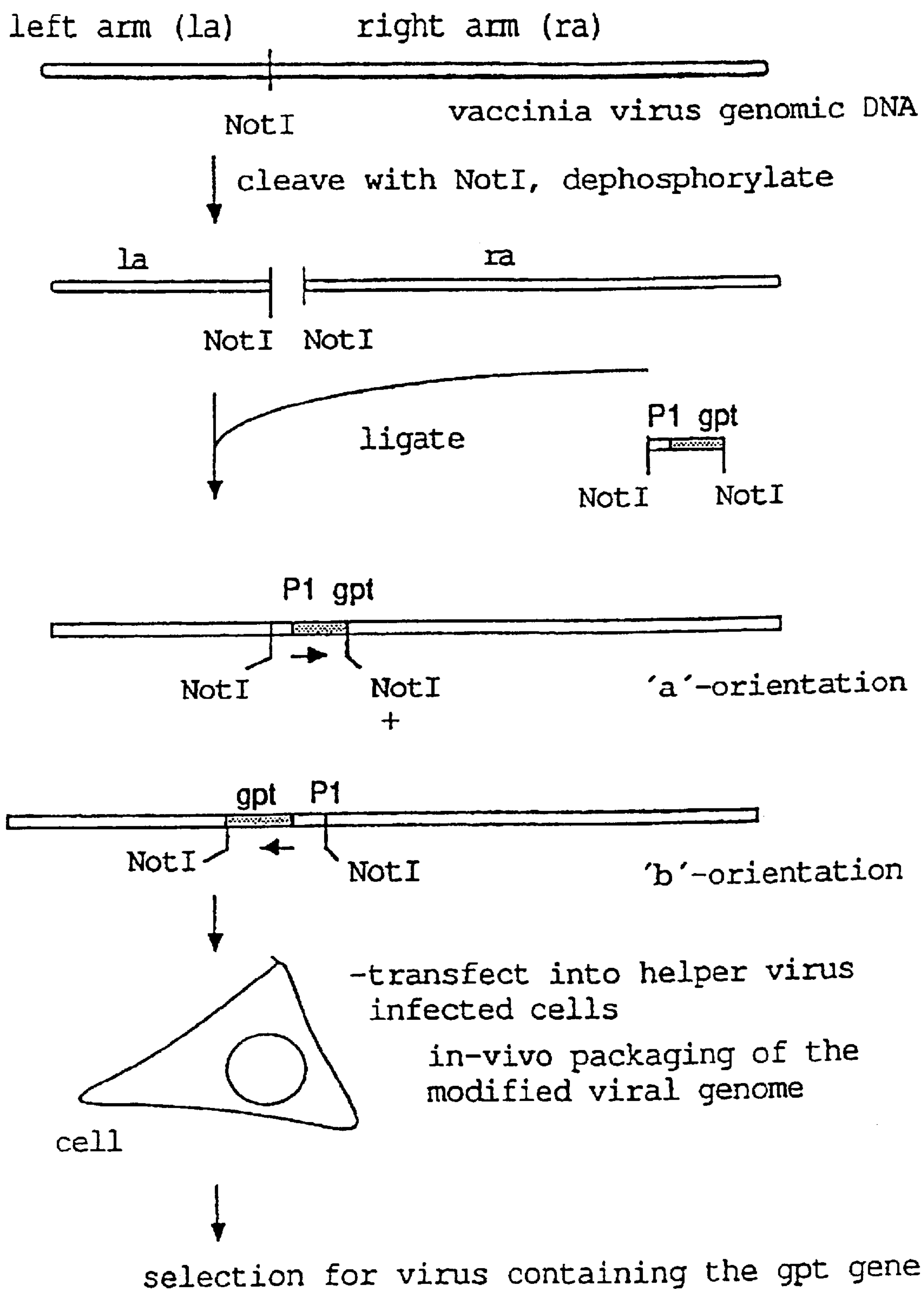

FIG. 1.3
Construction of the plasmids pN2-gpta and pN2-gptb
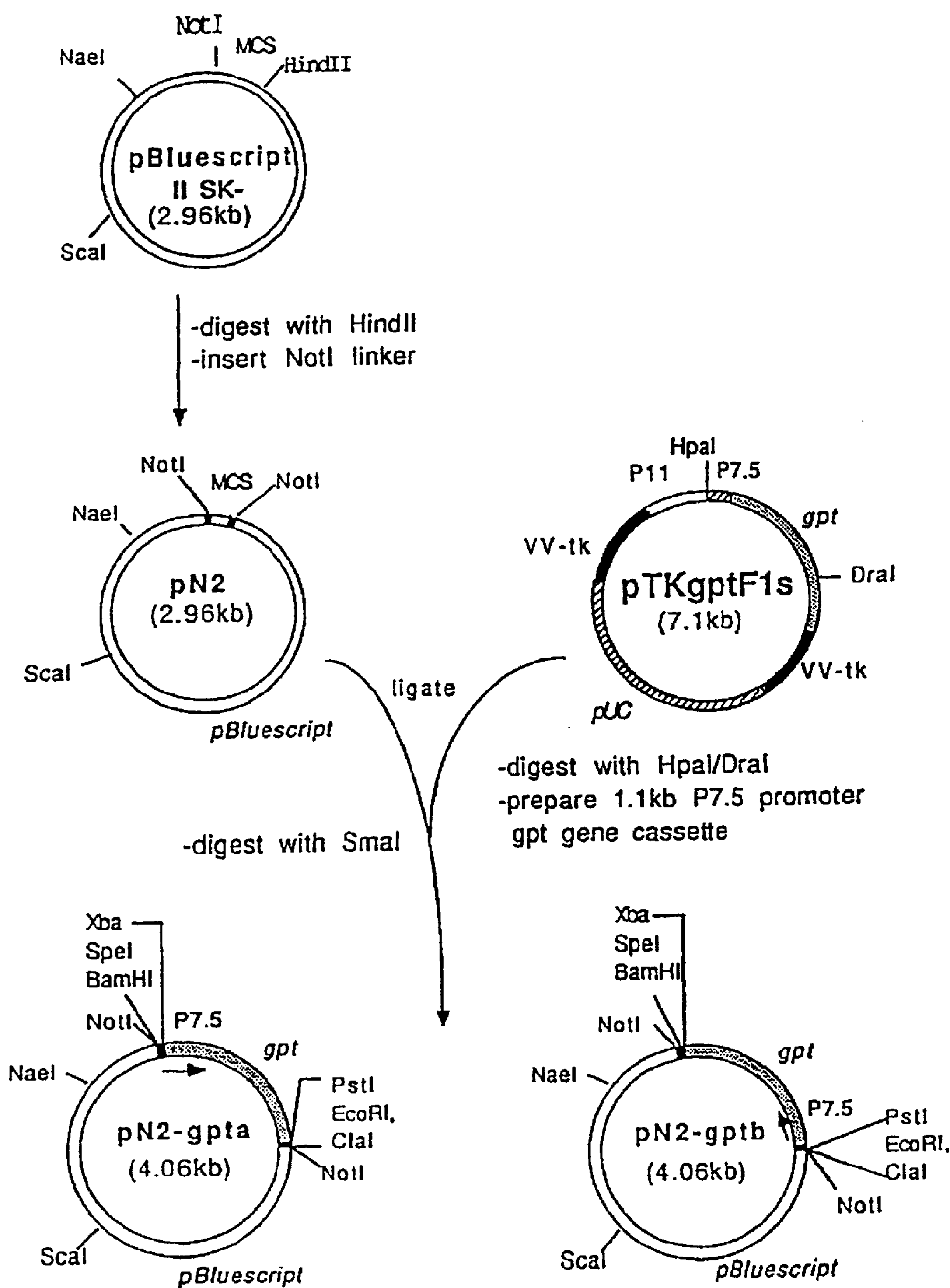

Fig. 1.4
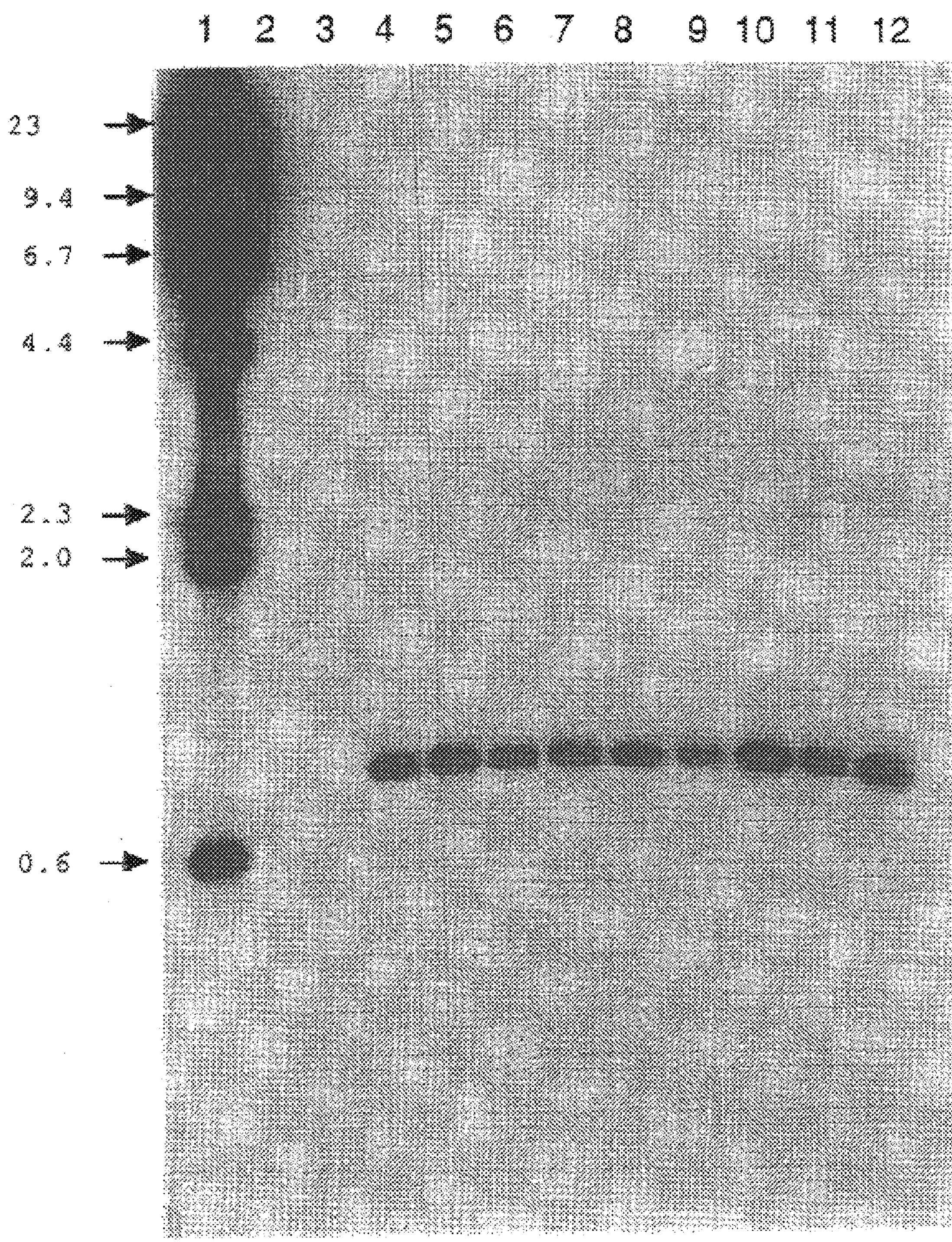

Fig.1.5
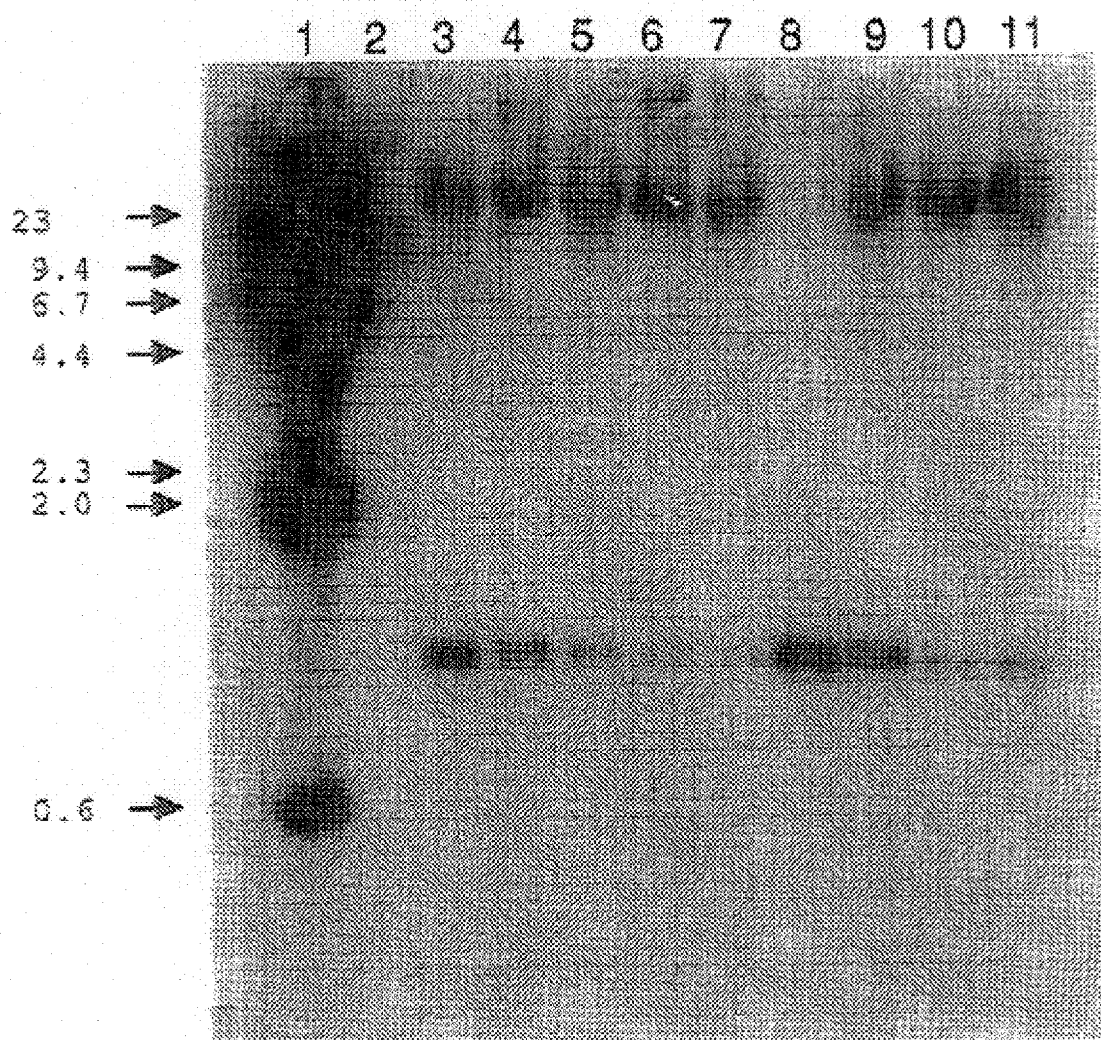

Fig.1.6
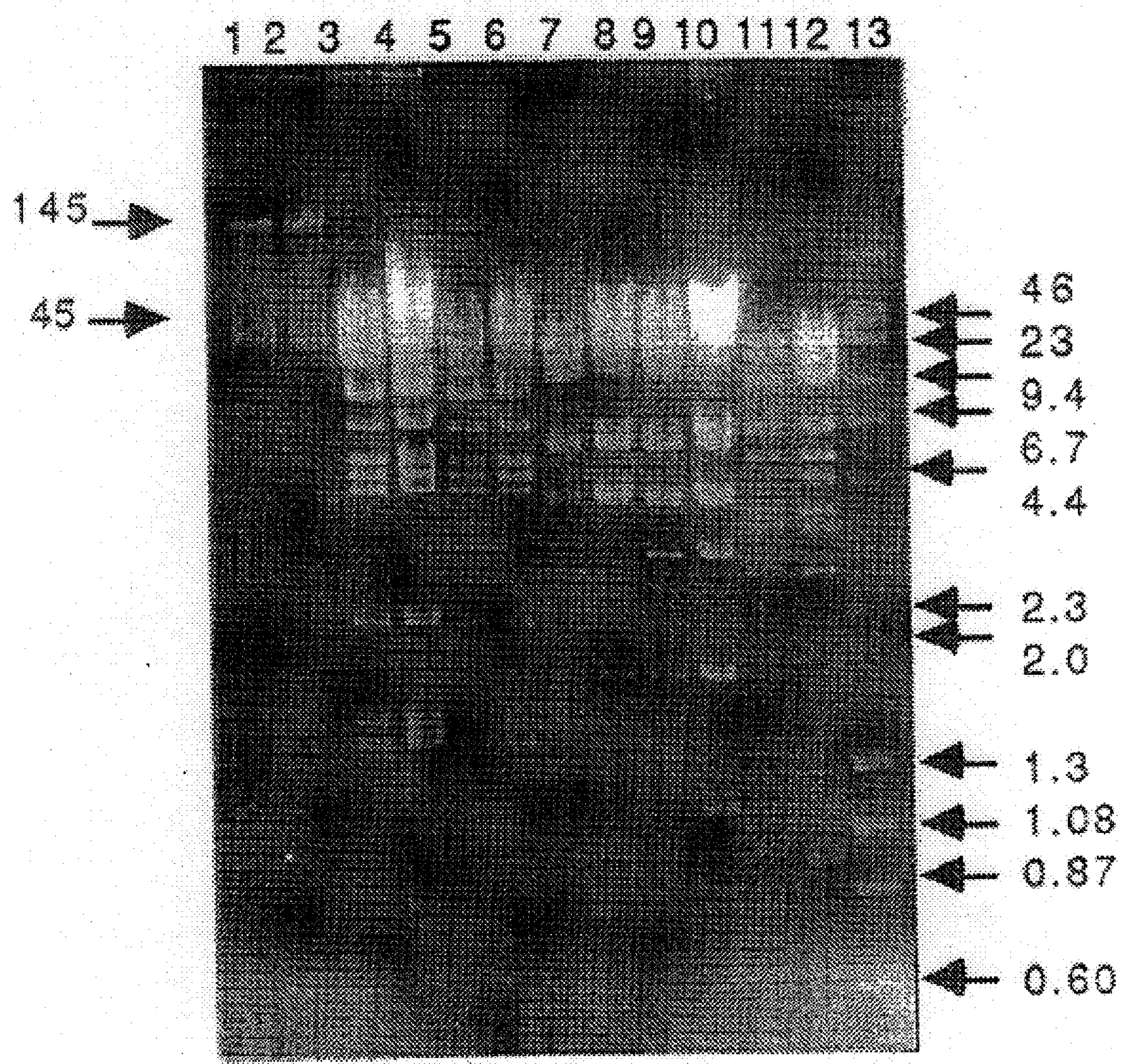

Fig.1.7
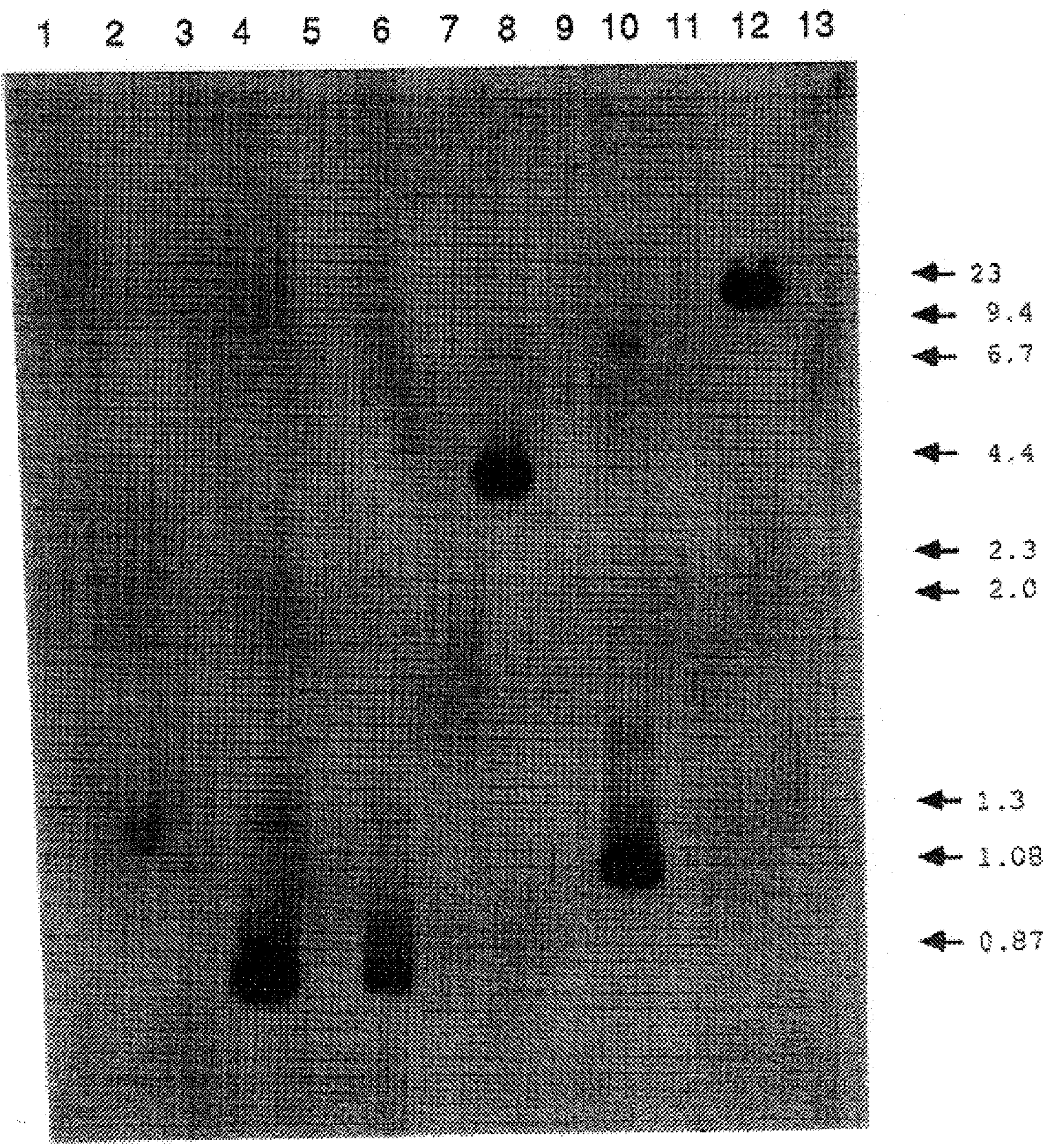

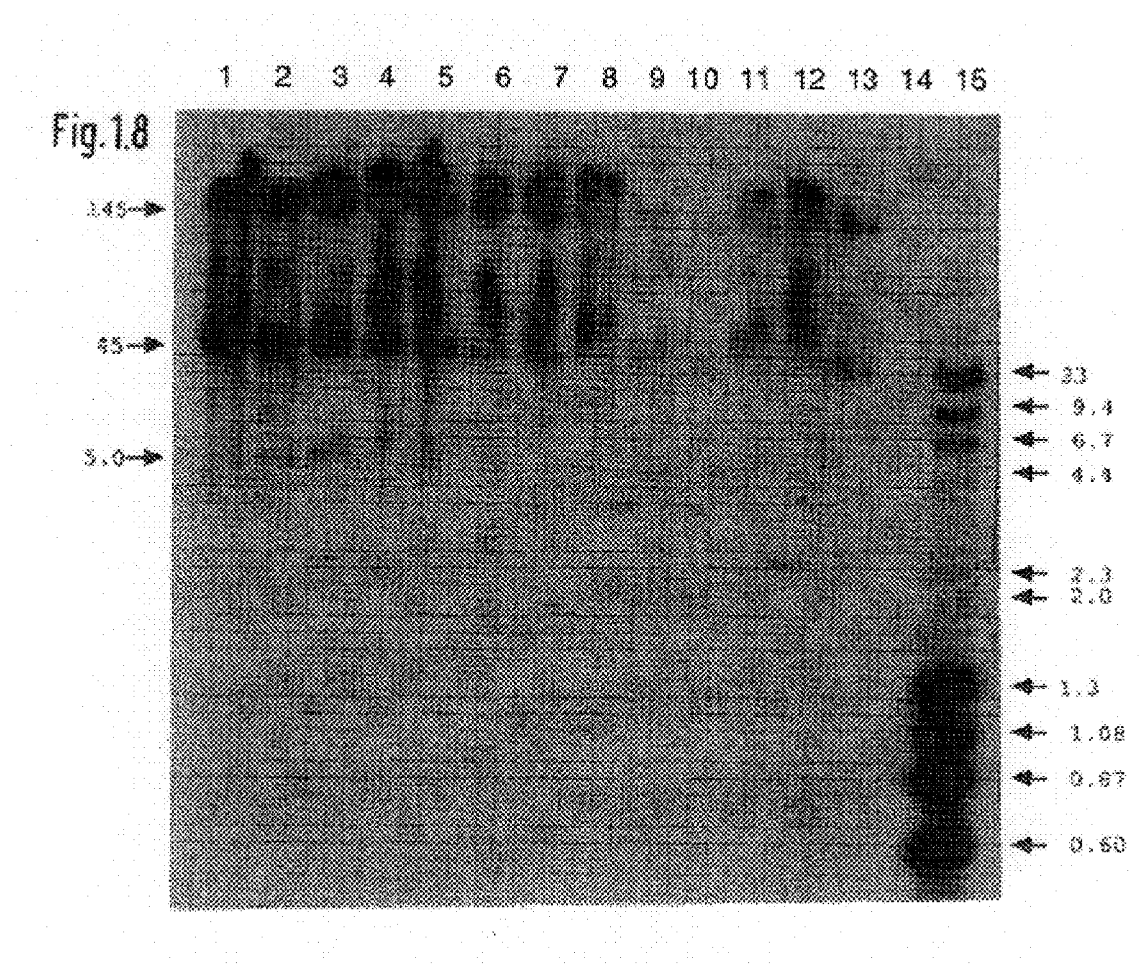
Fig.1.8
1
2
3
4
5
6
7
8
9
10
11
12
13
14
15
145
45
5.0
23
9.4
6.7
4.4
2.3
2.0
1.3
1.08
0.87
0.60

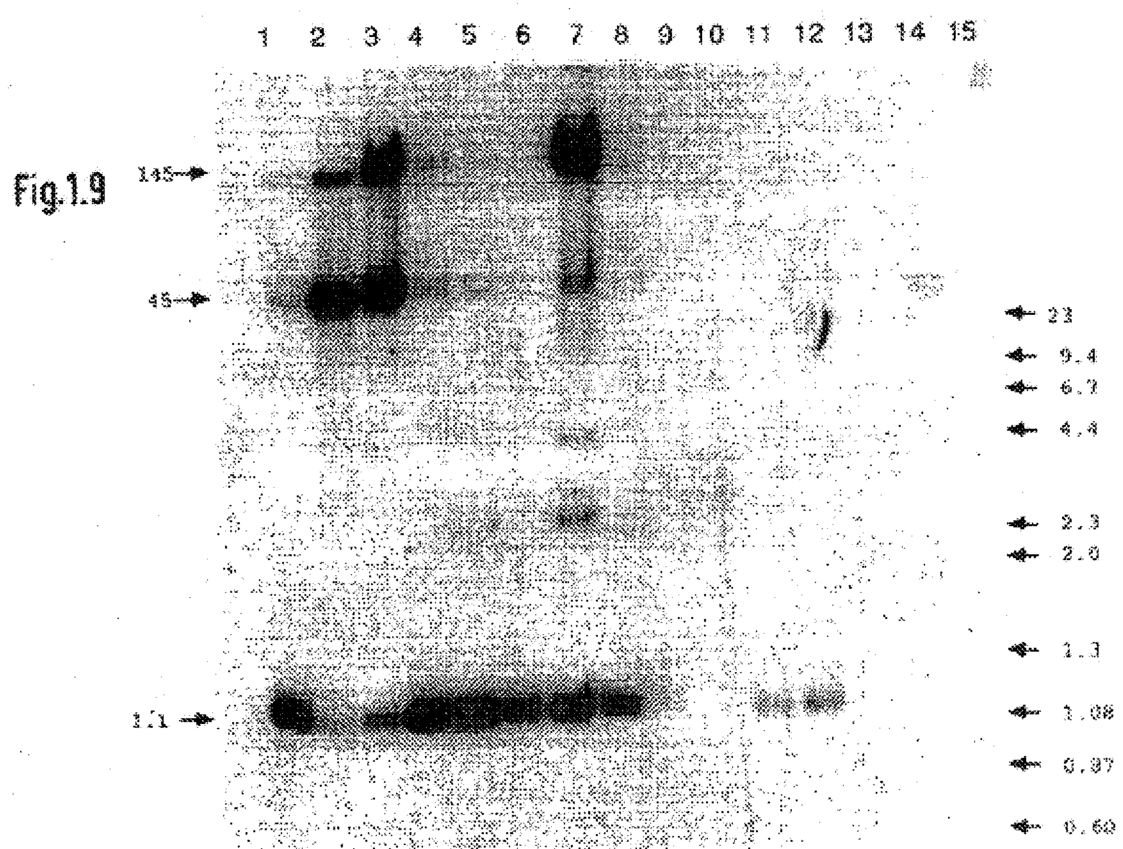
Fig.1.9
1 2 3 4 5 6 7 8 9 10 11 12 13 14 15
145
45
11
23
9.4
6.7
4.4
2.3
2.0
1.3
1.08
0.87
0.60

Fig.1.10
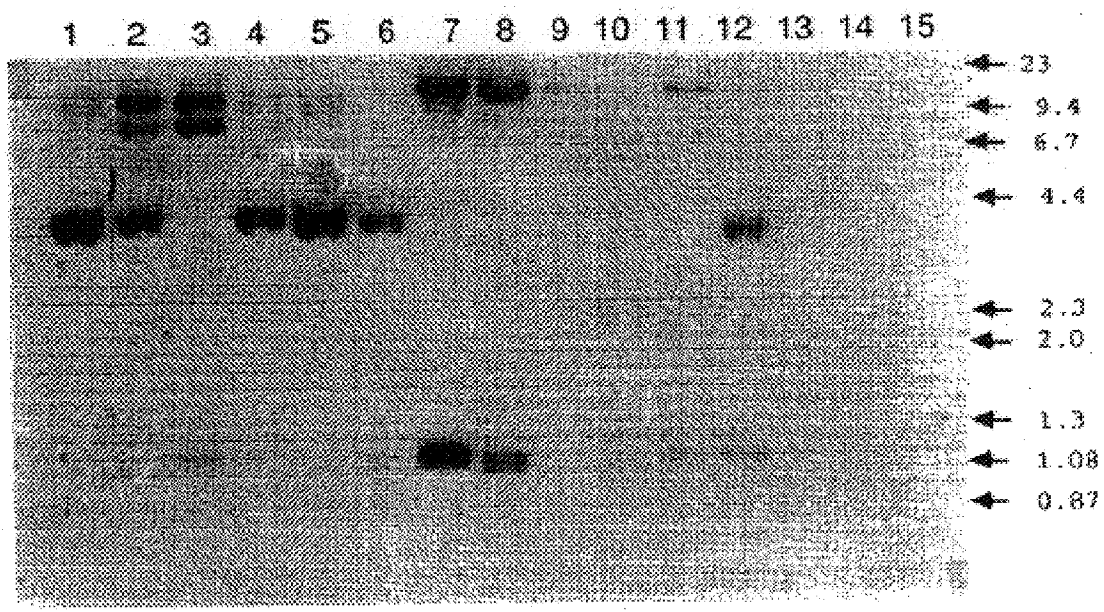

FIG. 1.11
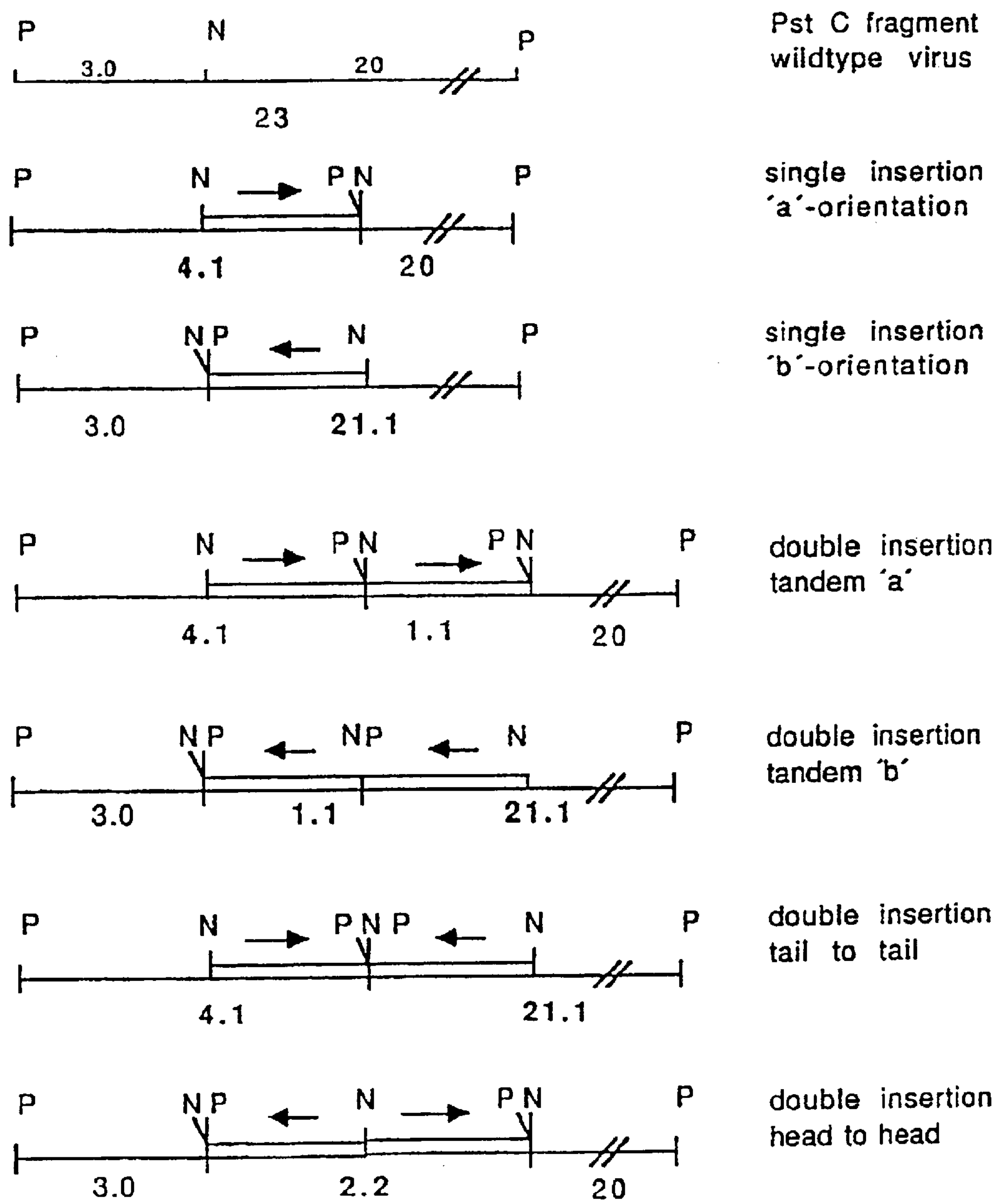

FIG. 2.2
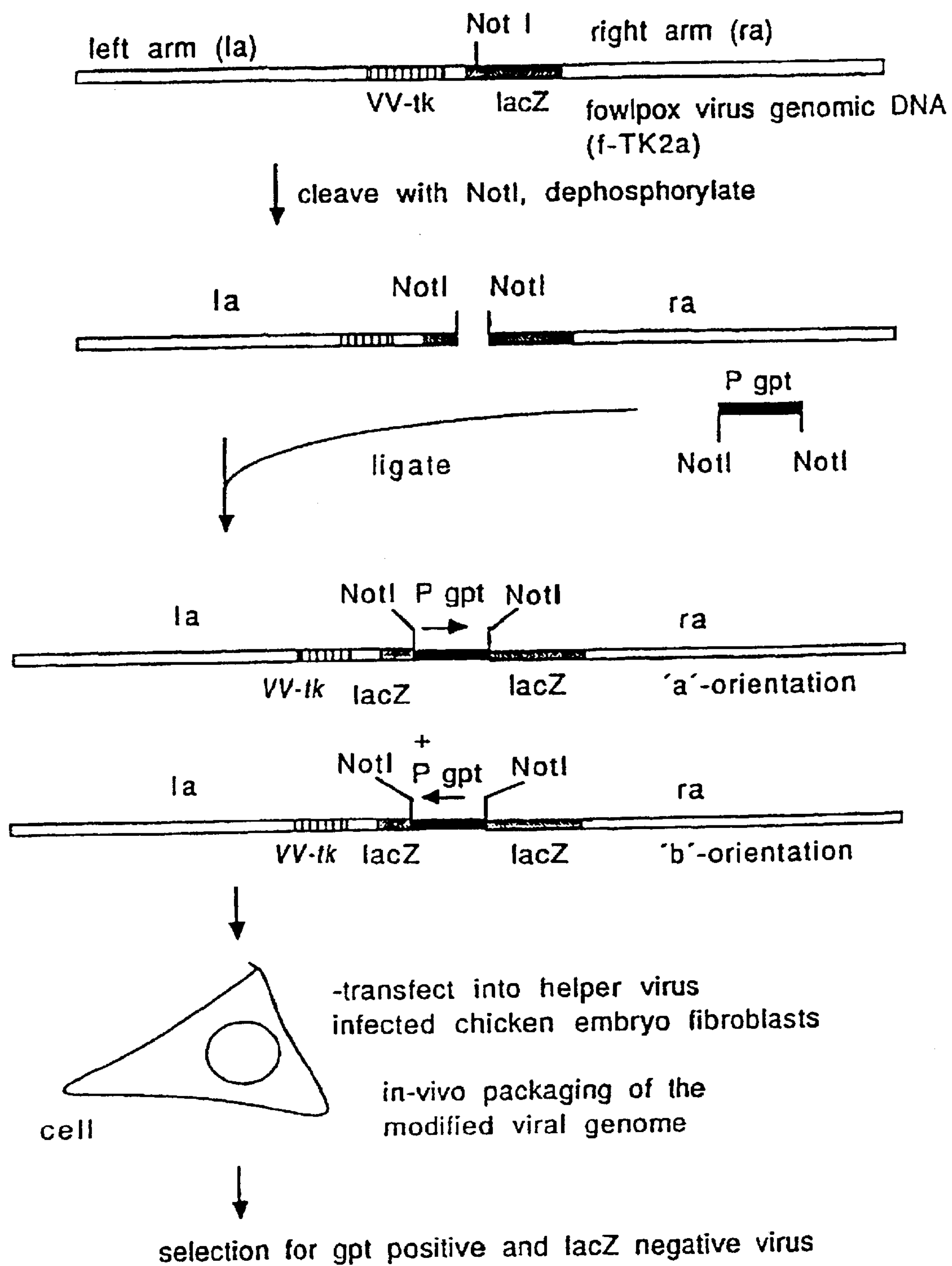

FIG. 3.1
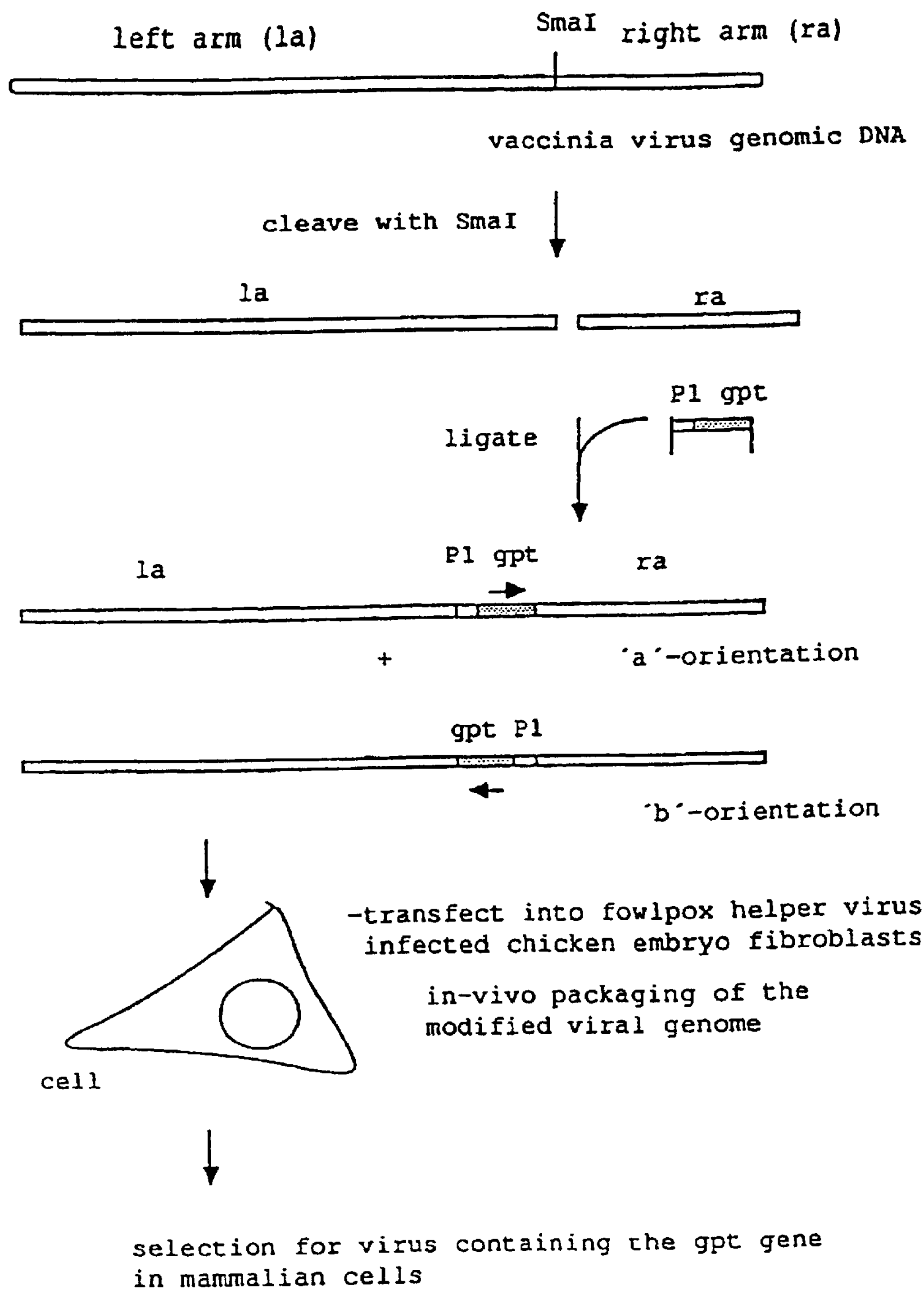

Fig. 3.2
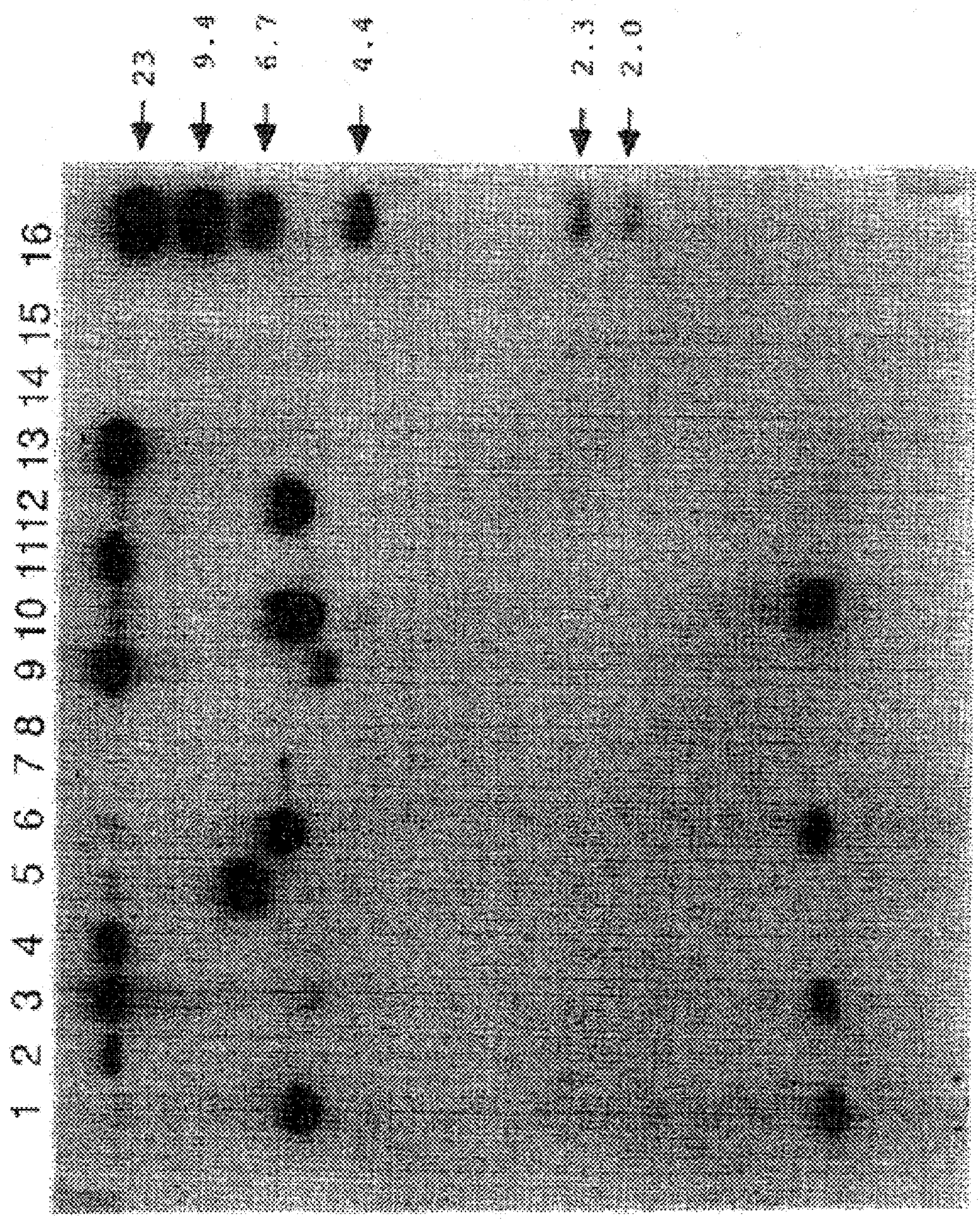

FIG. 3.3A
H S H
1.
44.6 4.9
Hind III A Fragment vaccinia wild type virus
FIG. 3.3B
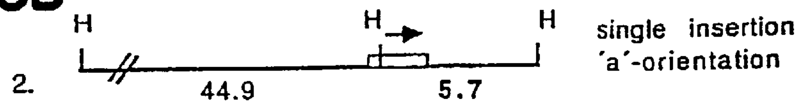
FIG. 3.3C
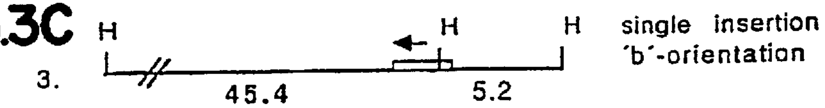
FIG. 3.3D
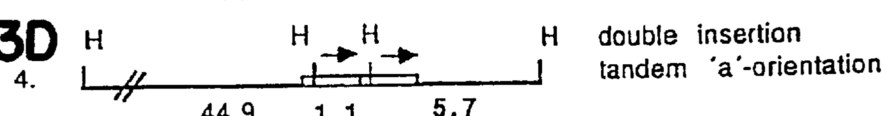
FIG. 3.3E
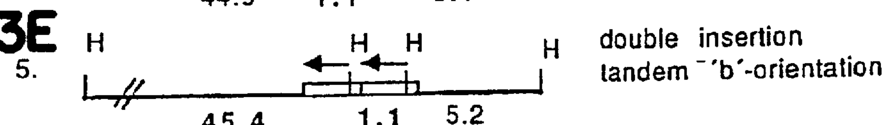
FIG. 3.3F
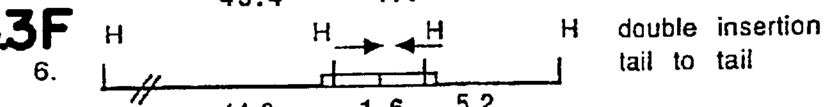
FIG. 3.3G
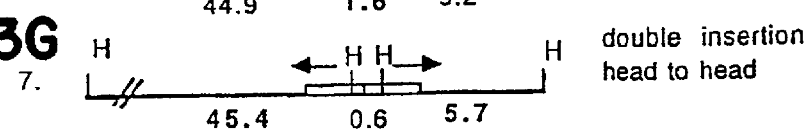

FIG. 4.1A
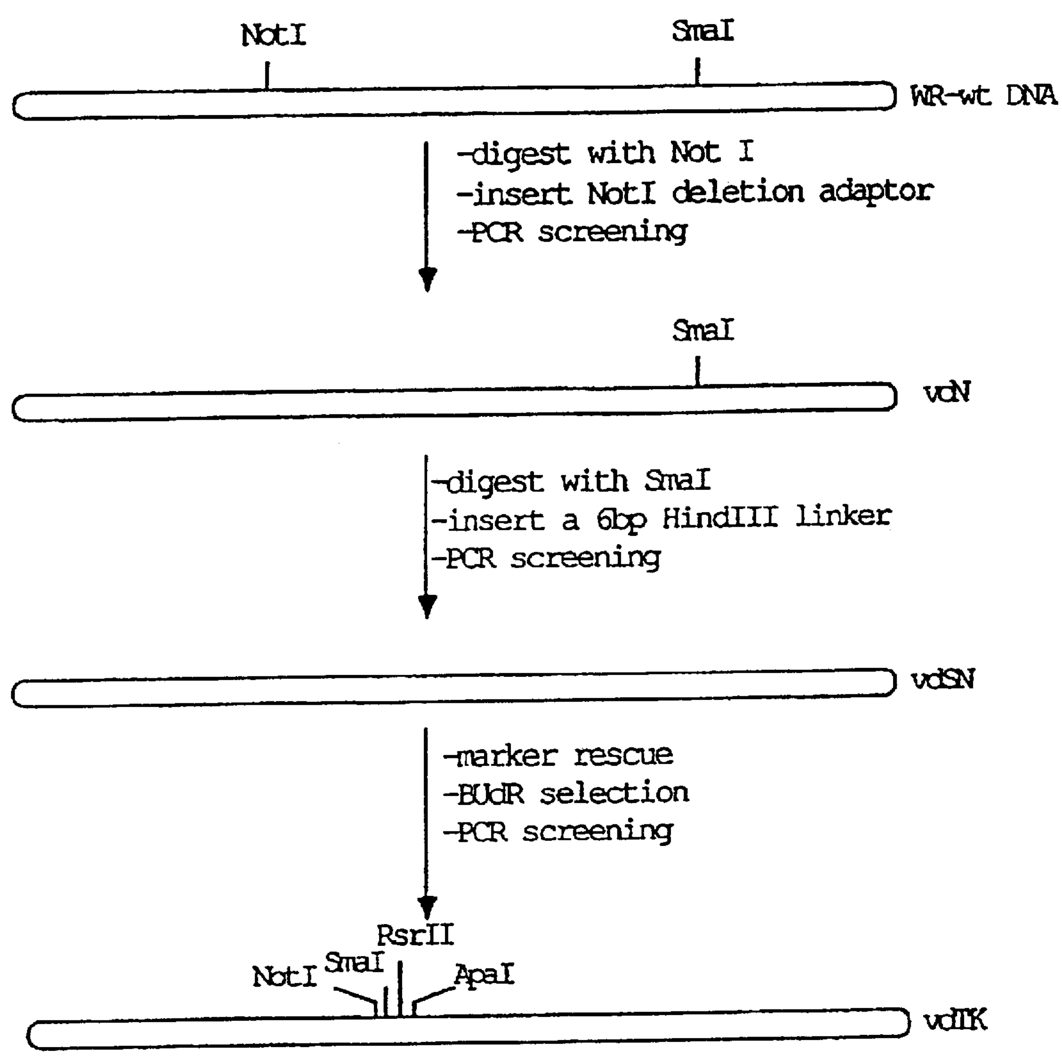

Construction of the plasmid pTZ-SacI
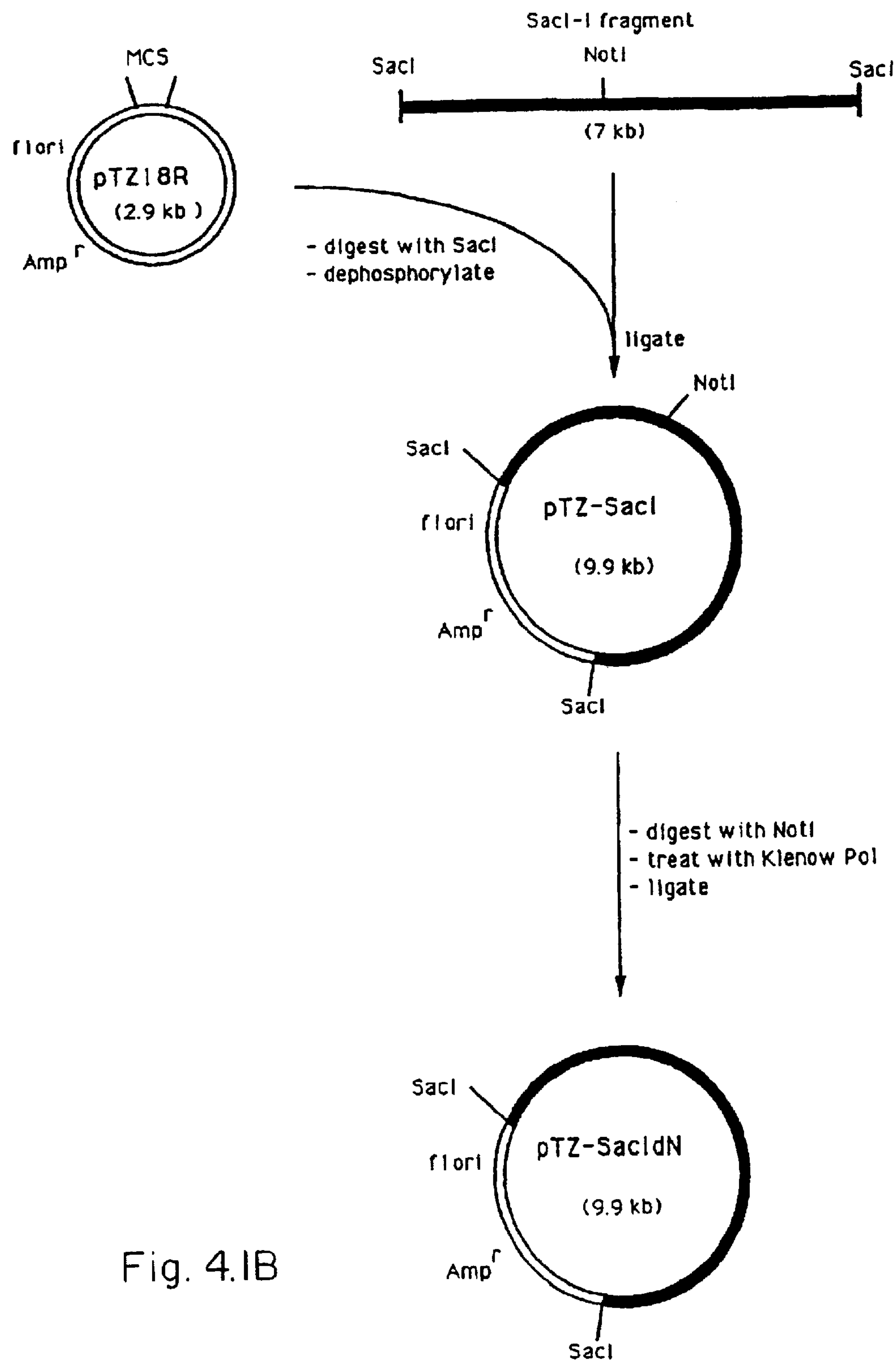
Fig. 4.1B

Construction of the plasmid pTZ-SalFH
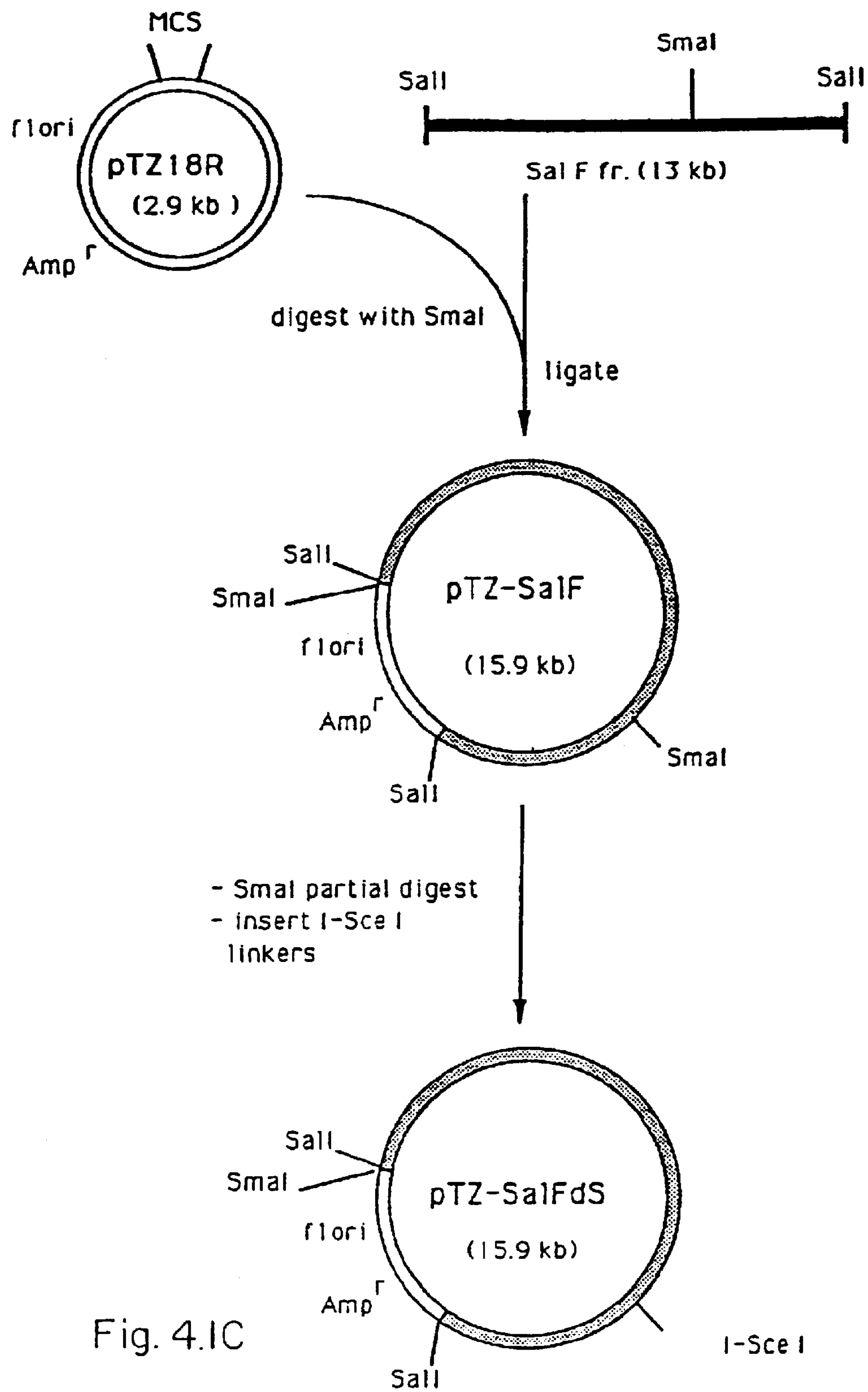
Fig. 4.1C

*FIG. 4.2*
CONSTRUCTION OF THE PLASMID pHindJ-3
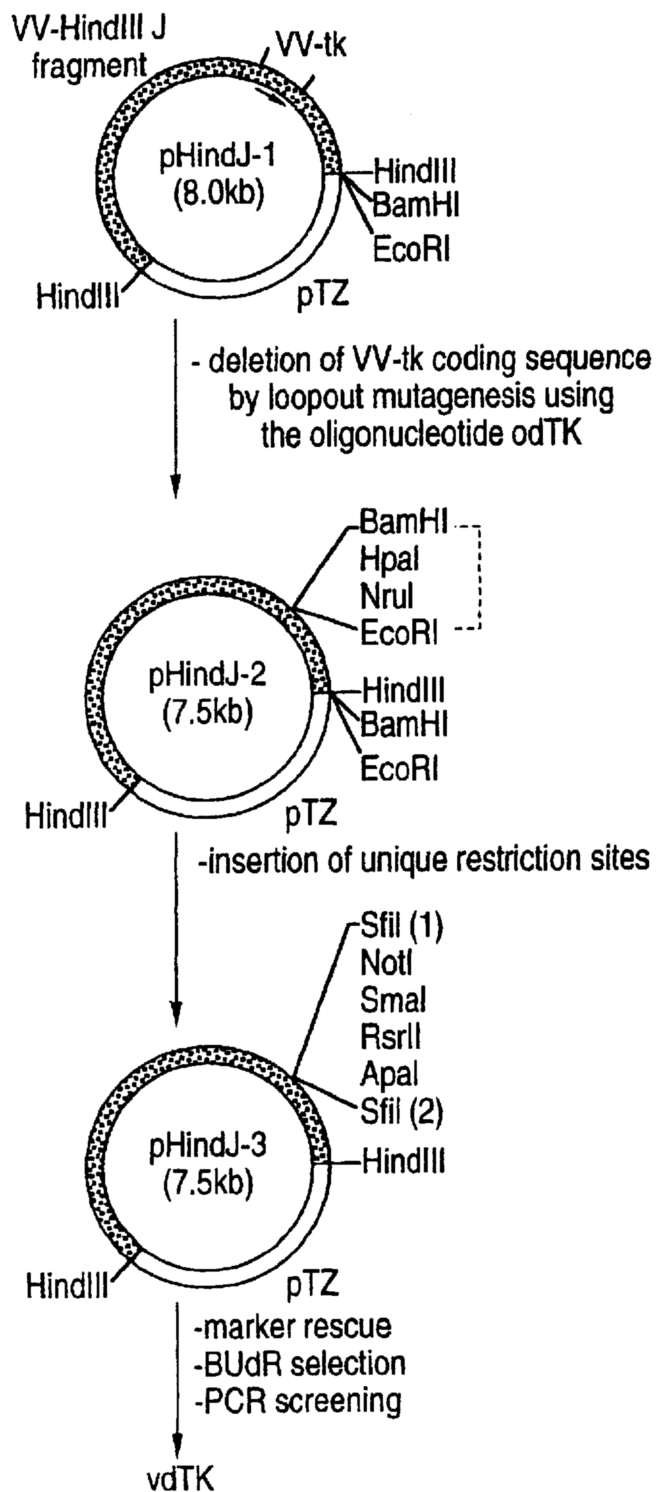

Construction of the plasmids pA1 and pA2
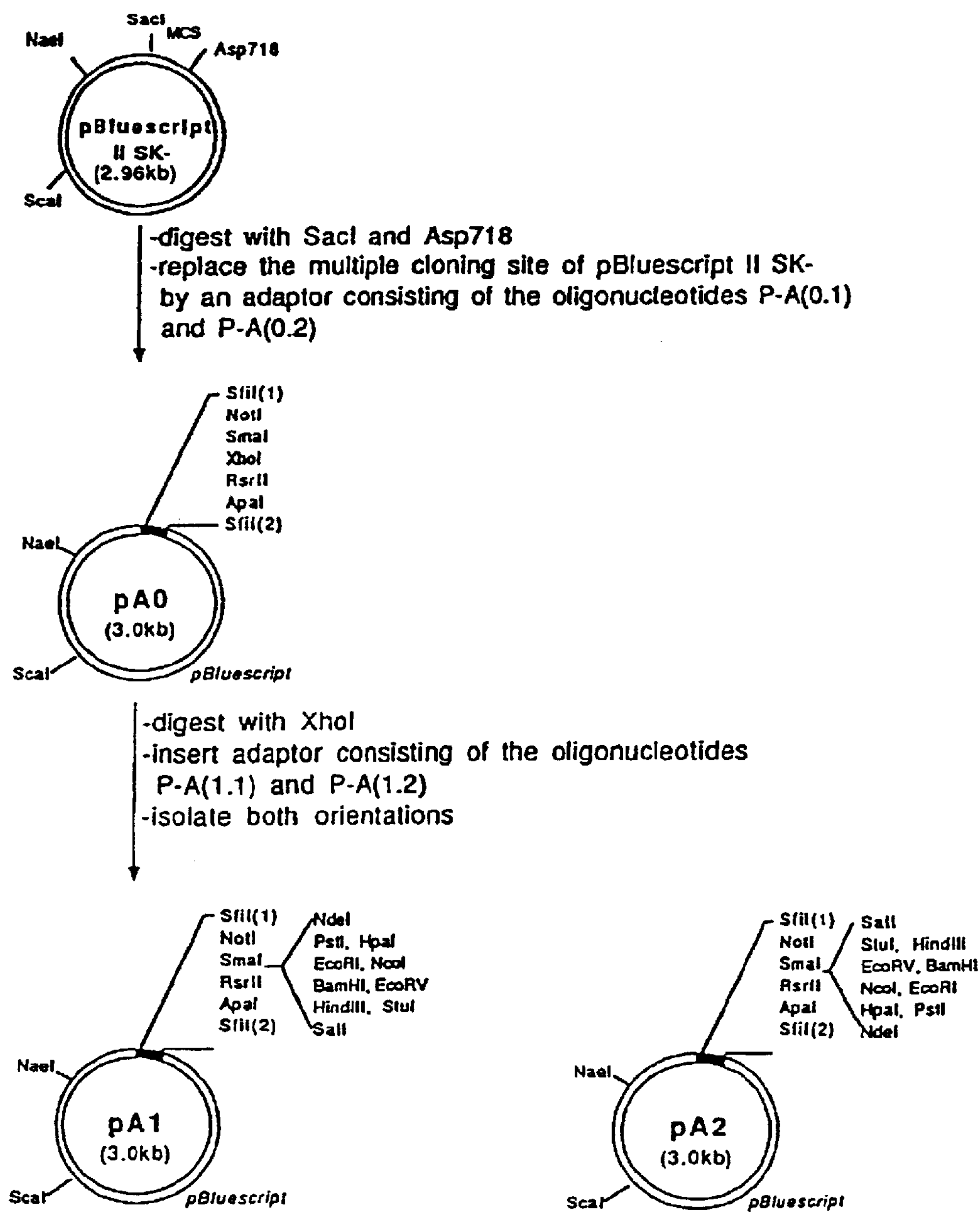
FIGURE 4.3

FIG. 4.4A
Construction of the plasmids pA1-S1 and pA2-S1
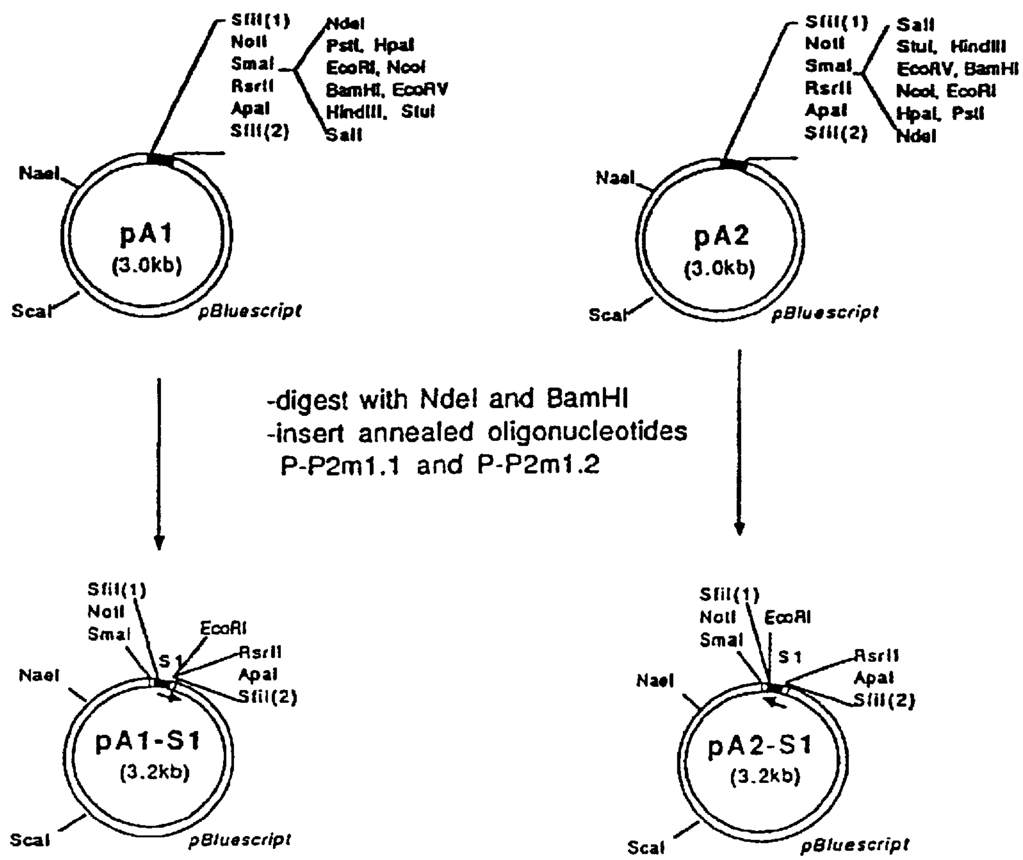
FIG. 4.4B
*Structure of the promoter S1:*
TACGGCTTGG TATAGCGGAC AACTAAGTAA TTGTAAAGAA GAAAACGAAA CTATCAAAAC CGTTTATGAA
ATGATAGAAA AAAGAATATA AATAATCCTG TATTTTAGTT TAAGTAACAG TAAAATAATG AGTAGAAAAT
EcoRI
ACTATTTTTT ATAGCCTATA AATCATGAATTCG

FIG. 4.5A
Construction of the plasmids pA1-S2 and pA2-S2
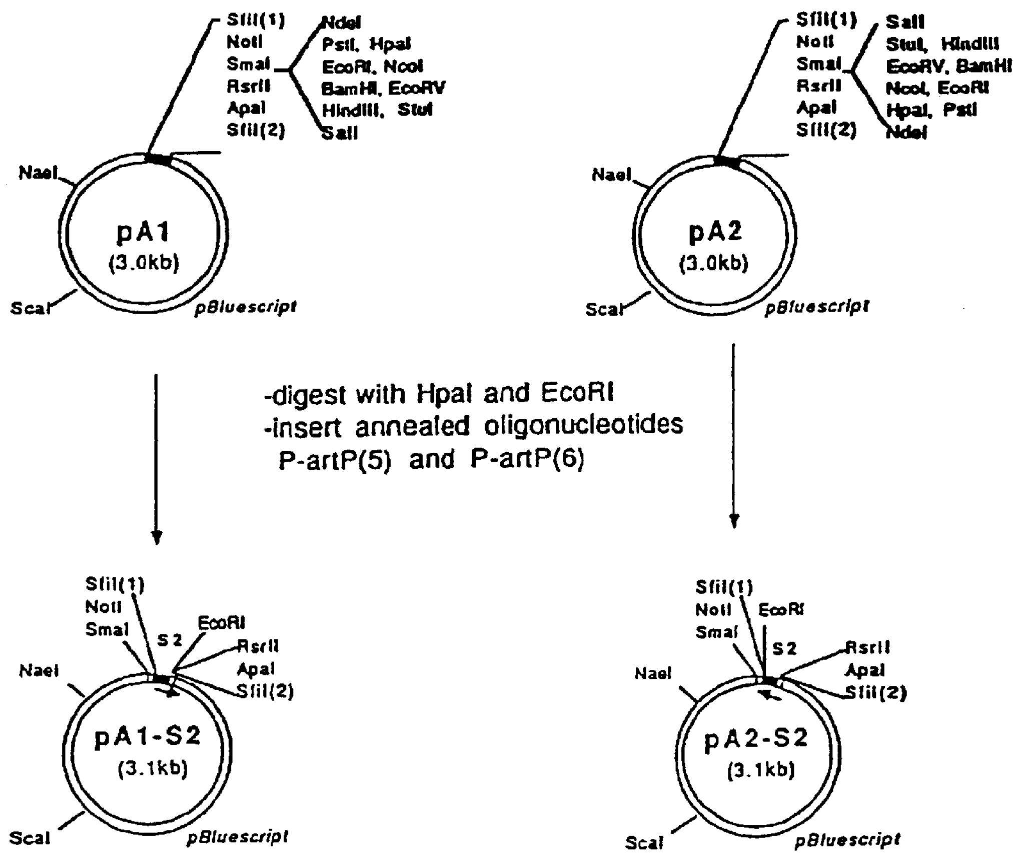
FIG. 4.5B
Structure of the promoter S2
PstI EcoRI
GGGAAGCTTT TTTTTTTTTT TTTTTTTGGC ATATAAATAG GCTGCAGG AATTC
vector DNA

FIG. 4.6
CONSTRUCTION OF THE PLASMIDS pN2-gpta AND pN2-gptb
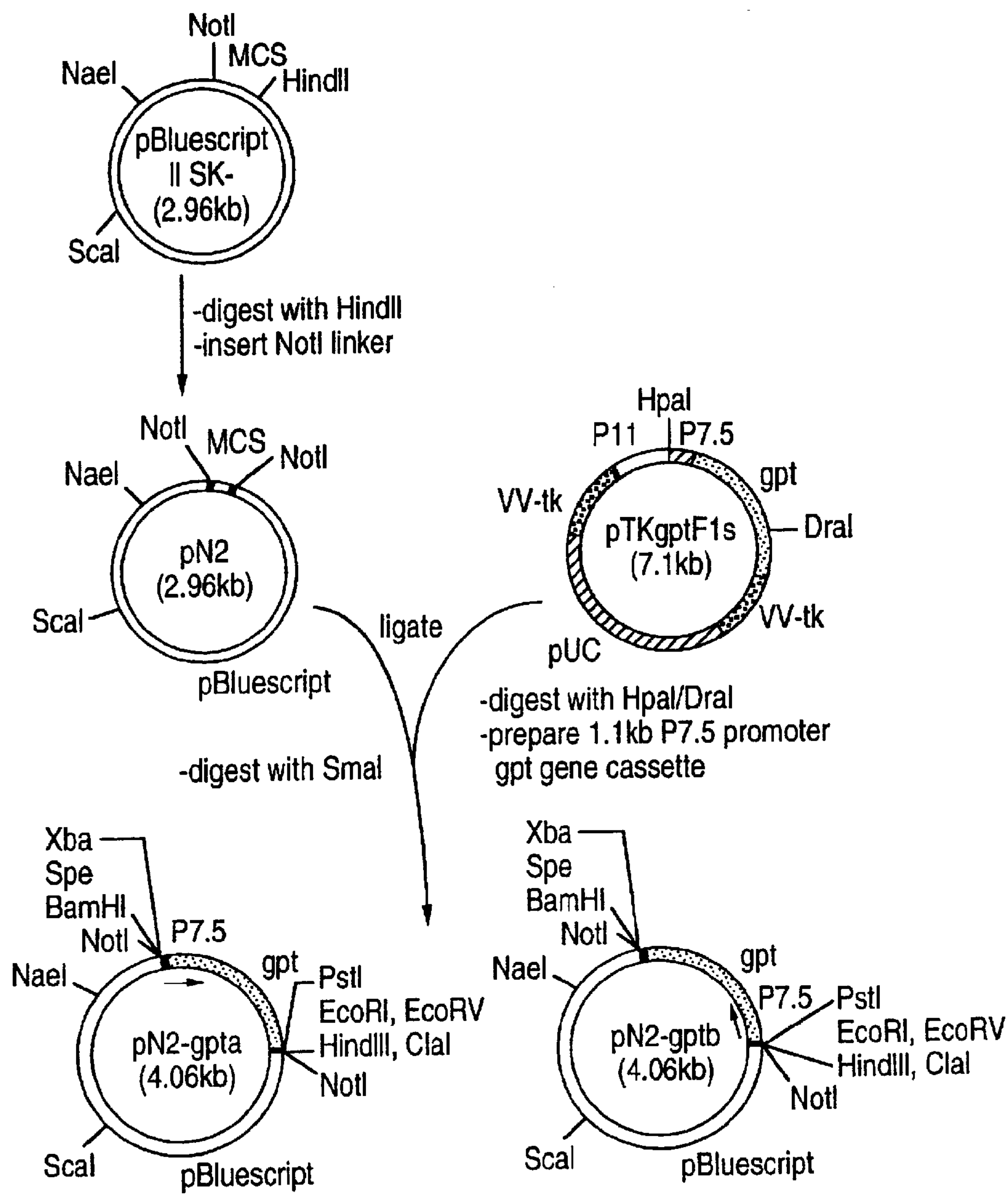

FIG. 4.7A

*Construction of the plasmids pN2gpt-S3A and pN2gpt-S4*

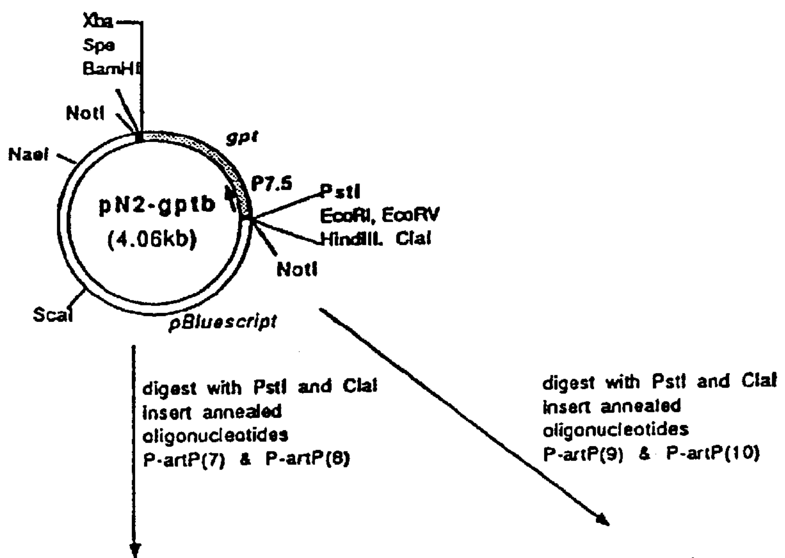

FIG. 4.7B

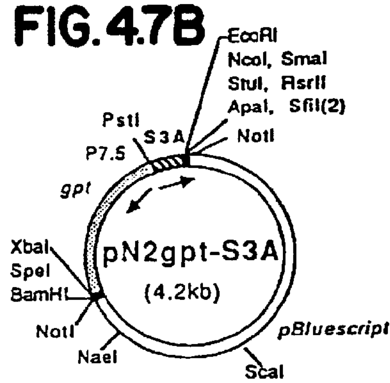

FIG. 4.7C

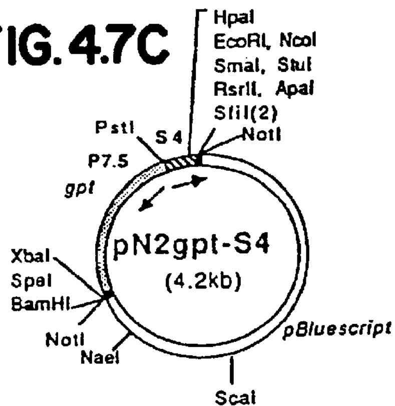

FIG. 4.7D

*Structure of the promoter S3A*

S3A → EcoRI NcoI SmaI StuI RsrII ApaI SfiI (2)

GAAGCTTTTTTTTTTTTTTTTTTTTTTGGCATATAAATGAATTCCATGGCCCGGGAGGCCTCGGACCGGGCCCGGCCATATAGGCCAG

FIG. 4.7E

*Structure of the promoter S4*

S4 → HpaI EcoRI NcoI SmaI StuI RsrII ApaI SfiI (2)

GAAGCTTTTTTTTTTTTTTTTTTTTGGCATATAAATCGTTAACGAATTCCATGGCCCGGGAGGCCTCGGACCGGGCCCGGCCATATAGGCCAG

FIG. 5.1
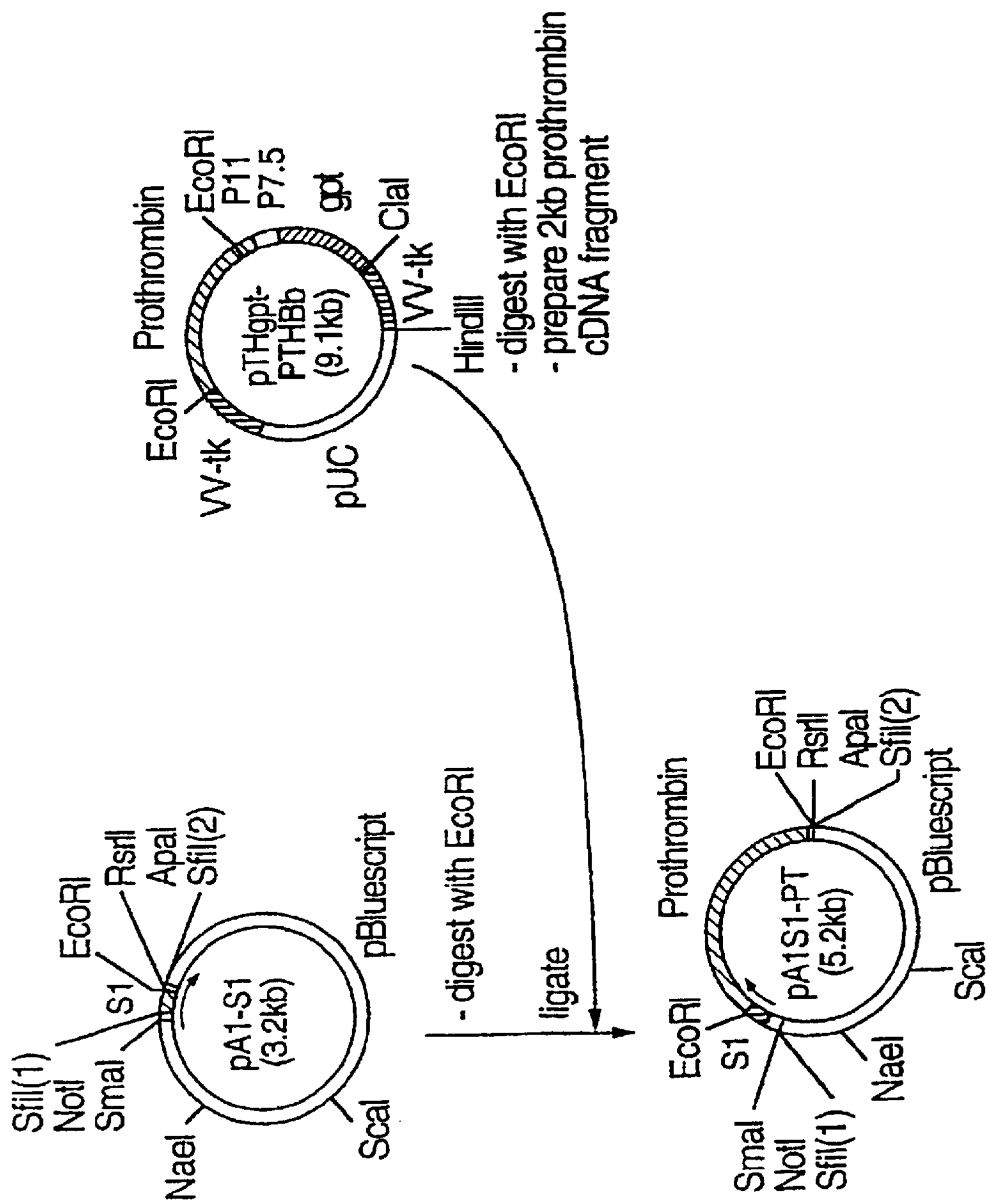

FIG. 5.2
Construction of the plasmid pN2gpt-GPg
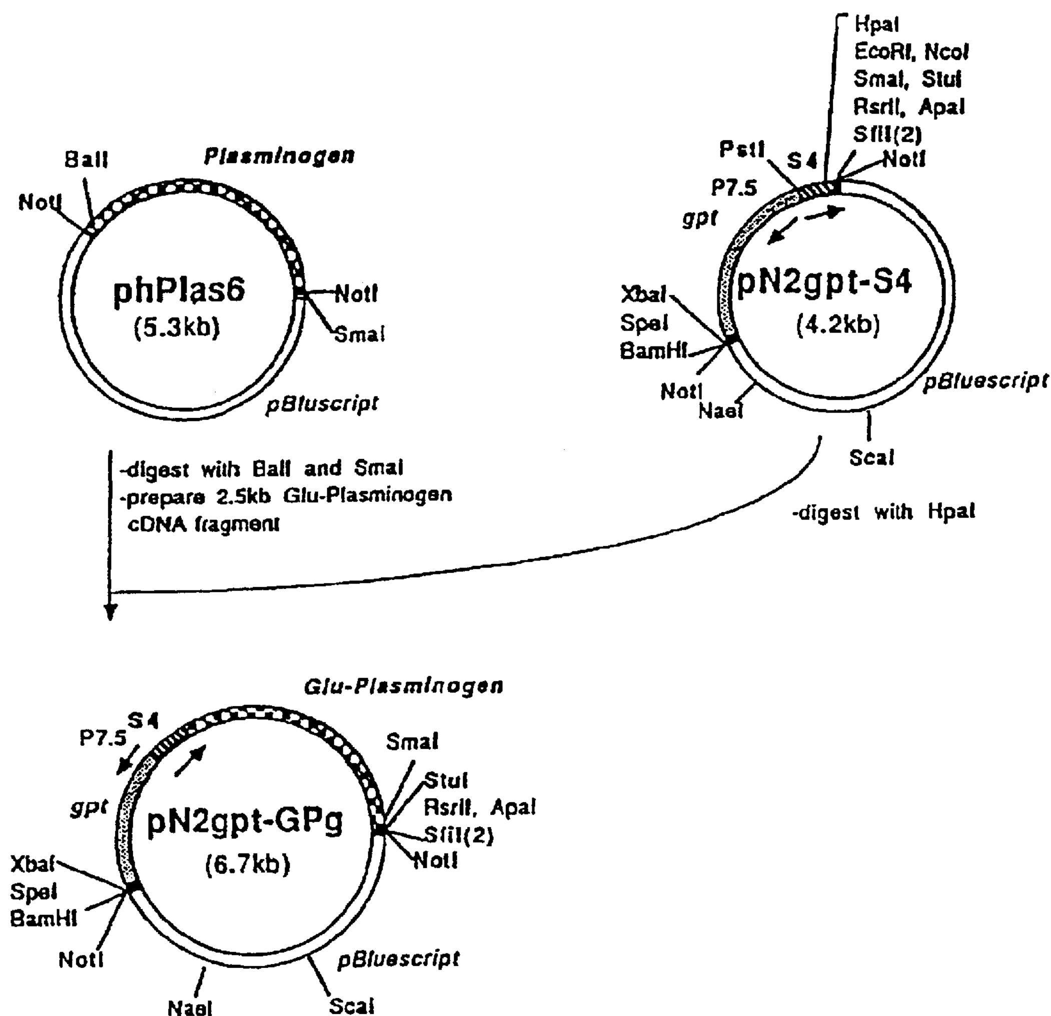

Construction of the plasmid pN2gpt-LPg
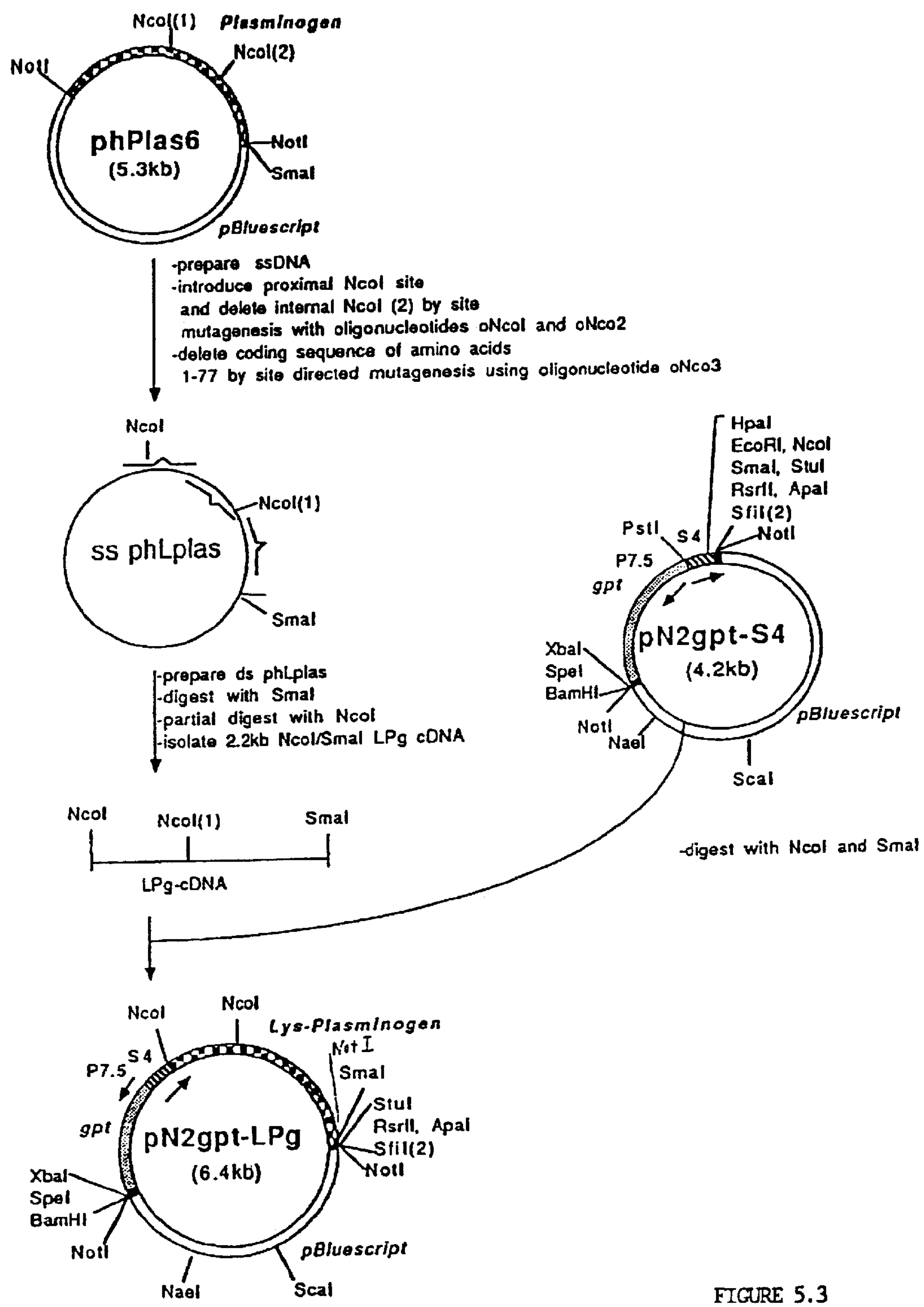
FIGURE 5.3

Construction of the plasmid pN2gpt-gp160
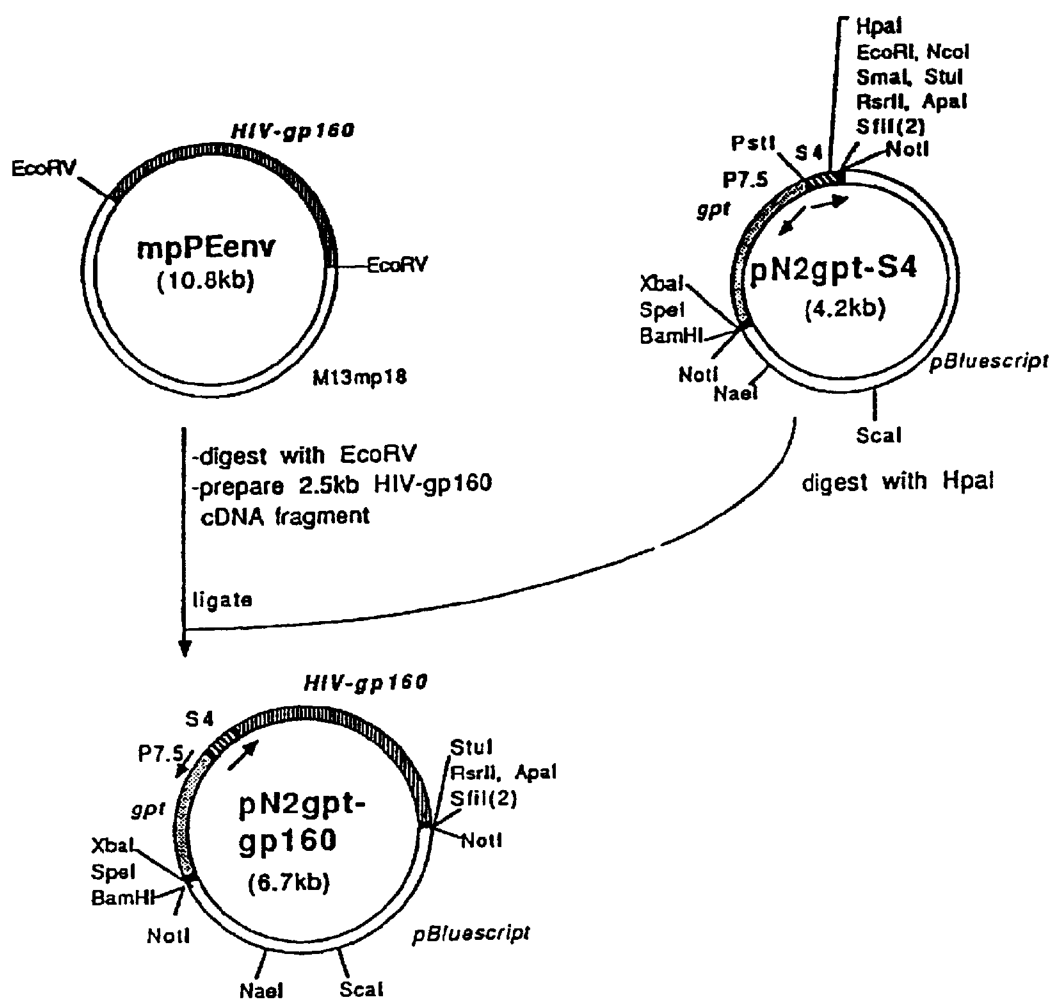
FIGURE 5.4

FIG. 5.5
Construction of the plasmid pTZgpt-S3AlacZ
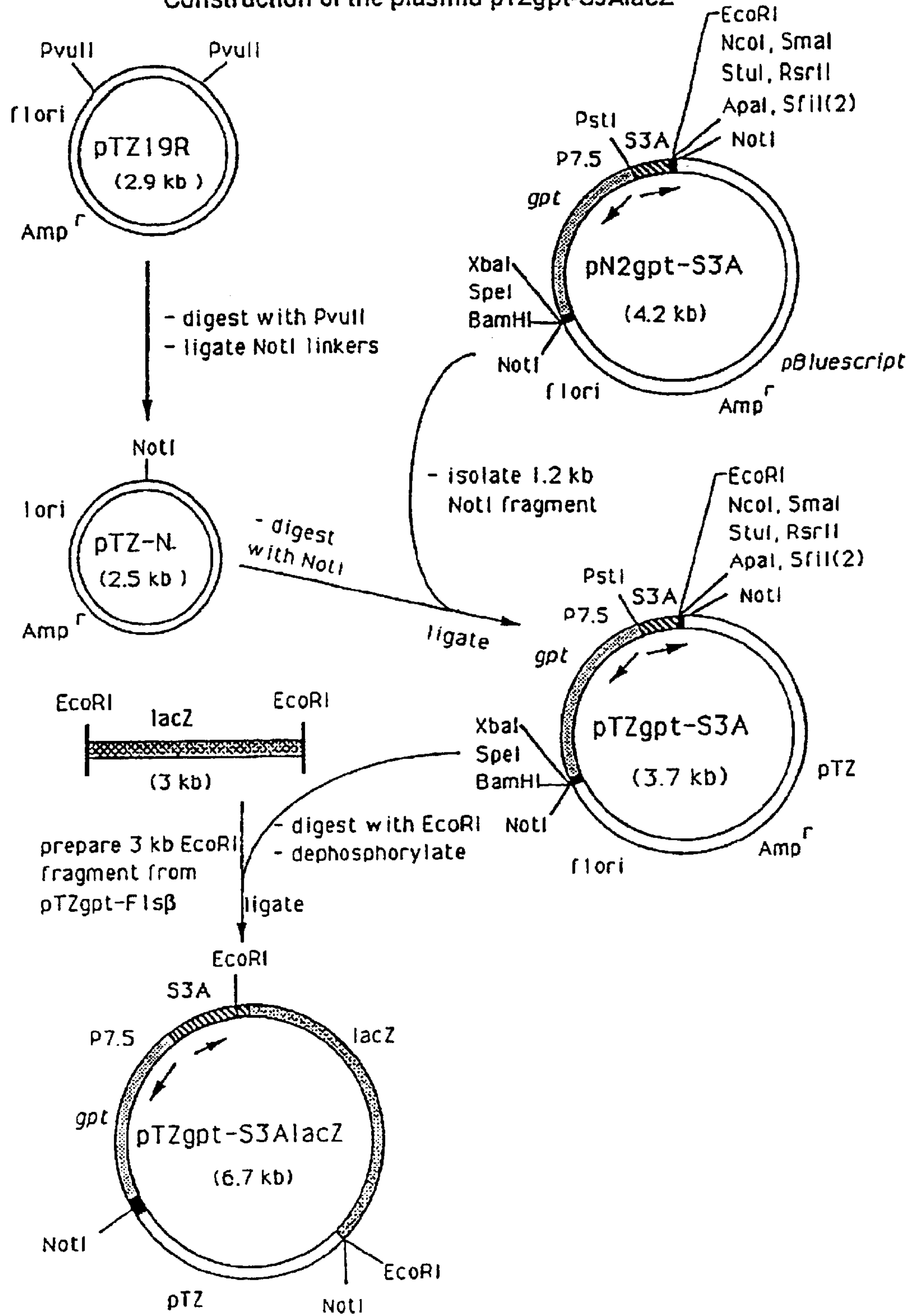

*FIG. 5.6*
CONSTRUCTION OF THE PLASMIDS pTZS4-lacZa/b
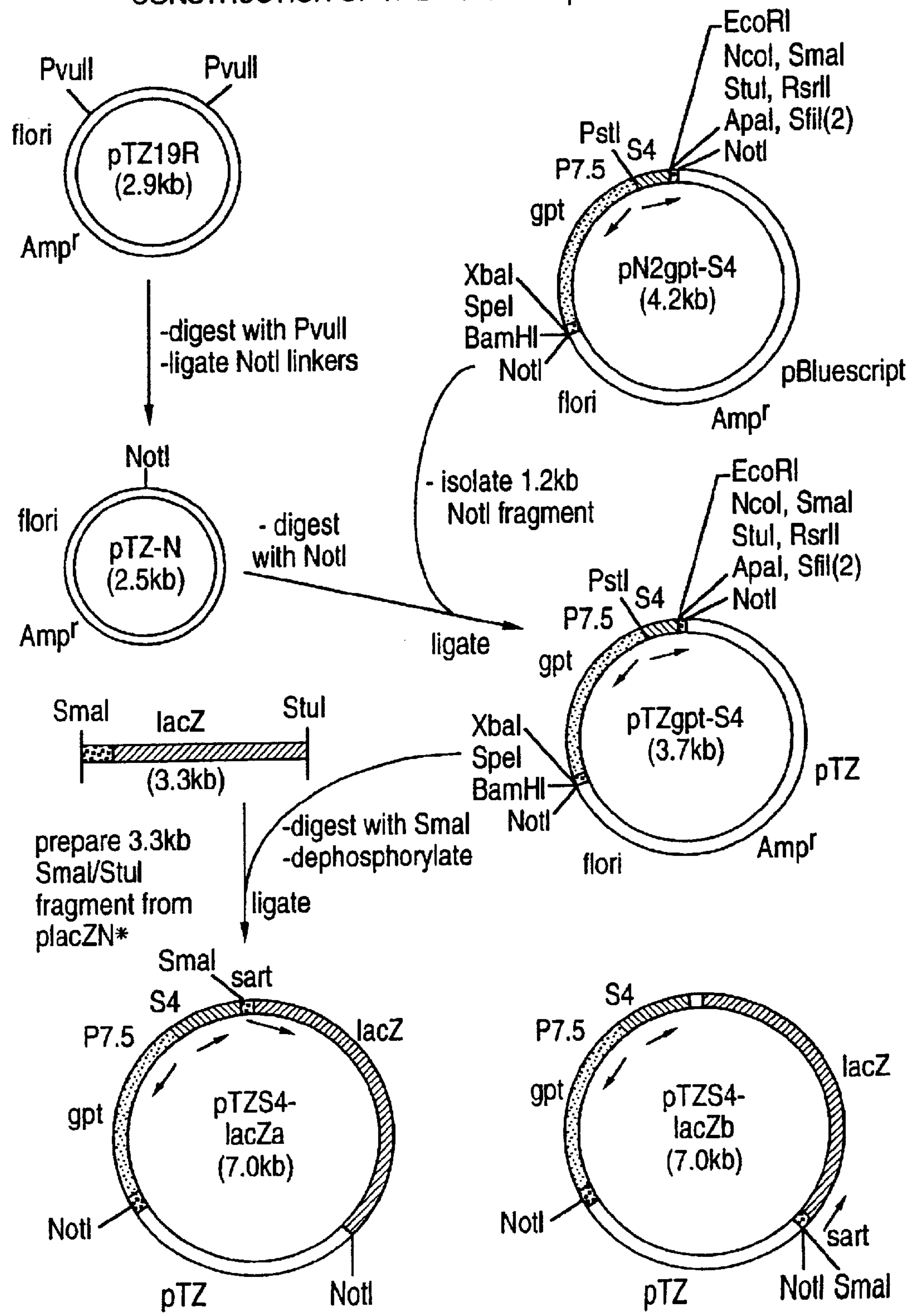

FIG. 6.1A
*Construction of the VV vector vS4*
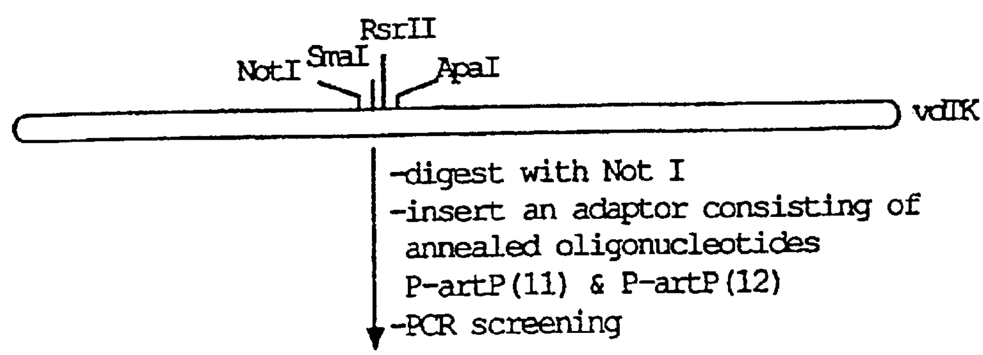
FIG. 6.1B
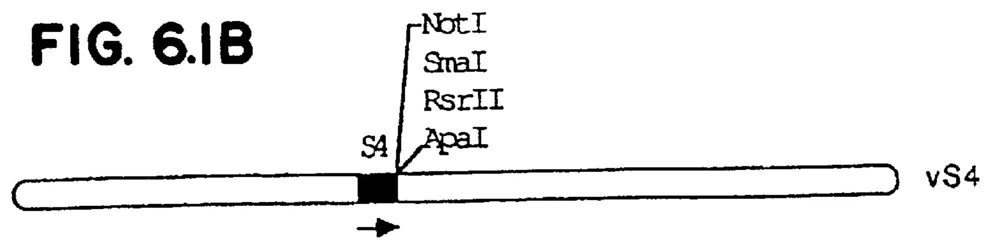
FIG. 6.1C
*Structure of the promoter-adaptor in vS4*
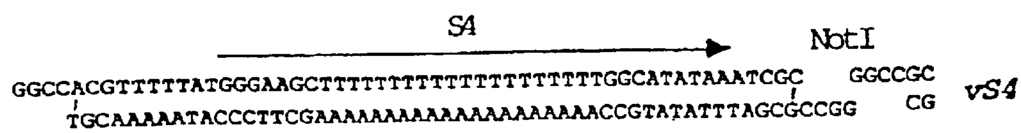

FIG. 6.2A
Construction of the vaccinia virus strain vvWF
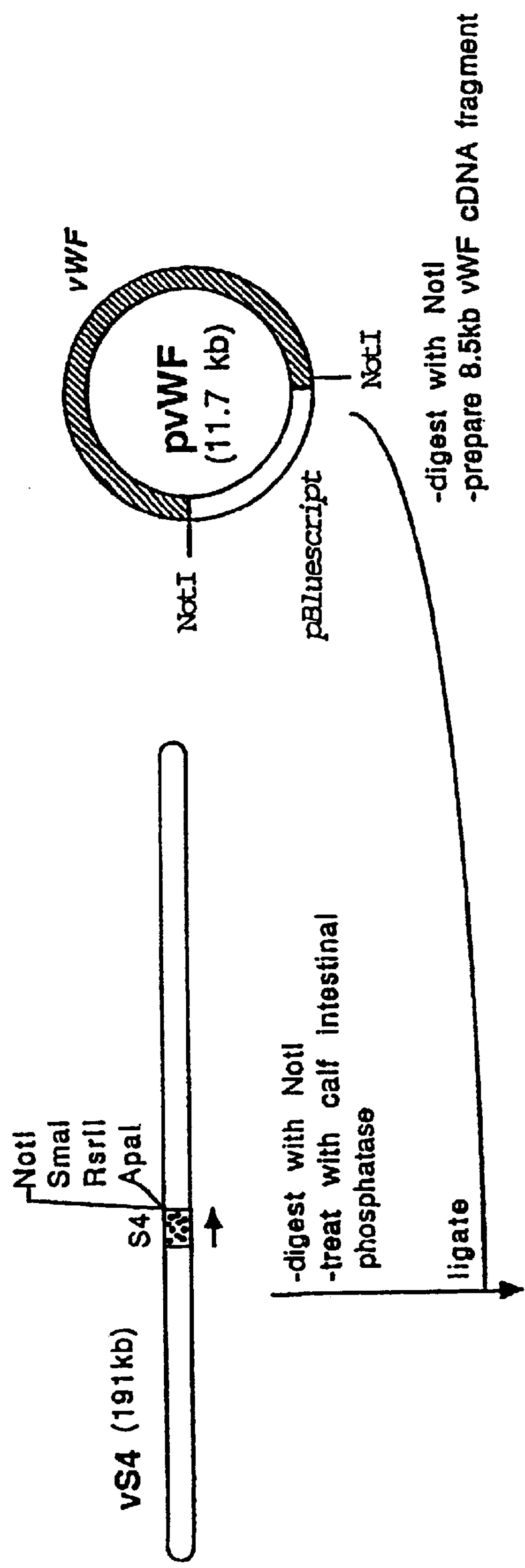
FIG. 6.2B

FIG. 7.1

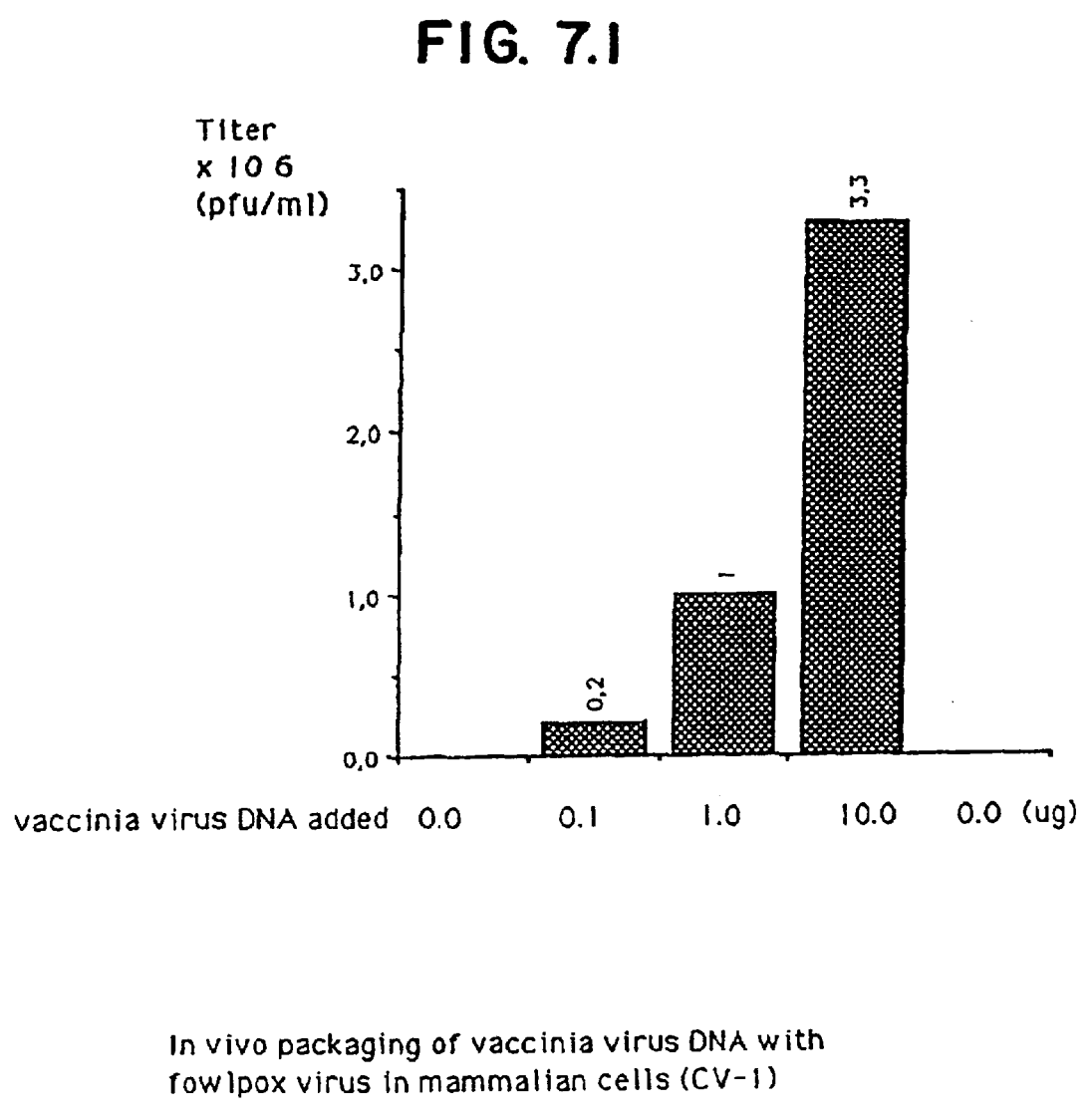

Titer
x 10 6
(pfu/ml)

3,0
2,0
1,0
0,0

0,2
1
3,3 vaccinia virus DNA added 0.0 0.1 1.0 10.0 0.0 (ug)

In vivo packaging of vaccinia virus DNA with fowlpox virus in mammalian cells (CV-1)

*FIG. 8.1*
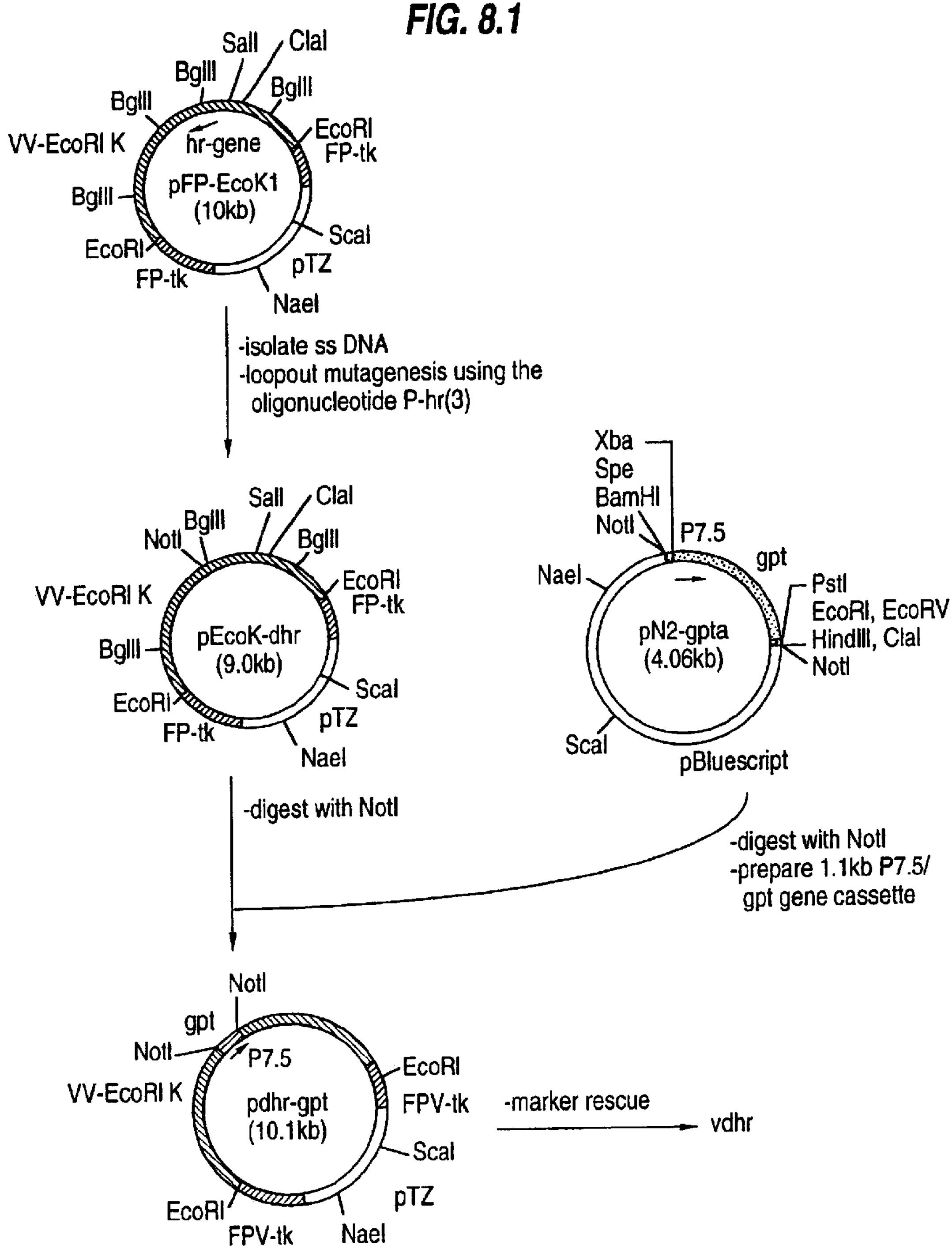

FIG. 9.1A
Construction of the plasmids pS2gpt-P2 and pP2gp160MN
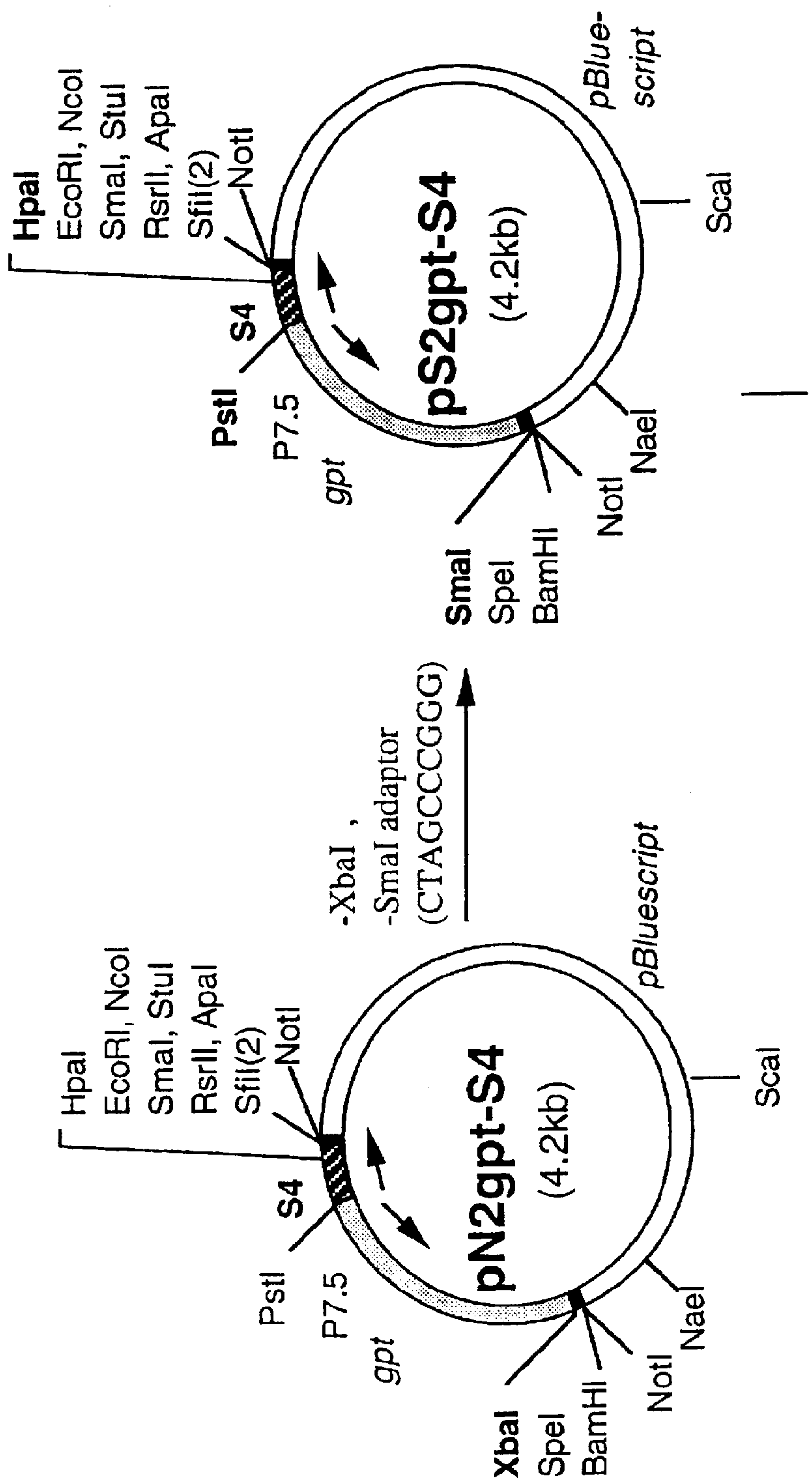

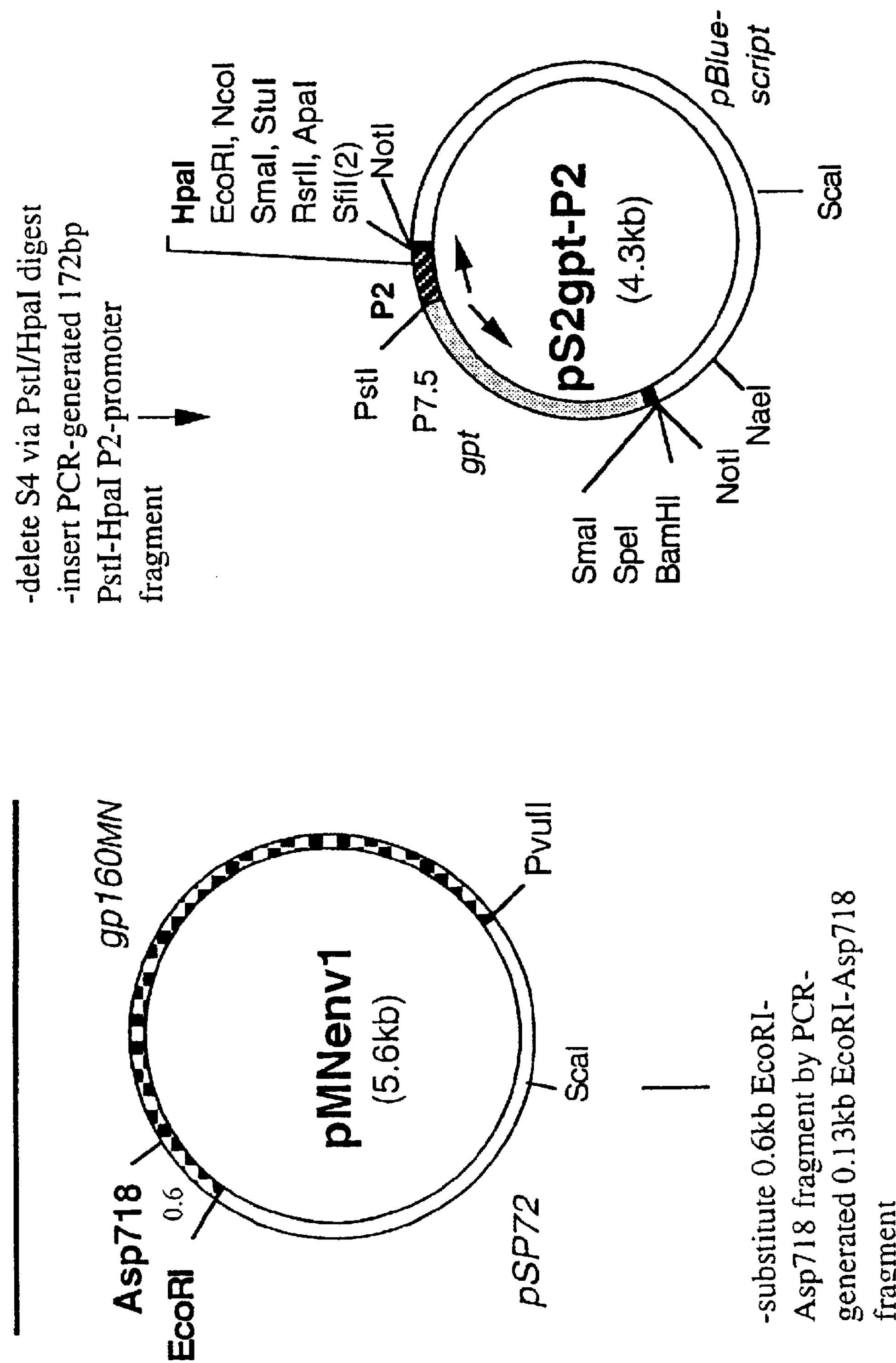
FIG. 9.1B
gp160MN
Asp718
EcoRI
0.6
pMNenv1
(5.6kb)
PvuII
ScaI
pSP72
-substitute 0.6kb EcoRI-Asp718 fragment by PCR-generated 0.13kb EcoRI-Asp718 fragment
-delete S4 via PstI/HpaI digest
-insert PCR-generated 172bp PstI-HpaI P2-promoter fragment
HpaI
EcoRI, NcoI
SmaI, StuI
RsrII, ApaI
SfiI(2)
NotI
P2
PstI
P7.5
gpt
pS2gpt-P2
(4.3kb)
pBlue-script
ScaI
NaeI
NotI
SmaI
SpeI
BamHI

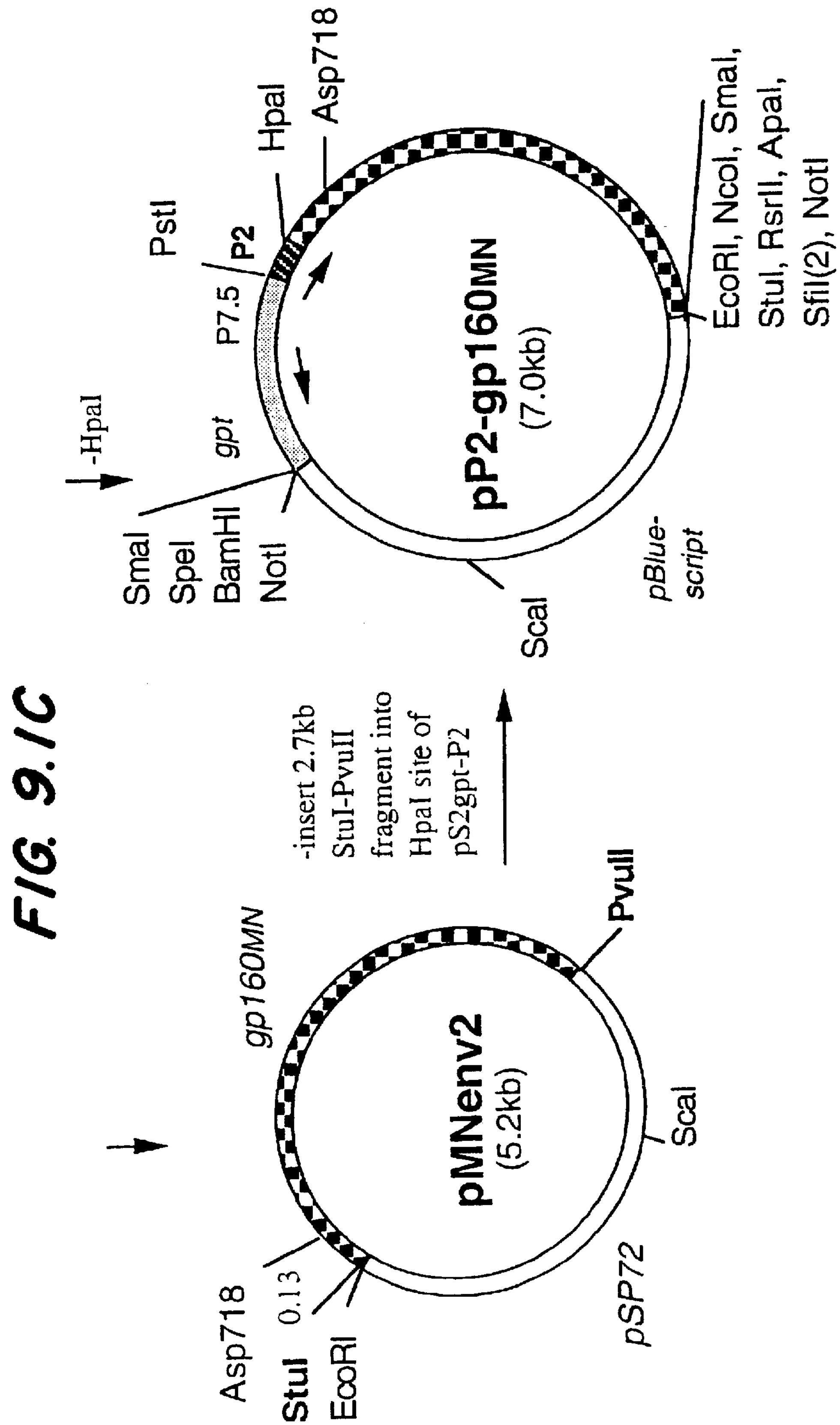
FIG. 9.1C
Asp718
StuI
EcoRI
0.13
gp160MN
pMNenv2
(5.2kb)
PvuII
ScaI
pSP72
-insert 2.7kb
StuI-PvuII
fragment into
HpaI site of
pS2gpt-P2
-HpaI
SmaI
SpeI
BamHI
NotI
gpt
P7.5
PstI
P2
HpaI
Asp718
pP2-gp160MN
(7.0kb)
EcoRI, NcoI, SmaI,
StuI, RsrII, ApaI,
SfiI(2), NotI
pBlue-
script
ScaI Construction of the chimaeric viruses vP2-gp160MNA and vP2-gp160MNB

Fig. 9.2

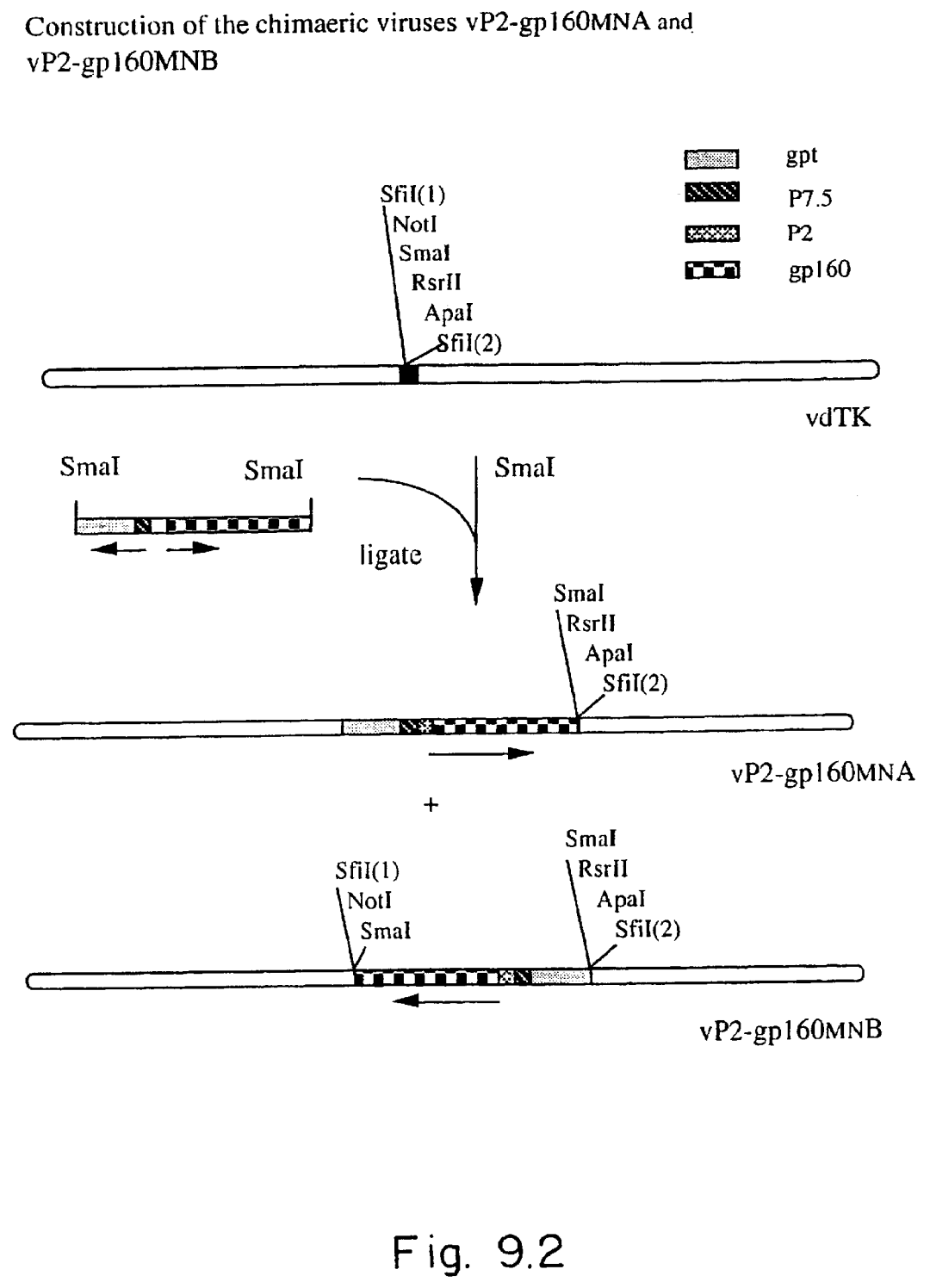

FIG. 9.3A
PstI-E-Fragment (wild-type virus)
P 5.8 E 11.4 P
1kb
17.2
PstI-Fragments
in vP2-gp160 MNA
FIG. 9.3B
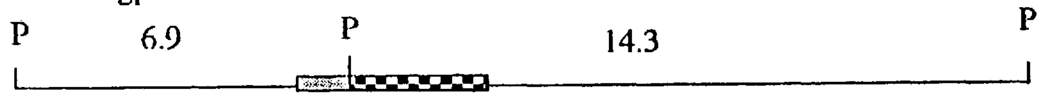
in vP2-gp160 MNB
FIG. 9.3C
P 8.7 P 12.5 P

FIG. 9.4A
Construction of the plasmids pTZ-L2, pTZselP-L2 and pselP-gpt-L2
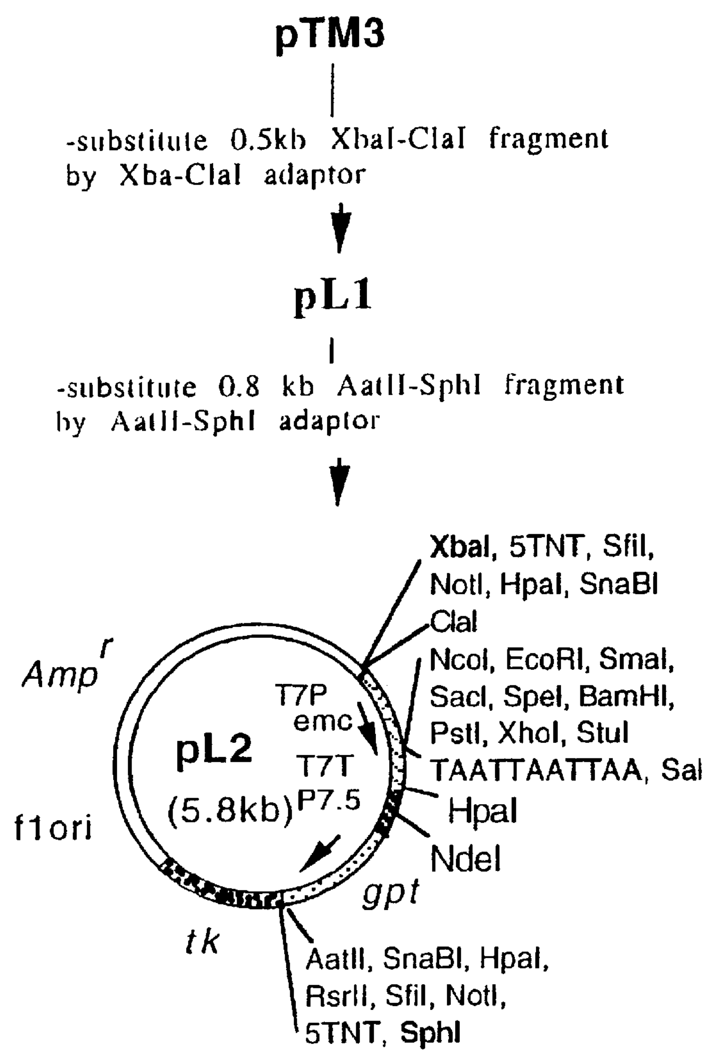

FIG. 9.4B
-insert XbaI-SphI T7-marker gene cassette between PvuII sites of pTZ19R
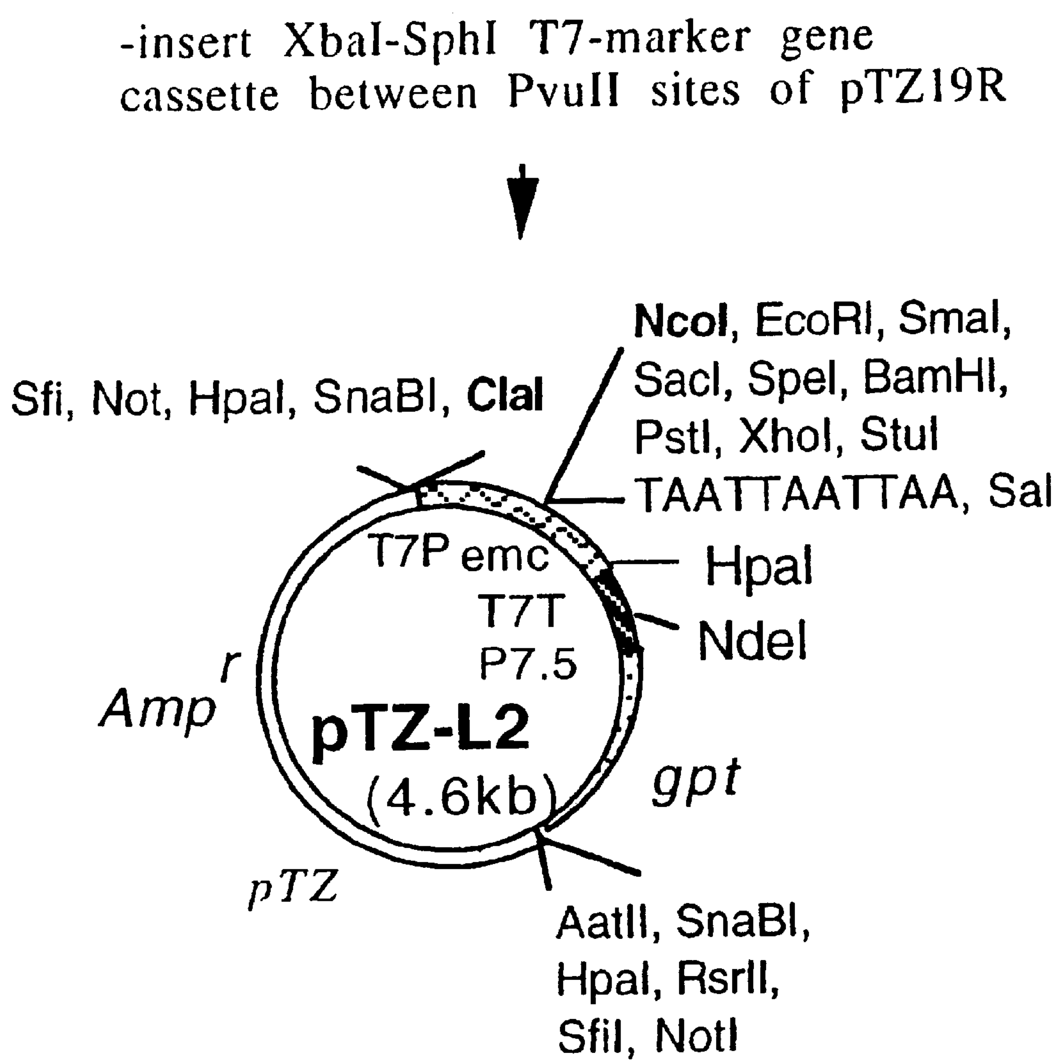

FIG. 9.4C
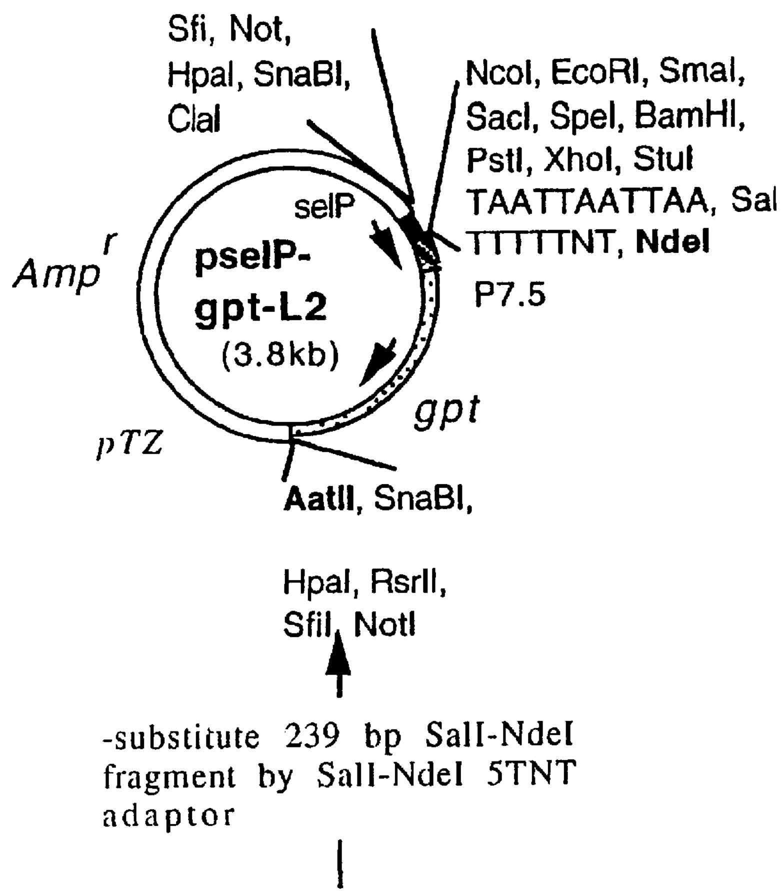
-substitute 239 bp SalI-NdeI fragment by SalI-NdeI 5TNT adaptor
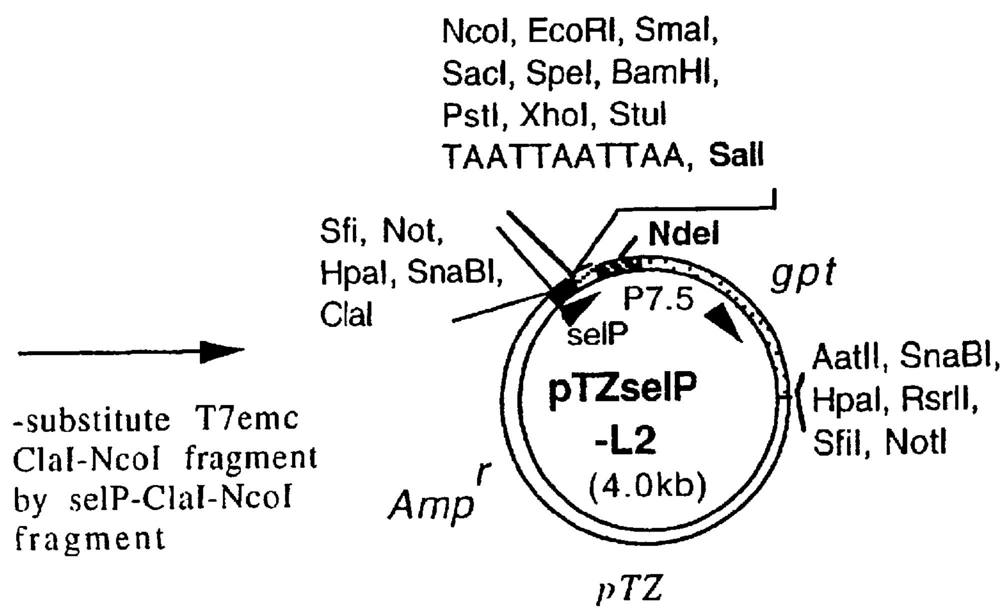
-substitute T7emc ClaI-NcoI fragment by selP-ClaI-NcoI fragment FIG. 9.5A1 Construction of the plasmid pselP-gp160MN
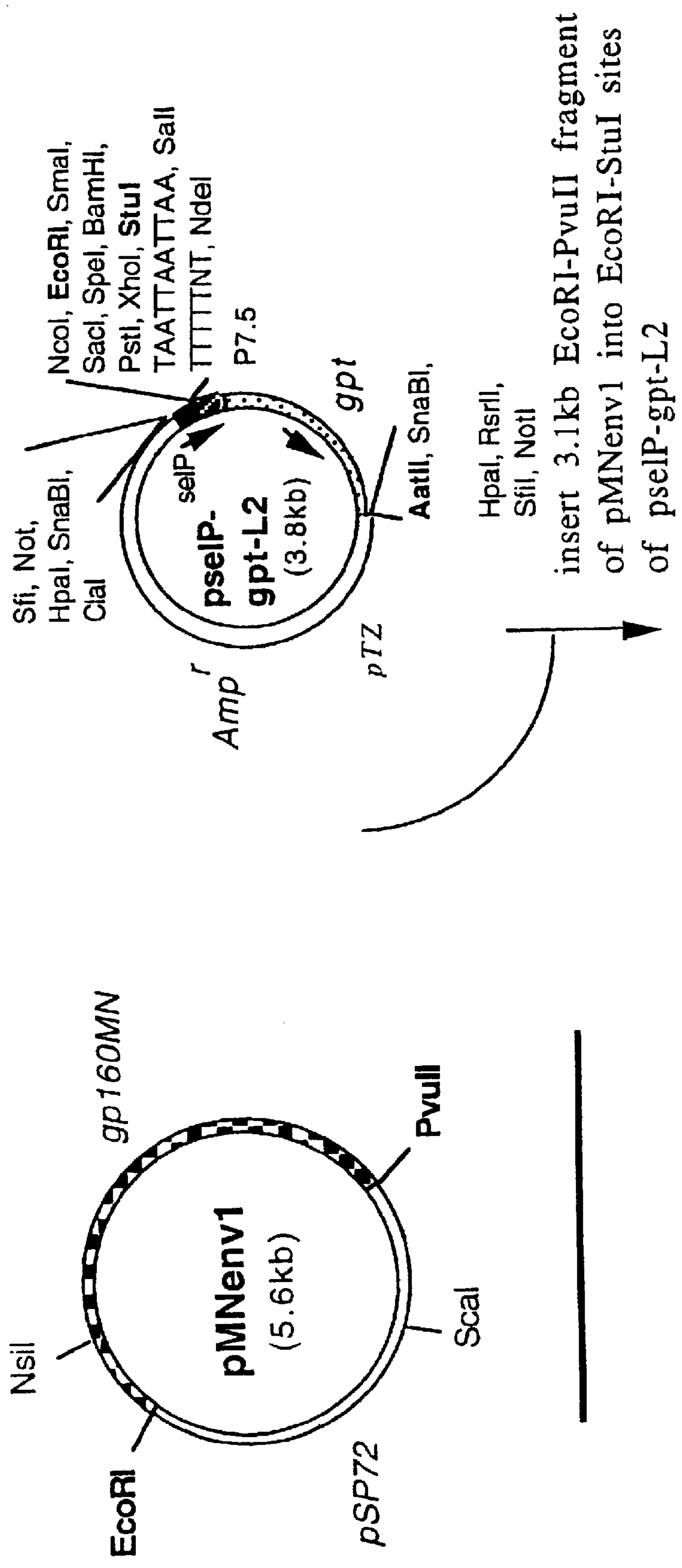

FIG. 9.5A2
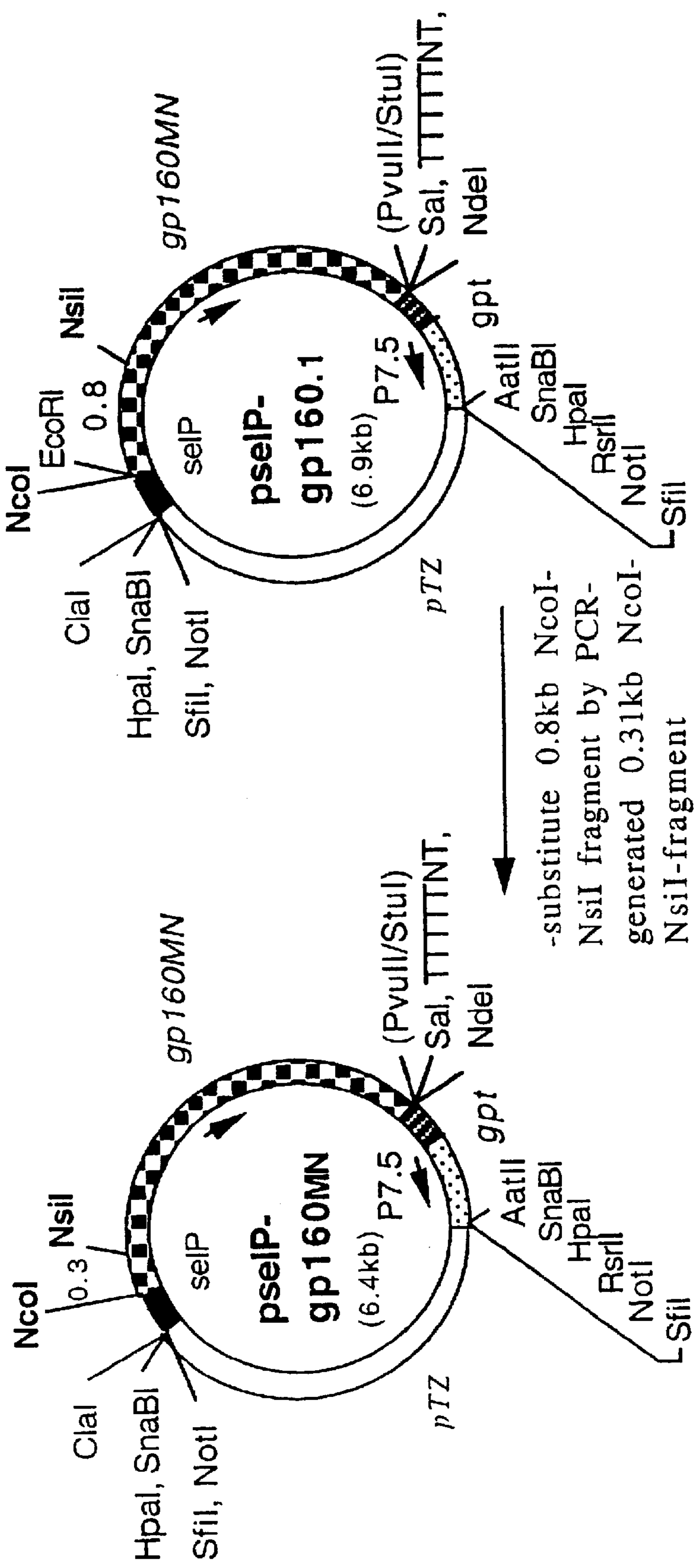

Fig. 9.5 B

```
wild-type gp160MN:                     MET ARG VAL  LYS
                                    CA ATG AGA GTG AAG

gp 160 in vselP-gp160-virus:           MET  ALA VAL  LYS
                                    CC ATG GCC GTG AAG
                                     NcoI
```

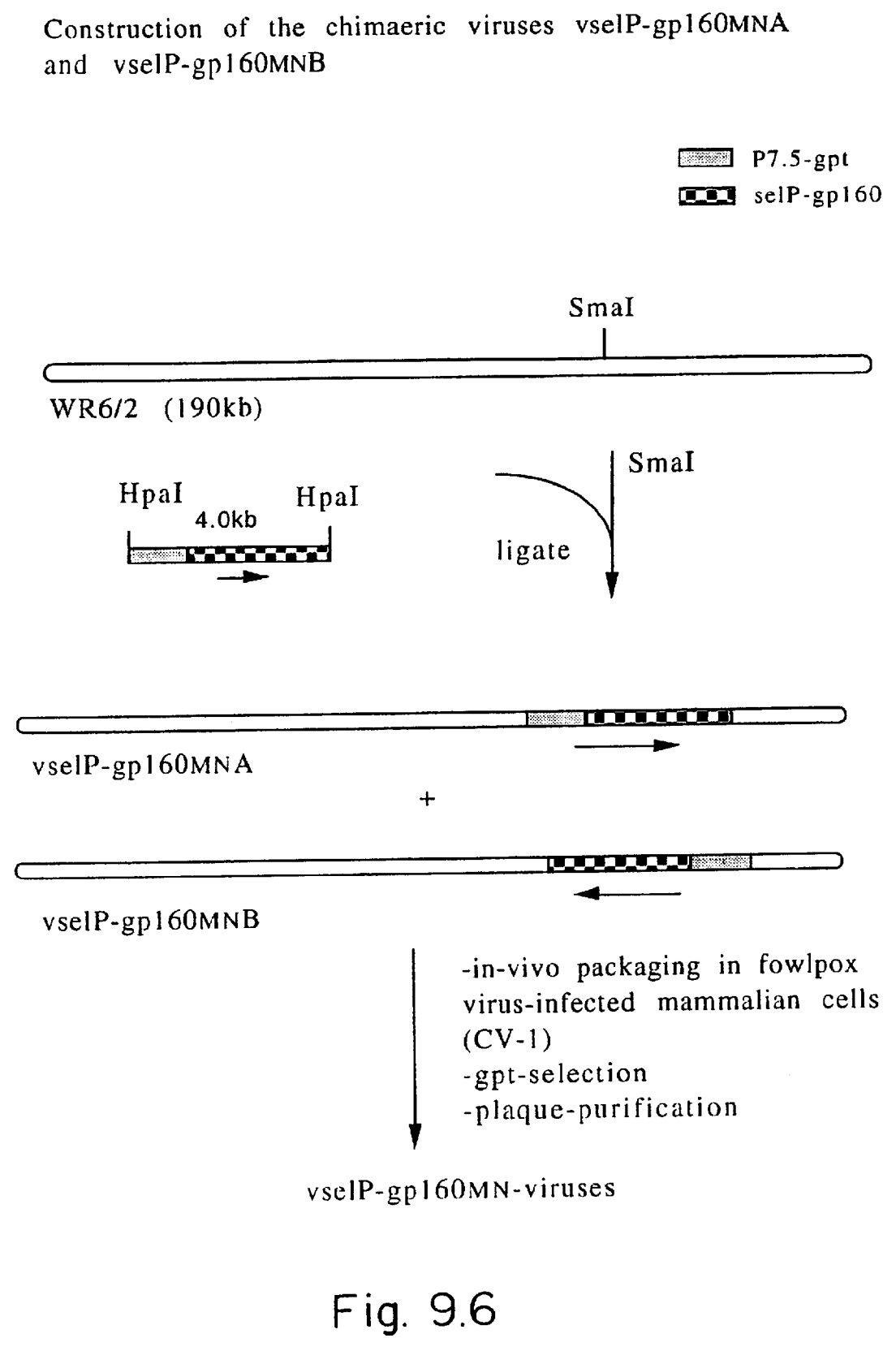

Construction of the chimaeric viruses vselP-gp160MNA and vselP-gp160MNB

P7.5-gpt
selP-gp160

SmaI

WR6/2 (190kb)

HpaI 4.0kb HpaI

SmaI ligate vselP-gp160MNA

+ vselP-gp160MNB

-in-vivo packaging in fowlpox virus-infected mammalian cells (CV-1)
-gpt-selection
-plaque-purification vselP-gp160MN-viruses

Fig. 9.6

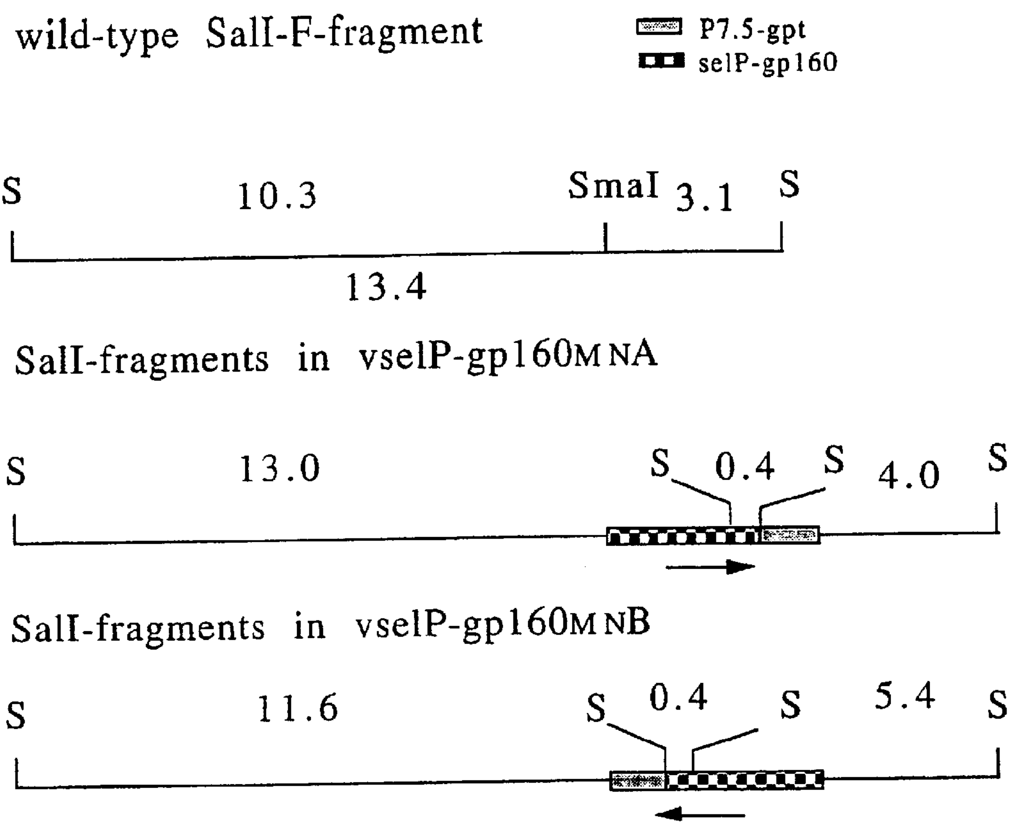
Figure 9.7

Structure of the plasmid pN2-gptaProtS
Fig. 10.1 A
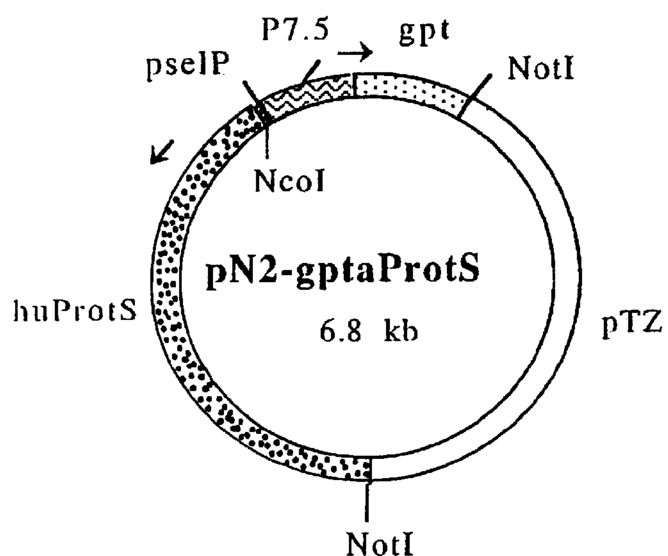
Fig. 10.1 B
| | | met | arg | val | leu | gly |
|---|---|---|---|---|---|---|
| Wild-type Protein S: | GAA | **ATG** | AGG | GTC | CTG | GGT |
| | | met | ala | val | leu | gly |
| Protein S in the chimeras: | GCC | **ATG** | GCG | GTC | CTG | GGT |
| | | NcoI | | | | |

FIG. 10.2A
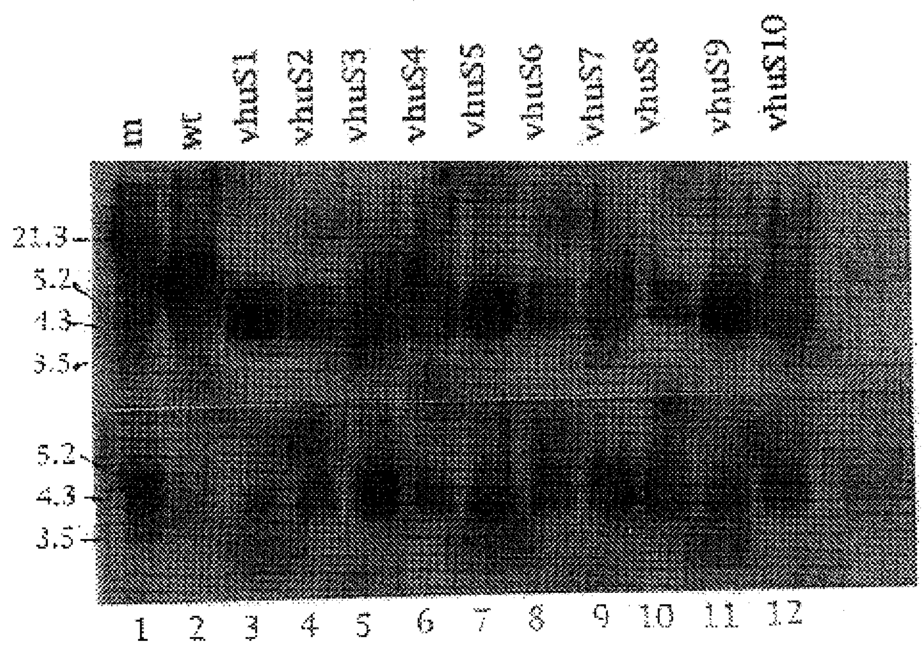
FIG. 10.2B
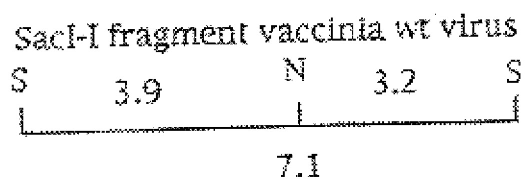
FIG. 10.2C
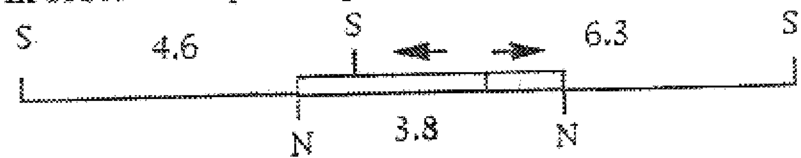

Fig. 10.3
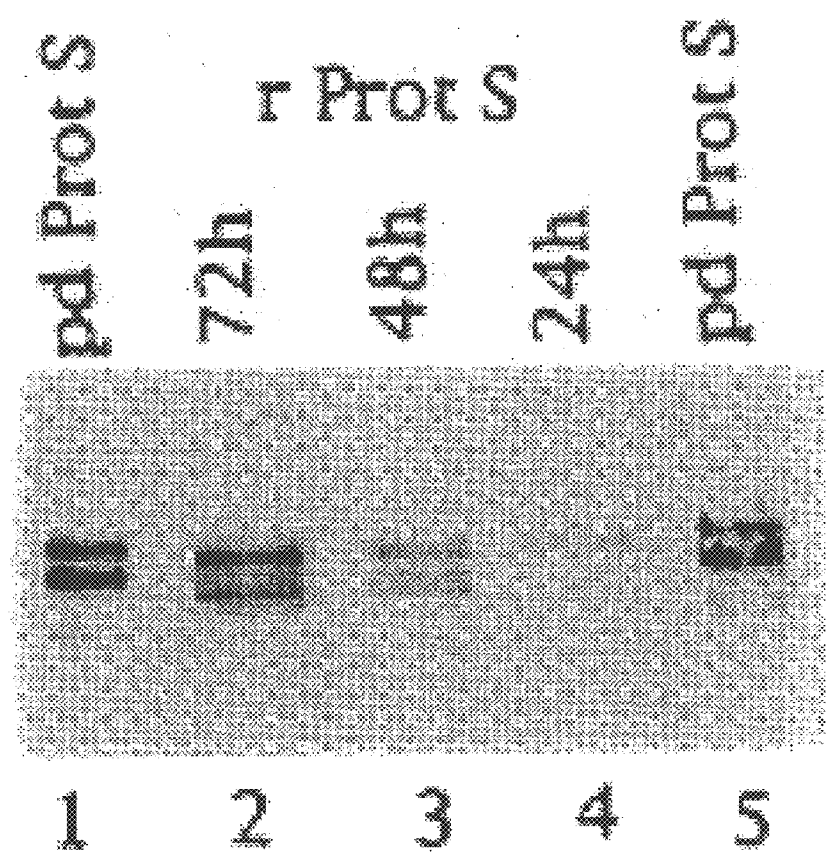

Structure of the plasmid pN2gpta-FIX
Fig. 11.1 A
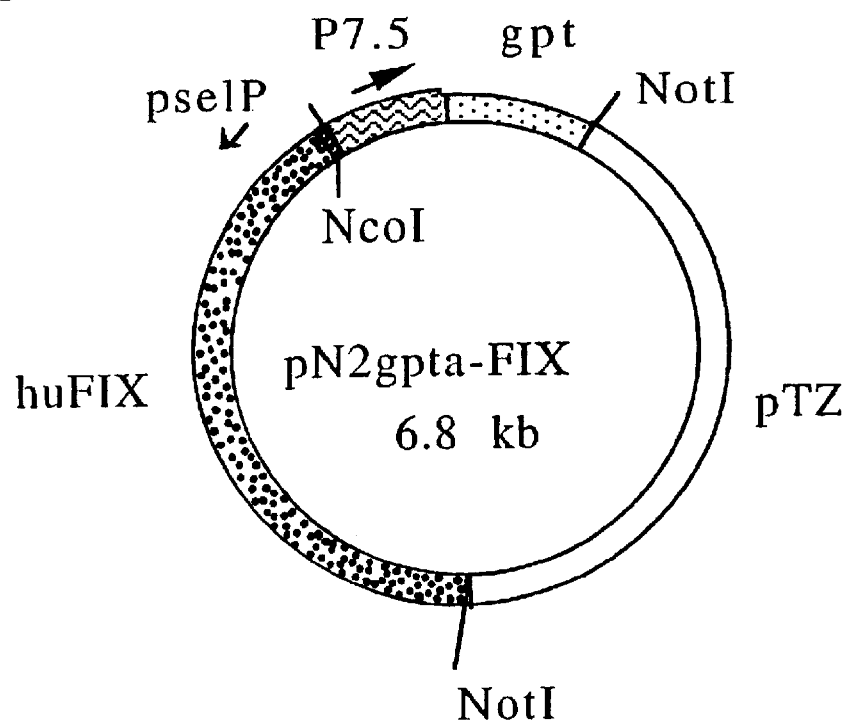
Fig. 11.1 B
| | met gln arg val asn |
|---|---|
| wild-type factor IX: | TT **ATG** CAG CGC GTG AAC |
| | met glu arg val asn |
|---|---|
| factor IX vFIX#5: | CC **ATG** GAG CGC GTG AAC |

FIG. 11.2A
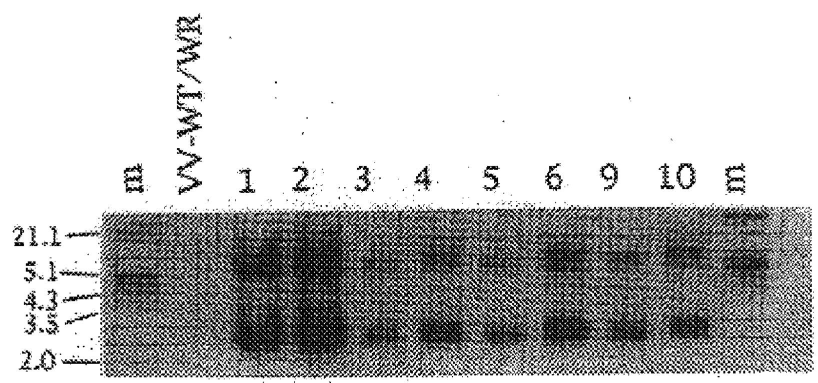
FIG. 11.2B1
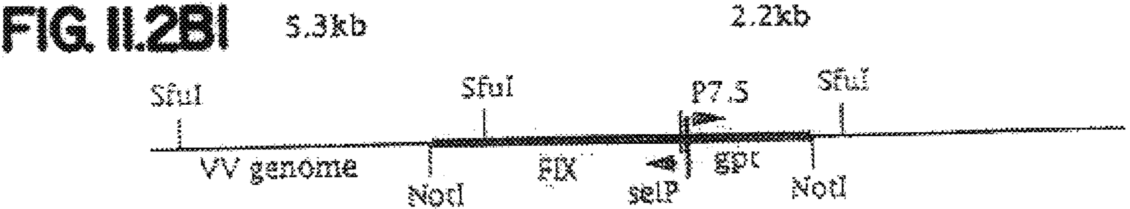
FIG. 11.2B2
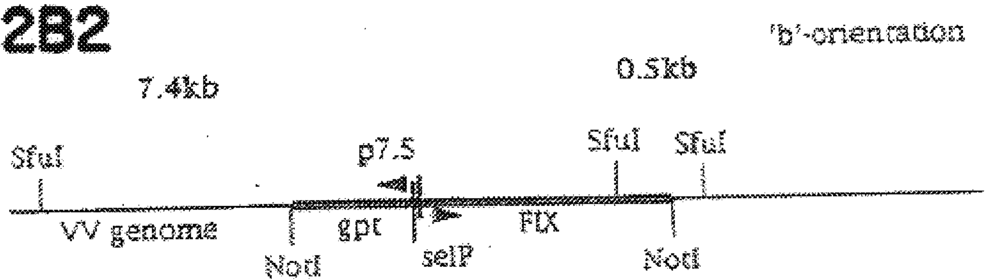
Southern blot analysis of the factor IX chimeras Fig. 11.3
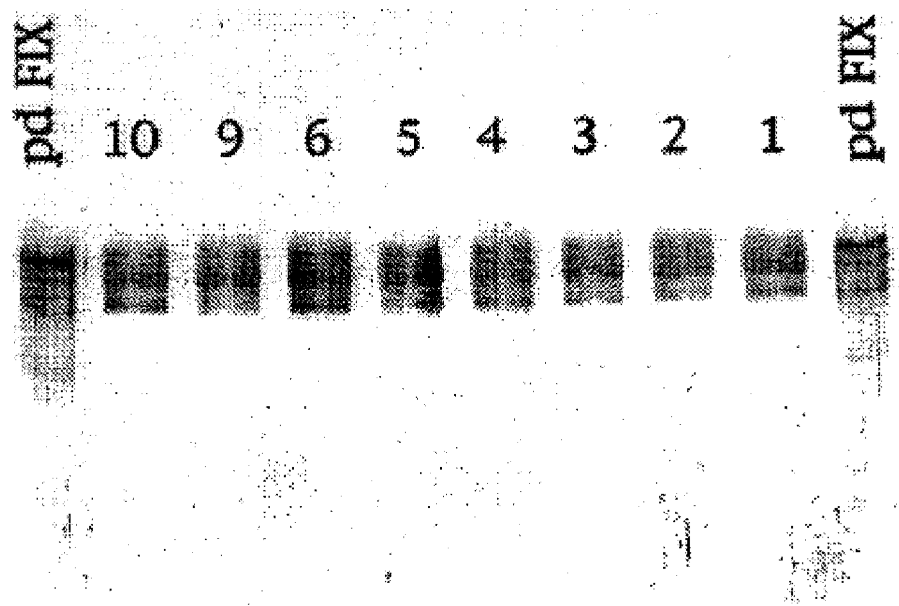
Western Blot analysis
Factor IX expression in Vero cells

Construction of the chimeric fowlpox virus f-env IIIB by direct molecular cloning
FPV recombinant f-TK2a (300kb)
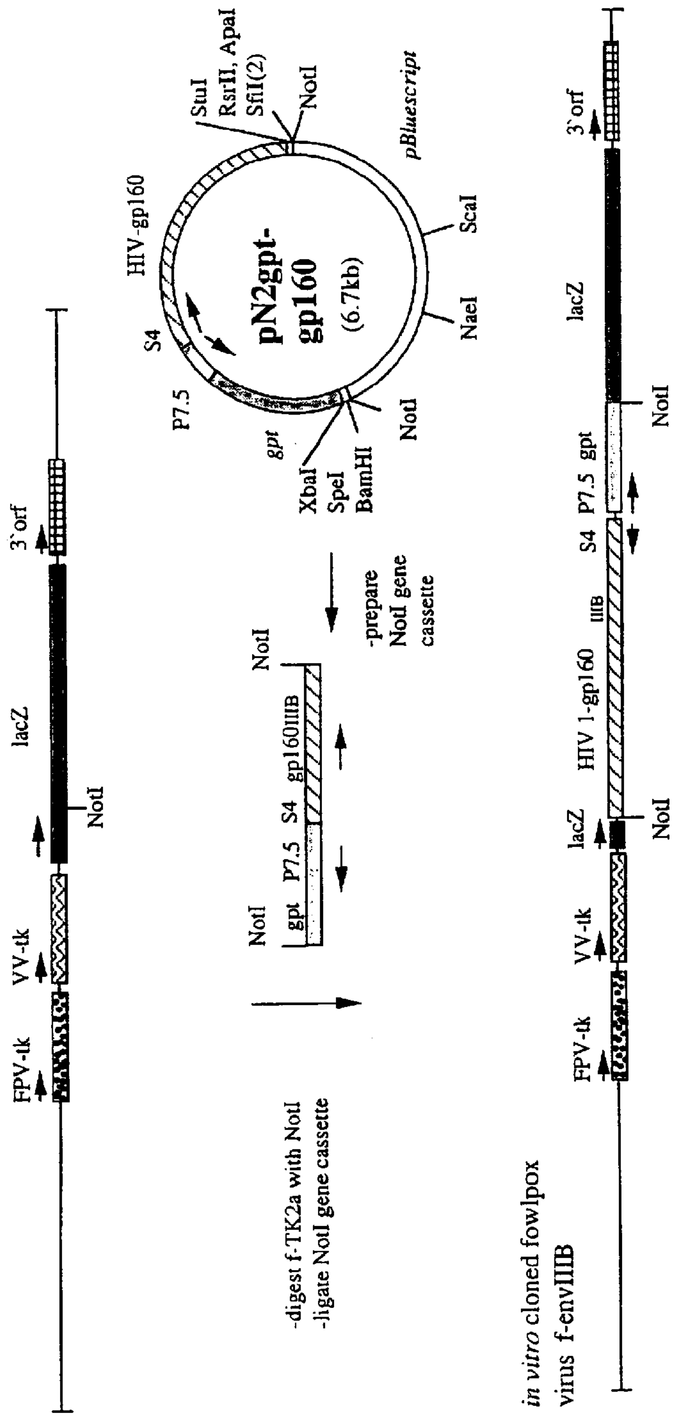
figure 12.1

Figure 12:
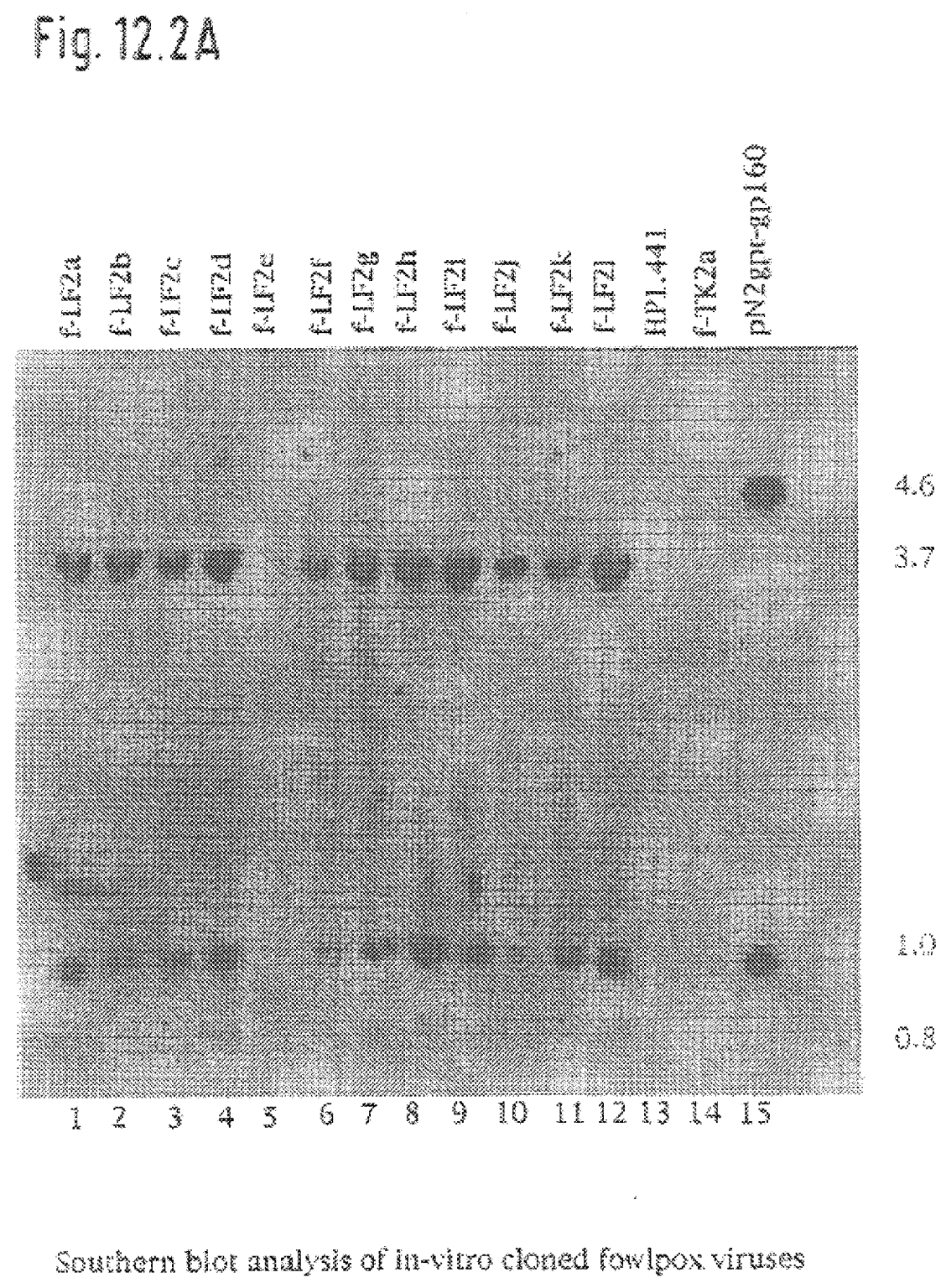

Fig. 12.2A

Southern blot analysis of in-vitro cloned fowlpox viruses

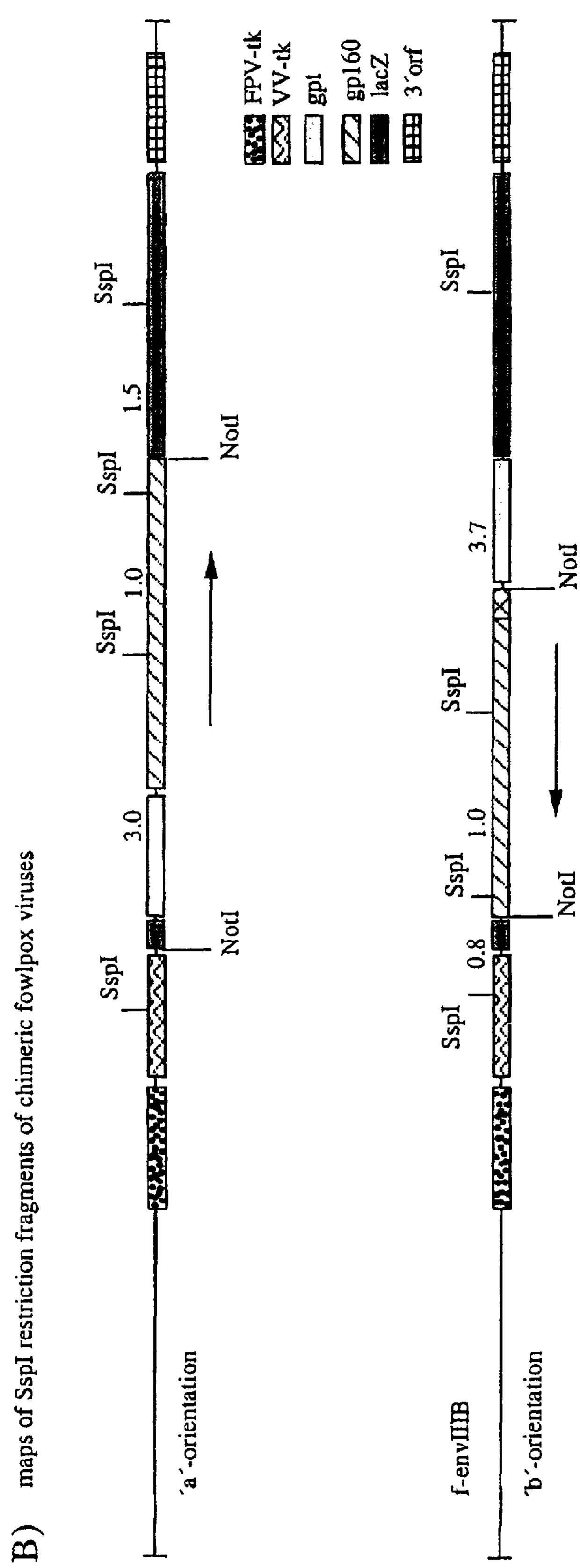
Fig. 12.2B

Fig.12.3
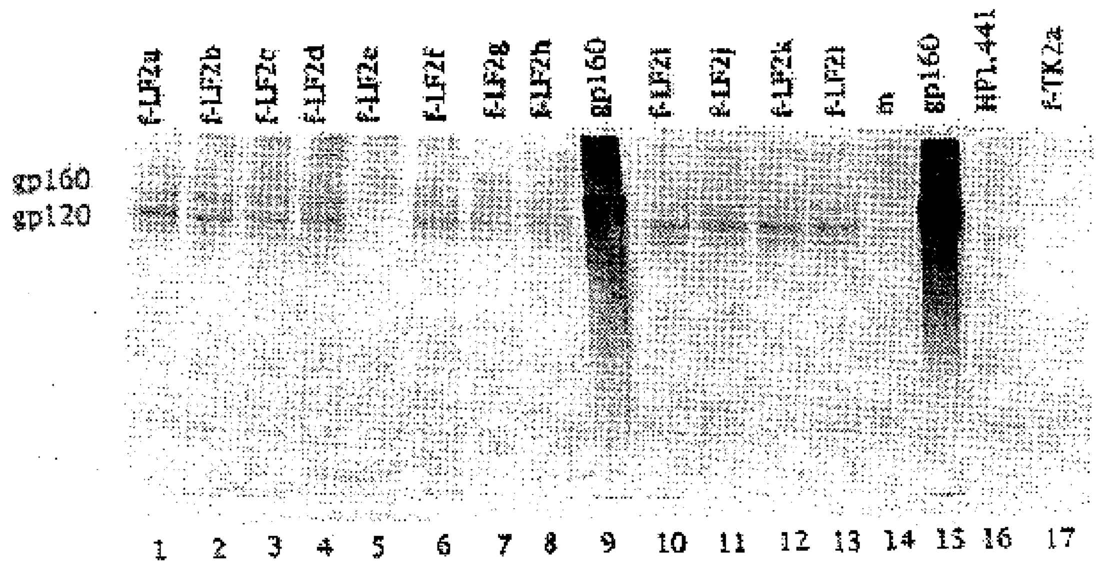
Western blot analysis / gp160 expression in chicken embryo fibroblasts infected with chimeric fowlpox viruses

Fig.12.4

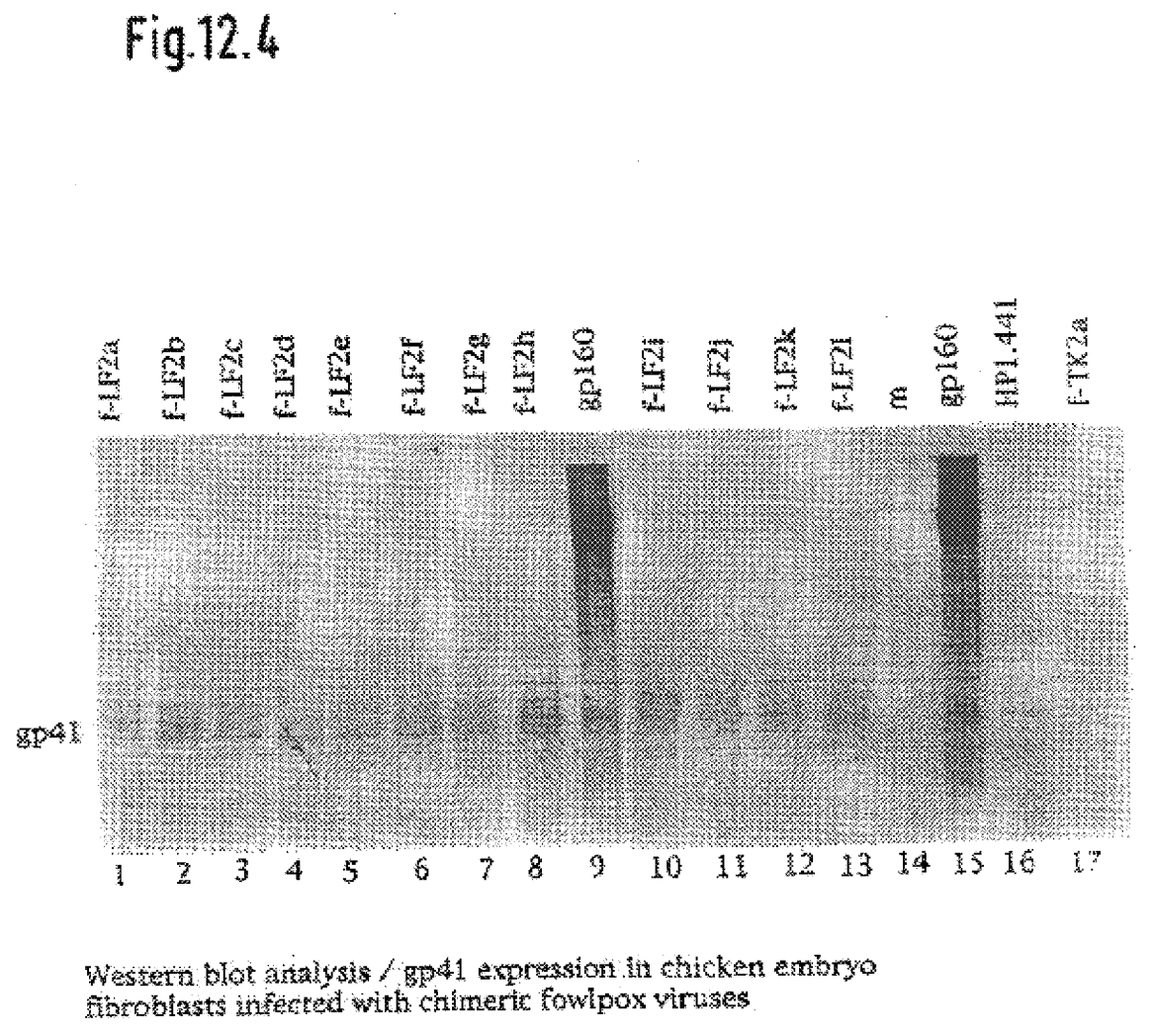

Western blot analysis / gp41 expression in chicken embryo fibroblasts infected with chimeric fowlpox viruses Construction of the insertion plasmid pSep-ST2
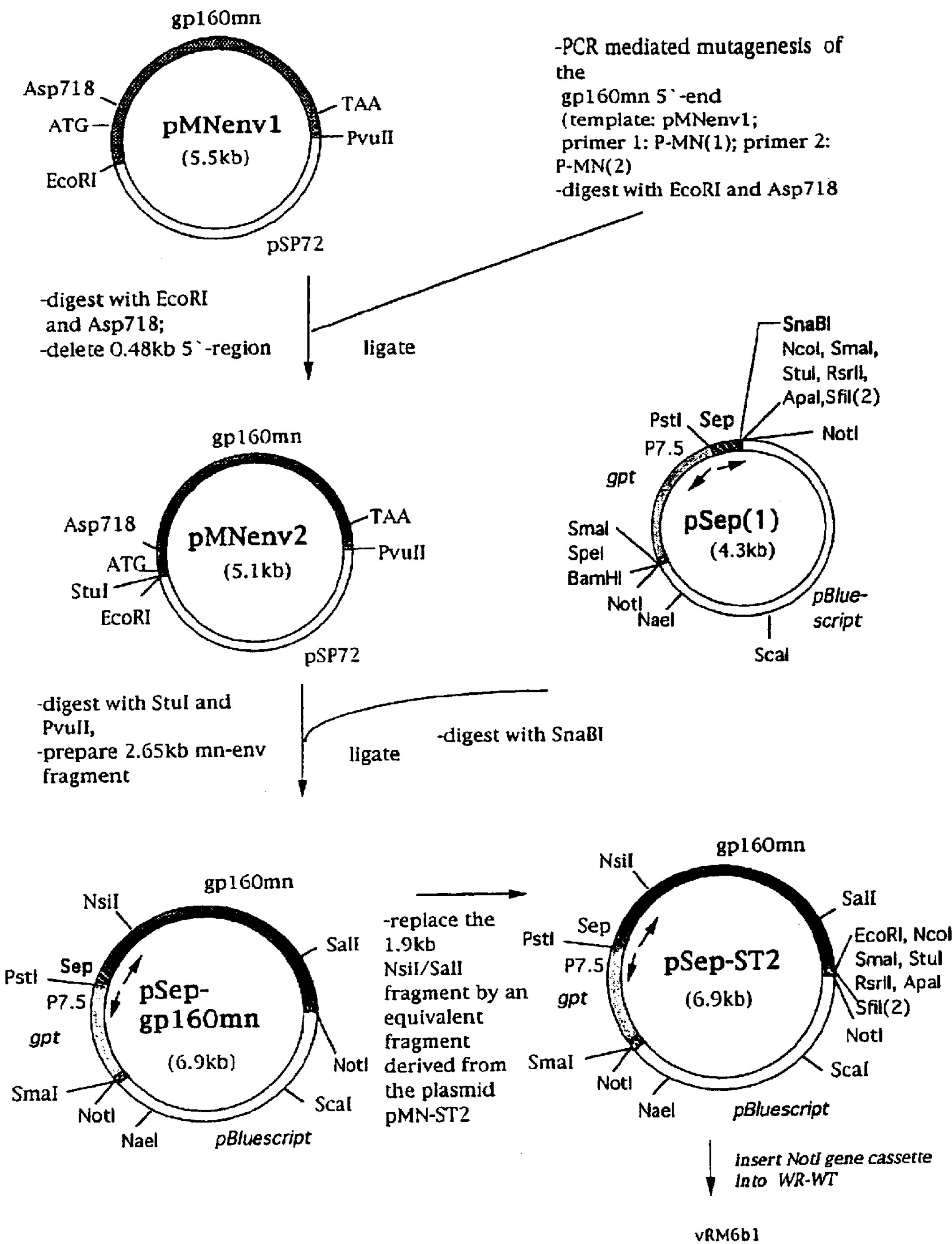
Fig. 13.1

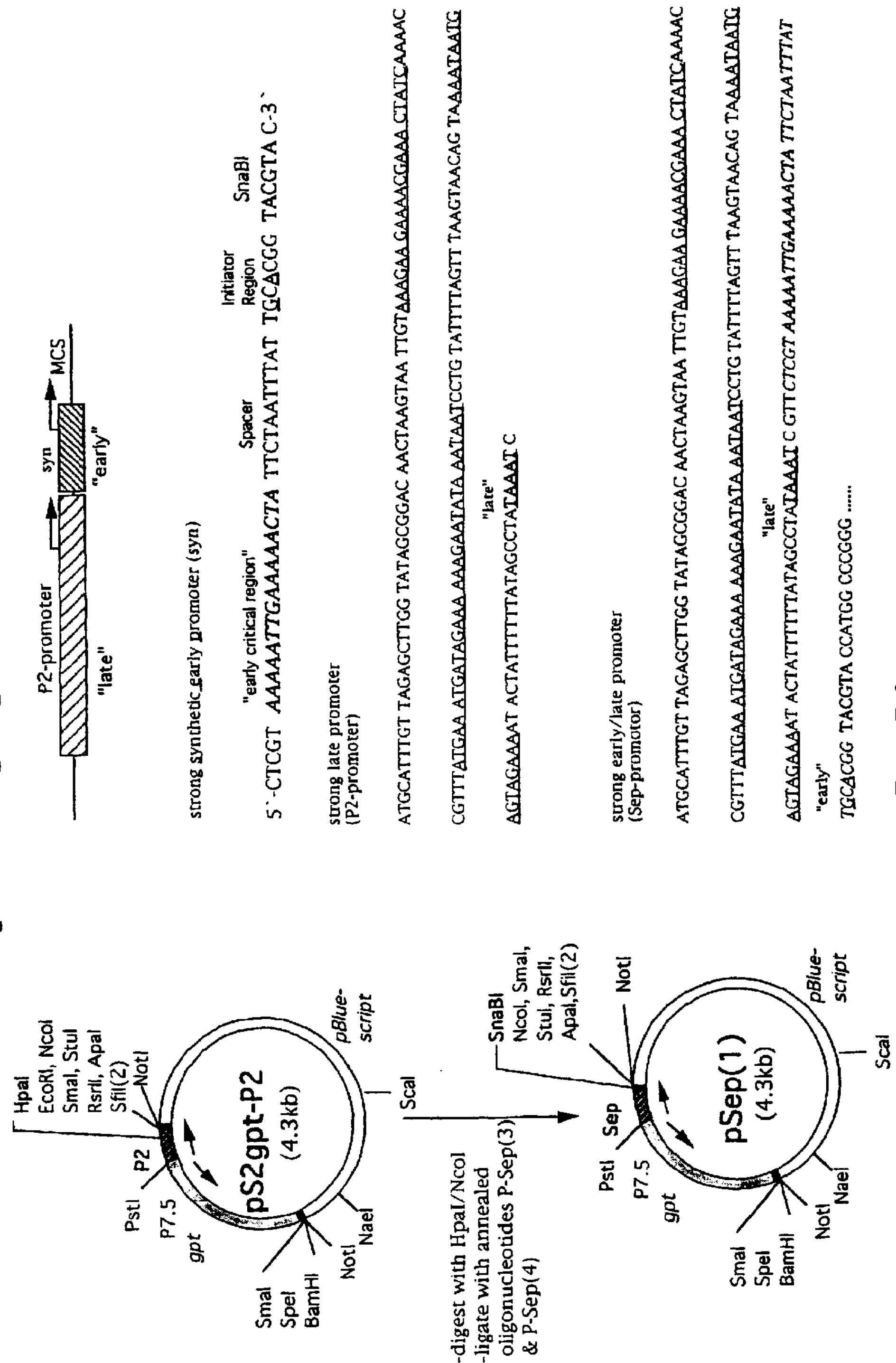
Fig. 13.2

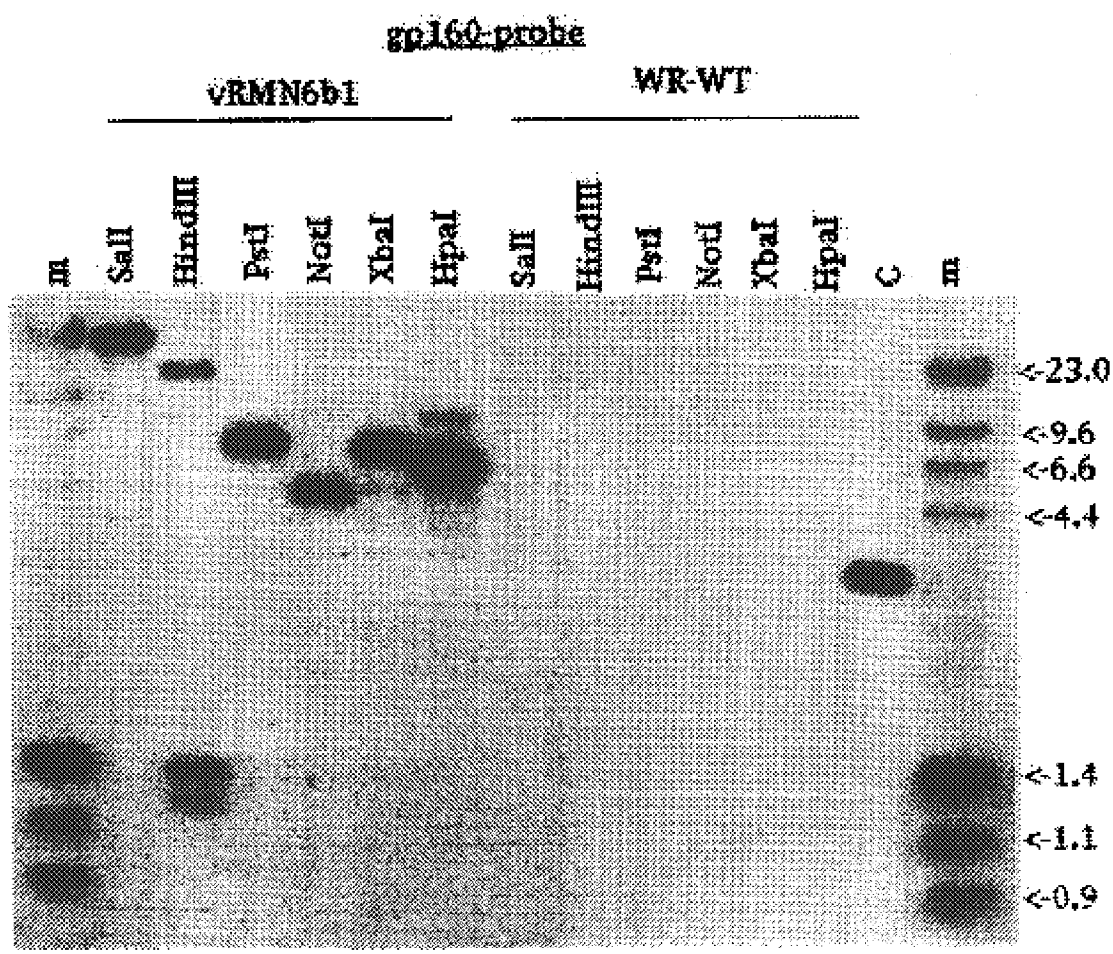
Fig. 13.3

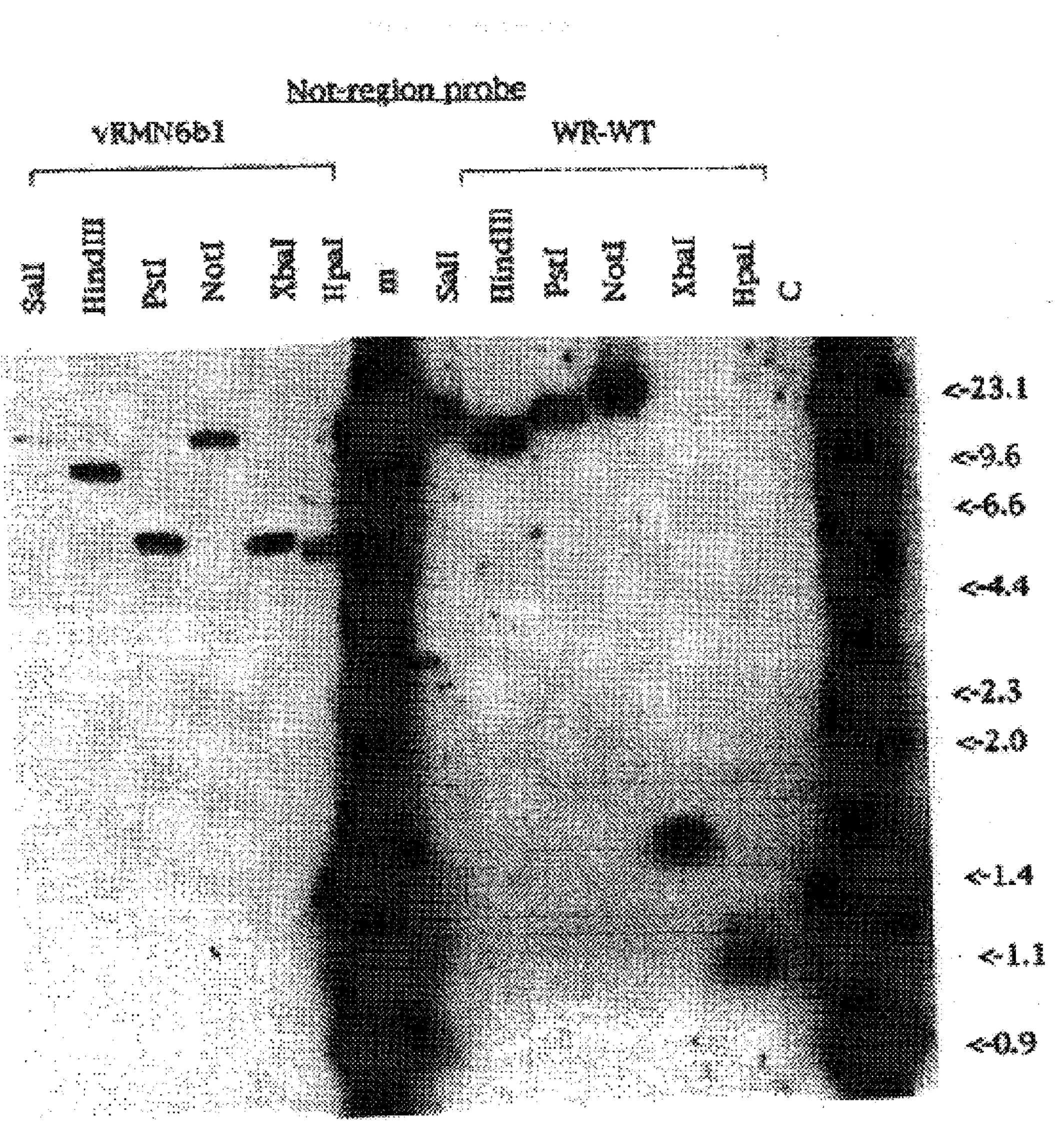
Fig. 13.4

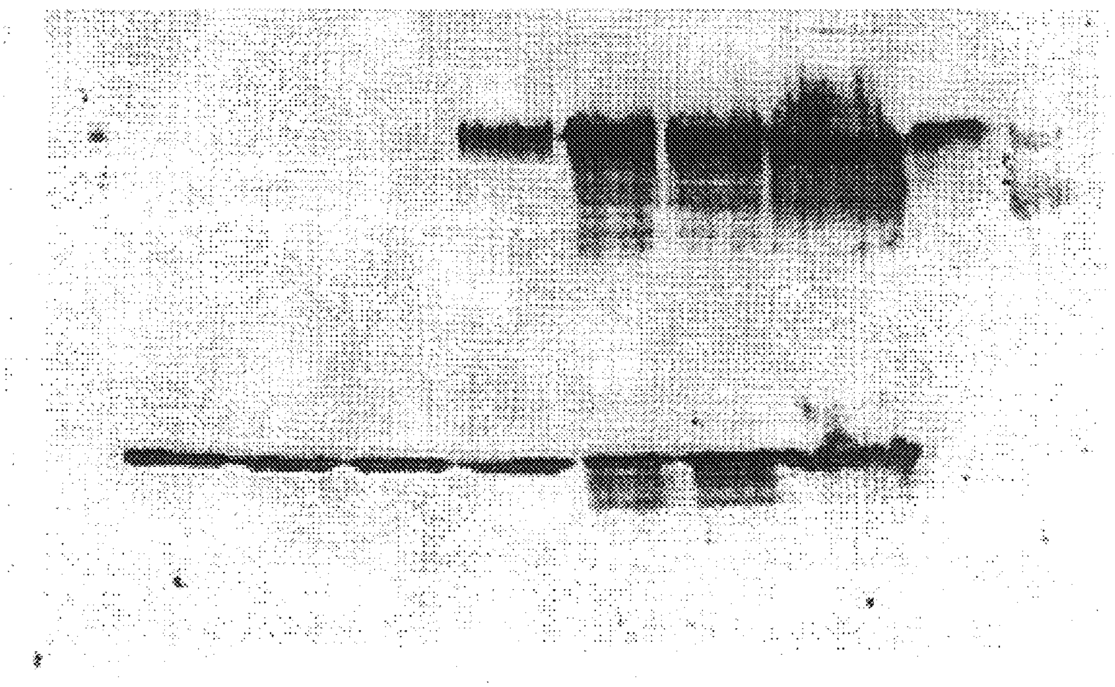
Fig. 13.5

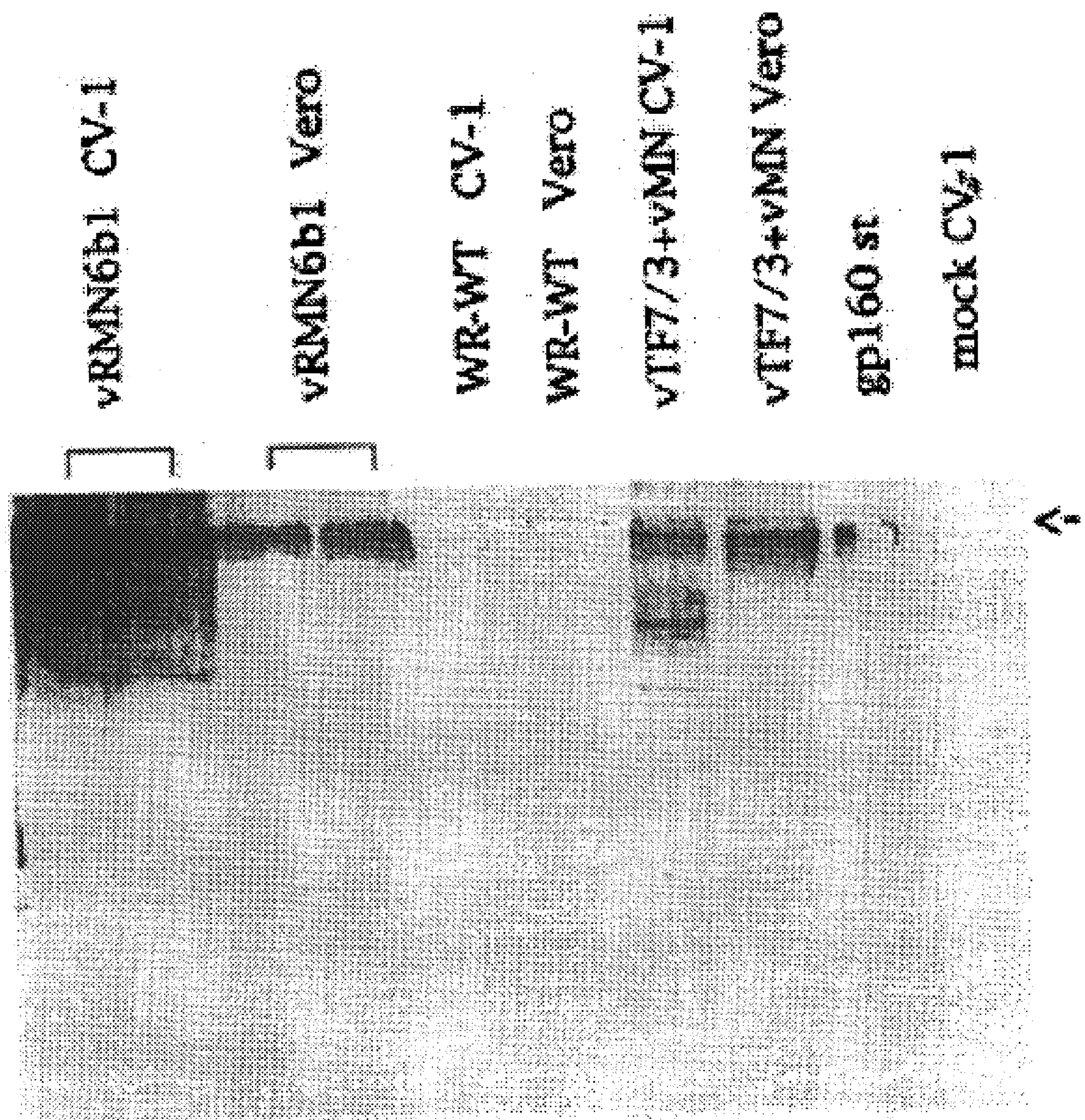
Fig. 13.6

Construction of pSep-gag
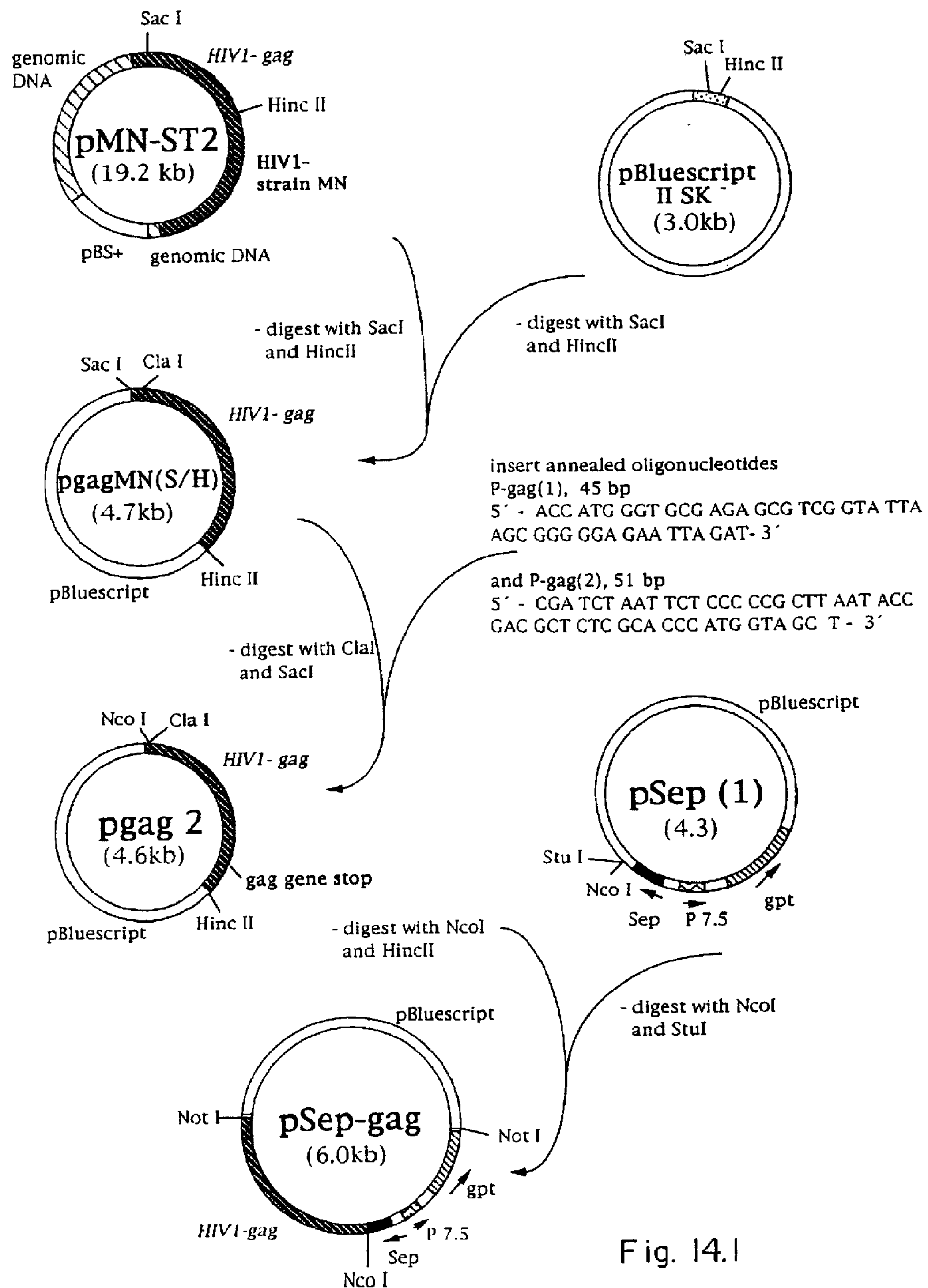
Fig. 14.1

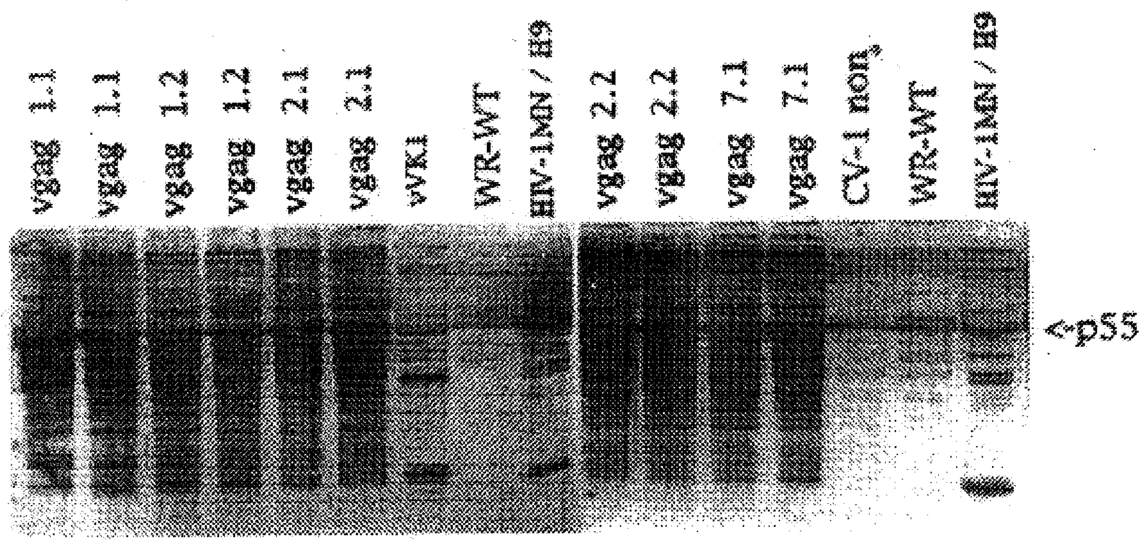
Fig. 14.2

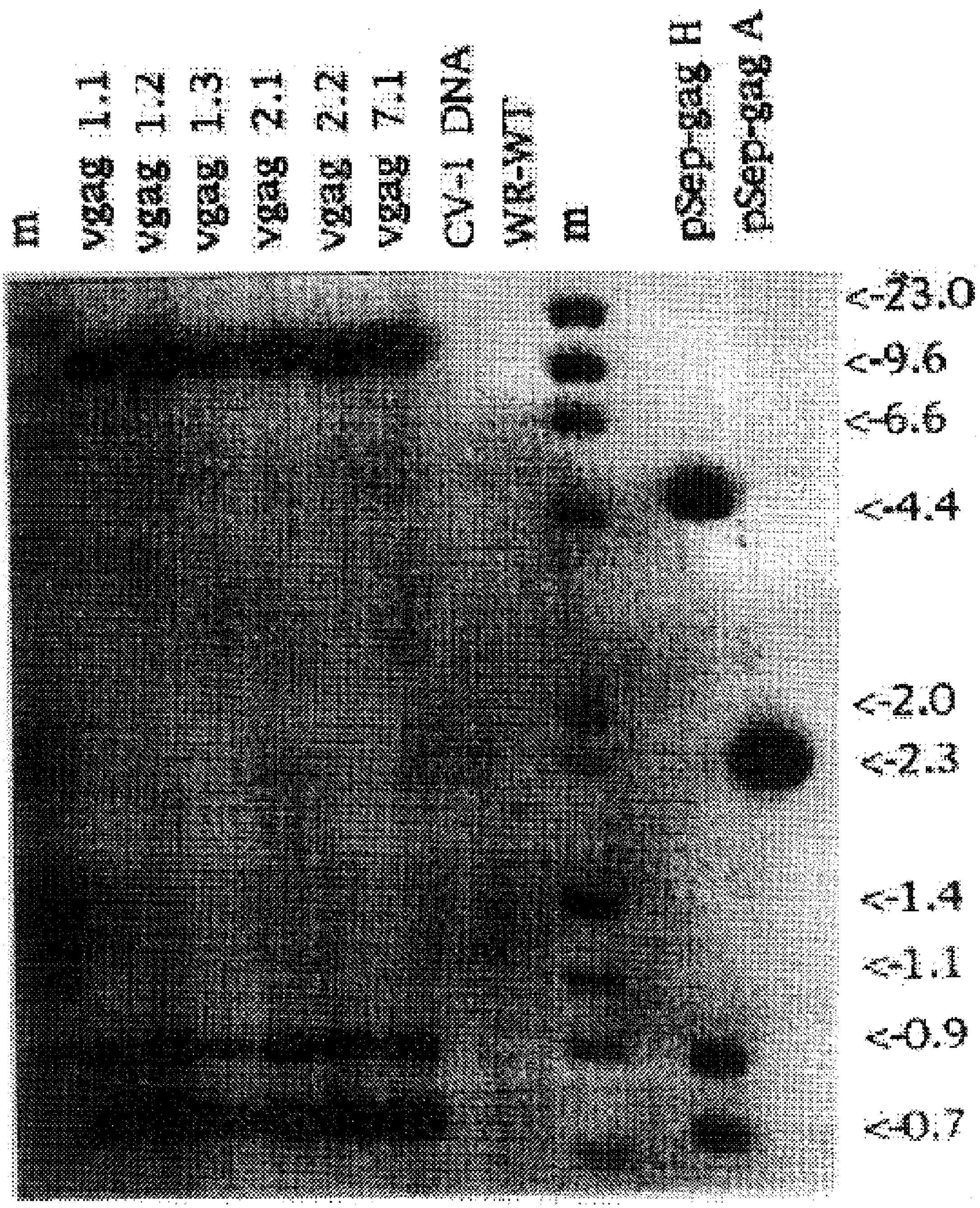
Fig. 14.3

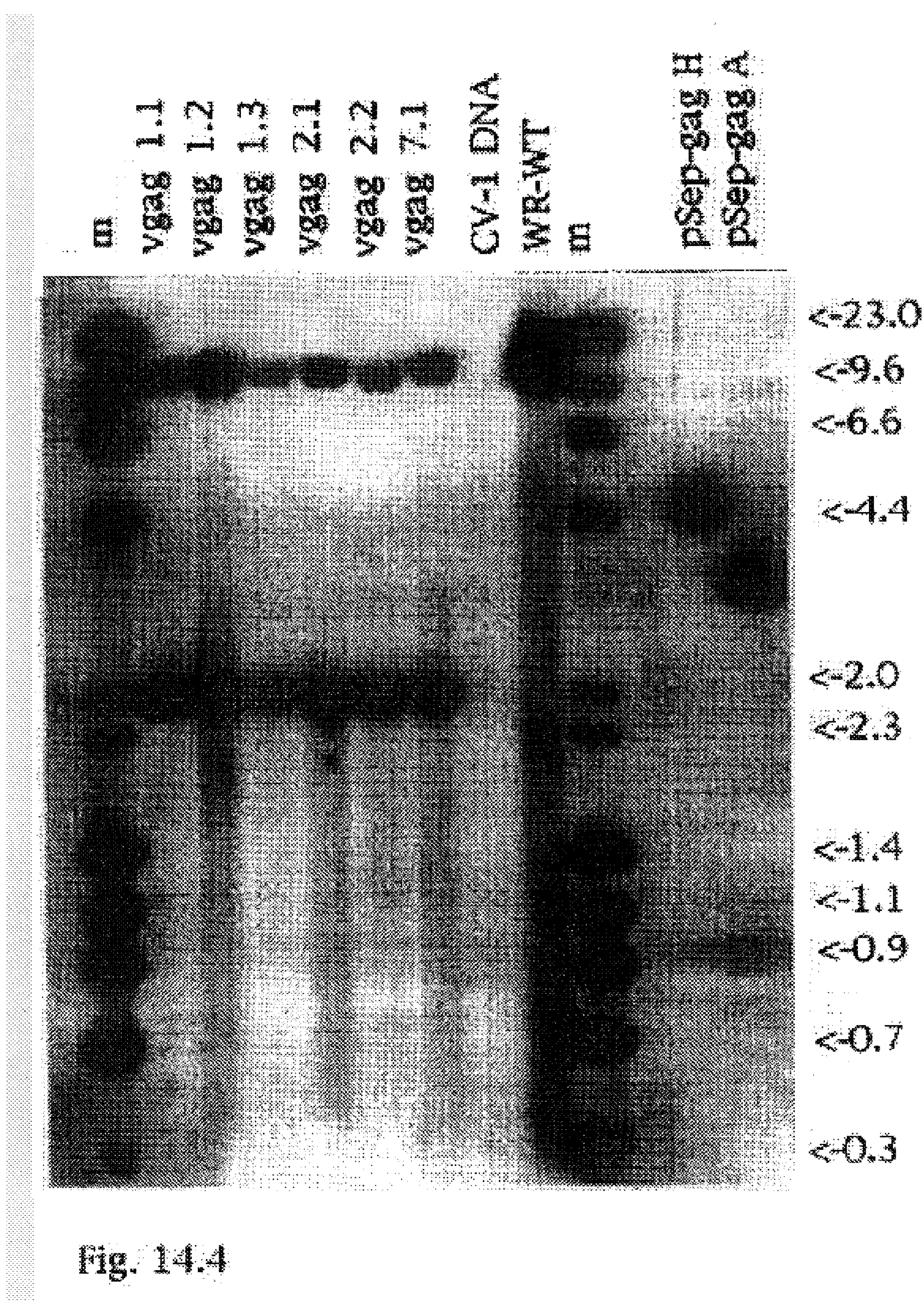
Fig. 14.4

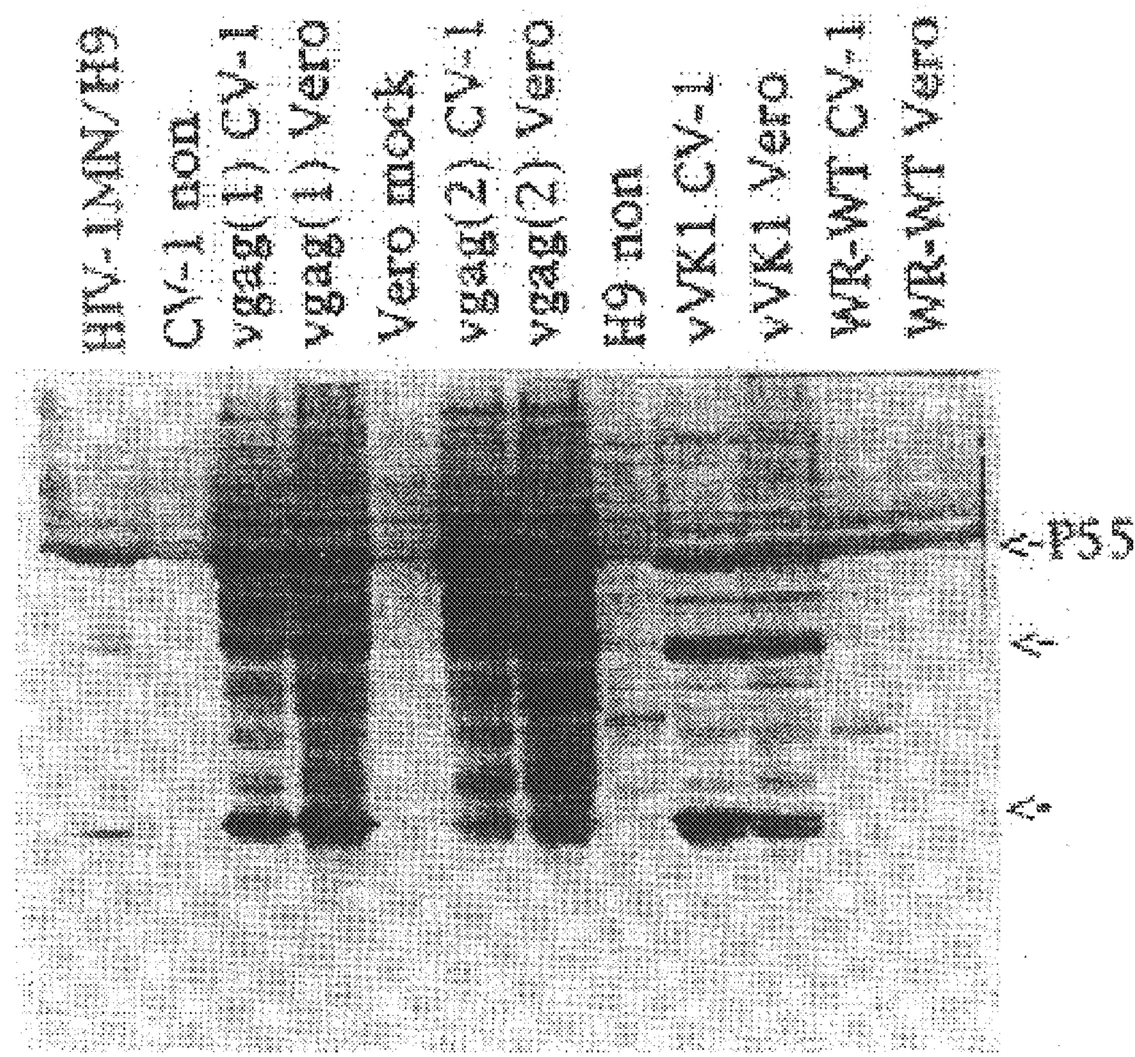
Fig. 14.5

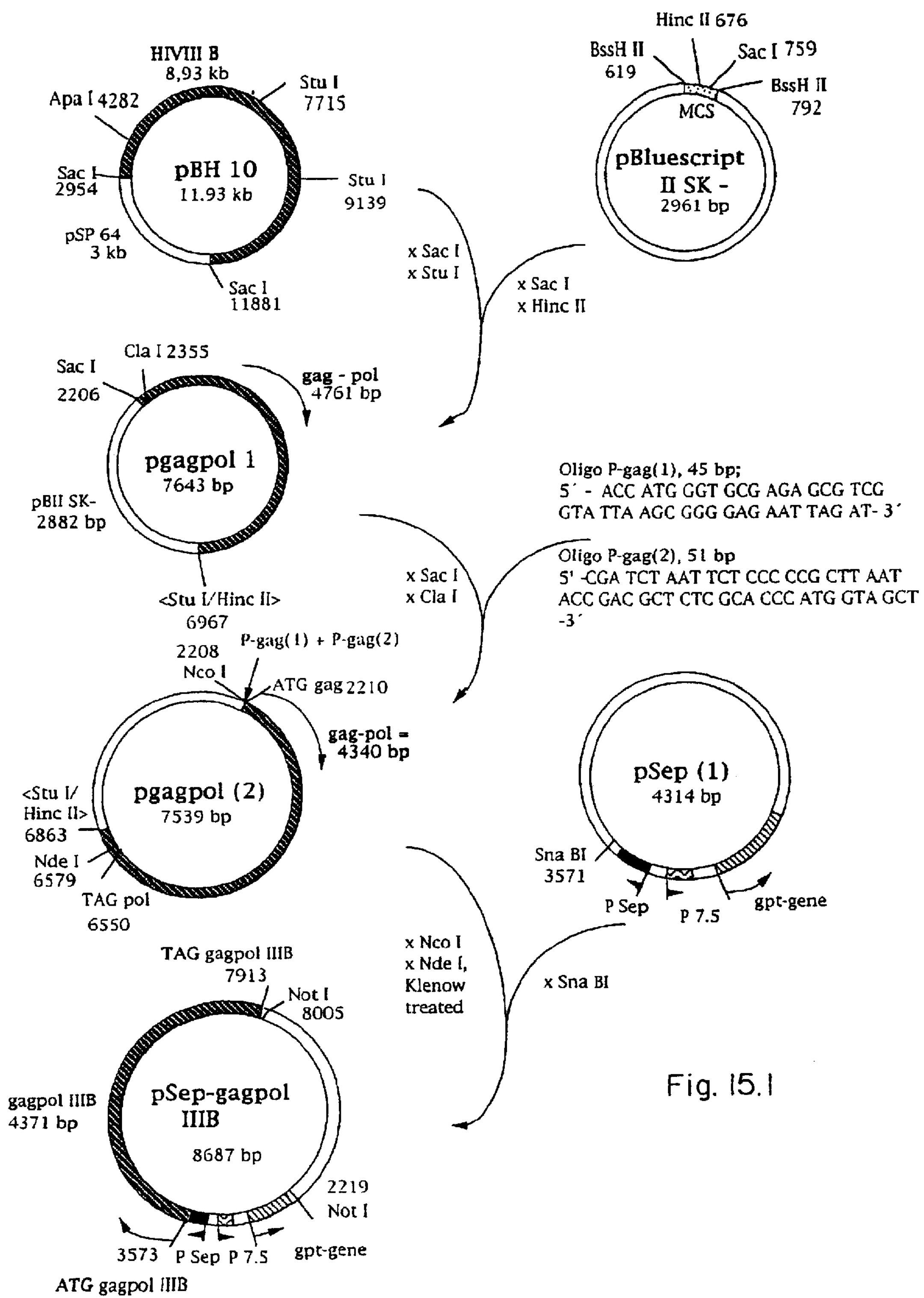
Fig. 15.1

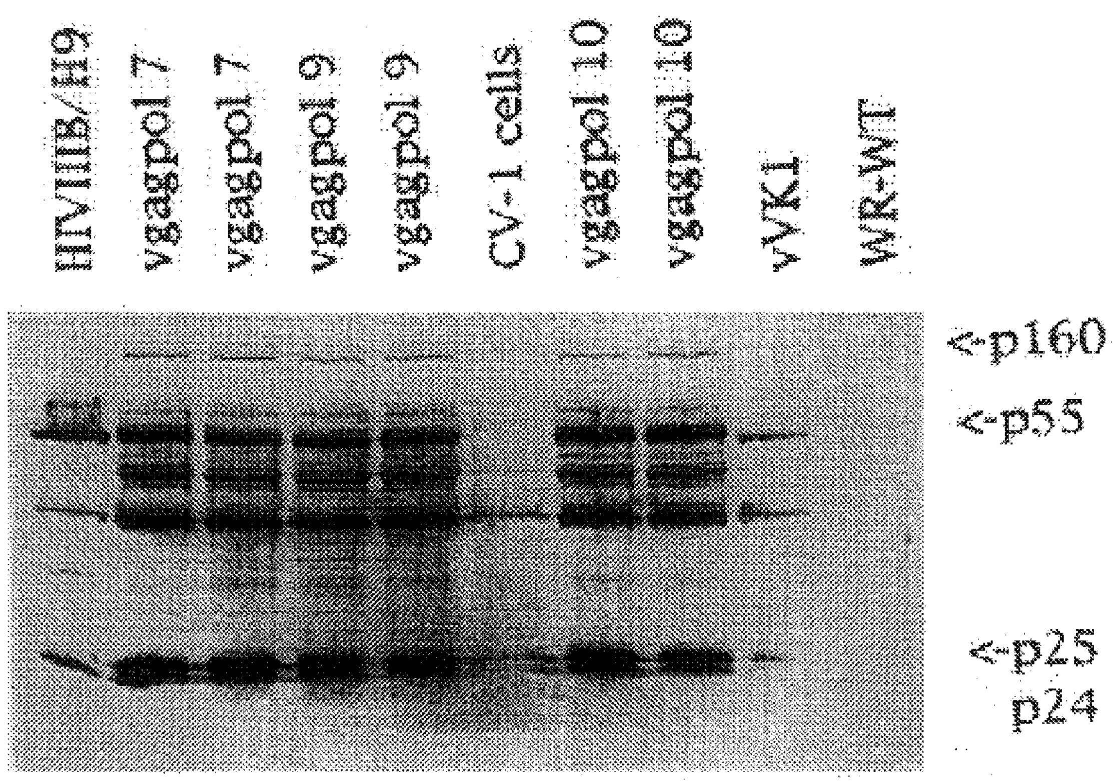
Fig. 15.2

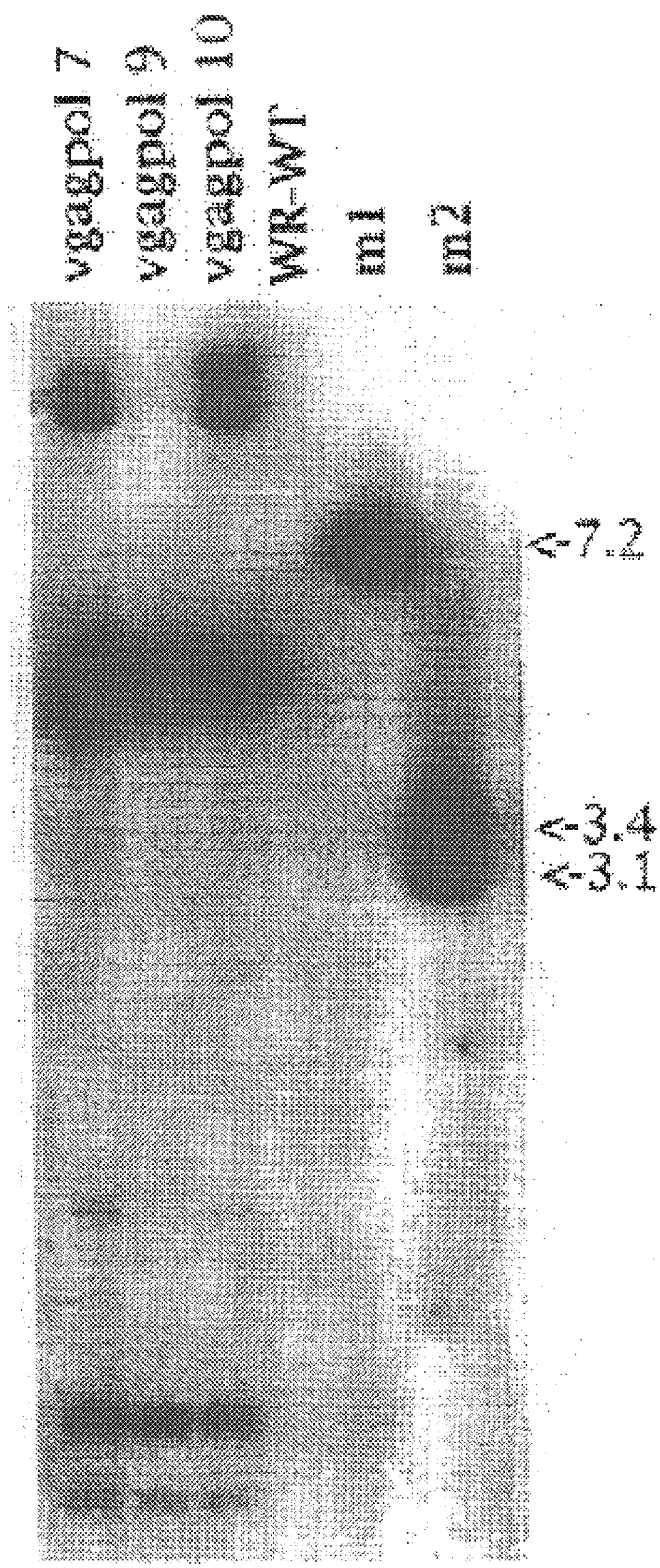
Fig. 15.3

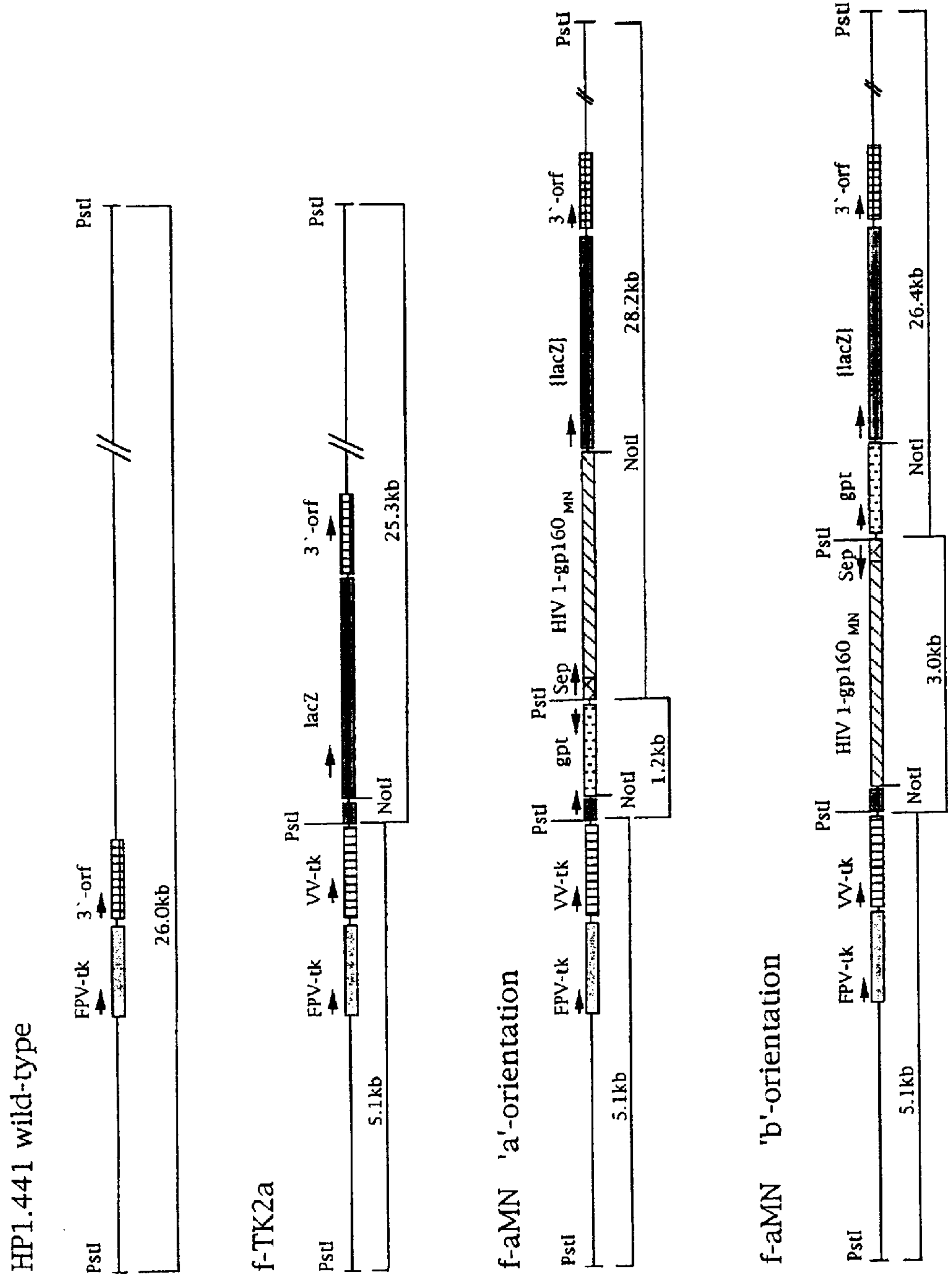
Fig. 16.1

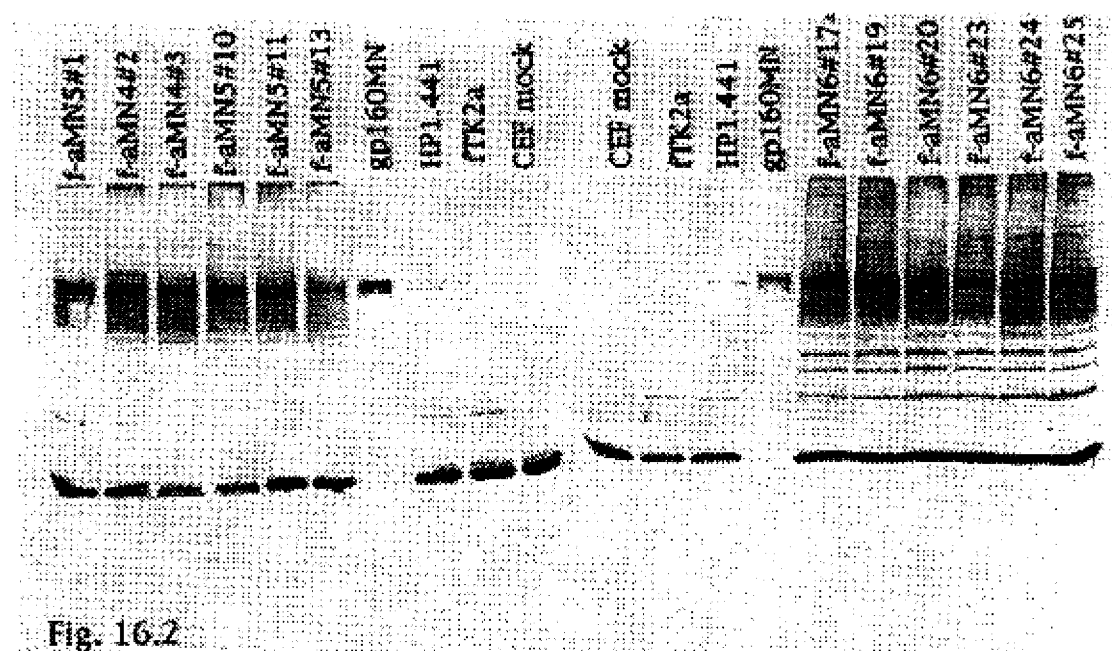
Fig. 16.2

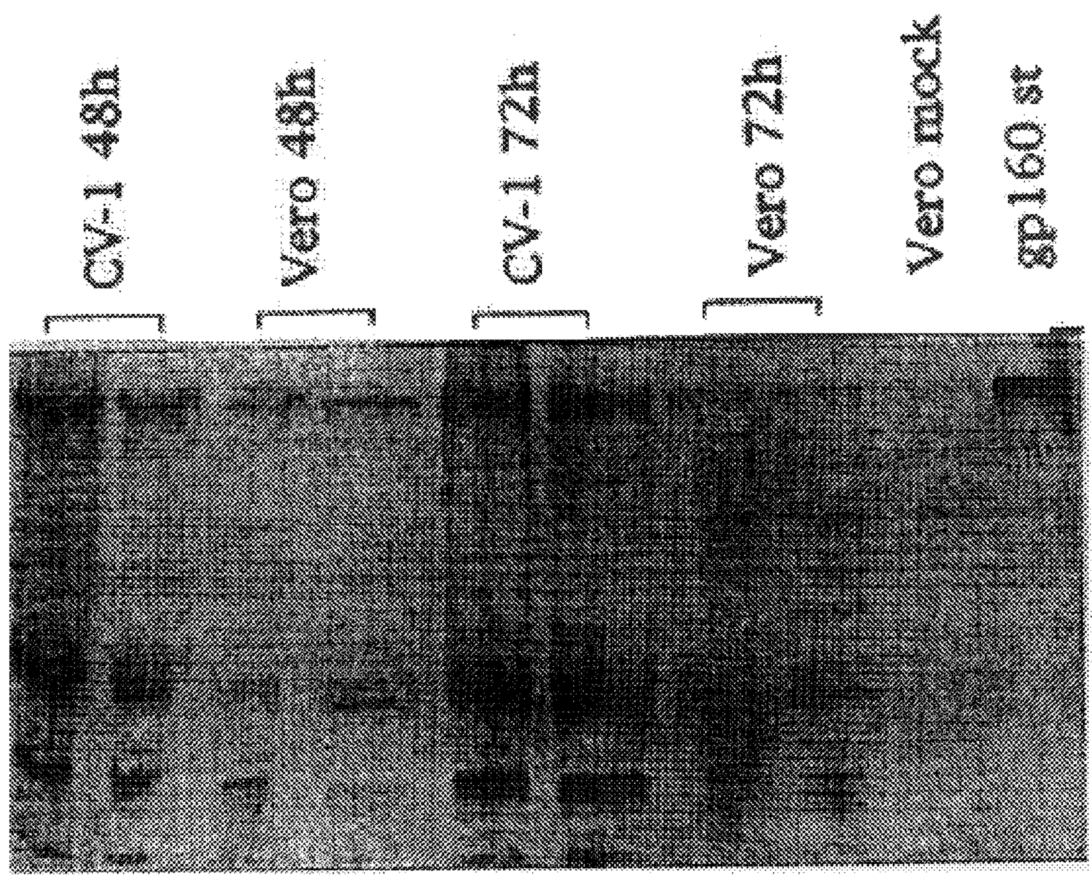
Fig. 16.3

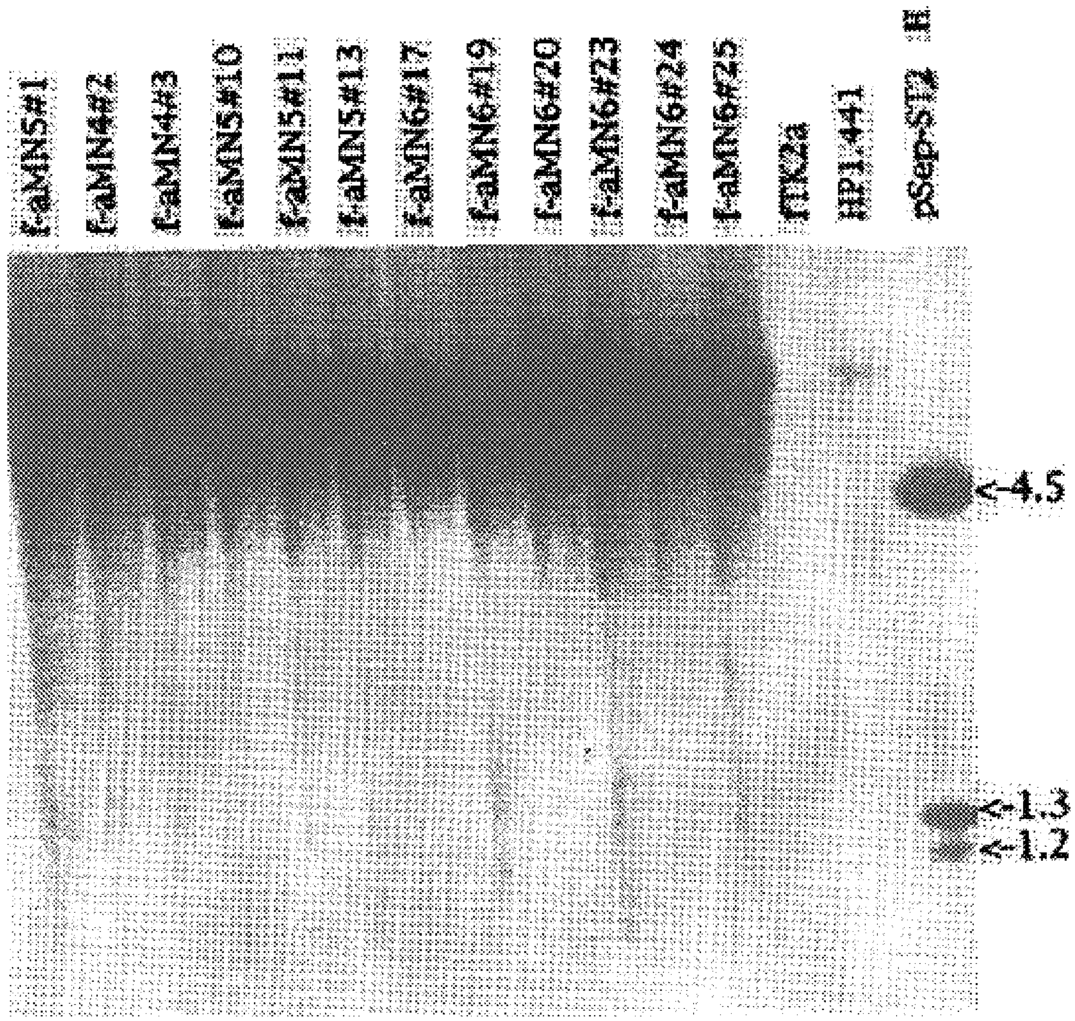
Fig. 16.4

SEQUENCE LISTING (1) GENERAL INFORMATION:

(iii) NUMBER OF SEQUENCES: 95

(2) INFORMATION FOR SEQ ID NO:1:

(i) SEQUENCE CHARACTERISTICS:
(A) LENGTH: 48 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: pN2

(xi) SEQUENCE DESCRIPTION: SEQ ID NO:1:

```
TCAAGCTTAT CGATACCGTC GCGGCCGCGA CCTCGAGGGG GGGCCCGG                 48
```

(2) INFORMATION FOR SEQ ID NO:2:

(i) SEQUENCE CHARACTERISTICS:
(A) LENGTH: 1133 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: pN2-gpta (xi) SEQUENCE DESCRIPTION: SEQ ID NO:2:

```
CTAGAACTAG TGGATCCCCC AACTTAAGGG TACCGCCTCG ACATCTATAT ACTATATAGT     60

AATACCAATA CTCAAGACTA CGAAACTGAT ACAATCTCTT ATCATGTGGG TAATGTTCTC    120

GATGTCGAAT AGCCATATGC CGGTAGTTGC GATATACATA AACTGATCAC TAATTCCAAA    180

CCCACCCGCT TTTTATAGTA AGTTTTTCAC CCATAAATAA TAAATACAAT AATTAATTTC    240

TCGTAAAAGT AGAAAATATA TTCTAATTTA TTGCACGGTA AGGAAGTAGA ATCATAAAGA    300

ACAGTGACGG ATGATCCCCA AGCTTGGACA CAAGACAGGC TTGCGAGATA TGTTTGAGAA    360

TACCACTTTA TCCCGCGTCA GGGAGAGGCA GTGCGTAAAA AGACGCGGAC TCATGTGAAA    420

TACTGGTTTT TAGTGCGCCA GATCTCTATA ATCTCGCGCA ACCTATTTTC CCCTCGAACA    480

CTTTTTAAGC CGTAGATAAA CAGGCTGGGA CACTTCACAT GAGCGAAAAA TACATCGTCA    540

CCTGGGACAT GTTGCAGATC CATGCACGTA AACTCGCAAG CCGACTGATG CCTTCTGAAC    600

AATGGAAAGG CATTATTGCC GTAAGCCGTG GCGGTCTGGT ACCGGGTGCG TTACTGGCGC    660

GTGAACTGGG TATTCGTCAT GTCGATACCG TTTGTATTTC CAGCTACGAT CACGACAACC    720

AGCGCGAGCT TAAAGTGCTG AAACGCGCAG AAGGCGATGG CGAAGGCTTC ATCGTTATTG    780

ATGACCTGGT GGATACCGGT GGTACTGCGG TTGCGATTCG TGAAATGTAT CCAAAAGCGC    840

ACTTTGTCAC CATCTTCGCA AAACCGGCTG GTCGTCCGCT GGTTGATGAC TATGTTGTTG    900

ATATCCCGCA AGATACCTGG ATTGAACAGC CGTGGGATAT GGGCGTCGTA TTCGTCCCGC    960

CAATCTCCGG TCGCTAATCT TTTCAACGCC TGGCACTGCC GGGCGTTGTT CTTTTTAACT   1020

TCAGGCGGGT TACAATAGTT TCCAGTAAGT ATTCTGGAGG CTGCATCCAT GACACAGGCA   1080
```

-continued

```
AACCTGAGCG AAACCCTGTT CAAACCCCGC TTTGGGCTGC AGGAATTCGA TAT         1133
```

(2) INFORMATION FOR SEQ ID NO:3:

(i) SEQUENCE CHARACTERISTICS:
(A) LENGTH: 1133 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: pN2-gptb (xi) SEQUENCE DESCRIPTION: SEQ ID NO:3:

```
CTAGAACTAG TGGATCCCCC AAAGCGGGGT TTGAACAGGG TTTCGCTCAG GTTTGCCTGT    60

GTCATGGATG CAGCCTCCAG AATACTTACT GGAAACTATT GTAACCCGCC TGAAGTTAAA   120

AAGAACAACG CCCGGCAGTG CCAGGCGTTG AAAAGATTAG CGACCGGAGA TTGGCGGGAC   180

GAATACGACG CCCATATCCC ACGGCTGTTC AATCCAGGTA TCTTGCGGGA TATCAACAAC   240

ATAGTCATCA ACCAGCGGAC GACCAGCCGG TTTTGCGAAG ATGGTGACAA AGTGCGCTTT   300

TGGATACATT TCACGAATCG CAACCGCAGT ACCACCGGTA TCCACCAGGT CATCAATAAC   360

GATGAAGCCT TCGCCATCGC CTTCTGCGCG TTTCAGCACT TTAAGCTCGC GCTGGTTGTC   420

GTGATCGTAG CTGGAAATAC AAACGGTATC GACATGACGA ATACCCAGTT CACGCGCCAG   480

TAACGCACCC GGTACCAGAC CGCCACGGCT TACGGCAATA ATGCCTTTCC ATTGTTCAGA   540

AGGCATCAGT CGGCTTGCGA GTTTACGTGC ATGGATCTGC AACATGTCCC AGGTGACGAT   600

GTATTTTTCG CTCATGTGAA GTGTCCCAGC CTGTTTATCT ACGGCTTAAA AAGTGTTCGA   660

GGGGAAAATA GGTTGCGCGA GATTATAGAG ATCTGGCGCA CTAAAAACCA GTATTTCACA   720

TGAGTCCGCG TCTTTTTACG CACTGCCTCT CCCTGACGCG GGATAAAGTG GTATTCTCAA   780

ACATATCTCG CAAGCCTGTC TTGTGTCCAA GCTTGGGGAT CATCCGTCAC TGTTCTTTAT   840

GATTCTACTT CCTTACCGTG CAATAAATTA GAATATATTT TCTACTTTTA CGAGAAATTA   900

ATTATTGTAT TTATTATTTA TGGGTGAAAA ACTTACTATA AAAAGCGGGT GGGTTTGGAA   960

TTAGTGATCA GTTTATGTAT ATCGCAACTA CCGGCATATG GCTATTCGAC ATCGAGAACA  1020

TTACCCACAT GATAAGAGAT TGTATCAGTT TCGTAGTCTT GAGTATTGGT ATTACTATAT  1080

AGTATATAGA TGTCGAGGCG GTACCCTTAA GTTGGGCTGC AGGAATTCGA TAT         1133
```

(2) INFORMATION FOR SEQ ID NO:4:

(i) SEQUENCE CHARACTERISTICS:
(A) LENGTH: 66 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: pHindJ-2

(xi) SEQUENCE DESCRIPTION: SEQ ID NO:4:

```
CGCATTTTCT AACGTGATGG GATCCGTTAA CTCGCGAGAA TTCTGTAGAA AGTGTTACAT    60

CGACTC                                                               66
```

-continued (2) INFORMATION FOR SEQ ID NO:5:

(i) SEQUENCE CHARACTERISTICS:
(A) LENGTH: 127 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: pHindJ-3

(xi) SEQUENCE DESCRIPTION: SEQ ID NO:5:

```
CGCATTTTCT AACGTGATGG GATCCGGCCG GCTAGGCCGC GGCCGCCCGG GTTTTTATCT     60

CGAGACAAAA AGACGGACCG GGCCCGGCCA TATAGGCCCA ATTCTGTAGA AAGTGTTACA    120

TCGACTC                                                              127
```

(2) INFORMATION FOR SEQ ID NO:6:

(i) SEQUENCE CHARACTERISTICS:
(A) LENGTH: 115 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: pA0

(xi) SEQUENCE DESCRIPTION: SEQ ID NO:6:

```
AGGGAACAAA AGCTGGAGCT AGGCCGGCTA GGCCGCGGCC GCCCGGGTTT TTATCTCGAG     60

ACAAAAAGAC GGACCGGGCC CGGCCATATA GGCCAGTACC CAATTCGCCC TATAG         115
```

(2) INFORMATION FOR SEQ ID NO:7:

(i) SEQUENCE CHARACTERISTICS:
(A) LENGTH: 103 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: pA1

(xi) SEQUENCE DESCRIPTION: SEQ ID NO:7:

```
CGGCCGCCCG GGTTTTTATC TCGACATATG CTGCAGTTAA CGAATTCCAT GGGGATCCGA     60

TATCAAGCTT AGGCCTGTCG ACGTCGAGAC AAAAAGACGG ACC                      103
```

(2) INFORMATION FOR SEQ ID NO:8:

(i) SEQUENCE CHARACTERISTICS:
(A) LENGTH: 103 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: pA2

-continued (xi) SEQUENCE DESCRIPTION: SEQ ID NO:8:

```
CGGCCGCCCG GGTTTTTATC TCGACGTCGA CAGGCCTAAG CTTGATATCG GATCCCCATG     60

GAATTCGTTA ACTGCAGCAT ATGTCGAGAC AAAAAGACGG ACC                      103
```

(2) INFORMATION FOR SEQ ID NO:9:

(i) SEQUENCE CHARACTERISTICS:
(A) LENGTH: 213 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: pA1-S1

(xi) SEQUENCE DESCRIPTION: SEQ ID NO:9:

```
CCCGGGTTTT TATCTCGACA TACGGCTTGG TATAGCGGAC AACTAAGTAA TTGTAAAGAA     60

GAAAACGAAA CTATCAAAAC CGTTTATGAA ATGATAGAAA AAAGAATATA AATAATCCTG    120

TATTTTAGTT TAAGTAACAG TAAAATAATG AGTAGAAAAT ACTATTTTTT ATAGCCTATA    180

AATCATGAAT TCGGATCCGA TATCAAGCTT AGG                                 213
```

(2) INFORMATION FOR SEQ ID NO:10:

(i) SEQUENCE CHARACTERISTICS:
(A) LENGTH: 215 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: pA2-S1

(xi) SEQUENCE DESCRIPTION: SEQ ID NO:10:

```
CAGGCCTAAG CTTGATATCG GATCCGAATT CATGATTTAT AGGCTATAAA AAATAGTATT     60

TTCTACTCAT TATTTTACTG TTACTTAAAC TAAAATACAG GATTATTTAT ATTCTTTTTT    120

CTATCATTTC ATAAACGGTT TTGATAGTTT CGTTTTCTTC TTTACAATTA CTTAGTTGTC    180

CGCTATACCA AGCCGTATGT CGAGACAAAA AGACG                               215
```

(2) INFORMATION FOR SEQ ID NO:11:

(i) SEQUENCE CHARACTERISTICS:
(A) LENGTH: 88 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: pA1-S2

(xi) SEQUENCE DESCRIPTION: SEQ ID NO:11:

```
TCTCGACATA TGCTGCAGTT GGGAAGCTTT TTTTTTTTTT TTTTTTTGGC ATATAAATAG     60

GCTGCAGGAA TTCCATGGGG ATCCGATA                                        88
```

(2) INFORMATION FOR SEQ ID NO:12:

-continued (i) SEQUENCE CHARACTERISTICS:
(A) LENGTH: 92 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: pA2-S2

(xi) SEQUENCE DESCRIPTION: SEQ ID NO:12:

```
TTGATATCGG ATCCCCATGG AATTCCTGCA GCCTATTTAT ATGCCAAAAA AAAAAAAAAA     60

AAAAAGCTTC CCAACTGCAG CATATGTCGA GA                                   92
```

(2) INFORMATION FOR SEQ ID NO:13:

(i) SEQUENCE CHARACTERISTICS:
(A) LENGTH: 127 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: pN2gpt-S3A (fig. 4.7)

(xi) SEQUENCE DESCRIPTION: SEQ ID NO:13:

```
TACCCTTAAG TTGGGCTGCA GAAGCTTTTT TTTTTTTTTT TTTTTGGCAT ATAAATGAAT     60

TCCATGGCCC GGGAAGGCCT CGGACCGGGC CCGGCCATAT AGGCCAGCGA TACCGTCGCG    120

GCCGCGA                                                              127
```

(2) INFORMATION FOR SEQ ID NO:14:

(i) SEQUENCE CHARACTERISTICS:
(A) LENGTH: 134 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: pN2gpt-S4

(xi) SEQUENCE DESCRIPTION: SEQ ID NO:14:

```
TACCCTTAAG TTGGGCTGCA GAAGCTTTTT TTTTTTTTTT TTTTTGGCAT ATAAATCGTT     60

AACGAATTCC ATGGCCCGGG AAGGCCTCGG ACCGGGCCCG GCCATATAGG CCAGCGATAC    120

CGTCGCGGCC GCGA                                                      134
```

(2) INFORMATION FOR SEQ ID NO:15:

(i) SEQUENCE CHARACTERISTICS:
(A) LENGTH: 1988 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: pA1S1-PT -continued (xi) SEQUENCE DESCRIPTION: SEQ ID NO:15:

```
TTTTATAGCC TATAAATCAT GAATTCCGCG CACGTCCGAG GCTTGCAGCT GCCTGGCTGC     60
CTGGCCCTGG CTGCCCTGTG TAGCCTTGTG CACAGCCAGC ATGTGTTCCT GGCTCCTCAG    120
CAAGCACGGT CGCTGCTCCA GCGGGTCCGG CGAGCCAACA CCTTCTTGGA GGAGGTGCGC    180
AAGGGCAACC TAGAGCGAGA GTGCGTGGAG GAGACGTGCA GCTACGAGGA GGCCTTCGAG    240
GCTCTGGAGT CCTCCACGGC TACGGATGTG TTCTGGGCCA AGTACACAGC TTGTGAGACA    300
GCGAGGACGC CTCGAGATAA GCTTGCTGCA TGTCTGGAAG GTAACTGTGC TGAGGGTCTG    360
GGTACGAACT ACCGAGGGCA TGTGAACATC ACCCGGTCAG GCATTGAGTG CCAGCTATGG    420
AGGAGTCGCT ACCCACATAA GCCTGAAATC AACTCCACTA CCCATCCTGG GGCCGACCTA    480
CAGGAGAATT TCTGCCGCAA CCCCGACAGC AGCAACACGG GACCATGGTG CTACACTACA    540
GACCCCACCG TGAGGAGGCA GGAATGCAGC ATCCCTGTCT GTGGCCAGGA TCAAGTCACT    600
GTAGCGATGA CTCCACGCTC CGAAGGCTCC AGTGTGAATC TGTCACCTCC ATTGGAGCAG    660
TGTGTCCCTG ATCGGGGGCA GCAGTACCAG GGGCGCCTGG CGGTGACCAC ACATGGGCTC    720
CCCTGCCTGG CCTGGGCCAG CGCACAGGCC AAGGCCCTGA GCAAGCACCA GGACTTCAAC    780
TCAGCTGTGC AGCTGGTGGA GAACTTCTGC CGCAACCCAG ACGGGGATGA GGAGGGCGTG    840
TGGTGCTATG TGGCCGGGAA GCCTGGCGAC TTTGGGTACT GCGACCTCAA CTATTGTGAG    900
GAGGCCGTGG AGGAGGAGAC AGGAGATGGG CTGGATGAGG ACTCAGACAG GGCCATCGAA    960
GGGCGTACCG CCACAAGTGA GTACCAGACT TTCTTCAATC CGAGGACCTT TGGCTCGGGA   1020
GAGGCAGACT GTGGGCTGCG ACCTCTGTTC GAGAAGAAGT CGCTGGAGGA CAAAACCGAA   1080
AGAGAGCTCC TGGAATCCTA CATCGACGGG CGCATTGTGG AGGGCTCGGA TGCAGAGATC   1140
GGCATGTCAC CTTGGCAGGT GATGCTTTTC CGGAAGAGTC CCCAGGAGCT GCTGTGTGGG   1200
GCCAGCCTCA TCAGTGACCG CTGGGTCCTC ACCGCCGCCC ACTGCCTCCT GTACCCGCCC   1260
TGGGACAAGA ACTTCACCGA GAATGACCTT CTGGTGCGCA TTGGCAAGCA CTCCCGCACC   1320
AGGTACGAGC GAAACATTGA AAAGATATCC ATGTTGGAAA AGATCTACAT CCACCCCAGG   1380
TACAACTGGC GGGAGAACCT GGACCGGGAC ATTGCCCTGA TGAAGCTGAA GAAGCCTGTT   1440
GCCTTCAGTG ACTACATTCA CCCTGTGTGT CTGCCCGACA GGGAGACGGC AGCCAGCTTG   1500
CTCCAGGCTG GATACAAGGG GCGGGTGACA GGCTGGGGCA ACCTGAAGGA GACGTGGACA   1560
GCCAACGTTG GTAAGGGGCA GCCCAGTGTC CTGCAGGTGG TGAACCTGCC CATTGTGGAG   1620
CGGCCGGTCT GCAAGGACTC CACCCGGATC CGCATCACTG ACAACATGTT CTGTGCTGGT   1680
TACAAGCCTG ATGAAGGGAA ACGAGGGGAT GCCTGTGAAG GTGACAGTGG GGGACCCTTT   1740
GTCATGAAGA GCCCCTTTAA CAACCGCTGG TATCAAATGG GCATCGTCTC ATGGGGTGAA   1800
GGCTGTGACC GGGATGGGAA ATATGGCTTC TACACACATG TGTTCCGCCT GAAGAAGTGG   1860
ATACAGAAGG TCATTGATCA GTTTGGAGAG TAGGGGGCCA CTCATATTCT GGGCTCCTGG   1920
AACCAATCCC GTGAAAGAAT TATTTTTGTG TTTCTAAAAC TAGAATTCGG ATTCGATATC   1980
AAGCTTAG                                                            1988
```

(2) INFORMATION FOR SEQ ID NO:16:

(i) SEQUENCE CHARACTERISTICS:
(A) LENGTH: 26 base pairs
(B) TYPE: nucleic acid
(C) STRANDEDNESS: single
(D) TOPOLOGY: linear -continued (ii) MOLECULE TYPE: Other nucleic acid;
(A) DESCRIPTION: Synthetic DNA oligonucleotide (vii) IMMEDIATE SOURCE:
(B) CLONE: odN1

(xi) SEQUENCE DESCRIPTION: SEQ ID NO:16:

```
GGCCAGGCCT TTTAAATTAA GATATC                                         26
```

(2) INFORMATION FOR SEQ ID NO:17:

(i) SEQUENCE CHARACTERISTICS:
(A) LENGTH: 111 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: pN2gpt-GPg (xi) SEQUENCE DESCRIPTION: SEQ ID NO:17:

```
TTTTTGGCAT ATAAATCGTT CCAGTCCCAA AATGTAATTG GACGGGAGAC AGAGTGACGC     60

ACGCGGCCGC TCTAGAACTA GTGGATCCCC CAACGAATTC CATGGCCCGG G             111
```

(2) INFORMATION FOR SEQ ID NO:18:

(i) SEQUENCE CHARACTERISTICS:
(A) LENGTH: 2296 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: pN2gpt-LPg (xi) SEQUENCE DESCRIPTION: SEQ ID NO:18:

```
ATAAATCGTT AACGAATTCC ATGGAACATA AGGAAGTGGT TCTTCTACTT CTTTTATTTC     60

TGAAATCAGG TCAAGGAAAA GTGTATCTCT CAGAGTGCAA GACTGGGAAT GGAAAGAACT    120

ACAGAGGGAC GATGTCCAAA ACAAAAAATG GCATCACCTG TCAAAAATGG AGTTCCACTT    180

CTCCCCACAG ACCTAGATTC TCACCTGCTA CACACCCCTC AGAGGGACTG GAGGAGAACT    240

ACTGCAGGAA TCCAGACAAC GATCCGCAGG GGCCCTGGTG CTATACTACT GATCCAGAAA    300

AGAGATATGA CTACTGCGAC ATTCTTGAGT GTGAAGAGGA ATGTATGCAT TGCAGTGGAG    360

AAAACTATGA CGGCAAAATT TCCAAGACCA TGTCTGGACT GGAATGCCAG GCCTGGGACT    420

CTCAGAGCCC ACACGCTCAT GGATACATTC CTTCCAAATT TCCAAACAAG AACCTGAAGA    480

AGAATTACTG TCGTAACCCC GATAGGGAGC TGCGGCCTTG GTGTTTCACC ACCGACCCCA    540

ACAAGCGCTG GGAACTTTGC GACATCCCCC GCTGCACAAC ACCTCCACCA TCTTCTGGTC    600

CCACCTACCA GTGTCTGAAG GGAACAGGTG AAAACTATCG CGGGAATGTG GCTGTTACCG    660

TTTCCGGGCA CACCTGTCAG CACTGGAGTG CACAGACCCC TCACACACAT AACAGGACAC    720

CAGAAAACTT CCCCTGCAAA AATTTGGATG AAAACTACTG CCGCAATCCT GACGGAAAAA    780

GGGCCCCATG GTGCCATACA ACCAACAGCC AAGTGCGGTG GGAGTACTGT AAGATACCGT    840

CCTGTGACTC CTCCCCAGTA TCCACGGAAC AATTGGCTCC CACAGCACCA CCTGAGCTAA    900
```

-continued

```
CCCCTGTGGT CCAGGACTGC TACCACGGTG ATGGACAGAG CTACCGAGGC ACATCCTCCA    960

CCACCACCAC AGGAAAGAAG TGTCAGTCTT GGTCATCTAT GACACCACAC CGGCACCAGA   1020

AGACCCCAGA AAACTACCCA AATGCTGGCC TGACAATGAA CTACTGCAGG AATCCAGATG   1080

CCGATAAAGG CCCCTGGTGT TTTACCACAG ACCCCAGCGT CAGGTGGGAG TACTGCAACC   1140

TGAAAAAATG CTCAGGAACA GAAGCGAGTG TTGTAGCACC TCCGCCTGTT GTCCTGCTTC   1200

CAGATGTAGA GACTCCTTCC GAAGAAGACT GTATGTTTGG GAATGGGAAA GGATACCGAG   1260

GCAAGAGGGC GACCACTGTT ACTGGGACGC CATGCCAGGA CTGGGCTGCC CAGGAGCCCC   1320

ATAGACACAG CATTTTCACT CCAGAGACAA ATCCACGGGC GGGTCTGGAA AAAAATTACT   1380

GCCGTAACCC TGATGGTGAT GTAGGTGGTC CCTGGTGCTA CACGACAAAT CCAAGAAAAC   1440

TTTACGACTA CTGTGATGTC CCTCAGTGTG CGGCCCCTTC ATTTGATTGT GGGAAGCCTC   1500

AAGTGGAGCC GAAGAAATGT CCTGGAAGGG TTGTGGGGGG GTGTGTGGCC CACCCACATT   1560

CCTGGCCCTG GCAAGTCAGT CTTAGAACAA GGTTTGGAAT GCACTTCTGT GGAGGCACCT   1620

TGATATCCCC AGAGTGGGTG TTGACTGCTG CCCACTGCTT GGAGAAGTCC CCAAGGCCTT   1680

CATCCTACAA GGTCATCCTG GGTGCACACC AAGAAGTGAA TCTCGAACCG CATGTTCAGG   1740

AAATAGAAGT GTCTAGGCTG TTCTTGGAGC CCACACGAAA AGATATTGCC TTGCTAAAGC   1800

TAAGCAGTCC TGCCGTCATC ACTGACAAAG TAATCCCAGC TTGTCTGCCA TCCCCAAATT   1860

ATGTGGTCGC TGACCGGACC GAATGTTTCA TCACTGGCTG GGGAGAAACC CAAGGTACTT   1920

TTGGAGCTGG CCTTCTCAAG GAAGCCCAGC TCCCTGTGAT TGAGAATAAA GTGTGCAATC   1980

GCTATGAGTT TCTGAATGGA AGAGTCCAAT CCACCGAACT CTGTGCTGGG CATTTGGCCG   2040

GAGGCACTGA CAGTTGCCAG GGTGACAGTG GAGGTCCTCT GGTTTGCTTC GAGAAGGACA   2100

AATACATTTT ACAAGGAGTC ACTTCTTGGG GTCTTGGCTG TGCACGCCCC AATAAGCCTG   2160

GTGTCTATGT TCGTGTTTCA AGGTTTGTTA CTTGGATTGA GGGAGTGATG AGAAATAATT   2220

AATTGGACGG GAGACAGAGT GACGCACGCG GCCGCTCTAG AACTAGTGGA TCCCCCGGGA   2280

AGGCCTCGGA CCGGGC                                                   2296
```

(2) INFORMATION FOR SEQ ID NO:19:

(i) SEQUENCE CHARACTERISTICS:
(A) LENGTH: 56 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: pN2gpt-gp160

(xi) SEQUENCE DESCRIPTION: SEQ ID NO:19:

```
TTTTTGGCAT ATAAATCGTT ATCCACCATG TAAGATAACG AATTCCATGG CCCGGG         56
```

(2) INFORMATION FOR SEQ ID NO:20:

(i) SEQUENCE CHARACTERISTICS:
(A) LENGTH: 331 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide -continued (vii) IMMEDIATE SOURCE:
(B) CLONE: pvWF (xi) SEQUENCE DESCRIPTION: SEQ ID NO:20:

```
TTTTTTTTGG CATATAAATC GCGGCCGCGG GTGGTTGGTG GATGTCACAG CTTGGGCTTT     60

ATCTCCCCCA GCAGTGGGAT TCCACAGCCC CTGGGCTACA TAACAGCAAG ACAGTCCGGA    120

GCTGTAGCAG ACCTGATTGA GCCTTTGCAG CAGCTGAGAG CATGGCCTAG GGTGGGCGGC    180

ACCATTGTCC AGCAGCTGAG TTTCCCAGGG ACCTTGGAGA TAGCCGCAGC CCTCATTTGC    240

AGGGGAAGAT GTGAGGCTGC TGCAGCTGCA TGGGTGCCTG CTGCTGCCTG CCTTGGCCTG    300

ATGGCGGCCG CCCGGGTTTT TATCTCGAGA C                                   331
```

(2) INFORMATION FOR SEQ ID NO:21:

(i) SEQUENCE CHARACTERISTICS:
(A) LENGTH: 50 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: pEcoK-dhr (xi) SEQUENCE DESCRIPTION: SEQ ID NO:21:

```
ATTAGCGTCT CGTTTCAGAC GCGGCCGCGG TAATTAGATT CTCCCACATT                50
```

(2) INFORMATION FOR SEQ ID NO:22:

(i) SEQUENCE CHARACTERISTICS:
(A) LENGTH: 1209 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: pdhr-gpt (xi) SEQUENCE DESCRIPTION: SEQ ID NO:22:

```
ATTAGCGTCT CGTTTCAGAC GCGGCCGCTC TAGAACTAGT GGATCCCCCA ACTTAAGGGT     60

ACCGCCTCGA CATCTATATA CTATATAGTA ATACCAATAC TCAAGACTAC GAAACTGATA    120

CAATCTCTTA TCATGTGGGT AATGTTCTCG ATGTCGAATA GCCATATGCC GGTAGTTGCG    180

ATATACATAA ACTGATCACT AATTCCAAAC CCACCCGCTT TTTATAGTAA GTTTTTCACC    240

CATAAATAAT AAATACAATA ATTAATTTCT CGTAAAAGTA GAAAATATAT TCTAATTTAT    300

TGCACGGTAA GGAAGTAGAA TCATAAAGAA CAGTGACGGA TGATCCCCAA GCTTGGACAC    360

AAGACAGGCT TGCGAGATAT GTTTGAGAAT ACCACTTTAT CCCGCGTCAG GGAGAGGCAG    420

TGCGTAAAAA GACGCGGACT CATGTGAAAT ACTGGTTTTT AGTGCGCCAG ATCTCTATAA    480

TCTCGCGCAA CCTATTTTCC CCTCGAACAC TTTTTAAGCC GTAGATAAAC AGGCTGGGAC    540

ACTTCACATG AGCGAAAAAT ACATCGTCAC CTGGGACATG TTGCAGATCC ATGCACGTAA    600

ACTCGCAAGC CGACTGATGC CTTCTGAACA ATGGAAAGGC ATTATTGCCG TAAGCCGTGG    660

CGGTCTGGTA CCGGGTGCGT TACTGGCGCG TGAACTGGGT ATTCGTCATG TCGATACCGT    720

TTGTATTTCC AGCTACGATC ACGACAACCA GCGCGAGCTT AAAGTGCTGA AACGCGCAGA    780
```

-continued

```
AGGCGATGGC GAAGGCTTCA TCGTTATTGA TGACCTGGTG GATACCGGTG GTACTGCGGT    840

TGCGATTCGT GAAATGTATC CAAAAGCGCA CTTTGTCACC ATCTTCGCAA AACCGGCTGG    900

TCGTCCGCTG GTTGATGACT ATGTTGTTGA TATCCCGCAA GATACCTGGA TTGAACAGCC    960

GTGGGATATG GGCGTCGTAT TCGTCCCGCC AATCTCCGGT CGCTAATCTT TTCAACGCCT   1020

GGCACTGCCG GGCGTTGTTC TTTTTAACTT CAGGCGGGTT ACAATAGTTT CCAGTAAGTA   1080

TTCTGGAGGC TGCATCCATG ACACAGGCAA ACCTGAGCGA AACCCTGTTC AAACCCCGCT   1140

TTGGGCTGCA GGAATTCGAT ATCAAGCTTA TCGATACCGT CGCGGCCGCG GTAATTAGAT   1200

TCTCCCACA                                                           1209
```

(2) INFORMATION FOR SEQ ID NO:23:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: odN2

(xi) SEQUENCE DESCRIPTION: SEQ ID NO:23:

```
GGCCGATATC TTAATTTAAA AGGCCT                                          26
```

(2) INFORMATION FOR SEQ ID NO:24:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: odN3

(xi) SEQUENCE DESCRIPTION: SEQ ID NO:24:

```
CCAATGTTAC GTGGGTTACA TCAG                                            24
```

(2) INFORMATION FOR SEQ ID NO:25:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: I-SceI linker 1

(xi) SEQUENCE DESCRIPTION: SEQ ID NO:25:

```
TAGGGATAAC AGGGTAAT                                                   18
```

(2) INFORMATION FOR SEQ ID NO:26:

(i) SEQUENCE CHARACTERISTICS:
(A) LENGTH: 18 base pairs
(B) TYPE: nucleic acid

-continued (C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: I-SceI linker 2

(xi) SEQUENCE DESCRIPTION: SEQ ID NO:26:

ATTACCCTGT TATCCCTA 18

(2) INFORMATION FOR SEQ ID NO:27:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: odS2

(xi) SEQUENCE DESCRIPTION: SEQ ID NO:27:

GTATAAAGTC CGACTATTGT TCT 23

(2) INFORMATION FOR SEQ ID NO:28:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: odS3

(xi) SEQUENCE DESCRIPTION: SEQ ID NO:28:

TCTGAGGCCT AATAGACCTC TGTACA 26

(2) INFORMATION FOR SEQ ID NO:29:

(i) SEQUENCE CHARACTERISTICS:
(A) LENGTH: 13 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: SfiI(1)

(xi) SEQUENCE DESCRIPTION: SEQ ID NO:29:

GGCCGGCTAG GCC 13

(2) INFORMATION FOR SEQ ID NO:30:

(i) SEQUENCE CHARACTERISTICS:
(A) LENGTH: 13 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: SfiI(2)

(xi) SEQUENCE DESCRIPTION: SEQ ID NO:30:

GGCCATATAG GCC 13

(2) INFORMATION FOR SEQ ID NO:31:

(i) SEQUENCE CHARACTERISTICS:
(A) LENGTH: 66 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: odTK1

(xi) SEQUENCE DESCRIPTION: SEQ ID NO:31:

GAGTCGATGT AACACTTTCT ACAGGATCCG TTAACTCGCG AGAATTCCAT CACGTTAGAA 60

AATGCG 66

(2) INFORMATION FOR SEQ ID NO:32:

(i) SEQUENCE CHARACTERISTICS:
(A) LENGTH: 79 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: P-J(1)

(xi) SEQUENCE DESCRIPTION: SEQ ID NO:32:

GATCCGGCCG GCTAGGCCGC GGCCGCCCGG GTTTTTATCT CGAGACAAAA AGACGGACCG 60

GGCCCGGCCA TATAGGCCC 79

(2) INFORMATION FOR SEQ ID NO:33:

(i) SEQUENCE CHARACTERISTICS:
(A) LENGTH: 79 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: P-J(2)

(xi) SEQUENCE DESCRIPTION: SEQ ID NO:33:

AATTGGGCCT ATATGGCCGG GCCCGGTCCG TCTTTTTGTC TCGAGATAAA AACCCGGGCG 60

GCCGCGGCCT AGCCGGCCG 79

(2) INFORMATION FOR SEQ ID NO:34:

(i) SEQUENCE CHARACTERISTICS:
(A) LENGTH: 18 base pairs
(B) TYPE: nucleic acid (C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: odTK2

(xi) SEQUENCE DESCRIPTION: SEQ ID NO:34:

AGAAGCCGTG GGTCATTG 18

(2) INFORMATION FOR SEQ ID NO:35:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: odTK3

(xi) SEQUENCE DESCRIPTION: SEQ ID NO:35:

TACCGTGTCG CTGTAACTTA C 21

(2) INFORMATION FOR SEQ ID NO:36:

(i) SEQUENCE CHARACTERISTICS:
(A) LENGTH: 75 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: P-A(0.1)

(xi) SEQUENCE DESCRIPTION: SEQ ID NO:36:

AGGCCGGCTA GGCCGCGGCC GCCCGGGTTT TTATCTCGAG ACAAAAAGAC GGACCGGGCC 60

CGGCCATATA GGCCA 75

(2) INFORMATION FOR SEQ ID NO:37:

(i) SEQUENCE CHARACTERISTICS:
(A) LENGTH: 83 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: P-A(0.2)

(xi) SEQUENCE DESCRIPTION: SEQ ID NO:37:

GTACTGGCCT ATATGGCCGG GCCCGGTCCG TCTTTTTGTC TCGAGATAAA AACCCGGGCG 60

GCCGCGGCCT AGCCGGCCTA GCT 83

(2) INFORMATION FOR SEQ ID NO:38:

(i) SEQUENCE CHARACTERISTICS:
(A) LENGTH: 55 base pairs

-continued (B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: P-artP(11)

(xi) SEQUENCE DESCRIPTION: SEQ ID NO:38:

GGCCACGTTT TTATGGGAAG CTTTTTTTTT TTTTTTTTTT TGGCATATAA ATCGC 55

(2) INFORMATION FOR SEQ ID NO:39:

(i) SEQUENCE CHARACTERISTICS:
(A) LENGTH: 55 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: P-artP(12)

(xi) SEQUENCE DESCRIPTION: SEQ ID NO:39:

GGCCGCGATT TATATGCCAA AAAAAAAAAA AAAAAAAAGC TTCCCATAAA AACGT 55

(2) INFORMATION FOR SEQ ID NO:40:

(i) SEQUENCE CHARACTERISTICS:
(A) LENGTH: 93 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: P-artP(8)

(xi) SEQUENCE DESCRIPTION: SEQ ID NO:40:

CGCTGGCCTA TATGGCCGGG CCCGGTCCGA GGCCTTCCCG GGCCATGGAA TTCATTTATA 60

TGCCAAAAAA AAAAAAAAAA AAAAGCTTCT GCA 93

(2) INFORMATION FOR SEQ ID NO:41:

(i) SEQUENCE CHARACTERISTICS:
(A) LENGTH: 97 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: P-artP(10)

(xi) SEQUENCE DESCRIPTION: SEQ ID NO:41:

CGCTGGCCTA TATGGCCGGG CGTCCGAGGC CTTCCCGGGC CATGGAATTC GTTAACGATT 60

TATATGCCAA AAAAAAAAAA AAAAAAAAGC TTCTGCA 97

(2) INFORMATION FOR SEQ ID NO:42:

(i) SEQUENCE CHARACTERISTICS:

(A) LENGTH: 50 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: oligonucleotide P-hr(3)

(xi) SEQUENCE DESCRIPTION: SEQ ID NO:42:

ATTAGCGTCT CGTTTCAGAC GCGGCCGCGG TAATTAGATT CTCCCACATT 50

(2) INFORMATION FOR SEQ ID NO:43:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (xi) SEQUENCE DESCRIPTION: SEQ ID NO:43:

CTAGCCCGGG 10

(2) INFORMATION FOR SEQ ID NO:44:

(i) SEQUENCE CHARACTERISTICS:
(A) LENGTH: 47 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: P-P2 5'(1)

(xi) SEQUENCE DESCRIPTION: SEQ ID NO:44:

GTACGTACGG CTGCAGTTGT TAGAGCTTGG TATAGCGGAC AACTAAG 47

(2) INFORMATION FOR SEQ ID NO:45:

(i) SEQUENCE CHARACTERISTICS:
(A) LENGTH: 50 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: P-P2 3'(1)

(xi) SEQUENCE DESCRIPTION: SEQ ID NO:45:

TCTGACTGAC GTTAACGATT TATAGGCTAT AAAAAATAGT ATTTTCTACT 50

(2) INFORMATION FOR SEQ ID NO:46:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: Other nucleic acid;

(A) DESCRIPTION: Synthetic DNA oligonucleotide (vii) IMMEDIATE SOURCE:
(B) CLONE: P-SM(2)

(xi) SEQUENCE DESCRIPTION: SEQ ID NO:46:

GTCTTGAGTA TTGGTATTAC 20

(2) INFORMATION FOR SEQ ID NO:47:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: P-SM(3)

(xi) SEQUENCE DESCRIPTION: SEQ ID NO:47:

CGAAACTATC AAAACGCTTT ATG 23

(2) INFORMATION FOR SEQ ID NO:48:

(i) SEQUENCE CHARACTERISTICS:
(A) LENGTH: 53 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: P-MN(1)

(xi) SEQUENCE DESCRIPTION: SEQ ID NO:48:

AGCTAGCTGA ATTCAGGCCT CATGAGAGTG AAGGGGATCA GGAGGAATTA TCA 53

(2) INFORMATION FOR SEQ ID NO:49:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: P-MN(2)

(xi) SEQUENCE DESCRIPTION: SEQ ID NO:49:

CATCTGATGC ACAAAATAGA GTGGTGGTTG 30

(2) INFORMATION FOR SEQ ID NO:50:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:

(B) CLONE: P-Seq(2)

(xi) SEQUENCE DESCRIPTION: SEQ ID NO:50:

CTGTGGGTAC ACAGGCTTGT GTGGCCC 27

(2) INFORMATION FOR SEQ ID NO:51:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: P-Seq(3)

(xi) SEQUENCE DESCRIPTION: SEQ ID NO:51:

CAATTTTTCT GTAGCACTAC AGATC 25

(2) INFORMATION FOR SEQ ID NO:52:

(i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: o-542

(xi) SEQUENCE DESCRIPTION: SEQ ID NO:52:

CGATTACGTA GTTAACGCGG CCGCGGCCTA GCCGGCCATA AAAAT 45

(2) INFORMATION FOR SEQ ID NO:53:

(i) SEQUENCE CHARACTERISTICS:
(A) LENGTH: 47 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: o-544

(xi) SEQUENCE DESCRIPTION: SEQ ID NO:53:

CTAGATTTTT ATGGCCGGCT AGGCCGCGGC CGCGTTAACT ACGTAAT 47

(2) INFORMATION FOR SEQ ID NO:54:

(i) SEQUENCE CHARACTERISTICS:
(A) LENGTH: 50 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: o-541

(xi) SEQUENCE DESCRIPTION: SEQ ID NO:54:

-continued

CTTTTTCTGC GGCCGCGGAT ATGGCCCGGT CCGGTTAACT ACGTAGACGT 50

(2) INFORMATION FOR SEQ ID NO:55:

(i) SEQUENCE CHARACTERISTICS:
(A) LENGTH: 53 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: o-543

(xi) SEQUENCE DESCRIPTION: SEQ ID NO:55:

CTACGTAGTT AACCGGACCG GGCCATATAG GCCGCGGCCG CAGAAAAAGC ATG 53

(2) INFORMATION FOR SEQ ID NO:56:

(i) SEQUENCE CHARACTERISTICS:
(A) LENGTH: 51 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: o-selPI (xi) SEQUENCE DESCRIPTION: SEQ ID NO:56:

CGATAAAAAT TGAAATTTTA TTTTTTTTTT TTGGAATATA AATAAGGCCT C 51

(2) INFORMATION FOR SEQ ID NO:57:

(i) SEQUENCE CHARACTERISTICS:
(A) LENGTH: 53 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: o-selPII (xi) SEQUENCE DESCRIPTION: SEQ ID NO:57:

CATGGAGGCC TTATTTATAT TCCAAAAAAA AAAAATAAAA TTTCAATTTT TAT 53

(2) INFORMATION FOR SEQ ID NO:58:

(i) SEQUENCE CHARACTERISTICS:
(A) LENGTH: 14 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: o-830

(xi) SEQUENCE DESCRIPTION: SEQ ID NO:58:

TCGACTTTTT ATCA 14

(2) INFORMATION FOR SEQ ID NO:59:

(i) SEQUENCE CHARACTERISTICS:
(A) LENGTH: 12 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: o-857

(xi) SEQUENCE DESCRIPTION: SEQ ID NO:59:

```
TATGATAAAA AC                                                 12
```

(2) INFORMATION FOR SEQ ID NO:60:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: o-NcoI (xi) SEQUENCE DESCRIPTION: SEQ ID NO:60:

```
GAGCAGAAGA CAGTGGCCAT GGCCGTGAAG GGGATCAGGA                   40
```

(2) INFORMATION FOR SEQ ID NO:61:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: o-NsiI (xi) SEQUENCE DESCRIPTION: SEQ ID NO:61:

```
CATAAACTGA TTATATCCTC ATGCATCTGT                              30
```

(2) INFORMATION FOR SEQ ID NO:62:

(i) SEQUENCE CHARACTERISTICS:
(A) LENGTH: 4145 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: pS2gpt-S4

(xi) SEQUENCE DESCRIPTION: SEQ ID NO:62:

```
GTGGCACTTT TCGGGGAAAT GTGCGCGGAA CCCCTATTTG TTTATTTTTC TAAATACATT     60

CAAATATGTA TCCGCTCATG AGACAATAAC CCTGATAAAT GCTTCAATAA TATTGAAAAA    120

GGAAGAGTAT GAGTATTCAA CATTTCCGTG TCGCCCTTAT TCCCTTTTTT GCGGCATTTT    180
```

-continued

```
GCCTTCCTGT TTTTGCTCAC CCAGAAACGC TGGTGAAAGT AAAAGATGCT GAAGATCAGT    240
TGGGTGCACG AGTGGGTTAC ATCGAACTGG ATCTCAACAG CGGTAAGATC CTTGAGAGTT    300
TTCGCCCCGA AGAACGTTTT CCAATGATGA GCACTTTTAA AGTTCTGCTA TGTGGCGCGG    360
TATTATCCCG TATTGACGCC GGGCAAGAGC AACTCGGTCG CCGCATACAC TATTCTCAGA    420
ATGACTTGGT TGAGTACTCA CCAGTCACAG AAAAGCATCT TACGGATGGC ATGACAGTAA    480
GAGAATTATG CAGTGCTGCC ATAACCATGA GTGATAACAC TGCGGCCAAC TTACTTCTGA    540
CAACGATCGG AGGACCGAAG GAGCTAACCG CTTTTTTGCA CAACATGGGG GATCATGTAA    600
CTCGCCTTGA TCGTTGGGAA CCGGAGCTGA ATGAAGCCAT ACCAAACGAC GAGCGTGACA    660
CCACGATGCC TGTAGCAATG GCAACAACGT TGCGCAAACT ATTAACTGGC GAACTACTTA    720
CTCTAGCTTC CCGGCAACAA TTAATAGACT GGATGGAGGC GGATAAAGTT GCAGGACCAC    780
TTCTGCGCTC GGCCCTTCCG GCTGGCTGGT TTATTGCTGA TAAATCTGGA GCCGGTGAGC    840
GTGGGTCTCG CGGTATCATT GCAGCACTGG GGCCAGATGG TAAGCCCTCC CGTATCGTAG    900
TTATCTACAC GACGGGGAGT CAGGCAACTA TGGATGAACG AAATAGACAG ATCGCTGAGA    960
TAGGTGCCTC ACTGATTAAG CATTGGTAAC TGTCAGACCA AGTTTACTCA TATATACTTT   1020
AGATTGATTT AAAACTTCAT TTTTAATTTA AAAGGATCTA GGTGAAGATC CTTTTTGATA   1080
ATCTCATGAC CAAAATCCCT TAACGTGAGT TTTCGTTCCA CTGAGCGTCA GACCCCGTAG   1140
AAAAGATCAA AGGATCTTCT TGAGATCCTT TTTTTCTGCG CGTAATCTGC TGCTTGCAAA   1200
CAAAAAAACC ACCGCTACCA GCGGTGGTTT GTTTGCCGGA TCAAGAGCTA CCAACTCTTT   1260
TTCCGAAGGT AACTGGCTTC AGCAGAGCGC AGATACCAAA TACTGTCCTT CTAGTGTAGC   1320
CGTAGTTAGG CCACCACTTC AAGAACTCTG TAGCACCGCC TACATACCTC GCTCTGCTAA   1380
TCCTGTTACC AGTGGCTGCT GCCAGTGGCG ATAAGTCGTG TCTTACCGGG TTGGACTCAA   1440
GACGATAGTT ACCGGATAAG GCGCAGCGGT CGGGCTGAAC GGGGGGTTCG TGCACACAGC   1500
CCAGCTTGGA GCGAACGACC TACACCGAAC TGAGATACCT ACAGCGTGAG CTATGAGAAA   1560
GCGCCACGCT TCCCGAAGGG AGAAAGGCGG ACAGGTATCC GGTAAGCGGC AGGGTCGGAA   1620
CAGGAGAGCG CACGAGGGAG CTTCCAGGGG GAAACGCCTG GTATCTTTAT AGTCCTGTCG   1680
GGTTTCGCCA CCTCTGACTT GAGCGTCGAT TTTTGTGATG CTCGTCAGGG GGGCGGAGCC   1740
TATGGAAAAA CGCCAGCAAC GCGGCCTTTT TACGGTTCCT GGCCTTTTGC TGGCCTTTTG   1800
CTCACATGTT CTTTCCTGCG TTATCCCCTG ATTCTGTGGA TAACCGTATT ACCGCCTTTG   1860
AGTGAGCTGA TACCGCTCGC CGCAGCCGAA CGACCGAGCG CAGCGAGTCA GTGAGCGAGG   1920
AAGCGGAAGA GCGCCCAATA CGCAAACCGC CTCTCCCCGC GCGTTGGCCG ATTCATTAAT   1980
GCAGCTGGCA CGACAGGTTT CCCGACTGGA AAGCGGGCAG TGAGCGCAAC GCAATTAATG   2040
TGAGTTAGCT CACTCATTAG GCACCCCAGG CTTTACACTT TATGCTTCCG GCTCGTATGT   2100
TGTGTGGAAT TGTGAGCGGA TAACAATTTC ACACAGGAAA CAGCTATGAC CATGATTACG   2160
CCAAGCGCGC AATTAACCCT CACTAAAGGG AACAAAAGCT GGAGCTCCAC CGCGGTGGCG   2220
GCCGCTCTAG CCCGGGCTAG AACTAGTGGA TCCCCCAAAG CGGGGTTTGA ACAGGGTTTC   2280
GCTCAGGTTT GCCTGTGTCA TGGATGCAGC CTCCAGAATA CTTACTGGAA ACTATTGTAA   2340
CCCGCCTGAA GTTAAAAAGA ACAACGCCCG GCAGTGCCAG GCGTTGAAAA GATTAGCGAC   2400
CGGAGATTGG CGGGACGAAT ACGACGCCCA TATCCCACGG CTGTTCAATC CAGGTATCTT   2460
GCGGGATATC AACAACATAG TCATCAACCA GCGGACGACC AGCCGGTTTT GCGAAGATGG   2520
```

-continued

```
TGACAAAGTG CGCTTTTGGA TACATTTCAC GAATCGCAAC CGCAGTACCA CCGGTATCCA   2580

CCAGGTCATC AATAACGATG AAGCCTTCGC CATCGCCTTC TGCGCGTTTC AGCACTTTAA   2640

GCTCGCGCTG GTTGTCGTGA TCGTAGCTGG AAATACAAAC GGTATCGACA TGACGAATAC   2700

CCAGTTCACG CGCCAGTAAC GCACCCGGTA CCAGACCGCC ACGGCTTACG GCAATAATGC   2760

CTTTCCATTG TTCAGAAGGC ATCAGTCGGC TTGCGAGTTT ACGTGCATGG ATCTGCAACA   2820

TGTCCCAGGT GACGATGTAT TTTTCGCTCA TGTGAAGTGT CCCAGCCTGT TTATCTACGG   2880

CTTAAAAAGT GTTCGAGGGG AAAATAGGTT GCGCGAGATT ATAGAGATCT GGCGCACTAA   2940

AAACCAGTAT TTCACATGAG TCCGCGTCTT TTTACGCACT GCCTCTCCCT GACGCGGGAT   3000

AAAGTGGTAT TCTCAAACAT ATCTCGCAAG CCTGTCTTGT GTCCAAGCTT GGGGATCATC   3060

CGTCACTGTT CTTTATGATT CTACTTCCTT ACCGTGCAAT AAATTAGAAT ATATTTTCTA   3120

CTTTTACGAG AAATTAATTA TTGTATTTAT TATTTATGGG TGAAAAACTT ACTATAAAAA   3180

GCGGGTGGGT TTGGAATTAG TGATCAGTTT ATGTATATCG CAACTACCGG CATATGGCTA   3240

TTCGACATCG AGAACATTAC CCACATGATA AGAGATTGTA TCAGTTTCGT AGTCTTGAGT   3300

ATTGGTATTA CTATATAGTA TATAGATGTC GAGGCGGTAC CCTTAAGTTG GGCTGCAGAA   3360

GCTTTTTTTT TTTTTTTTTT TTGGCATATA AATCGTTAAC GAATTCCATG GCCCGGGAAG   3420

GCCTCGGACC GGGCCCGGCC ATATAGGCCA GCGATACCGT CGCGGCCGCG ACCTCGAGGG   3480

GGGGCCCGGT ACCCAATTCG CCCTATAGTG AGTCGTATTA CGCGCGCTCA CTGGCCGTCG   3540

TTTTACAACG TCGTGACTGG GAAAACCCTG GCGTTACCCA ACTTAATCGC CTTGCAGCAC   3600

ATCCCCCTTT CGCCAGCTGG CGTAATAGCG AAGAGGCCCG CACCGATCGC CCTTCCCAAC   3660

AGTTGCGCAG CCTGAATGGC GAATGGAAAT TGTAAGCGTT AATATTTTGT TAAAATTCGC   3720

GTTAAATTTT TGTTAAATCA GCTCATTTTT TAACCAATAG GCCGAAATCG GCAAAATCCC   3780

TTATAAATCA AAAGAATAGA CCGAGATAGG GTTGAGTGTT GTTCCAGTTT GGAACAAGAG   3840

TCCACTATTA AAGAACGTGG ACTCCAACGT CAAAGGGCGA AAAACCGTCT ATCAGGGCGA   3900

TGGCCCACTA CGTGAACCAT CACCCTAATC AAGTTTTTTG GGGTCGAGGT GCCGTAAAGC   3960

ACTAAATCGG AACCCTAAAG GGAGCCCCCG ATTTAGAGCT TGACGGGGAA AGCCGGCGAA   4020

CGTGGCGAGA AAGGAAGGGA AGAAAGCGAA AGGAGCGGGC GCTAGGGCGC TGGCAAGTGT   4080

AGCGGTCACG CTGCGCGTAA CCACCACACC CGCCGCGCTT AATGCGCCGC TACAGGGCGC   4140

GTCAG                                                               4145
```

(2) INFORMATION FOR SEQ ID NO:63:

(i) SEQUENCE CHARACTERISTICS:
(A) LENGTH: 4277 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: pS2gpt-P2

(xi) SEQUENCE DESCRIPTION: SEQ ID NO:63:

```
GTGGCACTTT TCGGGGAAAT GTGCGCGGAA CCCCTATTTG TTTATTTTTC TAAATACATT     60

CAAATATGTA TCCGCTCATG AGACAATAAC CCTGATAAAT GCTTCAATAA TATTGAAAAA    120

GGAAGAGTAT GAGTATTCAA CATTTCCGTG TCGCCCTTAT TCCCTTTTTT GCGGCATTTT    180
```

-continued

```
GCCTTCCTGT TTTTGCTCAC CCAGAAACGC TGGTGAAAGT AAAAGATGCT GAAGATCAGT    240
TGGGTGCACG AGTGGGTTAC ATCGAACTGG ATCTCAACAG CGGTAAGATC CTTGAGAGTT    300
TTCGCCCCGA AGAACGTTTT CCAATGATGA GCACTTTTAA AGTTCTGCTA TGTGGCGCGG    360
TATTATCCCG TATTGACGCC GGGCAAGAGC AACTCGGTCG CCGCATACAC TATTCTCAGA    420
ATGACTTGGT TGAGTACTCA CCAGTCACAG AAAAGCATCT TACGGATGGC ATGACAGTAA    480
GAGAATTATG CAGTGCTGCC ATAACCATGA GTGATAACAC TGCGGCCAAC TTACTTCTGA    540
CAACGATCGG AGGACCGAAG GAGCTAACCG CTTTTTTGCA CAACATGGGG GATCATGTAA    600
CTCGCCTTGA TCGTTGGGAA CCGGAGCTGA ATGAAGCCAT ACCAAACGAC GAGCGTGACA    660
CCACGATGCC TGTAGCAATG GCAACAACGT TGCGCAAACT ATTAACTGGC GAACTACTTA    720
CTCTAGCTTC CCGGCAACAA TTAATAGACT GGATGGAGGC GGATAAAGTT GCAGGACCAC    780
TTCTGCGCTC GGCCCTTCCG GCTGGCTGGT TTATTGCTGA TAAATCTGGA GCCGGTGAGC    840
GTGGGTCTCG CGGTATCATT GCAGCACTGG GGCCAGATGG TAAGCCCTCC CGTATCGTAG    900
TTATCTACAC GACGGGGAGT CAGGCAACTA TGGATGAACG AAATAGACAG ATCGCTGAGA    960
TAGGTGCCTC ACTGATTAAG CATTGGTAAC TGTCAGACCA AGTTTACTCA TATATACTTT   1020
AGATTGATTT AAAACTTCAT TTTTAATTTA AAAGGATCTA GGTGAAGATC CTTTTTGATA   1080
ATCTCATGAC CAAAATCCCT TAACGTGAGT TTTCGTTCCA CTGAGCGTCA GACCCCGTAG   1140
AAAAGATCAA AGGATCTTCT TGAGATCCTT TTTTTCTGCG CGTAATCTGC TGCTTGCAAA   1200
CAAAAAAACC ACCGCTACCA GCGGTGGTTT GTTTGCCGGA TCAAGAGCTA CCAACTCTTT   1260
TTCCGAAGGT AACTGGCTTC AGCAGAGCGC AGATACCAAA TACTGTCCTT CTAGTGTAGC   1320
CGTAGTTAGG CCACCACTTC AAGAACTCTG TAGCACCGCC TACATACCTC GCTCTGCTAA   1380
TCCTGTTACC AGTGGCTGCT GCCAGTGGCG ATAAGTCGTG TCTTACCGGG TTGGACTCAA   1440
GACGATAGTT ACCGGATAAG GCGCAGCGGT CGGGCTGAAC GGGGGGTTCG TGCACACAGC   1500
CCAGCTTGGA GCGAACGACC TACACCGAAC TGAGATACCT ACAGCGTGAG CTATGAGAAA   1560
GCGCCACGCT TCCCGAAGGG AGAAAGGCGG ACAGGTATCC GGTAAGCGGC AGGGTCGGAA   1620
CAGGAGAGCG CACGAGGGAG CTTCCAGGGG GAAACGCCTG GTATCTTTAT AGTCCTGTCG   1680
GGTTTCGCCA CCTCTGACTT GAGCGTCGAT TTTTGTGATG CTCGTCAGGG GGGCGGAGCC   1740
TATGGAAAAA CGCCAGCAAC GCGGCCTTTT TACGGTTCCT GGCCTTTTGC TGGCCTTTTG   1800
CTCACATGTT CTTTCCTGCG TTATCCCCTG ATTCTGTGGA TAACCGTATT ACCGCCTTTG   1860
AGTGAGCTGA TACCGCTCGC CGCAGCCGAA CGACCGAGCG CAGCGAGTCA GTGAGCGAGG   1920
AAGCGGAAGA GCGCCCAATA CGCAAACCGC CTCTCCCCGC GCGTTGGCCG ATTCATTAAT   1980
GCAGCTGGCA CGACAGGTTT CCCGACTGGA AAGCGGGCAG TGAGCGCAAC GCAATTAATG   2040
TGAGTTAGCT CACTCATTAG GCACCCCAGG CTTTACACTT TATGCTTCCG GCTCGTATGT   2100
TGTGTGGAAT TGTGAGCGGA TAACAATTTC ACACAGGAAA CAGCTATGAC CATGATTACG   2160
CCAAGCGCGC AATTAACCCT CACTAAAGGG AACAAAAGCT GGAGCTCCAC CGCGGTGGCG   2220
GCCGCTCTAG CCCGGGCTAG AACTAGTGGA TCCCCCAAAG CGGGGTTTGA ACAGGGTTTC   2280
GCTCAGGTTT GCCTGTGTCA TGGATGCAGC CTCCAGAATA CTTACTGGAA ACTATTGTAA   2340
CCCGCCTGAA GTTAAAAAGA ACAACGCCCG GCAGTGCCAG GCGTTGAAAA GATTAGCGAC   2400
CGGAGATTGG CGGGACGAAT ACGACGCCCA TATCCCACGG CTGTTCAATC CAGGTATCTT   2460
GCGGGATATC AACAACATAG TCATCAACCA GCGGACGACC AGCCGGTTTT GCGAAGATGG   2520
TGACAAAGTG CGCTTTTGGA TACATTTCAC GAATCGCAAC CGCAGTACCA CCGGTATCCA   2580
```

```
CCAGGTCATC AATAACGATG AAGCCTTCGC CATCGCCTTC TGCGCGTTTC AGCACTTTAA   2640

GCTCGCGCTG GTTGTCGTGA TCGTAGCTGG AAATACAAAC GGTATCGACA TGACGAATAC   2700

CCAGTTCACG CGCCAGTAAC GCACCCGGTA CCAGACCGCC ACGGCTTACG GCAATAATGC   2760

CTTTCCATTG TTCAGAAGGC ATCAGTCGGC TTGCGAGTTT ACGTGCATGG ATCTGCAACA   2820

TGTCCCAGGT GACGATGTAT TTTTCGCTCA TGTGAAGTGT CCCAGCCTGT TTATCTACGG   2880

CTTAAAAAGT GTTCGAGGGG AAAATAGGTT GCGCGAGATT ATAGAGATCT GGCGCACTAA   2940

AAACCAGTAT TTCACATGAG TCCGCGTCTT TTTACGCACT GCCTCTCCCT GACGCGGGAT   3000

AAAGTGGTAT TCTCAAACAT ATCTCGCAAG CCTGTCTTGT GTCCAAGCTT GGGGATCATC   3060

CGTCACTGTT CTTTATGATT CTACTTCCTT ACCGTGCAAT AAATTAGAAT ATATTTTCTA   3120

CTTTTACGAG AAATTAATTA TTGTATTTAT TATTTATGGG TGAAAAACTT ACTATAAAAA   3180

GCGGGTGGGT TTGGAATTAG TGATCAGTTT ATGTATATCG CAACTACCGG CATATGGCTA   3240

TTCGACATCG AGAACATTAC CCACATGATA AGAGATTGTA TCAGTTTCGT AGTCTTGAGT   3300

ATTGGTATTA CTATATAGTA TATAGATGTC GAGGCGGTAC CCTTAAGTTG GGCTGCAGTT   3360

GTTAGAGCTT GGTATAGCGG ACAACTAAGT AATTGTAAAG AAGAAAACGA AACTATCAAA   3420

ACCGTTTATG AAATGATAGA AAAAAGAATA TAAATAATCC TGTATTTTAG TTTAAGTAAC   3480

AGTAAAATAA TGAGTAGAAA ATACTATTTT TTATAGCCTA TAAATCGTTA ACGAATTCCA   3540

TGGCCCGGGA AGGCCTCGGA CCGGGCCCGG CCATATAGGC CAGCGATACC GTCGCGGCCG   3600

CGACCTCGAG GGGGGGCCCG GTACCCAATT CGCCCTATAG TGAGTCGTAT TACGCGCGCT   3660

CACTGGCCGT CGTTTTACAA CGTCGTGACT GGGAAAACCC TGGCGTTACC CAACTTAATC   3720

GCCTTGCAGC ACATCCCCCT TTCGCCAGCT GGCGTAATAG CGAAGAGGCC CGCACCGATC   3780

GCCCTTCCCA ACAGTTGCGC AGCCTGAATG GCGAATGGAA ATTGTAAGCG TTAATATTTT   3840

GTTAAAATTC GCGTTAAATT TTTGTTAAAT CAGCTCATTT TTTAACCAAT AGGCCGAAAT   3900

CGGCAAAATC CCTTATAAAT CAAAAGAATA GACCGAGATA GGGTTGAGTG TTGTTCCAGT   3960

TTGGAACAAG AGTCCACTAT TAAAGAACGT GGACTCCAAC GTCAAAGGGC GAAAAACCGT   4020

CTATCAGGGC GATGGCCCAC TACGTGAACC ATCACCCTAA TCAAGTTTTT TGGGGTCGAG   4080

GTGCCGTAAA GCACTAAATC GGAACCCTAA AGGGAGCCCC CGATTTAGAG CTTGACGGGG   4140

AAAGCCGGCG AACGTGGCGA GAAAGGAAGG GAAGAAAGCG AAAGGAGCGG GCGCTAGGGC   4200

GCTGGCAAGT GTAGCGGTCA CGCTGCGCGT AACCACCACA CCCGCCGCGC TTAATGCGCC   4260

GCTACAGGGC GCGTCAG                                                  4277
```

(2) INFORMATION FOR SEQ ID NO:64:

(i) SEQUENCE CHARACTERISTICS:
(A) LENGTH: 4701 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: pTZ-L2

(xi) SEQUENCE DESCRIPTION: SEQ ID NO:64:

```
AGCGCCCAAT ACGCAAACCG CCTCTCCCCG CGCGTTGGCC GATTCATTAA TGCAGCTTTT     60

TCTGCGGCCG CGGCCTATAT GGCCCGGTCC GGTTAACTAC GTAGACGTCG AGGATTTCGC    120
```

-continued

```
GTGGGTCAAT GCCGCGCCAG ATCCACATCA GACGGTTAAT CATGCGATAC CAGTGAGGGA    180
TGGTTTTACC ATCAAGGGCC GACTGCACAG GCGGTTGTGC GCCGTGATTA AAGCGGCGGA    240
CTAGCGTCGA GGTTTCAGGA TGTTTAAAGC GGGGTTTGAA CAGGGTTTCG CTCAGGTTTG    300
CCTGTGTCAT GGATGCAGCC TCCAGAATAC TTACTGGAAA CTATTGTAAC CCGCCTGAAG    360
TTAAAAAGAA CAACGCCCGG CAGTGCCAGG CGTTGAAAAG ATTAGCGACC GGAGATTGGC    420
GGGACGAATA CGACGCCCAT ATCCCACGGC TGTTCAATCC AGGTATCTTG CGGGATATCA    480
ACAACATAGT CATCAACCAG CGGACGACCA GCCGGTTTTG CGAAGATGGT GACAAAGTGC    540
GCTTTTGGAT ACATTTCACG AATCGCAACC GCAGTACCAC CGGTATCCAC CAGGTCATCA    600
ATAACGATGA AGCCTTCGCC ATCGCCTTCT GCGCGTTTCA GCACTTTAAG CTCGCGCTGG    660
TTGTCGTGAT CGTAGCTGGA AATACAAACG GTATCGACAT GACGAATACC CAGTTCACGC    720
GCCAGTAACG CACCCGGTAC CAGACCGCCA CGGCTTACGG CAATAATGCC TTTCCATTGT    780
TCAGAAGGCA TCAGTCGGCT TGCGAGTTTA CGTGCATGGA TCTGCAACAT GTCCCAGGTG    840
ACGATGTATT TTTCGCTCAT GTGAAGTGTC CCAGCCTGTT TATCTACGGC TTAAAAAGTG    900
TTCGAGGGGA AAATAGGTTG CGCGAGATTA TAGAGATCTG GCGCACTAAA AACCAGTATT    960
TCACATGAGT CCGCGTCTTT TTACGCACTG CCTCTCCCTG ACGCGGGATA AAGTGGTATT   1020
CTCAAACATA TCTCGCAAGC CTGTCTTGTG TCCAAGCTTG GGGATCATCC GTCACTGTTC   1080
TTTATGATTC TACTTCCTTA CCGTGCAATA AATTAGAATA TATTTTCTAC TTTTACGAGA   1140
AATTAATTAT TGTATTTATT ATTTATGGGT GAAAAACTTA CTATAAAAAG CGGGTGGGTT   1200
TGGAATTAGT GATCAGTTTA TGTATATCGC AACTACCGGC ATATGGCTAT TCGACATCGA   1260
GAACATTACC CACATGATAA GAGATTGTAT CAGTTTCGTA GTCTTGAGTA TTGGTATTAC   1320
TATATAGTAT ATNNNNNNGG TAACNNNNNN NNNNNNNNNN NNNNNNNNNN NNNNNNNNNN   1380
NNNNNNNAGA TCTCGATCCG GATATAGTTC CTCCTTTCAG CAAAAAACCC CTCAAGACCC   1440
GTTTAGAGGC CCCAAGGGGT TATGCTAGTT ATTGCTCANN NNNNNNNNGT CGACTTAATT   1500
AATTAGGCCT CTCGAGCTGC AGGGATCCAC TAGTGAGCTC CCCGGGGAAT TCCCATGGTA   1560
TTATCGTGTT TTTCAAAGGA AAAAAACGTC CCGTGGTTCG GGGGGCTCTN NNNNNNNNNN   1620
NNNNNNNNNN NNNNNNNNNN NNNNNNNNNN NNNNNNNNNN NNNNNNNNNN NNNNNNNNNN   1680
NNNNNNNNNN NNNNNNNNNN NNNNNNNNNN NNNNNNNNNN NNNNNNNNNN NNNNNNNNNN   1740
NNNNNNNNNN NNNNNNNNNN NNNNNNNNNN NNNNNNNNNN NNNNNNNNNN NNNNNNNNNN   1800
NNNNNNNNNN NNNNNNNNNN NNNNNNNNNN NNNNNNNNNN NNNNNNNNNN NNNNNNNNNN   1860
NNNNNNNNNN NNNNNNNNNN NNNNNNNNNN NNNNNNNNNN NNNNNNNNNN NNNNNNNNNN   1920
NNNNNNNNNN NNNNNNNNNN NNNNNNNNNN NNNNNNNNNN NNNNNNNNNN NNNNNNNNNN   1980
NNNNNNNNNN NNNNNNNNNN NNNNNNNNNN NNNNNNNNNN NNNNNNNNNN NNNNNNNNNN   2040
NNNNNNNNNN NNNNNNNNNN NNNNNNNNNN NNNNNNNNNN NNNNNNNNNN NNNNNNNNNN   2100
NNNNNNNNNN NNNNNNNNNN NNNNNNNNNN NCCGCTAGAG GGAAACCGTT GTGGTCTCCC   2160
TATAGTGAGT CGTATTAATT TCGCGGGATC GATCGATTAC GTAGTTAACG CGGCCGCGGC   2220
CTAGCCGGCC ATAAAAATCT AGCTGGCGTA ATAGCGAAGA GGCCCGCACC GATCGCCCTT   2280
CCCAACAGTT GCGCAGCCTG AATGGCGAAT GGGAAATTGT AAACGTTAAT ATTTTGTTAA   2340
AATTCGCGTT AAATTTTTGT TAAATCAGCT CATTTTTTAA CCAATAGGCC GAAATCGGCA   2400
AAATCCCTTA TAAATCAAAA GAATAGACCG AGATAGGGTT GAGTGTTGTT CCAGTTTGGA   2460
```

-continued

```
ACAAGAGTCC ACTATTAAAG AACGTGGACT CCAACGTCAA AGGGCGAAAA ACCGTCTATC   2520

AGGGCGATGG CCCACTACGT GAACCATCAC CCTAATCAAG TTTTTTGGGG TCGAGGTGCC   2580

GTAAAGCACT AAATCGGAAC CCTAAAGGGA GCCCCCGATT TAGAGCTTGA CGGGGAAAGC   2640

CGGCGAACGT GGCGAGAAAG GAAGGGAAGA AAGCGAAAGG AGCGGGCGCT AGGGCGCTGG   2700

CAAGTGTAGC GGTCACGCTG CGCGTAACCA CCACACCCGC CGCGCTTAAT GCGCCGCTAC   2760

AGGGCGCGTC AGGTGGCACT TTTCGGGGAA ATGTGCGCGG AACCCCTATT TGTTTATTTT   2820

TCTAAATACA TTCAAATATG TATCCGCTCA TGAGACAATA ACCCTGATAA ATGCTTCAAT   2880

AATATTGAAA AAGGAAGAGT ATGAGTATTC AACATTTCCG TGTCGCCCTT ATTCCCTTTT   2940

TTGCGGCATT TTGCCTTCCT GTTTTTGCTC ACCCAGAAAC GCTGGTGAAA GTAAAAGATG   3000

CTGAAGATCA GTTGGGTGCA CGAGTGGGTT ACATCGAACT GGATCTCAAC AGCGGTAAGA   3060

TCCTTGAGAG TTTTCGCCCC GAAGAACGTT TTCCAATGAT GAGCACTTTT AAAGTTCTGC   3120

TATGTGGCGC GGTATTATCC CGTGTTGACG CCGGGCAAGA GCAACTCGGT CGCCGCATAC   3180

ACTATTCTCA GAATGACTTG GTTGAGTACT CACCAGTCAC AGAAAAGCAT CTTACGGATG   3240

GCATGACAGT AAGAGAATTA TGCAGTGCTG CCATAACCAT GAGTGATAAC ACTGCGGCCA   3300

ACTTACTTCT GACAACGATC GGAGGACCGA AGGAGCTAAC CGCTTTTTTG CACAACATGG   3360

GGGATCATGT AACTCGCCTT GATCGTTGGG AACCGGAGCT GAATGAAGCC ATACCAAACG   3420

ACGAGCGTGA CACCACGATG CCTGCAGCAA TGGCAACAAC GTTGCGCAAA CTATTAACTG   3480

GCGAACTACT TACTCTAGCT TCCCGGCAAC AATTAATAGA CTGGATGGAG GCGGATAAAG   3540

TTGCAGGACC ACTTCTGCGC TCGGCCCTTC CGGCTGGCTG GTTTATTGCT GATAAATCTG   3600

GAGCCGGTGA GCGTGGGTCT CGCGGTATCA TTGCAGCACT GGGGCCAGAT GGTAAGCCCT   3660

CCCGTATCGT AGTTATCTAC ACGACGGGGA GTCAGGCAAC TATGGATGAA CGAAATAGAC   3720

AGATCGCTGA GATAGGTGCC TCACTGATTA AGCATTGGTA ACTGTCAGAC CAAGTTTACT   3780

CATATATACT TTAGATTGAT TTAAAACTTC ATTTTTAATT TAAAAGGATC TAGGTGAAGA   3840

TCCTTTTTGA TAATCTCATG ACCAAAATCC CTTAACGTGA GTTTTCGTTC CACTGAGCGT   3900

CAGACCCCGT AGAAAAGATC AAAGGATCTT CTTGAGATCC TTTTTTTCTG CGCGTAATCT   3960

GCTGCTTGCA AACAAAAAAA CCACCGCTAC CAGCGGTGGT TTGTTTGCCG GATCAAGAGC   4020

TACCAACTCT TTTTCCGAAG GTAACTGGCT TCAGCAGAGC GCAGATACCA AATACTGTCC   4080

TTCTAGTGTA GCCGTAGTTA GGCCACCACT TCAAGAACTC TGTAGCACCG CCTACATACC   4140

TCGCTCTGCT AATCCTGTTA CCAGTGGCTG CTGCCAGTGG CGATAAGTCG TGTCTTACCG   4200

GGTTGGACTC AAGACGATAG TTACCGGATA AGGCGCAGCG GTCGGGCTGA ACGGGGGGTT   4260

CGTGCACACA GCCCAGCTTG GAGCGAACGA CCTACACCGA ACTGAGATAC CTACAGCGTG   4320

AGCATTGAGA AAGCGCCACG CTTCCCGAAG GGAGAAAGGC GGACAGGTAT CCGGTAAGCG   4380

GCAGGGTCGG AACAGGAGAG CGCACGAGGG AGCTTCCAGG GGGAAACGCC TGGTATCTTT   4440

ATAGTCCTGT CGGGTTTCGC CACCTCTGAC TTGAGCGTCG ATTTTTGTGA TGCTCGTCAG   4500

GGGGGCGGAG CCTATGGAAA AACGCCAGCA ACGCGGCCTT TTTACGGTTC CTGGCCTTTT   4560

GCTGGCCTTT TGCTCACATG TTCTTTCCTG CGTTATCCCC TGATTCTGTG GATAACCGTA   4620

TTACCGCCTT TGAGTGAGCT GATACCGCTC GCCGCAGCCG AACGACCGAG CGCAGCGAGT   4680

CAGTGAGCGA GGAAGCGGAA G                                             4701
```

(2) INFORMATION FOR SEQ ID NO:65:

(i) SEQUENCE CHARACTERISTICS:
(A) LENGTH: 3878 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: pselP-gpt-L2

(xi) SEQUENCE DESCRIPTION: SEQ ID NO:65:

```
AGCGCCCAAT ACGCAAACCG CCTCTCCCCG CGCGTTGGCC GATTCATTAA TGCAGCTTTT     60

TCTGCGGCCG CGGCCTATAT GGCCCGGTCC GGTTAACTAC GTAGACGTCG AGGATTTCGC    120

GTGGGTCAAT GCCGCGCCAG ATCCACATCA GACGGTTAAT CATGCGATAC CAGTGAGGGA    180

TGGTTTTACC ATCAAGGGCC GACTGCACAG GCGGTTGTGC GCCGTGATTA AAGCGGCGGA    240

CTAGCGTCGA GGTTTCAGGA TGTTTAAAGC GGGGTTTGAA CAGGGTTTCG CTCAGGTTTG    300

CCTGTGTCAT GGATGCAGCC TCCAGAATAC TTACTGGAAA CTATTGTAAC CCGCCTGAAG    360

TTAAAAAGAA CAACGCCCGG CAGTGCCAGG CGTTGAAAAG ATTAGCGACC GGAGATTGGC    420

GGGACGAATA CGACGCCCAT ATCCCACGGC TGTTCAATCC AGGTATCTTG CGGGATATCA    480

ACAACATAGT CATCAACCAG CGGACGACCA GCCGGTTTTG CGAAGATGGT GACAAAGTGC    540

GCTTTTGGAT ACATTTCACG AATCGCAACC GCAGTACCAC CGGTATCCAC CAGGTCATCA    600

ATAACGATGA AGCCTTCGCC ATCGCCTTCT GCGCGTTTCA GCACTTTAAG CTCGCGCTGG    660

TTGTCGTGAT CGTAGCTGGA AATACAAACG GTATCGACAT GACGAATACC CAGTTCACGC    720

GCCAGTAACG CACCCGGTAC CAGACCGCCA CGGCTTACGG CAATAATGCC TTTCCATTGT    780

TCAGAAGGCA TCAGTCGGCT TGCGAGTTTA CGTGCATGGA TCTGCAACAT GTCCCAGGTG    840

ACGATGTATT TTTCGCTCAT GTGAAGTGTC CCAGCCTGTT TATCTACGGC TTAAAAAGTG    900

TTCGAGGGGA AAATAGGTTG CGCGAGATTA TAGAGATCTG GCGCACTAAA AACCAGTATT    960

TCACATGAGT CCGCGTCTTT TTACGCACTG CCTCTCCCTG ACGCGGGATA AAGTGGTATT   1020

CTCAAACATA TCTCGCAAGC CTGTCTTGTG TCCAAGCTTG GGGATCATCC GTCACTGTTC   1080

TTTATGATTC TACTTCCTTA CCGTGCAATA AATTAGAATA TATTTTCTAC TTTTACGAGA   1140

AATTAATTAT TGTATTTATT ATTTATGGGT GAAAAACTTA CTATAAAAAG CGGGTGGGTT   1200

TGGAATTAGT GATCAGTTTA TGTATATCGC AACTACCGGC ATATGATAAA AAGTCGACTT   1260

AATTAATTAG GCCTCTCGAG CTGCAGGGAT CCACTAGTGA GCTCCCCGGG GAATTCCCAT   1320

GGAGGCCTTA TTTATATTCC AAAAAAAAAA AATAAAATTT CAATTTTTAT CGATTACGTA   1380

GTTAACGCGG CCGCGGCCTA GCCGGCCATA AAAATCTAGC TGGCGTAATA GCGAAGAGGC   1440

CCGCACCGAT CGCCCTTCCC AACAGTTGCG CAGCCTGAAT GGCGAATGGG AAATTGTAAA   1500

CGTTAATATT TTGTTAAAAT TCGCGTTAAA TTTTTGTTAA ATCAGCTCAT TTTTTAACCA   1560

ATAGGCCGAA ATCGGCAAAA TCCCTTATAA ATCAAAAGAA TAGACCGAGA TAGGGTTGAG   1620

TGTTGTTCCA GTTTGGAACA AGAGTCCACT ATTAAAGAAC GTGGACTCCA ACGTCAAAGG   1680

GCGAAAAACC GTCTATCAGG GCGATGGCCC ACTACGTGAA CCATCACCCT AATCAAGTTT   1740

TTTGGGGTCG AGGTGCCGTA AAGCACTAAA TCGGAACCCT AAAGGGAGCC CCCGATTTAG   1800

AGCTTGACGG GGAAAGCCGG CGAACGTGGC GAGAAAGGAA GGGAAGAAAG CGAAAGGAGC   1860

GGGCGCTAGG GCGCTGGCAA GTGTAGCGGT CACGCTGCGC GTAACCACCA CACCCGCCGC   1920

GCTTAATGCG CCGCTACAGG GCGCGTCAGG TGGCACTTTT CGGGGAAATG TGCGCGGAAC   1980
```

-continued

```
CCCTATTTGT TTATTTTTCT AAATACATTC AAATATGTAT CCGCTCATGA GACAATAACC   2040

CTGATAAATG CTTCAATAAT ATTGAAAAAG GAAGAGTATG AGTATTCAAC ATTTCCGTGT   2100

CGCCCTTATT CCCTTTTTTG CGGCATTTTG CCTTCCTGTT TTTGCTCACC CAGAAACGCT   2160

GGTGAAAGTA AAAGATGCTG AAGATCAGTT GGGTGCACGA GTGGGTTACA TCGAACTGGA   2220

TCTCAACAGC GGTAAGATCC TTGAGAGTTT TCGCCCCGAA GAACGTTTTC CAATGATGAG   2280

CACTTTTAAA GTTCTGCTAT GTGGCGCGGT ATTATCCCGT GTTGACGCCG GGCAAGAGCA   2340

ACTCGGTCGC CGCATACACT ATTCTCAGAA TGACTTGGTT GAGTACTCAC CAGTCACAGA   2400

AAAGCATCTT ACGGATGGCA TGACAGTAAG AGAATTATGC AGTGCTGCCA TAACCATGAG   2460

TGATAACACT GCGGCCAACT TACTTCTGAC AACGATCGGA GGACCGAAGG AGCTAACCGC   2520

TTTTTTGCAC AACATGGGGG ATCATGTAAC TCGCCTTGAT CGTTGGGAAC CGGAGCTGAA   2580

TGAAGCCATA CCAAACGACG AGCGTGACAC CACGATGCCT GCAGCAATGG CAACAACGTT   2640

GCGCAAACTA TTAACTGGCG AACTACTTAC TCTAGCTTCC CGGCAACAAT TAATAGACTG   2700

GATGGAGGCG GATAAAGTTG CAGGACCACT TCTGCGCTCG GCCCTTCCGG CTGGCTGGTT   2760

TATTGCTGAT AAATCTGGAG CCGGTGAGCG TGGGTCTCGC GGTATCATTG CAGCACTGGG   2820

GCCAGATGGT AAGCCCTCCC GTATCGTAGT TATCTACACG ACGGGGAGTC AGGCAACTAT   2880

GGATGAACGA AATAGACAGA TCGCTGAGAT AGGTGCCTCA CTGATTAAGC ATTGGTAACT   2940

GTCAGACCAA GTTTACTCAT ATATACTTTA GATTGATTTA AAACTTCATT TTTAATTTAA   3000

AAGGATCTAG GTGAAGATCC TTTTTGATAA TCTCATGACC AAAATCCCTT AACGTGAGTT   3060

TTCGTTCCAC TGAGCGTCAG ACCCCGTAGA AAAGATCAAA GGATCTTCTT GAGATCCTTT   3120

TTTTCTGCGC GTAATCTGCT GCTTGCAAAC AAAAAAACCA CCGCTACCAG CGGTGGTTTG   3180

TTTGCCGGAT CAAGAGCTAC CAACTCTTTT TCCGAAGGTA ACTGGCTTCA GCAGAGCGCA   3240

GATACCAAAT ACTGTCCTTC TAGTGTAGCC GTAGTTAGGC CACCACTTCA AGAACTCTGT   3300

AGCACCGCCT ACATACCTCG CTCTGCTAAT CCTGTTACCA GTGGCTGCTG CCAGTGGCGA   3360

TAAGTCGTGT CTTACCGGGT TGGACTCAAG ACGATAGTTA CCGGATAAGG CGCAGCGGTC   3420

GGGCTGAACG GGGGGTTCGT GCACACAGCC CAGCTTGGAG CGAACGACCT ACACCGAACT   3480

GAGATACCTA CAGCGTGAGC ATTGAGAAAG CGCCACGCTT CCCGAAGGGA GAAAGGCGGA   3540

CAGGTATCCG GTAAGCGGCA GGGTCGGAAC AGGAGAGCGC ACGAGGGAGC TTCCAGGGGG   3600

AAACGCCTGG TATCTTTATA GTCCTGTCGG GTTTCGCCAC CTCTGACTTG AGCGTCGATT   3660

TTTGTGATGC TCGTCAGGGG GGCGGAGCCT ATGGAAAAAC GCCAGCAACG CGGCCTTTTT   3720

ACGGTTCCTG GCCTTTTGCT GGCCTTTTGC TCACATGTTC TTTCCTGCGT TATCCCCTGA   3780

TTCTGTGGAT AACCGTATTA CCGCCTTTGA GTGAGCTGAT ACCGCTCGCC GCAGCCGAAC   3840

GACCGAGCGC AGCGAGTCAG TGAGCGAGGA AGCGGAAG                           3878
```

(2) INFORMATION FOR SEQ ID NO:66:

(i) SEQUENCE CHARACTERISTICS:
(A) LENGTH: 6474 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: pselP-gp160MN -continued (xi) SEQUENCE DESCRIPTION: SEQ ID NO:66:

```
AGCGCCCAAT ACGCAAACCG CCTCTCCCCG CGCGTTGGCC GATTCATTAA TGCAGCTTTT     60
TCTGCGGCCG CGGCCTATAT GGCCCGGTCC GGTTAACTAC GTAGACGTCG AGGATTTCGC    120
GTGGGTCAAT GCCGCGCCAG ATCCACATCA GACGGTTAAT CATGCGATAC CAGTGAGGGA    180
TGGTTTTACC ATCAAGGGCC GACTGCACAG GCGGTTGTGC GCCGTGATTA AAGCGGCGGA    240
CTAGCGTCGA GGTTTCAGGA TGTTTAAAGC GGGGTTTGAA CAGGGTTTCG CTCAGGTTTG    300
CCTGTGTCAT GGATGCAGCC TCCAGAATAC TTACTGGAAA CTATTGTAAC CCGCCTGAAG    360
TTAAAAAGAA CAACGCCCGG CAGTGCCAGG CGTTGAAAAG ATTAGCGACC GGAGATTGGC    420
GGGACGAATA CGACGCCCAT ATCCCACGGC TGTTCAATCC AGGTATCTTG CGGGATATCA    480
ACAACATAGT CATCAACCAG CGGACGACCA GCCGGTTTTG CGAAGATGGT GACAAAGTGC    540
GCTTTTGGAT ACATTTCACG AATCGCAACC GCAGTACCAC CGGTATCCAC CAGGTCATCA    600
ATAACGATGA AGCCTTCGCC ATCGCCTTCT GCGCGTTTCA GCACTTTAAG CTCGCGCTGG    660
TTGTCGTGAT CGTAGCTGGA AATACAAACG GTATCGACAT GACGAATACC CAGTTCACGC    720
GCCAGTAACG CACCCGGTAC CAGACCGCCA CGGCTTACGG CAATAATGCC TTTCCATTGT    780
TCAGAAGGCA TCAGTCGGCT TGCGAGTTTA CGTGCATGGA TCTGCAACAT GTCCCAGGTG    840
ACGATGTATT TTTCGCTCAT GTGAAGTGTC CCAGCCTGTT TATCTACGGC TTAAAAAGTG    900
TTCGAGGGGA AAATAGGTTG CGCGAGATTA TAGAGATCTG GCGCACTAAA AACCAGTATT    960
TCACATGAGT CCGCGTCTTT TTACGCACTG CCTCTCCCTG ACGCGGGATA AAGTGGTATT   1020
CTCAAACATA TCTCGCAAGC CTGTCTTGTG TCCAAGCTTG GGGATCATCC GTCACTGTTC   1080
TTTATGATTC TACTTCCTTA CCGTGCAATA AATTAGAATA TATTTTCTAC TTTTACGAGA   1140
AATTAATTAT TGTATTTATT ATTTATGGGT GAAAAACTTA CTATAAAAAG CGGGTGGGTT   1200
TGGAATTAGT GATCAGTTTA TGTATATCGC AACTACCGGC ATATGATAAA AAGTCGACTT   1260
AATTAATTAG GCTGGTTCAG CTCGTCTCAT TCTTTCCCTT ACAGTAGGCC ATCCAGTCAC   1320
ACGTTTTGAC CATTTGCCAC CCATCTTATA GCAAAGCCCT TTCCAAGCCC TGTCTTATTC   1380
TTGTAGGTAT GTGGAGAATA GCTCTACCAG CTCTTTGCAG TACTTCTATA ACCCTATCTG   1440
TCCCCTCAGC TACTGCTATA GCTGTGGCAT TAAGCAAGCT AACAGCACTA CTCTTTAGTT   1500
CCTGACTCCA ATACTGTAGG AGATTCCACC AATATTTGAG GACTTCCCAC CCCCTGCGTC   1560
CCAGAAGTTC CACAATCCTC GCTGCAATCA AGAGTAAGTC TCTGTGGTGG TAGCTGAAGA   1620
GGAACAGGCT CCGCAGGTCG ACCCAGATAA TTGCTAAGAA TCCATGCACT AATCGACCGG   1680
ATGTGTCTCT GTCTCTCTCT CCACCTTCTT CTTCGATTCC TTCGGGCCTG TCGGGTCCCC   1740
TCGGAACTGG GGGGCGGGTC TGCAACGACA ATGGTGAGTA TCCCTGCCTA ACTCTATTCA   1800
CTATAGAAAG TACAGCAAAA ACTATTCTTA AACCTACCAA GCCTCCTACT ATCATTATGA   1860
ATATTTTTAT ATACCACAGC CAATTTGTTA TGTCAAACCA ATTCCACAAA CTTGCCCATT   1920
TATCCAATTC CAATAATTCT TGTTCATTCT TTTCTTGTTG GGTTTGCGAT TTTTCTAGTA   1980
ATGAGTATAT TAAGCTTGTG TAATTGTCAA TTTCTCTTTC CCACTGCATC CAGGTCATGT   2040
TATTCCAAAT ATCATCCAGA GATTTATTAC TCCAACTAGC ATTCCAAGGC ACAGTAGTGG   2100
TGCAAATGAG TTTTCCAGAG CAACCCCAAA ACCCCAGGAG CTGTTGATCC TTTAGGTATC   2160
TTTCCACAGC CAGGACTCTT GCCTGGAGCT GCTTGATGCC CCAGACTGTG AGTTGCAACA   2220
TATGCTGTTG CGCCTCAATG GCCCTCAGCA AATTGTTCTG CTGTTGCACT ATACCAGACA   2280
```

-continued

```
ATAATAGTCT GGCCTGTACC GTCAGCGTCA CTGACGCTGC GCCCATAGTG CTTCCTGCTG   2340
CTCCTAAGAA CCCAAGGAAC AGAGCTCCTA TCGCTGCTCT TTTTTCTCTC TGCACCACTC   2400
TTCTCTTTGC CTTGGTGGGT GCTACTCCTA ATGGTTCAAT TGTTACTACT TTATATTTAT   2460
ATAATTCACT TCTCCAATTG TCCCTCATAT CTCCTCCTCC AGGTCTGAAG ATCTCGGTGT   2520
CGTTCGTGTC CGTGTCCTTA CCACCATCTC TTGTTAATAG TAGCCCTGTA ATATTTGATG   2580
AACATCTAAT TTGTCCTTCA ATGGGAGGGG CATACATTGC TTTTCCTACT TCCTGCCACA   2640
TGTTTATAAT TTGTTTTATT TTGCATTGAA GTGTGATATT GTTATTTGAC CCTGTAGTAT   2700
TATTCCAAGT ATTATTACCA TTCCAAGTAC TATTAAACAG TGGTGATGTA TTACAGTAGA   2760
AAAATTCCCC TCCACAATTA AAACTGTGCA TTACAATTTC TGGGTCCCCT CCTGAGGATT   2820
GATTAAAGAC TATTGTTTTA TTCTTAAATT GTTCTTTTAA TTTGCTAACT ATCTGTCTTA   2880
AAGTGTCATT CCATTTTGCT CTACTAATGT TACAATGTGC TTGTCTTATA GTTCCTATTA   2940
TATTTTTTGT TGTATAAAAT GCTCTCCCTG GTCCTATATG TATCCTTTTT CTTTTATTGT   3000
AGTTGGGTCT TGTACAATTA ATTTGTACAG ATTCATTCAG ATGTACTATG ATGGTTTTAG   3060
CATTATCAGT GAAATTCTCA GATCTAATTA CTACCTCTTC TTCTGCTAGA CTGCCATTTA   3120
ACAGCAGTTG AGTTGATACT ACTGGCCTAA TTCCATGTGT ACATTGTACT GTGCTGACAT   3180
TTTTACATGA TCCTTTTCCA CTGAACTTTT TATCGTTACA TTTTAGAATC GCAAAACCAG   3240
CCGGGGCACA ATAGTGTATG GGAATTGGCT CAAAGGATAT CTTTGGACAA GCTTGTGTAA   3300
TGACTGAGGT ATTACAACTT ATCAACCTAT AGCTGGTACT ATCATTATCT ATTGATACTA   3360
TATCAAGTTT ATAAAGAAGT GCATATTCTT TCTGCATCTT ATCTCTTATG CTTGTGGTGA   3420
TATTGAAAGA GCAGTTTTTC ATTTCTCCTC CCTTTATTGT TCCCTCGCTA TTACTATTGT   3480
TATTAGCAGT ACTATTATTG GTATTAGTAG TATTCCTCAA ATCAGTGCAA TTTAAAGTAA   3540
CACAGAGTGG GGTTAATTTT ACACATGGCT TTAGGCTTTG ATCCCATAAA CTGATTATAT   3600
CCTCATGCAT CTGTTCTACC ATGTTATTTT TCCACATGTT AAAATTTTCT GTCACATTTA   3660
CCAATTCTAC TTCTTGTGGG TTGGGGTCTG TGGGTACACA GGCTTGTGTG GCCCAAACAT   3720
TATGTACCTC TGTATCATAT GCTTTAGCAT CTGATGCACA AAATAGAGTG GTGGTTGCTT   3780
CTTTCCACAC AGGTACCCCA TAATAGACTG TGACCCACAA TTTTTCTGTA GCACTACAGA   3840
TCATTAATAA CCCAAGGAGC ATCGTGCCCC ATCCCCACCA GTGCTGATAA TTCCTCCTGA   3900
TCCCCTTCAC GGCCATGGAG GCCTTATTTA TATTCCAAAA AAAAAAAATA AAATTTCAAT   3960
TTTTATCGAT TACGTAGTTA ACGCGGCCGC GGCCTAGCCG GCCATAAAAA TCTAGCTGGC   4020
GTAATAGCGA AGAGGCCCGC ACCGATCGCC CTTCCCAACA GTTGCGCAGC CTGAATGGCG   4080
AATGGGAAAT TGTAAACGTT AATATTTTGT TAAAATTCGC GTTAAATTTT TGTTAAATCA   4140
GCTCATTTTT TAACCAATAG GCCGAAATCG GCAAAATCCC TTATAAATCA AAAGAATAGA   4200
CCGAGATAGG GTTGAGTGTT GTTCCAGTTT GGAACAAGAG TCCACTATTA AAGAACGTGG   4260
ACTCCAACGT CAAAGGGCGA AAAACCGTCT ATCAGGGCGA TGGCCCACTA CGTGAACCAT   4320
CACCCTAATC AAGTTTTTTG GGGTCGAGGT GCCGTAAAGC ACTAAATCGG AACCCTAAAG   4380
GGAGCCCCCG ATTTAGAGCT TGACGGGGAA AGCCGGCGAA CGTGGCGAGA AAGGAAGGGA   4440
AGAAAGCGAA AGGAGCGGGC GCTAGGGCGC TGGCAAGTGT AGCGGTCACG CTGCGCGTAA   4500
CCACCACACC CGCCGCGCTT AATGCGCCGC TACAGGGCGC GTCAGGTGGC ACTTTTCGGG   4560
GAAATGTGCG CGGAACCCCT ATTTGTTTAT TTTTCTAAAT ACATTCAAAT ATGTATCCGC   4620
TCATGAGACA ATAACCCTGA TAAATGCTTC AATAATATTG AAAAAGGAAG AGTATGAGTA   4680
```

```
TTCAACATTT CCGTGTCGCC CTTATTCCCT TTTTTGCGGC ATTTTGCCTT CCTGTTTTTG   4740

CTCACCCAGA AACGCTGGTG AAAGTAAAAG ATGCTGAAGA TCAGTTGGGT GCACGAGTGG   4800

GTTACATCGA ACTGGATCTC AACAGCGGTA AGATCCTTGA GAGTTTTCGC CCCGAAGAAC   4860

GTTTTCCAAT GATGAGCACT TTTAAAGTTC TGCTATGTGG CGCGGTATTA TCCCGTGTTG   4920

ACGCCGGGCA AGAGCAACTC GGTCGCCGCA TACACTATTC TCAGAATGAC TTGGTTGAGT   4980

ACTCACCAGT CACAGAAAAG CATCTTACGG ATGGCATGAC AGTAAGAGAA TTATGCAGTG   5040

CTGCCATAAC CATGAGTGAT AACACTGCGG CCAACTTACT TCTGACAACG ATCGGAGGAC   5100

CGAAGGAGCT AACCGCTTTT TTGCACAACA TGGGGGATCA TGTAACTCGC CTTGATCGTT   5160

GGGAACCGGA GCTGAATGAA GCCATACCAA ACGACGAGCG TGACACCACG ATGCCTGCAG   5220

CAATGGCAAC AACGTTGCGC AAACTATTAA CTGGCGAACT ACTTACTCTA GCTTCCCGGC   5280

AACAATTAAT AGACTGGATG GAGGCGGATA AAGTTGCAGG ACCACTTCTG CGCTCGGCCC   5340

TTCCGGCTGG CTGGTTTATT GCTGATAAAT CTGGAGCCGG TGAGCGTGGG TCTCGCGGTA   5400

TCATTGCAGC ACTGGGGCCA GATGGTAAGC CCTCCCGTAT CGTAGTTATC TACACGACGG   5460

GGAGTCAGGC AACTATGGAT GAACGAAATA GACAGATCGC TGAGATAGGT GCCTCACTGA   5520

TTAAGCATTG GTAACTGTCA GACCAAGTTT ACTCATATAT ACTTTAGATT GATTTAAAAC   5580

TTCATTTTTA ATTTAAAAGG ATCTAGGTGA AGATCCTTTT TGATAATCTC ATGACCAAAA   5640

TCCCTTAACG TGAGTTTTCG TTCCACTGAG CGTCAGACCC CGTAGAAAAG ATCAAAGGAT   5700

CTTCTTGAGA TCCTTTTTTT CTGCGCGTAA TCTGCTGCTT GCAAACAAAA AAACCACCGC   5760

TACCAGCGGT GGTTTGTTTG CCGGATCAAG AGCTACCAAC TCTTTTTCCG AAGGTAACTG   5820

GCTTCAGCAG AGCGCAGATA CCAAATACTG TCCTTCTAGT GTAGCCGTAG TTAGGCCACC   5880

ACTTCAAGAA CTCTGTAGCA CCGCCTACAT ACCTCGCTCT GCTAATCCTG TTACCAGTGG   5940

CTGCTGCCAG TGGCGATAAG TCGTGTCTTA CCGGGTTGGA CTCAAGACGA TAGTTACCGG   6000

ATAAGGCGCA GCGGTCGGGC TGAACGGGGG GTTCGTGCAC ACAGCCCAGC TTGGAGCGAA   6060

CGACCTACAC CGAACTGAGA TACCTACAGC GTGAGCATTG AGAAAGCGCC ACGCTTCCCG   6120

AAGGGAGAAA GGCGGACAGG TATCCGGTAA GCGGCAGGGT CGGAACAGGA GAGCGCACGA   6180

GGGAGCTTCC AGGGGGAAAC GCCTGGTATC TTTATAGTCC TGTCGGGTTT CGCCACCTCT   6240

GACTTGAGCG TCGATTTTTG TGATGCTCGT CAGGGGGGCG GAGCCTATGG AAAAACGCCA   6300

GCAACGCGGC CTTTTTACGG TTCCTGGCCT TTTGCTGGCC TTTTGCTCAC ATGTTCTTTC   6360

CTGCGTTATC CCCTGATTCT GTGGATAACC GTATTACCGC CTTTGAGTGA GCTGATACCG   6420

CTCGCCGCAG CCGAACGACC GAGCGCAGCG AGTCAGTGAG CGAGGAAGCG GAAG         6474
```

(2) INFORMATION FOR SEQ ID NO:67:

(i) SEQUENCE CHARACTERISTICS:
(A) LENGTH: 6811 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: pN2-gpta ProtS (xi) SEQUENCE DESCRIPTION: SEQ ID NO:67:

```
GTGGCACTTT TCGGGGAAAT GTGCGCGGAA CCCCTATTTG TTTATTTTTC TAAATACATT     60
```

-continued

```
CAAATATGTA TCCGCTCATG AGACAATAAC CCTGATAAAT GCTTCAATAA TATTGAAAAA    120
GGAAGAGTAT GAGTATTCAA CATTTCCGTG TCGCCCTTAT TCCCTTTTTT GCGGCATTTT    180
GCCTTCCTGT TTTTGCTCAC CCAGAAACGC TGGTGAAAGT AAAAGATGCT GAAGATCAGT    240
TGGGTGCACG AGTGGGTTAC ATCGAACTGG ATCTCAACAG CGGTAAGATC CTTGAGAGTT    300
TTCGCCCCGA AGAACGTTTT CCAATGATGA GCACTTTTAA AGTTCTGCTA TGTGGCGCGG    360
TATTATCCCG TATTGACGCC GGGCAAGAGC AACTCGGTCG CCGCATACAC TATTCTCAGA    420
ATGACTTGGT TGAGTACTCA CCAGTCACAG AAAAGCATCT TACGGATGGC ATGACAGTAA    480
GAGAATTATG CAGTGCTGCC ATAACCATGA GTGATAACAC TGCGGCCAAC TTACTTCTGA    540
CAACGATCGG AGGACCGAAG GAGCTAACCG CTTTTTTGCA CAACATGGGG GATCATGTAA    600
CTCGCCTTGA TCGTTGGGAA CCGGAGCTGA ATGAAGCCAT ACCAAACGAC GAGCGTGACA    660
CCACGATGCC TGTAGCAATG GCAACAACGT TGCGCAAACT ATTAACTGGC GAACTACTTA    720
CTCTAGCTTC CCGGCAACAA TTAATAGACT GGATGGAGGC GGATAAAGTT GCAGGACCAC    780
TTCTGCGCTC GGCCCTTCCG GCTGGCTGGT TTATTGCTGA TAAATCTGGA GCCGGTGAGC    840
GTGGGTCTCG CGGTATCATT GCAGCACTGG GGCCAGATGG TAAGCCCTCC CGTATCGTAG    900
TTATCTACAC GACGGGGAGT CAGGCAACTA TGGATGAACG AAATAGACAG ATCGCTGAGA    960
TAGGTGCCTC ACTGATTAAG CATTGGTAAC TGTCAGACCA AGTTTACTCA TATATACTTT   1020
AGATTGATTT AAAACTTCAT TTTTAATTTA AAAGGATCTA GGTGAAGATC CTTTTTGATA   1080
ATCTCATGAC CAAAATCCCT TAACGTGAGT TTTCGTTCCA CTGAGCGTCA GACCCCGTAG   1140
AAAAGATCAA AGGATCTTCT TGAGATCCTT TTTTTCTGCG CGTAATCTGC TGCTTGCAAA   1200
CAAAAAAACC ACCGCTACCA GCGGTGGTTT GTTTGCCGGA TCAAGAGCTA CCAACTCTTT   1260
TTCCGAAGGT AACTGGCTTC AGCAGAGCGC AGATACCAAA TACTGTCCTT CTAGTGTAGC   1320
CGTAGTTAGG CCACCACTTC AAGAACTCTG TAGCACCGCC TACATACCTC GCTCTGCTAA   1380
TCCTGTTACC AGTGGCTGCT GCCAGTGGCG ATAAGTCGTG TCTTACCGGG TTGGACTCAA   1440
GACGATAGTT ACCGGATAAG GCGCAGCGGT CGGGCTGAAC GGGGGGTTCG TGCACACAGC   1500
CCAGCTTGGA GCGAACGACC TACACCGAAC TGAGATACCT ACAGCGTGAG CTATGAGAAA   1560
GCGCCACGCT TCCCGAAGGG AGAAAGGCGG ACAGGTATCC GGTAAGCGGC AGGGTCGGAA   1620
CAGGAGAGCG CACGAGGGAG CTTCCAGGGG GAAACGCCTG GTATCTTTAT AGTCCTGTCG   1680
GGTTTCGCCA CCTCTGACTT GAGCGTCGAT TTTTGTGATG CTCGTCAGGG GGGCGGAGCC   1740
TATGGAAAAA CGCCAGCAAC GCGGCCTTTT TACGGTTCCT GGCCTTTTGC TGGCCTTTTG   1800
CTCACATGTT CTTTCCTGCG TTATCCCCTG ATTCTGTGGA TAACCGTATT ACCGCCTTTG   1860
AGTGAGCTGA TACCGCTCGC CGCAGCCGAA CGACCGAGCG CAGCGAGTCA GTGAGCGAGG   1920
AAGCGGAAGA GCGCCCAATA CGCAAACCGC CTCTCCCCGC GCGTTGGCCG ATTCATTAAT   1980
GCAGCTGGCA CGACAGGTTT CCCGACTGGA AAGCGGGCAG TGAGCGCAAC GCAATTAATG   2040
TGAGTTAGCT CACTCATTAG GCACCCCAGG CTTTACACTT TATGCTTCCG GCTCGTATGT   2100
TGTGTGGAAT TGTGAGCGGA TAACAATTTC ACACAGGAAA CAGCTATGAC CATGATTACG   2160
CCAAGCGCGC AATTAACCCT CACTAAAGGG AACAAAAGCT GGAGCTCCAC CGCGGTGGCG   2220
GCCGCGTCGA CAGAAAAATT AATTAATTAT GGCCTCTCGA GCTGCAGCTG CCAAGAAGAA   2280
GATTCCTGTG CTGCTCTCAG GAAAATATGT CCCACTTGTT TTCTAATTCA ATAAAGATAC   2340
TGGTTTAAAT GTGAAGCCAC ACAAGAGAAA GATGAAGCCA AAGCTGGTCC CCCTGAGGAA   2400
```

-continued

```
TTGTTTTGAA ATAAGGCATT AGGACCCTCC ATTCAATTCA TATTTAATAG ACCACCATCT   2460
CTTCTGCCTT CATCAGGAAA AAAACAAAAA CATAAACAAA ATAGTATCTG CCTATGATTA   2520
ATAGTATTTA ATTACACGCA CTTTTGTTTG AGTTTACTTC CTTGCTTTCT GAAAAAAACA   2580
TAGGTATTTA GACACTAGTT CATGATGATA AAATTAAAAA TTTAGTTTTA CAAACAAAAA   2640
TTGAAACTGT CATTTGTAGG AAAAAAATTC AAATTTAAAA TTGTTATTTT TCACTATTCT   2700
TAGATAGCAA GAGAAGTAAG AATTTCTTTA CTGTGATTTA TATCACAACA GAATTTTTTT   2760
CCTTGACAAA GGACCTTTTA AAAATCCCAG GAAAGGACCA CAAAATAATC AAAGACTGCA   2820
CATTGTAAAT AAAACCCTTC AGCTGTTATT GAAACATAAG TATAATTACA CACAAGGAAA   2880
AGGTATTATA AGCAGAGAAA AGATGCCTTA AGAATTCTTT GTCTTTTTCC AAACTGATGG   2940
ACATGAGTGA GCTCTAATAT CATTATGTTT AGAAATGGCT TCATCCAGAT CCAACTGTAC   3000
ACCATTAATA TTCACTTCCA TGCAGCCATT ATAAAAGGCA TTCACTGGTG TGGCACTGAA   3060
TGGAACATCT GGAAGGCCAC CCAGGTATGT GGCCACTTTT GCTTTCATTG CTTTGTCCAA   3120
GACGGCAAGT TGTCTTTGAA GGTCTTCATG GGAGATGGTT TCTATTTTAA GTGGTGTCGA   3180
CAACTCCAGA TTGTTTCTGT TGACTCTAAA TTCCAGATGA GATTGTTGAT CGGAACATAG   3240
ACTTAGGGCC TGTATCCGAT ATATTACAGT ATTTTCAACA GATAACAGAA TATCCTGTGA   3300
TTTTTCAGAG GTGGAGTCCA CCAAGGACAC AGCAAAGGGC ACTGTGTTGT TACCAGAAAC   3360
CAAGGCAAGC ATAACACCAG TGCCCGTGGA TGGACGAATA TTCAAGGTCA CATTTACATG   3420
CCAACCCTCA GCACTGGATA CATTATTATA ATCTATGTGA AATTGAGCAA TTCCAGAACC   3480
AGGATAGTAG GAGCCCTTCT CCACAGTAAC CAGGCAATGC TTATTTTGTT TTTCTTGAAT   3540
AATTTCCTTT ATTCCAGAAG CTCCTTGCTT CATCAAATTC CAGCTTCGTA TACATCCATC   3600
TAGACGAGGG TTAATCGGTT TAATGAGTTC ACTTTCCACT TTCCGAGGGA ATCCTGCAAA   3660
GTATACTTTG GTTTCCAGCA ATCCATTTTC CGGCTTAAAA AGGGGTCCAG GTTTATTTAT   3720
ATCCATCACA GCTTCTTTAG CTATTTTAAT GCTAATACTA TGTTCTAATT CTTCCACAGA   3780
CACCATATTC CATAGACCAT TATTAATAAC ATCACCTCCA GTTGTGATTT TGGATGTATG   3840
TTCATTCTTA AGCTGAACTT CAATCTTTCC ACCACGAAGT GCAATCAGGA GCCACGCTGA   3900
GTGATCGATA GATTCTGCGT ACAGTATCAC GCCTTCTGAA TCATATGTCC GGAAATCAAA   3960
TTCTGCTGAA AATCTGCTGA TTTCTGGCAA ACGAAATTTT AAATATAAAA CAACCCCTGC   4020
AAACTGCTCC GCCAAGTAAA GTAATTCATA CTTTGTGTCA AGGTTCAAGG GAAGGCACAC   4080
TGAAACAACC TCACAACTCT TCTGATCTTG GGCAAGTTTG AATCCTTTCT TCCCATCACA   4140
ATAGCAAGTG TAACCTCCAG GGTAATTGAC ACAAAGCTGA GCACACATGT TCTCAGAGCA   4200
TTCATCTATA TCTTCACAAG ACTTTGATTT GAGATTATAT CTGTAGCCTT CGGGGCATTC   4260
ACATTCAAAA TCTCCTGGGA TGTTCTTGCA CACAGCTGTG CCACAAATGC TTGGCTTCAA   4320
AGAGCATTCA TCCACATCTT TACAATCTTT CTTATTTGAA AGCATAACAA AACCATTTTT   4380
ACAGGAACAG TGGTAACTTC CAGGTGTATT ATCACAAATT TGACTGCAAC CTCCATTTAT   4440
ATTTGAGGGA TCTTTGCATT CATTTATGTC AAATTCACAC TTTTCTCCTT GCCAACCTGG   4500
TTTACAAGTG CAAGTAAAAG AAGCTTTTCC ATCTTTGCAG CTCATATATC CATCTTCATT   4560
GCATGGCAGA GGACTACACT GGTCTGGAAT GGCATTGACA CAGCTTCTTA GGTCAGGATA   4620
AGCATTAGTT GACTGACGTG CAGCAGTGAA TAACCCAGTT TGAAAAGAGC GAAGACAAAC   4680
TAAGTATTTT GGATAAAAAT AATCCGTTTC CGGGTCATTT TCAAAGACCT CCCTGGCTTC   4740
TTCTTTATTG CACAGTTCTT CGATGCATTC TCTTTCAAGA TTACCCTGTT TGGTTTCTTC   4800
```

-continued

```
AAGTAAAGAA TTTGCACGAC GCTTCCTAAC CAGGACTTGT GAAGCCTGTT GCTTTGACAA   4860

AAAGTTTGCC TCTGAGACGG GAAGCACTAG GAGGAGACAC GCCAGCAACG CCCCGCAGCG   4920

CCCACCCAGG ACCCCCATGG AGGCCTTATT TATATTCCAA AAAAAAAAAA TAAAATTTCA   4980

ATTTTTAGAT CCCCCAACTT AAGGGTACCG CCTCGACATC TATATACTAT ATAGTAATAC   5040

CAATACTCAA GACTACGAAA CTGATACAAT CTCTTATCAT GTGGGTAATG TTCTCGATGT   5100

CGAATAGCCA TATGCCGGTA GTTGCGATAT ACATAAACTG ATCACTAATT CCAAACCCAC   5160

CCGCTTTTTA TAGTAAGTTT TTCACCCATA AATAATAAAT ACAATAATTA ATTTCTCGTA   5220

AAAGTAGAAA ATATATTCTA ATTTATTGCA CGGTAAGGAA GTAGAATCAT AAAGAACAGT   5280

GACGGATGAT CCCCAAGCTT GGACACAAGA CAGGCTTGCG AGATATGTTT GAGAATACCA   5340

CTTTATCCCG CGTCAGGGAG AGGCAGTGCG TAAAAAGACG CGGACTCATG TGAAATACTG   5400

GTTTTTAGTG CGCCAGATCT CTATAATCTC GCGCAACCTA TTTTCCCCTC GAACACTTTT   5460

TAAGCCGTAG ATAAACAGGC TGGGACACTT CACATGAGCG AAAAATACAT CGTCACCTGG   5520

GACATGTTGC AGATCCATGC ACGTAAACTC GCAAGCCGAC TGATGCCTTC TGAACAATGG   5580

AAAGGCATTA TTGCCGTAAG CCGTGGCGGT CTGGTACCGG GTGCGTTACT GGCGCGTGAA   5640

CTGGGTATTC GTCATGTCGA TACCGTTTGT ATTTCCAGCT ACGATCACGA CAACCAGCGC   5700

GAGCTTAAAG TGCTGAAACG CGCAGAAGGC GATGGCGAAG GCTTCATCGT TATTGATGAC   5760

CTGGTGGATA CCGGTGGTAC TGCGGTTGCG ATTCGTGAAA TGTATCCAAA AGCGCACTTT   5820

GTCACCATCT TCGCAAAACC GGCTGGTCGT CCGCTGGTTG ATGACTATGT TGTTGATATC   5880

CCGCAAGATA CCTGGATTGA ACAGCCGTGG GATATGGGCG TCGTATTCGT CCCGCCAATC   5940

TCCGGTCGCT AATCTTTTCA ACGCCTGGCA CTGCCGGGCG TTGTTCTTTT TAACTTCAGG   6000

CGGGTTACAA TAGTTTCCAG TAAGTATTCT GGAGGCTGCA TCCATGACAC AGGCAAACCT   6060

GAGCGAAACC CTGTTCAAAC CCCGCTTTGG GCTGCAGGAA TTCGATATCA AGCTTATCGA   6120

TACCGTCGCG GCCGCGACCT CGAGGGGGGG CCCGGTACCC AATTCGCCCT ATAGTGAGTC   6180

GTATTACGCG CGCTCACTGG CCGTCGTTTT ACAACGTCGT GACTGGGAAA ACCCTGGCGT   6240

TACCCAACTT AATCGCCTTG CAGCACATCC CCCTTTCGCC AGCTGGCGTA ATAGCGAAGA   6300

GGCCCGCACC GATCGCCCTT CCCAACAGTT GCGCAGCCTG AATGGCGAAT GGAAATTGTA   6360

AGCGTTAATA TTTTGTTAAA ATTCGCGTTA AATTTTTGTT AAATCAGCTC ATTTTTTAAC   6420

CAATAGGCCG AAATCGGCAA AATCCCTTAT AAATCAAAAG AATAGACCGA GATAGGGTTG   6480

AGTGTTGTTC CAGTTTGGAA CAAGAGTCCA CTATTAAAGA ACGTGGACTC CAACGTCAAA   6540

GGGCGAAAAA CCGTCTATCA GGGCGATGGC CCACTACGTG AACCATCACC CTAATCAAGT   6600

TTTTTGGGGT CGAGGTGCCG TAAAGCACTA AATCGGAACC CTAAAGGGAG CCCCCGATTT   6660

AGAGCTTGAC GGGGAAAGCC GGCGAACGTG GCGAGAAAGG AAGGGAAGAA AGCGAAAGGA   6720

GCGGGCGCTA GGGCGCTGGC AAGTGTAGCG GTCACGCTGC GCGTAACCAC CACACCCGCC   6780

GCGCTTAATG CGCCGCTACA GGGCGCGTCA G                                  6811
```

(2) INFORMATION FOR SEQ ID NO:68:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: Other nucleic acid;

(A) DESCRIPTION: Synthetic DNA oligonucleotide (vii) IMMEDIATE SOURCE:
(B) CLONE: oProtS1

(xi) SEQUENCE DESCRIPTION: SEQ ID NO:68:

```
ACCCAGGACC GCCATGGCGA AGCGCGC                                27
```

(2) INFORMATION FOR SEQ ID NO:69:

(i) SEQUENCE CHARACTERISTICS:
(A) LENGTH: 6926 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: pP2-gp160MN (xi) SEQUENCE DESCRIPTION: SEQ ID NO:69:

```
GTGGCACTTT TCGGGGAAAT GTGCGCGGAA CCCCTATTTG TTTATTTTTC TAAATACATT     60
CAAATATGTA TCCGCTCATG AGACAATAAC CCTGATAAAT GCTTCAATAA TATTGAAAAA    120
GGAAGAGTAT GAGTATTCAA CATTTCCGTG TCGCCCTTAT TCCCTTTTTT GCGGCATTTT    180
GCCTTCCTGT TTTTGCTCAC CCAGAAACGC TGGTGAAAGT AAAAGATGCT GAAGATCAGT    240
TGGGTGCACG AGTGGGTTAC ATCGAACTGG ATCTCAACAG CGGTAAGATC CTTGAGAGTT    300
TTCGCCCCGA AGAACGTTTT CCAATGATGA GCACTTTTAA AGTTCTGCTA TGTGGCGCGG    360
TATTATCCCG TATTGACGCC GGGCAAGAGC AACTCGGTCG CCGCATACAC TATTCTCAGA    420
ATGACTTGGT TGAGTACTCA CCAGTCACAG AAAAGCATCT TACGGATGGC ATGACAGTAA    480
GAGAATTATG CAGTGCTGCC ATAACCATGA GTGATAACAC TGCGGCCAAC TTACTTCTGA    540
CAACGATCGG AGGACCGAAG GAGCTAACCG CTTTTTTGCA CAACATGGGG GATCATGTAA    600
CTCGCCTTGA TCGTTGGGAA CCGGAGCTGA ATGAAGCCAT ACCAAACGAC GAGCGTGACA    660
CCACGATGCC TGTAGCAATG GCAACAACGT TGCGCAAACT ATTAACTGGC GAACTACTTA    720
CTCTAGCTTC CCGGCAACAA TTAATAGACT GGATGGAGGC GGATAAAGTT GCAGGACCAC    780
TTCTGCGCTC GGCCCTTCCG GCTGGCTGGT TTATTGCTGA TAAATCTGGA GCCGGTGAGC    840
GTGGGTCTCG CGGTATCATT GCAGCACTGG GGCCAGATGG TAAGCCCTCC CGTATCGTAG    900
TTATCTACAC GACGGGGAGT CAGGCAACTA TGGATGAACG AAATAGACAG ATCGCTGAGA    960
TAGGTGCCTC ACTGATTAAG CATTGGTAAC TGTCAGACCA AGTTTACTCA TATATACTTT   1020
AGATTGATTT AAAACTTCAT TTTTAATTTA AAAGGATCTA GGTGAAGATC CTTTTTGATA   1080
ATCTCATGAC CAAAATCCCT TAACGTGAGT TTTCGTTCCA CTGAGCGTCA GACCCCGTAG   1140
AAAAGATCAA AGGATCTTCT TGAGATCCTT TTTTTCTGCG CGTAATCTGC TGCTTGCAAA   1200
CAAAAAAACC ACCGCTACCA GCGGTGGTTT GTTTGCCGGA TCAAGAGCTA CCAACTCTTT   1260
TTCCGAAGGT AACTGGCTTC AGCAGAGCGC AGATACCAAA TACTGTCCTT CTAGTGTAGC   1320
CGTAGTTAGG CCACCACTTC AAGAACTCTG TAGCACCGCC TACATACCTC GCTCTGCTAA   1380
TCCTGTTACC AGTGGCTGCT GCCAGTGGCG ATAAGTCGTG TCTTACCGGG TTGGACTCAA   1440
GACGATAGTT ACCGGATAAG GCGCAGCGGT CGGGCTGAAC GGGGGGTTCG TGCACACAGC   1500
CCAGCTTGGA GCGAACGACC TACACCGAAC TGAGATACCT ACAGCGTGAG CTATGAGAAA   1560
GCGCCACGCT TCCCGAAGGG AGAAAGGCGG ACAGGTATCC GGTAAGCGGC AGGGTCGGAA   1620
```

-continued

```
CAGGAGAGCG CACGAGGGAG CTTCCAGGGG GAAACGCCTG GTATCTTTAT AGTCCTGTCG   1680
GGTTTCGCCA CCTCTGACTT GAGCGTCGAT TTTTGTGATG CTCGTCAGGG GGGCGGAGCC   1740
TATGGAAAAA CGCCAGCAAC GCGGCCTTTT TACGGTTCCT GGCCTTTTGC TGGCCTTTTG   1800
CTCACATGTT CTTTCCTGCG TTATCCCCTG ATTCTGTGGA TAACCGTATT ACCGCCTTTG   1860
AGTGAGCTGA TACCGCTCGC CGCAGCCGAA CGACCGAGCG CAGCGAGTCA GTGAGCGAGG   1920
AAGCGGAAGA GCGCCCAATA CGCAAACCGC CTCTCCCCGC GCGTTGGCCG ATTCATTAAT   1980
GCAGCTGGCA CGACAGGTTT CCCGACTGGA AAGCGGGCAG TGAGCGCAAC GCAATTAATG   2040
TGAGTTAGCT CACTCATTAG GCACCCCAGG CTTTACACTT TATGCTTCCG GCTCGTATGT   2100
TGTGTGGAAT TGTGAGCGGA TAACAATTTC ACACAGGAAA CAGCTATGAC CATGATTACG   2160
CCAAGCGCGC AATTAACCCT CACTAAAGGG AACAAAAGCT GGAGCTCCAC CGCGGTGGCG   2220
GCCGCTCTAG CCCGGGCTAG AACTAGTGGA TCCCCCAAAG CGGGGTTTGA ACAGGGTTTC   2280
GCTCAGGTTT GCCTGTGTCA TGGATGCAGC CTCCAGAATA CTTACTGGAA ACTATTGTAA   2340
CCCGCCTGAA GTTAAAAAGA ACAACGCCCG GCAGTGCCAG GCGTTGAAAA GATTAGCGAC   2400
CGGAGATTGG CGGGACGAAT ACGACGCCCA TATCCCACGG CTGTTCAATC CAGGTATCTT   2460
GCGGGATATC AACAACATAG TCATCAACCA GCGGACGACC AGCCGGTTTT GCGAAGATGG   2520
TGACAAAGTG CGCTTTTGGA TACATTTCAC GAATCGCAAC CGCAGTACCA CCGGTATCCA   2580
CCAGGTCATC AATAACGATG AAGCCTTCGC CATCGCCTTC TGCGCGTTTC AGCACTTTAA   2640
GCTCGCGCTG GTTGTCGTGA TCGTAGCTGG AAATACAAAC GGTATCGACA TGACGAATAC   2700
CCAGTTCACG CGCCAGTAAC GCACCCGGTA CCAGACCGCC ACGGCTTACG GCAATAATGC   2760
CTTTCCATTG TTCAGAAGGC ATCAGTCGGC TTGCGAGTTT ACGTGCATGG ATCTGCAACA   2820
TGTCCCAGGT GACGATGTAT TTTTCGCTCA TGTGAAGTGT CCCAGCCTGT TTATCTACGG   2880
CTTAAAAAGT GTTCGAGGGG AAAATAGGTT GCGCGAGATT ATAGAGATCT GGCGCACTAA   2940
AAACCAGTAT TTCACATGAG TCCGCGTCTT TTTACGCACT GCCTCTCCCT GACGCGGGAT   3000
AAAGTGGTAT TCTCAAACAT ATCTCGCAAG CCTGTCTTGT GTCCAAGCTT GGGGATCATC   3060
CGTCACTGTT CTTTATGATT CTACTTCCTT ACCGTGCAAT AAATTAGAAT ATATTTTCTA   3120
CTTTTACGAG AAATTAATTA TTGTATTTAT TATTTATGGG TGAAAAACTT ACTATAAAAA   3180
GCGGGTGGGT TTGGAATTAG TGATCAGTTT ATGTATATCG CAACTACCGG CATATGGCTA   3240
TTCGACATCG AGAACATTAC CCACATGATA AGAGATTGTA TCAGTTTCGT AGTCTTGAGT   3300
ATTGGTATTA CTATATAGTA TATAGATGTC GAGGCGGTAC CCTTAAGTTG GGCTGCAGTT   3360
GTTAGAGCTT GGTATAGCGG ACAACTAAGT AATTGTAAAG AAGAAAACGA AACTATCAAA   3420
ACCGTTTATG AAATGATAGA AAAAAGAATA TAAATAATCC TGTATTTTAG TTTAAGTAAC   3480
AGTAAAATAA TGAGTAGAAA ATACTATTTT TTATAGCCTA TAAATCGTTC CTCATGAGAG   3540
TGAAGGGGAT CAGGAGGAAT TATCAGCACT GGTGGGGATG GGGCACGATG CTCCTTGGGT   3600
TATTAATGAT CTGTAGTGCT ACAGAAAAAT TGTGGGTCAC AGTCTATTAT GGGGTACCTG   3660
TGTGGAAAGA AGCAACCACC ACTCTATTTT GTGCATCAGA TGCTAAAGCA TATGATACAG   3720
AGGTACATAA TGTTTGGGCC ACACAAGCCT GTGTACCCAC AGACCCCAAC CCACAAGAAG   3780
TAGAATTGGT AAATGTGACA GAAAATTTTA ACATGTGGAA AAATAACATG GTAGAACAGA   3840
TGCATGAGGA TATAATCAGT TTATGGGATC AAAGCCTAAA GCCATGTGTA AAATTAACCC   3900
CACTCTGTGT TACTTTAAAT TGCACTGATT TGAGGAATAC TACTAATACC AATAATAGTA   3960
```

-continued

```
CTGCTAATAA CAATAGTAAT AGCGAGGGAA CAATAAAGGG AGGAGAAATG AAAAACTGCT   4020

CTTTCAATAT CACCACAAGC ATAAGAGATA AGATGCAGAA AGAATATGCA CTTCTTTATA   4080

AACTTGATAT AGTATCAATA GATAATGATA GTACCAGCTA TAGGTTGATA AGTTGTAATA   4140

CCTCAGTCAT TACACAAGCT TGTCCAAAGA TATCCTTTGA GCCAATTCCC ATACACTATT   4200

GTGCCCCGGC TGGTTTTGCG ATTCTAAAAT GTAACGATAA AAAGTTCAGT GGAAAAGGAT   4260

CATGTAAAAA TGTCAGCACA GTACAATGTA CACATGGAAT TAGGCCAGTA GTATCAACTC   4320

AACTGCTGTT AAATGGCAGT CTAGCAGAAG AAGAGGTAGT AATTAGATCT GAGAATTTCA   4380

CTGATAATGC TAAAACCATC ATAGTACATC TGAATGAATC TGTACAAATT AATTGTACAA   4440

GACCCAACTA CAATAAAAGA AAAAGGATAC ATATAGGACC AGGGAGAGCA TTTTATACAA   4500

CAAAAAATAT AATAGGAACT ATAAGACAAG CACATTGTAA CATTAGTAGA GCAAAATGGA   4560

ATGACACTTT AAGACAGATA GTTAGCAAAT TAAAAGAACA ATTTAAGAAT AAAACAATAG   4620

TCTTTAATCA ATCCTCAGGA GGGGACCCAG AAATTGTAAT GCACAGTTTT AATTGTGGAG   4680

GGGAATTTTT CTACTGTAAT ACATCACCAC TGTTTAATAG TACTTGGAAT GGTAATAATA   4740

CTTGGAATAA TACTACAGGG TCAAATAACA ATATCACACT TCAATGCAAA ATAAAACAAA   4800

TTATAAACAT GTGGCAGGAA GTAGGAAAAG CAATGTATGC CCCTCCCATT GAAGGACAAA   4860

TTAGATGTTC ATCAAATATT ACAGGGCTAC TATTAACAAG AGATGGTGGT AAGGACACGG   4920

ACACGAACGA CACCGAGATC TTCAGACCTG GAGGAGGAGA TATGAGGGAC AATTGGAGAA   4980

GTGAATTATA TAAATATAAA GTAGTAACAA TTGAACCATT AGGAGTAGCA CCCACCAAGG   5040

CAAAGAGAAG AGTGGTGCAG AGAGAAAAAA GAGCAGCGAT AGGAGCTCTG TTCCTTGGGT   5100

TCTTAGGAGC AGCAGGAAGC ACTATGGGCG CAGCGTCAGT GACGCTGACG GTACAGGCCA   5160

GACTATTATT GTCTGGTATA GTGCAACAGC AGAACAATTT GCTGAGGGCC ATTGAGGCGC   5220

AACAGCATAT GTTGCAACTC ACAGTCTGGG GCATCAAGCA GCTCCAGGCA AGAGTCCTGG   5280

CTGTGGAAAG ATACCTAAAG GATCAACAGC TCCTGGGGTT TTGGGGTTGC TCTGGAAAAC   5340

TCATTTGCAC CACTACTGTG CCTTGGAATG CTAGTTGGAG TAATAAATCT CTGGATGATA   5400

TTTGGAATAA CATGACCTGG ATGCAGTGGG AAAGAGAAAT TGACAATTAC ACAAGCTTAA   5460

TATACTCATT ACTAGAAAAA TCGCAAACCC AACAAGAAAA GAATGAACAA GAATTATTGG   5520

AATTGGATAA ATGGGCAAGT TTGTGGAATT GGTTTGACAT AACAAATTGG CTGTGGTATA   5580

TAAAAATATT CATAATGATA GTAGGAGGCT TGGTAGGTTT AAGAATAGTT TTTGCTGTAC   5640

TTTCTATAGT GAATAGAGTT AGGCAGGGAT ACTCACCATT GTCGTTGCAG ACCCGCCCCC   5700

CAGTTCCGAG GGGACCCGAC AGGCCCGAAG GAATCGAAGA AGAAGGTGGA GAGAGAGACA   5760

GAGACACATC CGGTCGATTA GTGCATGGAT TCTTAGCAAT TATCTGGGTC GACCTGCGGA   5820

GCCTGTTCCT CTTCAGCTAC CACCACAGAG ACTTACTCTT GATTGCAGCG AGGATTGTGG   5880

AACTTCTGGG ACGCAGGGGG TGGGAAGTCC TCAAATATTG GTGGAATCTC CTACAGTATT   5940

GGAGTCAGGA ACTAAAGAGT AGTGCTGTTA GCTTGCTTAA TGCCACAGCT ATAGCAGTAG   6000

CTGAGGGGAC AGATAGGGTT ATAGAAGTAC TGCAAAGAGC TGGTAGAGCT ATTCTCCACA   6060

TACCTACAAG AATAAGACAG GGCTTGGAAA GGGCTTTGCT ATAAGATGGG TGGCAAATGG   6120

TCAAAACGTG TGACTGGATG GCCTACTGTA AGGGAAAGAA TGAGACGAGC TGAACCAGAA   6180

CGAATTCCAT GGCCCGGGAA GGCCTCGGAC CGGGCCCGGC CATATAGGCC AGCGATACCG   6240

TCGCGGCCGC GACCTCGAGG GGGGGCCCGG TACCCAATTC GCCCTATAGT GAGTCGTATT   6300

ACGCGCGCTC ACTGGCCGTC GTTTTACAAC GTCGTGACTG GAAAACCCT GGCGTTACCC    6360
```

-continued

```
AACTTAATCG CCTTGCAGCA CATCCCCCTT TCGCCAGCTG GCGTAATAGC GAAGAGGCCC   6420

GCACCGATCG CCCTTCCCAA CAGTTGCGCA GCCTGAATGG CGAATGGAAA TTGTAAGCGT   6480

TAATATTTTG TTAAAATTCG CGTTAAATTT TTGTTAAATC AGCTCATTTT TTAACCAATA   6540

GGCCGAAATC GGCAAAATCC CTTATAAATC AAAAGAATAG ACCGAGATAG GGTTGAGTGT   6600

TGTTCCAGTT TGGAACAAGA GTCCACTATT AAAGAACGTG GACTCCAACG TCAAAGGGCG   6660

AAAAACCGTC TATCAGGGCG ATGGCCCACT ACGTGAACCA TCACCCTAAT CAAGTTTTTT   6720

GGGGTCGAGG TGCCGTAAAG CACTAAATCG GAACCCTAAA GGGAGCCCCC GATTTAGAGC   6780

TTGACGGGGA AAGCCGGCGA ACGTGGCGAG AAAGGAAGGG AAGAAAGCGA AAGGAGCGGG   6840

CGCTAGGGCG CTGGCAAGTG TAGCGGTCAC GCTGCGCGTA ACCACCACAC CCGCCGCGCT   6900

TAATGCGCCG CTACAGGGCG CGTCAG                                        6926
```

(2) INFORMATION FOR SEQ ID NO:70:

(i) SEQUENCE CHARACTERISTICS:
(A) LENGTH: 49 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: selP promoter (xi) SEQUENCE DESCRIPTION: SEQ ID NO:70:

```
TATGAGATCT AAAAATTGAA ATTTTATTTT TTTTTTTTGG AATATAAAT                 49
```

(2) INFORMATION FOR SEQ ID NO:71:

(i) SEQUENCE CHARACTERISTICS:
(A) LENGTH: 34 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: oFIX.1

(xi) SEQUENCE DESCRIPTION: SEQ ID NO:71:

```
TCATGTTCAC GCGCTCCATG GCCGCGGCCG CACC                                 34
```

(2) INFORMATION FOR SEQ ID NO:72:

(i) SEQUENCE CHARACTERISTICS:
(A) LENGTH: 5532 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: pN2gpta-FIX (xi) SEQUENCE DESCRIPTION: SEQ ID NO:72:

```
GTGGCACTTT TCGGGGAAAT GTGCGCGGAA CCCCTATTTG TTTATTTTTC TAAATACATT     60

CAAATATGTA TCCGCTCATG AGACAATAAC CCTGATAAAT GCTTCAATAA TATTGAAAAA    120
```

-continued

```
GGAAGAGTAT GAGTATTCAA CATTTCCGTG TCGCCCTTAT TCCCTTTTTT GCGGCATTTT    180
GCCTTCCTGT TTTTGCTCAC CCAGAAACGC TGGTGAAAGT AAAAGATGCT GAAGATCAGT    240
TGGGTGCACG AGTGGGTTAC ATCGAACTGG ATCTCAACAG CGGTAAGATC CTTGAGAGTT    300
TTCGCCCCGA AGAACGTTTT CCAATGATGA GCACTTTTAA AGTTCTGCTA TGTGGCGCGG    360
TATTATCCCG TATTGACGCC GGGCAAGAGC AACTCGGTCG CCGCATACAC TATTCTCAGA    420
ATGACTTGGT TGAGTACTCA CCAGTCACAG AAAAGCATCT TACGGATGGC ATGACAGTAA    480
GAGAATTATG CAGTGCTGCC ATAACCATGA GTGATAACAC TGCGGCCAAC TTACTTCTGA    540
CAACGATCGG AGGACCGAAG GAGCTAACCG CTTTTTTGCA CAACATGGGG GATCATGTAA    600
CTCGCCTTGA TCGTTGGGAA CCGGAGCTGA ATGAAGCCAT ACCAAACGAC GAGCGTGACA    660
CCACGATGCC TGTAGCAATG GCAACAACGT TGCGCAAACT ATTAACTGGC GAACTACTTA    720
CTCTAGCTTC CCGGCAACAA TTAATAGACT GGATGGAGGC GGATAAAGTT GCAGGACCAC    780
TTCTGCGCTC GGCCCTTCCG GCTGGCTGGT TTATTGCTGA TAAATCTGGA GCCGGTGAGC    840
GTGGGTCTCG CGGTATCATT GCAGCACTGG GGCCAGATGG TAAGCCCTCC CGTATCGTAG    900
TTATCTACAC GACGGGGAGT CAGGCAACTA TGGATGAACG AAATAGACAG ATCGCTGAGA    960
TAGGTGCCTC ACTGATTAAG CATTGGTAAC TGTCAGACCA AGTTTACTCA TATATACTTT   1020
AGATTGATTT AAAACTTCAT TTTTAATTTA AAAGGATCTA GGTGAAGATC CTTTTTGATA   1080
ATCTCATGAC CAAAATCCCT TAACGTGAGT TTTCGTTCCA CTGAGCGTCA GACCCCGTAG   1140
AAAAGATCAA AGGATCTTCT TGAGATCCTT TTTTTCTGCG CGTAATCTGC TGCTTGCAAA   1200
CAAAAAAACC ACCGCTACCA GCGGTGGTTT GTTTGCCGGA TCAAGAGCTA CCAACTCTTT   1260
TTCCGAAGGT AACTGGCTTC AGCAGAGCGC AGATACCAAA TACTGTCCTT CTAGTGTAGC   1320
CGTAGTTAGG CCACCACTTC AAGAACTCTG TAGCACCGCC TACATACCTC GCTCTGCTAA   1380
TCCTGTTACC AGTGGCTGCT GCCAGTGGCG ATAAGTCGTG TCTTACCGGG TTGGACTCAA   1440
GACGATAGTT ACCGGATAAG GCGCAGCGGT CGGGCTGAAC GGGGGGTTCG TGCACACAGC   1500
CCAGCTTGGA GCGAACGACC TACACCGAAC TGAGATACCT ACAGCGTGAG CTATGAGAAA   1560
GCGCCACGCT TCCCGAAGGG AGAAAGGCGG ACAGGTATCC GGTAAGCGGC AGGGTCGGAA   1620
CAGGAGAGCG CACGAGGGAG CTTCCAGGGG GAAACGCCTG GTATCTTTAT AGTCCTGTCG   1680
GGTTTCGCCA CCTCTGACTT GAGCGTCGAT TTTTGTGATG CTCGTCAGGG GGGCGGAGCC   1740
TATGGAAAAA CGCCAGCAAC GCGGCCTTTT TACGGTTCCT GGCCTTTTGC TGGCCTTTTG   1800
CTCACATGTT CTTTCCTGCG TTATCCCCTG ATTCTGTGGA TAACCGTATT ACCGCCTTTG   1860
AGTGAGCTGA TACCGCTCGC CGCAGCCGAA CGACCGAGCG CAGCGAGTCA GTGAGCGAGG   1920
AAGCGGAAGA GCGCCCAATA CGCAAACCGC CTCTCCCCGC GCGTTGGCCG ATTCATTAAT   1980
GCAGCTGGCA CGACAGGTTT CCCGACTGGA AAGCGGGCAG TGAGCGCAAC GCAATTAATG   2040
TGAGTTAGCT CACTCATTAG GCACCCCAGG CTTTACACTT TATGCTTCCG GCTCGTATGT   2100
TGTGTGGAAT TGTGAGCGGA TAACAATTTC ACACAGGAAA CAGCTATGAC CATGATTACG   2160
CCAAGCGCGC AATTAACCCT CACTAAAGGG AACAAAAGCT GGAGCTCCAC CGCGGTGGCG   2220
GCCGCTTGTT AATTTTCAAT TCCAATGAAT TAACCTTGGA AATCCATCTT TCATTAAGTG   2280
AGCTTTGTTT TTTCCTTAAT CCAGTTGACA TACCGGGATA CCTTGGTATA TATTCCATAT   2340
TTGCCTTTCA TTGCACACTC TTCACCCCAG CTAATAATTC CAGTTAAGAA ACTGGTCCCT   2400
TCCACTTCAG TAACATGGGG TCCCCCACTA TCTCCTTGAC ATGAATCTCT ACCTCCTTCA   2460
```

-continued

```
TGGAAGCCAG CACAGAACAT GTTGTTATAG ATGGTGAACT TTGTAGATCG AAGACATGTG   2520
GCTCGGTCAA CAAGTGGAAC TCTAAGGTAC TGAAGAACTA AAGCTGATCT CCCTTTGTGG   2580
AAGACTCTTC CCCAGCCACT TACATAGCCA GATCCAAATT TGAGGAAGAT GTTCGTGTAT   2640
TCCTTGTCAG CAATGCAAAT AGGTGTAACG TAGCTGTTTA GCACTAAGGG TTCGTCCAGT   2700
TCCAGAAGGG CAATGTCATG GTTGTACTTA TTAATAGCTG CATTGTAGTT GTGGTGAGGA   2760
ATAATTCGAA TCACATTTCG CTTTTGCTCT GTATGTTCTG TCTCCTCAAT ATTATGTTCA   2820
CCTGCGACAA CTGTAATTTT AACACCAGTT TCAACACAGT GGGCAGCAGT TACAATCCAT   2880
TTTTCATTAA CGATAGAGCC TCCACAGAAT GCATCAACTT TACCATTCAA AACAACCTGC   2940
CAAGGGAATT GACCTGGTTT GGCATCTTCT CCACCAACAA CCCGAGTGAA GTCATTAAAT   3000
GATTGGGTGC TTTGAGTGAT GTTATCCAAA ATGGTTTCAG CTTCAGTAGA ATTTACATAG   3060
TCCACATCAG GAAAAACAGT CTCAGCACGG GTGAGCTTAG AAGTTTGTGA AACAGAAACT   3120
CTTCCACATG GAAATGGCAC TGCTGGTTCA CAGGACTTCT GGTTTTCTGC AAGTCGATAT   3180
CCCTCAGTAC AGGAGCAAAC CACCTTGTTA TCAGCACTAT TTTTACAAAA CTGCTCGCAT   3240
CTGCCATTCT TAATGTTACA TGTTACATCT AATTCACAGT TCTTTCCTTC AAATCCAAAG   3300
GGACACCAAC ATTCATAGGA ATTAATGTCA TCCTTGCAAC TGCCGCCATT TAAACATGGA   3360
TTGGACTCAC ACTGATCTCC ATCAACATAC TGCTTCCAAA ATTCAGTTGT TCTTTCAGTG   3420
TTTTCAAAAA CTTCTCGTGC TTCTTCAAAA CTACACTTTT CTTCCATACA TTCTCTCTCA   3480
AGGTTCCCTT GAACAAACTC TTCCAATTTA CCTGAATTAT ACCTCTTTGG CCGATTCAGA   3540
ATTTTGTTGG CGTTTTCATG ATCAAGAAAA ACTGTACATT CAGCACTGAG TAGATATCCT   3600
AAAAGGCAGA TGGTGATGAG GCCTGGTGAT TCTGCCATGA TCATGTTCAC GCGCTCCATG   3660
GAGGCCTTAT TTATATTCCA AAAAAAAAAA ATAAAATTTC AATTTTTAGA TCCCCCAACT   3720
TAAGGGTACC GCCTCGACAT CTATATACTA TATAGTAATA CCAATACTCA AGACTACGAA   3780
ACTGATACAA TCTCTTATCA TGTGGGTAAT GTTCTCGATG TCGAATAGCC ATATGCCGGT   3840
AGTTGCGATA TACATAAACT GATCACTAAT TCCAAACCCA CCCGCTTTTT ATAGTAAGTT   3900
TTTCACCCAT AAATAATAAA TACAATAATT AATTTCTCGT AAAAGTAGAA AATATATTCT   3960
AATTTATTGC ACGGTAAGGA AGTAGAATCA TAAAGAACAG TGACGGATGA TCCCCAAGCT   4020
TGGACACAAG ACAGGCTTGC GAGATATGTT TGAGAATACC ACTTTATCCC GCGTCAGGGA   4080
GAGGCAGTGC GTAAAAAGAC GCGGACTCAT GTGAAATACT GGTTTTTAGT GCGCCAGATC   4140
TCTATAATCT CGCGCAACCT ATTTTCCCCT CGAACACTTT TTAAGCCGTA GATAAACAGG   4200
CTGGGACACT TCACATGAGC GAAAAATACA TCGTCACCTG GGACATGTTG CAGATCCATG   4260
CACGTAAACT CGCAAGCCGA CTGATGCCTT CTGAACAATG GAAAGGCATT ATTGCCGTAA   4320
GCCGTGGCGG TCTGGTACCG GGTGCGTTAC TGGCGCGTGA ACTGGGTATT CGTCATGTCG   4380
ATACCGTTTG TATTTCCAGC TACGATCACG ACAACCAGCG CGAGCTTAAA GTGCTGAAAC   4440
GCGCAGAAGG CGATGGCGAA GGCTTCATCG TTATTGATGA CCTGGTGGAT ACCGGTGGTA   4500
CTGCGGTTGC GATTCGTGAA ATGTATCCAA AAGCGCACTT TGTCACCATC TTCGCAAAAC   4560
CGGCTGGTCG TCCGCTGGTT GATGACTATG TTGTTGATAT CCCGCAAGAT ACCTGGATTG   4620
AACAGCCGTG GGATATGGGC GTCGTATTCG TCCCGCCAAT CTCCGGTCGC TAATCTTTTC   4680
AACGCCTGGC ACTGCCGGGC GTTGTTCTTT TTAACTTCAG GCGGGTTACA ATAGTTTCCA   4740
GTAAGTATTC TGGAGGCTGC ATCCATGACA CAGGCAAACC TGAGCGAAAC CCTGTTCAAA   4800
CCCCGCTTTG GGCTGCAGGA ATTCGATATC AAGCTTATCG ATACCGTCGC GGCCGCGACC   4860
```

```
TCGAGGGGGG GCCCGGTACC CAATTCGCCC TATAGTGAGT CGTATTACGC GCGCTCACTG   4920

GCCGTCGTTT TACAACGTCG TGACTGGGAA AACCCTGGCG TTACCCAACT TAATCGCCTT   4980

GCAGCACATC CCCCTTTCGC CAGCTGGCGT AATAGCGAAG AGGCCCGCAC CGATCGCCCT   5040

TCCCAACAGT TGCGCAGCCT GAATGGCGAA TGGAAATTGT AAGCGTTAAT ATTTTGTTAA   5100

AATTCGCGTT AAATTTTTGT TAAATCAGCT CATTTTTTAA CCAATAGGCC GAAATCGGCA   5160

AAATCCCTTA TAAATCAAAA GAATAGACCG AGATAGGGTT GAGTGTTGTT CCAGTTTGGA   5220

ACAAGAGTCC ACTATTAAAG AACGTGGACT CCAACGTCAA AGGGCGAAAA ACCGTCTATC   5280

AGGGCGATGG CCCACTACGT GAACCATCAC CCTAATCAAG TTTTTTGGGG TCGAGGTGCC   5340

GTAAAGCACT AAATCGGAAC CCTAAAGGGA GCCCCCGATT TAGAGCTTGA CGGGGAAAGC   5400

CGGCGAACGT GGCGAGAAAG GAAGGGAAGA AAGCGAAAGG AGCGGGCGCT AGGGCGCTGG   5460

CAAGTGTAGC GGTCACGCTG CGCGTAACCA CCACACCCGC CGCGCTTAAT GCGCCGCTAC   5520

AGGGCGCGTC AG                                                       5532
```

(2) INFORMATION FOR SEQ ID NO:73:

(i) SEQUENCE CHARACTERISTICS:
(A) LENGTH: 14 base pairs
(B) TYPE: nucleic acid
(C) STRANDEDNESS: double
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: wild-type gp160MN (ix) FEATURE:
(A) NAME/KEY: CDS
(B) LOCATION: 3..14

(xi) SEQUENCE DESCRIPTION: SEQ ID NO:73:

```
CA ATG AGA GTG AAG                                                    14
   Met Arg Val Lys
     1
```

(2) INFORMATION FOR SEQ ID NO:74:

(i) SEQUENCE CHARACTERISTICS:
(A) LENGTH: 4 amino acids
(B) TYPE: amino acid
(D) TOPOLOGY: linear (ii) MOLECULE TYPE: protein (xi) SEQUENCE DESCRIPTION: SEQ ID NO:74:

```
Met Arg Val Lys
  1
```

(2) INFORMATION FOR SEQ ID NO:75:

(i) SEQUENCE CHARACTERISTICS:
(A) LENGTH: 14 base pairs
(B) TYPE: nucleic acid
(C) STRANDEDNESS: double
(D) TOPOLOGY: linear (ii) MOLECULE TYPE: Other nucleic acid;
(A) DESCRIPTION: Synthetic DNA oligonucleotide (vii) IMMEDIATE SOURCE:

-continued (B) CLONE: gp160 in vselP-gp160 virus (ix) FEATURE:
(A) NAME/KEY: CDS
(B) LOCATION: 3..14

(xi) SEQUENCE DESCRIPTION: SEQ ID NO:75:

```
CC ATG GCC GTG AAG                                                    14
   Met Ala Val Lys
     1
```

(2) INFORMATION FOR SEQ ID NO:76:

(i) SEQUENCE CHARACTERISTICS:
(A) LENGTH: 4 amino acids
(B) TYPE: amino acid
(D) TOPOLOGY: linear (ii) MOLECULE TYPE: protein (xi) SEQUENCE DESCRIPTION: SEQ ID NO:76:

```
Met Ala Val Lys
  1
```

(2) INFORMATION FOR SEQ ID NO:77:

(i) SEQUENCE CHARACTERISTICS:
(A) LENGTH: 18 base pairs
(B) TYPE: nucleic acid
(C) STRANDEDNESS: double
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: wild-type Protein S (ix) FEATURE:
(A) NAME/KEY: CDS
(B) LOCATION: 4..18

(xi) SEQUENCE DESCRIPTION: SEQ ID NO:77:

```
GAA ATG AGG GTC CTG GGT                                               18
    Met Arg Val Leu Gly
      1               5
```

(2) INFORMATION FOR SEQ ID NO:78:

(i) SEQUENCE CHARACTERISTICS:
(A) LENGTH: 5 amino acids
(B) TYPE: amino acid
(D) TOPOLOGY: linear (ii) MOLECULE TYPE: protein (xi) SEQUENCE DESCRIPTION: SEQ ID NO:78:

```
Met Arg Val Leu Gly
  1               5
```

(2) INFORMATION FOR SEQ ID NO:79:

(i) SEQUENCE CHARACTERISTICS:
(A) LENGTH: 18 base pairs
(B) TYPE: nucleic acid
(C) STRANDEDNESS: double
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: Protien S in the chimeras (ix) FEATURE:
(A) NAME/KEY: CDS
(B) LOCATION: 4..18

(xi) SEQUENCE DESCRIPTION: SEQ ID NO:79:

```
GCC ATG GCG GTC CTG GGT                                          18
    Met Ala Val Leu Gly
      1               5
```

(2) INFORMATION FOR SEQ ID NO:80:

(i) SEQUENCE CHARACTERISTICS:
(A) LENGTH: 5 amino acids
(B) TYPE: amino acid
(D) TOPOLOGY: linear (ii) MOLECULE TYPE: protein (xi) SEQUENCE DESCRIPTION: SEQ ID NO:80:

```
Met Ala Val Leu Gly
  1               5
```

(2) INFORMATION FOR SEQ ID NO:81:

(i) SEQUENCE CHARACTERISTICS:
(A) LENGTH: 17 base pairs
(B) TYPE: nucleic acid
(C) STRANDEDNESS: double
(D) TOPOLOGY: linear (ii) MOLECULE TYPE: Other nucleic acid;
(A) DESCRIPTION: Synthetic DNA oligonucleotide (vii) IMMEDIATE SOURCE:
(B) CLONE: wild-type factor IX (ix) FEATURE:
(A) NAME/KEY: CDS
(B) LOCATION: 3..17

(xi) SEQUENCE DESCRIPTION: SEQ ID NO:81:

```
TT ATG CAG CGC GTG AAC                                           17

   Met Gln Arg Val Asn
     1               5
```

(2) INFORMATION FOR SEQ ID NO:82:

(i) SEQUENCE CHARACTERISTICS:
(A) LENGTH: 5 amino acids
(B) TYPE: amino acid
(D) TOPOLOGY: linear (ii) MOLECULE TYPE: protein (xi) SEQUENCE DESCRIPTION: SEQ ID NO:82:

```
Met Gln Arg Val Asn
  1               5
```

(2) INFORMATION FOR SEQ ID NO:83:

(i) SEQUENCE CHARACTERISTICS:
(A) LENGTH: 17 base pairs
(B) TYPE: nucleic acid
(C) STRANDEDNESS: double
(D) TOPOLOGY: linear -continued

```
    (ii) MOLECULE TYPE: Other nucleic acid;
          (A) DESCRIPTION: Synthetic DNA oligonucleotide

   (vii) IMMEDIATE SOURCE:
          (B) CLONE: factor IX vFIX#5

    (ix) FEATURE:
          (A) NAME/KEY: CDS
          (B) LOCATION: 3..17

    (xi) SEQUENCE DESCRIPTION: SEQ ID NO:83:

CC ATG GAG CGC GTG AAC                                                      17
   Met Glu Arg Val Asn
     1               5


(2) INFORMATION FOR SEQ ID NO:84:

     (i) SEQUENCE CHARACTERISTICS:
          (A) LENGTH: 5 amino acids
          (B) TYPE: amino acid
          (D) TOPOLOGY: linear

    (ii) MOLECULE TYPE: protein

    (xi) SEQUENCE DESCRIPTION: SEQ ID NO:84:

Met Glu Arg Val Asn
  1               5


(2) INFORMATION FOR SEQ ID NO:85:

     (i) SEQUENCE CHARACTERISTICS:
          (A) LENGTH: 13 base pairs
          (B) TYPE: nucleic acid
          (C) STRANDEDNESS: single
          (D) TOPOLOGY: linear

    (xi) SEQUENCE DESCRIPTION: SEQ ID NO:85:

GGCCNNNNNG GCC                                                              13


(2) INFORMATION FOR SEQ ID NO:86:

     (i) SEQUENCE CHARACTERISTICS:
          (A) LENGTH: 11 base pairs
          (B) TYPE: nucleic acid
          (C) STRANDEDNESS: single
          (D) TOPOLOGY: linear

    (xi) SEQUENCE DESCRIPTION: SEQ ID NO:86:

TAATTAATTA A                                                                11


(2) INFORMATION FOR SEQ ID NO:87:

     (i) SEQUENCE CHARACTERISTICS:
          (A) LENGTH: 46 base pairs
          (B) TYPE: nucleic acid
          (C) STRANDEDNESS: single
          (D) TOPOLOGY: linear

    (xi) SEQUENCE DESCRIPTION: SEQ ID NO:87:

CTCGTAAAAA TTGAAAAACT ATTCTAATTT ATTGCACGGT ACGTAC                          46


(2) INFORMATION FOR SEQ ID NO:88:

     (i) SEQUENCE CHARACTERISTICS:
          (A) LENGTH: 174 base pairs
          (B) TYPE: nucleic acid
          (C) STRANDEDNESS: single
          (D) TOPOLOGY: linear
```

(xi) SEQUENCE DESCRIPTION: SEQ ID NO:88:

```
ATGCATTTGT TAGAGCTTGG TATAGCGGAC AACTAAGTAA TTGTAAAGAA GAAAACGAAA     60

CTATCAAAAC CGTTTATGAA ATGATAGAAA AAAGAATATA AATAATCCTG TATTTTAGTT    120

TAAGTAACAG TAAAATAATG AGTAGAAAAT ACTATTTTTT ATAGCCTATA AATC          174
```

(2) INFORMATION FOR SEQ ID NO:89:

(i) SEQUENCE CHARACTERISTICS:
(A) LENGTH: 234 base pairs
(B) TYPE: nucleic acid
(C) STRANDEDNESS: single
(D) TOPOLOGY: linear (xi) SEQUENCE DESCRIPTION: SEQ ID NO:89:

```
ATGCATTTGT TAGAGCTTGG TATAGCGGAC AACTAAGTAA TTGTAAAGAA GAAAACGAAA     60

CTATCAAAAC CGTTTATGAA ATGATAGAAA AAAGAATATA AATAATCCTG TATTTTAGTT    120

TAAGTAACAG TAAAATAATG AGTAGAAAAT ACTATTTTTT ATAGCCTATA AATCGTTCTC    180

GTAAAAATTG AAAAACTATT CTAATTTATT GCACGGTACG TACCATGGCC CGGG          234
```

(2) INFORMATION FOR SEQ ID NO:90:

(i) SEQUENCE CHARACTERISTICS:
(A) LENGTH: 45 base pairs
(B) TYPE: nucleic acid
(C) STRANDEDNESS: single
(D) TOPOLOGY: linear (xi) SEQUENCE DESCRIPTION: SEQ ID NO:90:

```
CTCGTAAAAA TTGAAAAACT ATTCTAATTT ATTGCACGGT CGCGA                     45
```

(2) INFORMATION FOR SEQ ID NO:91:

(i) SEQUENCE CHARACTERISTICS:
(A) LENGTH: 50 base pairs
(B) TYPE: nucleic acid
(C) STRANDEDNESS: single
(D) TOPOLOGY: linear (xi) SEQUENCE DESCRIPTION: SEQ ID NO:91:

```
CATGGTACGT ACCGTGCAAT AAATTAGAAT AGTTTTTCAA TTTTTACGAG                50
```

(2) INFORMATION FOR SEQ ID NO:92:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:92:

```
GCTCCCGCAG GTACCGATGC AAATGGCCAC                                      30
```

(2) INFORMATION FOR SEQ ID NO:93:

(i) SEQUENCE CHARACTERISTICS:
(A) LENGTH: 31 base pairs
(B) TYPE: nucleic acid
(C) STRANDEDNESS: single
(D) TOPOLOGY: linear (xi) SEQUENCE DESCRIPTION: SEQ ID NO:93:

```
GGGGAGAGAT CGAAAGTGAA TTTGACATAG C                                    31
```

-continued

```
(2) INFORMATION FOR SEQ ID NO:94:

     (i) SEQUENCE CHARACTERISTICS:
          (A) LENGTH: 45 base pairs
          (B) TYPE: nucleic acid
          (C) STRANDEDNESS: single
          (D) TOPOLOGY: linear

        (xi) SEQUENCE DESCRIPTION: SEQ ID NO:94:

ACCATGGGTG CGAGAGCGTC GGTATTAAGC GGGGGAGAAT TAGAT                    45


(2) INFORMATION FOR SEQ ID NO:95:

     (i) SEQUENCE CHARACTERISTICS:
          (A) LENGTH: 51 base pairs
          (B) TYPE: nucleic acid
          (C) STRANDEDNESS: single
          (D) TOPOLOGY: linear

        (xi) SEQUENCE DESCRIPTION: SEQ ID NO:95:

CGATCTAATT CTCCCCCGCT TAATACCGAC GCTCTCGCAC CCATGGTAGC T             51
```

DIRECT MOLECULAR CLONING OF FOREIGN GENES INTO POXVIRUSES AND METHODS FOR THE PREPARATION OF RECOMBINANT PROTEINS

This is a continuation-in-part of U.S. Ser. No. 07/914,738, filed on Jul. 20, 1992, now abandoned, which is a continuation-in-part of U.S. Ser. No. 07/750,080, filed Aug. 26, 1991, now U.S. Pat. No. 5,445,953.

BACKGROUND OF THE INVENTION

The present invention relates to modified genomes of eukaryotic DNA viruses which replicate in the cytoplasm of a host cell, such as poxviruses and iridoviruses. More specifically, the invention relates to direct molecular cloning of a modified cytoplasmic DNA virus genome that is produced by modifying under extracellular conditions a purified DNA molecule comprising a cytoplasmic DNA virus genome. The modified DNA molecule is then packaged into infectious virions in a cell infected with a helper cytoplasmic DNA virus. In a preferred embodiment of the present invention, a foreign DNA fragment comprising a desired gene is inserted directly into a genomic poxvirus DNA at a restriction endonuclease cleavage site that is unique in the viral genome, and the modified viral DNA is packaged into virions by transfection into cells infected with a helper poxvirus.

Cytoplasmic DNA viruses of eukaryotes include diverse poxviruses and iridoviruses found in vertebrates and insects. Poxviruses having recombinant genomes have been used for expression of a variety of inserted genes. Such poxviruses can be used to produce biologically active polypeptides in cell cultures, for instance, and to deliver vaccine antigens directly to an animal or a human immune system. Construction of recombinant iridovirus genomes for expression of foreign genes appears not to be documented in the literature pertaining to genetic engineering.

Conventional techniques for construction of recombinant poxvirus genomes comprised of foreign genes rely in part on in vivo (intracellular) recombination. The use of intracellular recombination was first described as a process of "marker rescue" with subgenomic fragments of viral DNA by Sam and Dumbell, *Ann. Virol.* (Institut Pasteur) 132E:135 (1981). These authors demonstrated that a temperature-sensitive vaccinia virus mutant could be "rescued" by intracellular recombination with a subgenomic DNA fragment of a rabbit poxvirus. The methods they used for intracellular recombination are still used today.

Construction of recombinant vaccinia viruses comprised of non-poxvirus ("foreign") genes was later described by Panicali and Paoletti, *Proc. Nat'l Acad. Sci. U.S.A.* 79:4927–4931 (1982); Mackett et al., *Proc. Nat'l Acad. Sci. U.S.A.* 79:7415–7419 (1982); and U.S. Pat. No. 4,769,330. More specifically, the extant technology for producing recombinant poxviruses involves two steps. First, a DNA fragment is prepared that has regions of homology to the poxvirus genome surrounding a foreign gene. Alternatively, an "insertion" plasmid is constructed by in vitro (extracellular) ligation of a foreign gene with a plasmid. This plasmid comprises short viral DNA sequences that are homologous to the region of the poxvirus genome where gene insertion is ultimately desired. The foreign gene is inserted into the plasmid at a site flanked by the viral DNA sequences and, typically, downstream of a poxvirus promoter that will control transcription of the inserted gene. In the second step, the insertion plasmid is introduced into host cells infected with the target poxvirus. The gene is then indirectly inserted into the poxvirus genome by intracellular recombination between homologous viral sequences in the poxvirus genome and the portion of the plasmid including the foreign gene. The resulting recombinant genome then replicates, producing infectious poxvirus.

Thus, insertion of each particular gene into a poxvirus genome has heretofore required a distinct plasmid comprised of the gene flanked viral sequences selected for a desired insertion location. A difficulty with this approach is that a new insertion plasmid is required for each recombinant poxvirus. Each plasmid must be constructed by extracellular recombinant DNA methods, amplified in a bacterial cell, and then laboriously isolated and rigorously purified before addition to a poxvirus-infected host cell.

Another problem with extant methodology in this regard is a low yield of recombinant genomes, which can necessitate screening hundreds of individual viruses to find a single desired recombinant. The poor yield is a function of the low frequency of individual intracellular recombination events, compounded by the requirement for multiple events of this sort to achieve integration of the insertion plasmid into a viral genome. As a result, the majority of viral genomes produced by intracellular recombination methods are parental genomes that lack a foreign gene. It is often necessary, therefore, to introduce a selective marker gene into a poxvirus genome, along with any other desired sequence, to permit ready detection of the required rare recombinants without the need of characterizing isolated DNA's from numerous individual virus clones.

Purified DNA's of eukaryotic cytoplasmic DNA viruses are incapable of replicating when introduced into susceptible host cells using methods that initiate infections with viral DNA's that replicate in the nucleus. This lack of infectivity of DNA's of cytoplasmic DNA viruses results from the fact that viral transcription must be initiated in infected cells by a virus-specific RNA polymerase which is normally provided inside infecting virions.

"Reactivation" of poxvirus DNA, in which genomic DNA inside an inactivated, noninfectious poxvirus particle was packaged into infectious virions by coinfection with a viable helper poxvirus, has been known for decades. See, for instance, Fenner and Woodroofe, *Virology* 11:185–201 (1960). In 1981 Sam and Dumbell demonstrated that isolated, noninfectious genomic DNA of a first poxvirus could be packaged into infectious poxvirus virions in cells infected with a second, genetically distinct poxvirus. Sam and Dumbell, *Ann. Virol.* (Institut Pasteur) 132E:135 (1981). This packaging of naked poxvirus DNA was first demonstrated by transfection of unmodified DNA comprising a first wildtype orthopoxvirus genome, isolated from virions or infected cells, into cells infected with a second naturally-occurring orthopoxvirus genome. However, heterologous packaging, packaging of DNA from one poxvirus genus (orthopox, for example) by viable virions of another genus (e.g., avipox), has not been demonstrated yet.

The use of intracellular recombination for constructing a recombinant poxvirus genome expressing non-poxvirus genes was reported shortly after Sam and Dumbell first reported intracellular packaging of naked poxvirus DNA into poxvirus virions and marker rescue with DNA fragments by intracellular recombination. See Panicali and Paoletti, 1982; Mackett et al., 1982. The relevant literature of the succeeding decade, however, appears not to document the direct molecular cloning, i.e., construction solely by extracellular genetic engineering, of a modified genome of any eukaryotic cytoplasmic DNA virus, particularly a poxvirus. The literature does not even evidence widespread recognition of any advantage possibly realized from such a direct cloning approach. To the contrary, an authoritative treatise has stated that direct molecular cloning is not practical in the context of genetic engineering of poxviruses because poxvirus DNA is not infectious. F. Fenner et al., *THE POXVIRUSES*. Academic Press, 1989). Others working in the area have likewise discounted endonucleolytic cleavage and religation of poxvirus DNA's, even while recognizing a potential for rescue by infectious virus of isolated DNA comprising a recombinant poxvirus genome. See, for example, Mackett and Smith, *J. Gen. Virol.* 67:2067–2082 (1986). Moreover, recent reviews propound the thesis that the only way feasible to construct a recombinant poxvirus genome is by methods requiring intracellular recombination. See Miner and Hruby, *TIBTECH* 8:20–25 (1990), and Moss and Flexner, *Ann. Rev. Immunol.* 5:305–324 (1987).

Vaccinia virus is a member of the Orthopox genus of the Poxvirus family with little virulence for humans. Although the exact origin of vaccinia virus is obscure, it is related to the cowpox virus used by Jenner and strains of vaccinia virus became the vaccines of choice for the prevention of smallpox. Baxby, "Vaccinia Virus," in *VACCINIA VIRUSES AS VECTORS FOR VACCINE ANTIGENS*. G. V. Quinnan, ed., Elsevier, New York, N.Y., pp. 3–8 (1985). The smallpox vaccines used in the eradication effort were prepared on large scale by inoculating the shaved abdomens of calves, sheep or water buffalo with seed stocks of vaccinia virus and harvesting the infected exudative lymph from the inoculation sites. Henderson and Arita, "Utilization of Vaccine in the Global Eradication of Smallpox," *VACCINIA VIRUSES AS VECTORS FOR VACCINE ANTIGENS*. G. V. Quinnan, ed., Elsevier, New York, N.Y., pp. 61–67 (1985). The novelty of the vaccination procedure used by Jenner caused alarm with some of his contemporaries. The ultimate eradication of smallpox following implementation of the Intensified Smallpox Eradication Program of the World Health Organization proved that skepticism to be without foundation.

Vaccinia virus has several biological properties which make it an excellent candidate for use as a live vaccine. First, it possesses a high degree of physical and genetic stability under even severe field conditions, reducing problems and expense in transport and storage. In addition, genomic stability makes the incorporation of one or more foreign genes for the antigens to be expressed more feasible than in other systems. Second, vaccinia replicates in the cytoplasm of host cells and uses its own DNA and RNA polymerase. Its effects on the host cell's physiologic functions can be minimized. Third, vaccinia virus has a wide host range, thus permitting use of a single vaccine in a large number of species. Fourth, both humoral and cellular immunity are mediated by vaccinia virus-based vaccines. And fifth, the duration of effectiveness of vaccinia immunization is relatively long. See Haber et al., *Science* 243:51 (1989). Much of the early work geared towards a vaccinia virus vector was undertaken with vaccine development in mind. Weir et al., *Proc. Nat'l Acad. Sci. USA* 79:1210–14 (1982); Mackett et al., *Proc. Nat'l Acad. Sci. USA* 79:7415–19 (1982); Smith et al., *Nature* 302:490–95 (1983); Smith et al., *Proc. Nat'l Acad. Sci. USA* 80:7155–59 (1983).

As with any vaccine, safety is a major concern with the use of vaccinia virus as a immunizing agent. The adverse reaction rate of 1 in 50,000, reported during smallpox vaccinations, was tolerated only because the disease it prevented was so devastating. Baxby (1985). Generalized vaccinia among persons without underlying illnesses is characterized by a vesicular rash of varying extent that is usually self-limited. In the event of the formation of skin lesions as a result of virus replication, there is a risk of bacterial superinfection. In addition, there is also a risk of the formation of a scar at the site of skin lesions if they occur. Several attenuated smallpox vaccine strains were developed but, due to lower potency, were not adopted for general use. Recent efforts towards genetic engineering of vaccinia virus have resulted in strains with decreased virulence. These efforts targeted the viral thymidine kinase, growth factor, hemagglutinin, 13.8 kD secreted protein and ribonucleotide reductase genes. Buller et al., *Nature* 317:813 (1985); Buller et al., *J. Virol.* 62:866 (1988); Flexner et al., *Nature* 330:259 (1987); Shida et al., *J. Virol.* 62:4474 (1988); Kotwal et al., *Virology* 171:579 (1989); Child et al., *Virology* 174:626 (1990). There also is interest in using other members of the poxvirus family, such as avipoxviruses, as limited host range vaccine vectors. Taylor et al., *Virology* 6:497 (1988). For instance, U.S. Pat. No. 5,266,313, hereby incorporated by reference, discloses and claims a raccoon poxvirus-based vaccine for rabies virus.

Recombinant vaccinia viruses have been used to express genes of nonviral pathogens such as bacteria, rickettsia and protozoa and, in some cases, have protected experimental animals from infection. Fields, *Science* 252:1662–67 (1991). In addition, vaccinia-based rabies and rinderpest vaccines have been tested. Id. The human immunodeficiency virus type 1 (HIV-1) envelope glycoprotein (env) gene has been cloned into a vaccinia vector and a phase trial was conducted with this virus. The vaccine appeared safe, and demonstrated the development of readily detectable, persistent in vivo T-cell proliferative and serum antibody responses to HIV-1 in vaccinia-naive persons. Cooney et al., *Lancet* 337:567 (1991). A neutralizing antibody response was not seen but the expression of the env gene was low compared to levels now obtainable.

SUMMARY OF THE INVENTION

It is therefore an object of the present invention to provide a method for constructing modified genomes of eukaryotic cytoplasmic DNA viruses, particularly of poxviruses, which overcomes the aforementioned limitations associated with conventional techniques based on intracellular recombination.

It is another object of the present invention to provide cytoplasmic DNA virus genome-construction techniques that produce substantially higher yields of recombinants than existing methodology.

It is a further object of this invention to provide methods for modifying a genome of a cytoplasmic DNA virus by direct modification of genomic viral DNA and intracellular packaging of the modified viral DNA into virions with the aid of helper virus functions.

It is another object of this invention to provide methods for construction of a genome of a cytoplasmic DNA virus that produce in one recombination reaction step modified genomes having a foreign DNA segment inserted in each of the two possible orientations and modified genomes having multiple insertions of a foreign DNA segment.

It is still another object of this invention to provide modified DNA molecules suitable for direct molecular cloning of foreign genes in a modified cytoplasmic DNA virus genome, comprising two portions of a genomic viral DNA produced by cleavage with a sequence-specific endonuclease at a site that is unique in the viral genome.

It is yet a further object of this invention to provide a cytoplasmic DNA virus, particularly a poxvirus, having a modified genome comprised of a foreign DNA inserted into a unique cleavage site for a sequence-specific endonuclease.

It is another object of this invention to provide plasmids which facilitate construction and transfer of gene cassettes into a cytoplasmic DNA virus, particularly a poxvirus, using direct molecular cloning.

It is yet another object of this invention to provide a cytoplasmic DNA virus, particularly a poxvirus, having a modified genome comprised of a DNA encoding at least a portion of an HIV-1 antigen. Such a virus can be used to produce recombinant HIV-1 antigens in vitro.

It is another object of this invention to provide a subunit vaccine against HIV-1 infection using recombinant HIV-1 antigens generated using a cytoplasmic DNA virus, particularly a poxvirus, having a modified genome comprised of a DNA encoding at least a portion of an HIV-1 antigen.

It is yet a further object of this invention to provide a cytoplasmic DNA virus, particularly a poxvirus, having a modified genome comprised of a DNA encoding at least a portion of an HIV-1 antigen and suitable for use as a live vaccine against HIV-1.

In accomplishing these and other objects, there has been provided, in accordance with one aspect of the present invention, a method for producing a modified eukaryotic cytoplasmic DNA virus by direct molecular cloning of a modified DNA molecule comprising a modified cytoplasmic DNA virus genome. The inventive method comprises the steps of (I) modifying under extracellular conditions a purified DNA molecule comprising a first cytoplasmic DNA virus genome to produce a modified DNA molecule comprising the modified viral genome; (II) introducing the modified DNA molecule into a first host cell which packages the modified DNA molecule into infectious virions; and (III) recovering from the first host cell infectious virions comprised of the modified viral genome.

According to one embodiment of this method, the step of modifying the DNA molecule under extracellular conditions comprises a step of cleaving the DNA molecule with a sequence-specific endonuclease. According to another embodiment, the step of modifying the DNA molecule comprises a step of inserting a first DNA sequence into the first viral genome. Advantageously, this first DNA sequence is inserted into the first genome at a cleavage site for a sequence-specific endonuclease. It should be noted that where a particular sequence-specific endonuclease, such as a bacterial restriction enzyme, is described herein by name, that name also signifies any isoschizomer of the named nuclease.

Optionally, the step of modifying the DNA molecule according to this method also comprises a step of using a phosphatase to remove a phosphate moiety from an end of a DNA segment that is produced by cleaving the DNA molecule with a sequence-specific endonuclease.

In some embodiments of this method, the first viral genome is a vaccinia virus genome and the unique site is a cleavage site for the bacterial restriction endonuclease NotI or for the bacterial restriction endonuclease SmaI. The first genome also may comprise a second DNA sequence not naturally-occurring in a eukaryotic cytoplasmic DNA virus genome where that second DNA sequence is comprised of the unique cleavage site. For instance, the first genome may be a fowlpox virus genome comprising a sequence of an *Escherichia coli* β-galactosidase gene and the unique site is a cleavage site for the bacterial restriction endonuclease NotI that is located in that gene.

In other forms of this method, the first DNA sequence is inserted into the first viral genome between a first cleavage site for a first sequence-specific endonuclease and a second cleavage site for a second sequence-specific endonuclease. Optionally, each of the first and second cleavage sites is unique in the first viral genome.

According to other embodiments of the method of this invention, at least a portion of the first DNA sequence which is inserted into the first genome is under transcriptional control of a promoter. This promoter may be located in the first DNA sequence that is inserted into the first viral genome. Alternatively, the promoter is located in the modified viral genome upstream of the first DNA sequence that is inserted into the first genome. In some cases, the promoter is utilized by an RNA polymerase encoded by the modified viral genome. This promoter may also be suitable for initiation of transcription by an RNA polymerase of the eukaryotic cytoplasmic DNA virus to be modified. In certain methods, the promoter comprises a modification of a naturally-occurring promoter of the eukaryotic cytoplasmic DNA virus.

The step of modifying the DNA molecule according to the method of this invention may comprise a step of deleting a DNA sequence from the first genome. Alternatively, this step comprises a step of substituting a DNA sequence of the first genome.

The method of modifying a first viral genome may also comprise a step of infecting the first host cell with a second eukaryotic cytoplasmic DNA virus comprising a second genome which is expressed to package the modified viral genome into infectious virions. Advantageously, the step of introducing the modified DNA molecule into the first host cell is carried out about one hour after the step of infecting the first host cell with the second eukaryotic cytoplasmic DNA virus.

In one variation of this method, the first host cell is selected such that expression of the second genome in the first host cell does not produce infectious virions comprised of the second viral genome. For instance, where the modified viral genome is a modified vaccinia virus genome and the second genome is a fowlpox virus genome, the selected first host cell is a mammalian cell.

In some forms of the method of modifying a viral genome, the step of recovering infectious virions comprised of the modified viral genome comprises a step of infecting a second host cell with infectious virions produced by the first host cell. This is done under conditions such that expression of the second genome in the second host cell does not produce infectious virions comprised of the second genome. For instance, when the modified viral genome is a modified vaccinia virus genome, the second genome may be a fowlpox virus genome, and the second host cell is a mammalian cell. Alternatively, the modified viral genome comprises a functional host range gene required to produce infectious virions in the second host cell and the second genome lacks that functional host range gene. This is illustrated by the case where the modified viral genome is a modified vaccinia virus genome comprising a functional host range gene required to produce infectious virions in a human cell and the second host cell is a human cell.

In other forms of this method, the modified viral genome comprises a selective marker gene, the second genome lacks that selective marker gene, and the step of infecting the second host cell is carried out under conditions that select for a genome expressing that selective marker gene. Advantageously, expression of the selective marker gene in the second host cell confers on the second host cell resistance to a cytotoxic drug which is present during infection at a level sufficient to select for a genome expressing the selective marker gene.

According to another aspect of the present invention, there is provided a modified eukaryotic cytoplasmic DNA virus produced by direct molecular cloning of a modified viral genome according to methods summarized hereinabove.

Yet another aspect of the present invention relates to a modified eukaryotic cytoplasmic DNA virus comprised of a modified viral genome, wherein that modified viral genome comprises: (I) a first genome of a first eukaryotic cytoplasmic DNA virus. This first genome is comprised of a cleavage site for a sequence-specific endonuclease and this cleavage site is a unique site in the first genome. The modified genome further comprises (II) a first DNA sequence inserted into the unique site in the first genome.

According to a major embodiment of this aspect of the invention, the first DNA sequence is not naturally-occurring in a genome of a eukaryotic cytoplasmic DNA virus. In some preferred cases, the first genome is a vaccinia virus genome and the unique site is a cleavage site for a bacterial restriction endonuclease selected from the group consisting of NotI and SmaI.

The first genome may comprise a second DNA sequence not naturally-occurring in a genome of a eukaryotic cytoplasmic DNA virus and that second DNA sequence is comprised of the unique cleavage site. In one example, the first genome is a fowlpox virus genome comprising a second DNA sequence of an *Escherichia coli* β-galactosidase gene and the unique site in that gene is a cleavage site for the bacterial restriction endonuclease NotI.

In some modified viruses of this invention, at least a portion of said first DNA sequence that is inserted into the unique site is under transcriptional control of a promoter. This promoter is located in the first DNA sequence that is inserted into the first genome. In some cases the first genome is a poxvirus genome and the promoter comprises a poxvirus promoter, either a naturally-occurring poxvirus promoter or a modification thereof.

Yet another aspect of the present invention relates to a modified eukaryotic cytoplasmic DNA virus comprised of a modified viral genome in which the modified viral genome comprises (I) a first genome of a first eukaryotic cytoplasmic DNA virus. This first genome is comprised of a first cleavage site for a first sequence-specific endonuclease and a second cleavage site for a second sequence-specific endonuclease. Each of these cleavage sites is a unique site in the first genome.

The modified genome in this modified virus further comprises (II) a first DNA sequence inserted into the first genome between the first unique site and the second unique site. In some forms of this modified virus the first DNA sequence is not naturally-occurring in a genome of a eukaryotic cytoplasmic DNA virus. In some cases the first genome comprises a second DNA sequence not naturally-occurring in a genome of a eukaryotic cytoplasmic DNA virus and that second DNA sequence is comprised of the first DNA sequence inserted between the first unique site and the second unique site. For an example, this modified virus may comprise a first genome that is a vaccinia virus genome and each of the first unique site and the second unique site is a cleavage site for a bacterial restriction endonuclease selected from the group consisting of NotI, SmaI, ApaI and RsrII.

Yet another modified eukaryotic cytoplasmic DNA virus of the present invention is comprised of a modified viral genome which comprises (I) a first genome of a first eukaryotic cytoplasmic DNA virus. This first genome is comprised of a first DNA sequence and this first DNA sequence is comprised of a cleavage site for a sequence-specific endonuclease that is a unique site in this modified viral genome. This genome of this modified virus further comprises (II) a promoter located such that a DNA sequence inserted into the unique site in the viral genome is under transcriptional control of the promoter. In certain forms, this first DNA sequence lacks a translation start codon between the promoter and the unique insertion site. This first DNA sequence may be one that is not naturally-occurring in a genome of a eukaryotic cytoplasmic DNA virus. This modified virus is exemplified by one in which the first genome is a vaccinia virus genome and the first DNA sequence is comprised of a multiple cloning site comprising cleavage sites for the bacterial restriction endonucleases NotI, SmaI, ApaI and RsrII.

Yet another aspect of the present invention relates to a modified eukaryotic cytoplasmic DNA virus of this invention, wherein a first sequence in the modified viral genome (an inserted sequence of interest) is expressed in a host cell resulting in production of a protein.

In one preferred embodiment of the foregoing aspect, the sequence of interest is derived from HIV-1, in particular, from the HIV-1 gp160, gag and pol genes. A cytoplasmic DNA virus containing such sequences is useful for the production of recombinant HIV-1 antigens in tissue culture. Recombinant HIV-1 antigens can be used in subunit vaccines or as diagnostic agents. In addition, a cytoplasmic virus containing HIV-1 sequences is useful as a live vaccine against HIV-1 infection.

According to another aspect, the present invention also relates to a DNA molecule comprising a modified viral genome of a modified virus according to the present invention, In particular, some forms of this DNA molecule comprise one end of a modified viral genome of a eukaryotic cytoplasmic DNA virus in which (I) that end of the modified viral genome comprises a DNA sequence not naturally-occurring in a genome of a eukaryotic cytoplasmic DNA virus. In this DNA molecule, (II) the modified viral genome is comprised of a cleavage site for a sequence-specific endonuclease that is a unique site in the modified viral genome; and (III) the DNA molecule has a terminus that is homologous to a terminus that is produced by cleaving the unique site in the modified viral genome with the sequence-specific endonuclease.

In some forms of this DNA molecule, the DNA sequence not naturally-occurring in a genome of a eukaryotic cytoplasmic DNA virus is comprised of the cleavage site for a sequence-specific endonuclease that is a unique site in the modified viral genome.

Still another aspect of this invention relates to a kit for direct molecular cloning of a modified viral genome of a eukaryotic cytoplasmic DNA virus, comprising:

(I) purified DNA molecules according to this invention;

(II) a DNA ligase; and (III) solutions of a buffer and reagents suitable for ligation of DNA segments together to produce a modified DNA molecule comprising the modified viral genome. In one form, this kit further comprises a plasmid comprised of a gene expression cassette flanked by sites for cleavage with a sequence-specific endonuclease that are compatible for insertion of that cassette into a unique cleavage site of the modified viral genome encoded by the DNA molecule in the kit. The kit may further comprise a first host cell and a second virus suitable for packaging of the modified viral genome into infectious virions.

According to a further aspect, this invention relates to a plasmid comprising a DNA segment having a cleavage site for the bacterial restriction endonuclease NotI at each end. In this plasmid, this DNA segment comprises a sequence-specific endonuclease cleavage site that is unique in the plasmid. An example of this plasmid as shown in FIG. 1.3, is designated pN2. In this plasmid the DNA segment may further comprise a selective marker gene under transcriptional control of a poxvirus promoter. For instance, such plasmids include plasmids designated pN2-gpta and pN2-gptb.

Another plasmid of the invention contains a DNA segment that further comprises a poxvirus promoter operatively linked to a DNA sequence comprising a restriction endonuclease cleavage site. Thus, a DNA segment inserted into this cleavage site is under transcriptional control of this promoter. Examples are plasmids designated pA1-S2 and pA2-S2. An example of such a plasmid which further comprises a selective marker gene under control of a separate poxvirus promoter is plasmid pN2gpt-S4.

Still another plasmid comprises a segment of a poxvirus genome that comprises a thymidine kinase gene of that poxvirus. This thymidine kinase gene has been modified to prevent expression of active thymidine kinase, as in plasmids designated pHindJ-2 and pHindJ-3. Another plasmid comprises a poxvirus promoter operatively linked to a translational start codon. This start codon is immediately followed by a second restriction endonuclease cleavage site suitably arranged to permit translation of an open reading frame inserted into that second restriction endonuclease cleavage site. Examples of this plasmid include plasmids designated pA1-S1, pA2-S1 and plasmid pN2gpt-S3A.

One particular plasmid of this type further comprises a DNA sequence encoding human prothrombin, where that DNA sequence is operatively linked to the poxvirus promoter and a start codon, as illustrated in FIG. 5.1 by a plasmid designated plasmid pA1S1-PT.

Another plasmid further comprises a DNA sequence encoding human plasminogen and including a translation start codon, where that DNA sequence is operatively linked to the poxvirus promoter. As shown in FIG. 5.2, this is exemplified by plasmids derived from pN2gpt-S4, such as pN2gpt-GPg, encoding human glu-plasminogen and pN2gpt-LPg encoding lys-plasminogen.

Yet another plasmid of this invention, as above, further comprises a DNA sequence encoding human immunodeficiency virus (HIV) gp160, including a translation start codon, operatively linked to the poxvirus promoter, as shown in FIG. 5.4 by plasmid pN2gpt-gp160. Finally, another plasmid comprises a DNA sequence encoding human von Willebrand factor as shown in FIG. 6.2, an example being designated plasmid pvWF.

Some plasmids of this invention comprise a sequence-specific endonuclease cleavage site that is unique in the genome of the poxvirus. Examples are shown in FIG. 4.3, including pA0, pA1 and pA2.

Another plasmid comprises a modified EcoRI K fragment of vaccinia virus DNA from which the K1L host range gene is deleted, as depicted in FIG. 8.1. Two examples are pEcoK-dhr and pdhr-gpt.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1.1 illustrates expression of marker genes by modified genomes of poxviruses produced by reactivation of naked poxvirus DNA. A silver-stained polyacrylamide gel of proteins produced in culture supernatants of cells infected with packaged viruses (vpPg#1–vpPg#8) and with wildtype (WT) virus controls is shown. The upper arrow points to plasminogen marker band, the lower arrow, to the band of major secreted 35 K vaccinia marker protein. Lanes 1 and 9, marker proteins; lanes 2 and 10, human plasminogen standard (10 ng); lane 3, vaccinia recombinant vPgD (source of packaged DNA); lanes 4–7 and 11–14, vpPg#1–8; lanes 8 and 15, wildtype vaccinia (WR WT).

FIG. 1.2 is a schematic diagram illustrating direct molecular cloning of poxvirus genomes comprised of a gene cassette for expression of a marker gene (the *E. coli* gpt gene) under control of a vaccinia virus promoter.

FIG. 1.3 is a schematic illustration of construction of plasmids (pN2-gpta and pN2-gptb) which are precursors for construction of gene expression cassettes by insertion of a promoter and an open reading frame. Such cassettes are designed for direct molecular transfer into vaccinia virus vectors using a unique insertion site and a selectable marker gene (gpt) driven by a vaccinia virus promoter. MCS=multiple cloning site. P7.5=promoter for vaccinia 7.5K kDa polypeptide gene; P11=promoter for vaccinia 11K polypeptide gene. Arrows indicate the directions of transcription from the promoters.

FIG. 1.4 demonstrates that poxvirus genomes produced by direct molecular cloning contain the gpt marker gene cassette inserted at a unique (NotI) cleavage site, as shown by Southern blot analyses of plaque-purified viral DNA's digested with the HindIII endonuclease using a gpt-gene probe. Lane 1, marker DNA's (HindIII digested phage λ DNA); lanes 2 and 3, wildtype vaccinia virus (WR) DNA cut with HindIII (500 and 100 ng, respectively); lanes 4–9, DNA's of cells infected with plaques designated 2.1.1 through 7.1.1; lanes 10–12, DNA's of cells infected with plaques 10.1.1–12.1.1. Arrows indicate sizes of the restriction fragments of the marker in kilobase pairs.

FIG. 1.5 further illustrates structures of modified poxvirus DNA's using Southern blot analyses of NotI-digested DNA's of cells infected with various isolates and hybridized with a gpt-gene probe. Lane 1, marker DNA's (HindIII digested phage λ DNA); lane 2, vaccinia wildtype (WT) DNA cut with NotI (50 ng); lanes 3–8, DNA's of cells infected with recombinant plaques designated 2.1.1 through 7.1.1; lanes 9–11, DNA's of cells infected with plaques 10.1.1–12.1.1.

FIG. 1.6 shows a comparison of DNA's from wildtype (WT) vaccinia and a modified clone (vp7) using ethidium bromide staining of DNA fragments cleaved with indicated restriction endonucleases and separated on an agarose gel. Lanes 1 and 2, NotI digests of WT and vp7; lanes 3 and 4, HindIII digests of WT and vp7; lanes 5 and 6, HindIII and NotI combined digests of WT and vp7; lanes 7 and 8, PstI digests of WT and vp7; lanes 9 and 10, PstI and NotI combined digests of WT and vp7; lanes 11 and 12, SalI digests of WT and vp7; lane 13, marker DNA's (ligated and HindIII digested phage λ DNA; and phage øX cut with HaeIII). Arrows on the left indicate sizes of fragments (in kilobase pairs) of NotI digest of vaccinia WT; arrows on right, markers. Note that lanes 1 and 2 contain about tenfold less DNA than the other lanes.

FIG. 1.7 illustrates a Southern blot analysis of the gel shown in FIG. 1.6 using a gpt-gene probe. Arrows indicate marker sizes.

FIG. 1.8 presents Southern blot analyses of vaccinia virus DNA's from infected cells digested with NotI and hybridized to a vaccinia virus probe. Lanes 1–4, DNA's of cells infected with plaques designated A1–A4; lanes 5–8, plaques C1–C4; lanes 9–12, plaques E1–E4; lane 13, vaccinia WT DNA; lane 14, DNA of uninfected CV-1 host cells; lane 15, marker DNA's (HindIII digested phage λ DNA; and phage øX cut with HaeIII).

FIG. 1.9 shows a Southern blot analysis of the same samples as in the gel shown in FIG. 1.8 using a gpt-gene probe. Lanes 1–12 as in FIG. 1.8; lane 13, DNA of uninfected CV-1 host cells; lane 14, vaccinia WT DNA; lane 15, marker DNA's (HindIII digested phage λ DNA; and phage øX cut with HaeIII).

FIG. 1.10 shows a Southern blot analysis of the same viral DNA's as in the gel in FIG. 1.8, restricted with PstI, using a gpt-gene probe. Lanes 1–12 as in FIG. 1.8; lane 13, DNA of uninfected CV-1 host cells; lane 14, vaccinia WT DNA; lane 15, marker DNA's (HindIII digested phage λ DNA; and phage øX cut with HaeIII).

FIG. 1.11 outlines a schematic of the predicted structure of the modified PstI "C" fragments of vaccinia virus DNA's with single or double insertions of the gpt-gene cassette. P=PstI and N=NotI cleavage sites. The numbers indicates sizes of respective PstI fragments; bold type numbers indicate fragments expected to hybridize with a gpt-gene probe. Arrows indicate direction of transcription of the gpt-gene (800 bp) by the vaccinia virus promoter (300 bp).

FIG. 2.1 presents analyses of recombinant avipox (fowlpox, FP) genomes by digestion with the restriction endonuclease NotI and separation by FIGE on a 1% agarose gel. Lane 5, marker (phage λ HindIII fragments, uncut phage λ and vaccinia WR); lanes 1 and 2, fowlpox virus HP1.441 DNA, uncut and cut with NotI; lanes 3 and 4, recombinant fowlpox virus f-TK2a DNA, uncut and cut with NotI.

FIG. 2.2 illustrates construction of fowlpox viruses expressing foreign genes by direct molecular cloning. A gene expression cassette, consisting of the *E. coli* gpt gene controlled by a poxvirus promoter (P) is ligated with the right and left DNA arms (ra and la, respectively) of fowlpox virus (f-TK2a) obtained by cleavage with NotI. Packaging is performed by fowlpox helper virus (strain HP2) in chicken embryo fibroblasts.

FIG. 3.1 illustrates a process for construction of modified poxviruses by extracellular genome engineering and intracellular packaging. A gene cassette consisting of the gpt gene controlled by a vaccinia virus promoter, is ligated with the "right arm" (ra) and the "left arm" (la) of vaccinia virus DNA cleaved at a unique site with the endonuclease SmaI. Packaging is done by the fowlpox helper virus (strain HP1.441) in chicken embryo fibroblasts. P1=promoter of the vaccinia virus gene coding for the 7.5 kDA polypeptide.

FIG. 3.2 demonstrates that engineered vaccinia virus genomes packaged by fowlpox helper virus contain the expected insert at a unique SmaI cleavage site, as determined by Southern blot analyses. Total DNA isolated from infected cells was digested with HindIII, and the blot was hybridized with a gpt-gene probe. Lanes 1–8, DNA's from cells infected with plaques designated F12.2–F12.9; lanes 9–13, plaques F13.1–F13.5; lanes 14 and 15, HindIII-digested DNA isolated from uninfected cells and cells infected with vaccinia (WR wildtype) virus, respectively; lane 16, markers (HindIII-digested phage λ DNA). The DNA in lane 8 does not hybridize because the virus isolate #F12.9 did not replicate.

FIG. 3.3 presents a schematic outline of the expected structures of modified vaccinia virus genomes having a gene cassette inserted into a unique SmaI site, particularly the modified HindIII "A" fragments of viruses with single and double insertions. H=HindIII and S=SmaI restriction endonuclease cleavage sites. Numbers indicate sizes of the HindIII fragments, with those in bold type indicating fragments expected to hybridize with a gpt-gene probe. The gpt gene cassette consists of a vaccinia virus promoter (about 300 bp in size) separated by an internal HindIII site from the gpt sequences (about 800 bp). Arrows indicate the direction of transcription of the gpt gene.

FIG. 4.1A shows a schematic plan for the construction of vaccinia virus vector vdTK having a modified thymidine kinase (tk) gene using only direct molecular modification of the vaccinia virus genome, including deletion of undesired NotI and SmaI sites. WR-WT=wildtype (WT) Western Reserve (WR) strain of vaccinia virus (VV).

FIG. 4.1B outlines an alternative approach to that outlined in FIG. 4.1A for deletion of a NotI site using marker rescue techniques with vaccinia virus and a modified plasmid.

FIG. 4.1C outlines an alternative method to that outlined in FIG. 4.1A for deleting the SmaI site by marker rescue.

FIG. 4.2 illustrates construction of the vaccinia virus vector (vdTK) having the thymidine kinase (tk) gene replaced with a multiple cloning site. The arrow indicates the initiation and direction of transcription of the vaccinia virus tk gene (VV-tk) in the HindIII J fragment cloned in plasmid pHindJ-1. The tk gene was replaced, as shown, and the final plasmid pHindJ-3 was used to insert the modified HindIII J fragment into vaccinia virus.

FIG. 4.3 outlines construction of plasmids (pA1 and pA2) which are precursors for construction of gene expression cassettes by insertion of a promoter and an open reading frame. Such cassettes are suitable for direct molecular transfer into vaccinia virus vector vdTK using directional (forced) cloning.

FIG. 4.4A illustrates construction of plasmids (pA1-S1 and pA2-S1) comprised of gene expression cassettes suitable for association of open reading frames with a synthetic poxvirus promoter (S1) and a translation start codon. The cassettes are designed for direct molecular transfer into vaccinia virus vector vdTK by forced cloning. The S1 promoter is present in different orientations in the two plasmids, as indicated by the arrows showing the directions of transcription.

FIG. 4.4B shows the structure of the S1 promoter (bases 21–194 of SEQ ID NO:9).

FIG. 4.5A outlines the construction of plasmids (pA1-S2 and pA2-S2) comprised of gene expression cassettes suitable for association of open reading frames already having a translation start codon with a synthetic poxvirus promoter (S2), prior to direct molecular transfer into vaccinia virus vector vdTK by forced cloning. The S2 promoter is present in different orientations in the two plasmids, as indicated by the arrows showing the directions of transcription.

FIG. 4.5B shows the structure of the S2 promoter (bases 21–73 of SEQ ID NO:11).

FIG. 4.6 shows the construction of plasmids pN2-gpta and pN2-gptb.

FIG. 4.7 shows construction of plasmids (pN2gpt-S3A and pN2gpt-S4) comprised of gene expression cassettes suitable for association of an open reading frame, either lacking (S3A) or having (S4) a translation start codon, with a synthetic promoter (S3A, bases 21–107 of SEQ ID NO:13, or S4, bases 21–114 of SEQ ID NO:14, respectively), prior to direct molecular transfer into a unique site in vaccinia virus vector vdTK. Abbreviations as in FIG. 1.3.

FIG. 5.1 illustrates construction of a gene expression cassette plasmid (pA1S1-PT) for expression of human prothrombin in vaccinia virus vector vdTK. Abbreviations as in FIG. 1.3. Arrows indicate the direction of transcription.

FIG. 5.2 presents construction of a gene expression cassette plasmid (pN2gpt-GPg) for expression of human glu-plasminogen in vaccinia virus vector vdTK. S4=synthetic poxvirus promoter; other abbreviations as in FIG. 1.3.

FIG. 5.3 shows construction of a gene expression cassette plasmid (pN2gpt-LPg) for expression of human lys-plasminogen in vaccinia virus vector vdTK. Abbreviations as in FIG. 1.3.

FIG. 5.4 outlines construction of a gene expression cassette plasmid (pN2gpt-gp160) for expression of a human virus antigen (HIV gp160) in vaccinia virus vector vdTK. Abbreviations as in FIG. 1.3.

FIG. 5.5 illustrates an approach for screening of modified vaccinia viruses made by direct molecular cloning based on concurrent insertion of a marker gene (the *E. coli* lacZ gene) which confers a visually distinctive phenotype ("blue" plaque compared to normal "white" plaques of viruses lacking a lacZ gene).

FIG. 5.6 illustrates the construction of plasmids pTZS4-lacZa and pTZS4-lacZb.

FIG. 6.1 illustrates construction of a vaccinia virus vector (vS4) with a directional master cloning site under control of a strong late vaccinia virus promoter (S4). SEQ ID NOS 38 and 39 are shown in this Figure.

FIG. 6.2 presents construction of a modified vaccinia virus (vvwF) for expression of von-Willebrand factor by direct molecular insertion of an open reading frame into vaccinia virus vector vS4. vWF=von Willebrand factor cDNA. The arrow indicates the direction of transcription from the S4 promoter.

FIG. 7.1 illustrates the effect of amount of added DNA on packaging of vaccinia virus DNA by fowlpox helper virus in mammalian (CV-1) cells in which fowlpox virus does not completely replicate. Five cultures were infected with fowlpox virus and subsequently transfected with the indicated amounts of vaccinia virus DNA. The first column indicates a culture with no added DNA and no fowlpox virus, and the fifth column, no added DNA but infected with fowlpox virus.

FIG. 8.1 outlines construction of a vaccinia virus (vdhr) suitable for use as a helper virus having host range mutations which prevent replication in some human cell lines. hr-gene=host range gene located in the EcoRI K fragment of vaccinia virus; other abbreviations as in FIG. 1.3.

FIG. 9.1 shows the construction of the plasmids pS2gpt-P2 and pP2gp160MN. Arrows within plasmids show the direction of transcription of the respective genes. SEQ ID NO:43 is shown in this Figure.

FIG. 9.2 shows the schematic outline of the construction of the viruses vP2-gp160MN-A and vP2gp160MN-B.

FIG. 9.3 shows maps of the PstI-E-fragment of the wild-type vaccinia virus and of the PstI-fragments of the chimeric viruses comprising gp160 genes. Arrows indicate the direction of transcription of the gp160 gene. Numbers indicate sizes of fragments in kilobase pairs.

FIG. 9.4 shows construction of the plasmid pselP-gpt-L2. Arrows indicate the direction of transcription of the respective genes. SEQ ID NO:86 is shown in this Figure.

FIG. 9.5A shows construction of the plasmid pselP-gp160MN. SEQ ID NO:86 is shown in this Figure.

FIG. 9.5B shows sequences around translational start codons of wild-type (SEQ ID NOS 73 and 74) and modified (SEQ ID NOS 75 and 76) gp160 genes.

FIG. 9.6 is a schematic outline of construction of the chimeric vaccinia viruses vselP-gp160MNA and vP2-gp160MNB. Arrows indicate the direction of transcription of the gp160 gene.

FIG. 9.7 is a map of the SalI-F-fragment of the wild-type vaccinia virus and of SalI-fragments of chimeric vaccinia viruses vselP-gp160MNA and vP2-gp160MNB. Arrows indicate the direction of transcription of the gp160 gene. Numbers indicate sizes of the fragments in kilobase pairs.

FIG. 10.1A shows the structure of plasmid pN2-gptaProtS. The double gene cassette consisting of the gpt gene controlled by the vaccinia P7.5 promoter (P7.5) and the human Protein S gene (huProtS) controlled by a synthetic poxvirus promoter (selP) is flanked by NotI restriction sites.

FIG. 10.1B shows sequences around translational start codons of wild-type Protein S gene (SEQ ID NOS 77 and 78) and the Protein S gene in the chimeras (SEQ ID NOS 79 and 80).

FIG. 10.2A shows Southern blot analysis of chimeric vaccinia viruses carrying the Protein S gene. Total cellular DNAs digested with SacI and hybridized with vaccinia wild-type SacI fragment.

FIG. 10.2B shows the same material of FIG. 10.2A digested with NotI and probed with human Protein S sequences.

FIG. 10.2C shows schematic outline of the wild-type SacI-I-fragment and the chimeric SacI-fragment after ligation of the insert.

FIG. 10.3 shows Western blot analysis of plasma-derived Protein S (pdProtS; lanes 1 and 2) and of recombinant Protein S (rProtS). Cell culture supernatants (10 μl) of SK Hep1 cells were assayed after incubation periods of 24–72 h.

FIG. 11.1A shows the structure of plasmid pN2gpta-FIX. The double gene cassette consisting of the gpt gene controlled by the vaccinia P7.5 promoter (P7.5) and the human factor IX gene controlled by a synthetic poxvirus promoter (selP) is flanked by NotI restriction sites.

FIG. 11.1B shows sequences from wild-type factor IX (SEQ ID NOS 81 and 82) and factor IX vFIX#5 (SEQ ID NOS 83 and 84).

FIG. 11.2A shows Southern blot analysis of the chimeric viruses carrying a gene for human factor IX. Total cellular DNAs digested with SfuI and hybridized with the human factor IX gene probe (plasmid pBluescript-FIX). In all eight isolates (#1–6, 9 and 10), the insert had the 'a'-orientation. m=marker; VV-WT/WR=vaccinia wild-type, WR-strain.

FIG. 11.2B shows predicted genomic structures of the chimeric viruses.

FIG. 11.3 shows Western blot analysis of plasma-derived factor IX (pdFIX; lanes 1 and 2) and of recombinant factor IX expressed by chimeric vaccinia virus in Vero cells. Cell culture supernatants (10 μl) were assayed after incubation for 72 h. #1–6, 9 and 10=numbers of plaque isolates; pd FIX=plasma-derived factor IX.

FIG. 12.1 illustrates construction of the chimeric fowlpox virus f-envIIIB by direct molecular cloning of and HIV-$_{IIIB}$ env gene.

FIG. 12.2A shows Southern blot analyses of SspI-fragments of chimeric fowlpox virus isolates showing orientations of env gene inserts. Lanes 1–12, viral isolates f-LFa-l; lane 13 and 14, HP1.441 and f-TK2a (negative controls); lane 15, SspI digest (10 ng) of pN2gpt-gp160 (positive control).

FIG. 12.2B shows restriction maps of SspI fragments of inserts in the two possible orientations in the chimeric fowlpox virus of FIG. 12.2A. Numbers indicate sizes of SspI-fragments in kilobase pairs. Arrows indicate orientations of the insert which coincide with direction of transcription of the gp160 transcription unit.

FIG. 12.3 shows expression of HIV-1 envelope glycoproteins in chicken embryo fibroblasts (Western blot analysis). Lanes 1–8, viral isolates f-LF2a-h; lanes 9 and 15, gp160 standard, provided by A. Mitterer, Immuno Ag, Orth/Donau, Austria; lanes 10–13, viral isolates f-lF2i-l; lane 14, marker proteins; lanes 16 and 17, fowlpox viruses HP1.441 and f-TK2a (negative controls).

FIG. 12.4 shows detection of HIV gp41 produced by chimeric vaccinia viruses in infected chicken embryo fibroblasts (Western blot analysis). Lanes 1–8, viral isolates f-LF2a-h; lanes 9 and 15, gp160 standard; lanes 10–13, viral isolates f-LF2i-l; lane 14, marker proteins; lanes 16 and 17, fowlpox viruses HP1.441 and f-TK2a (negative controls).

FIG. 13.1 shows the construction scheme of the plasmid pSep-ST2.

FIG. 13.2 shows the structure, sequence and construction of the semi-synthetic poxvirus promoter Sep. SEQ ID NOS 87–89 are shown in this Figure.

FIG. 13.3 shows a Southern blot analysis of viral genomic DNA of the viruses vRMN6b1 and the Western Reserve wild-type strain (WR-WT).

FIG. 13.4 shows a Southern blot analysis of viral genomic DNA of the viruses vRMN6b1 and the Western Reserve wild-type strain (WR-WT).

FIG. 13.5 shows a comparison of the gpl6OMN expression levels of the different viral isolates.

FIG. 13.6 shows a comparison of gpl6OMN expression of vaccinia Sep-gpl6O constructs and vaccinia/bacterlophage T7 promoter constructs in CV-1 and Vero cells. The arrow points to the gpl6O protein band.

FIG. 14.1 shows the construction of the plasmid pSep-gag. Sep is a hybrid, early/late promoter; P7.5 is the vaccinia promoter for the P7.5 kDa product. Arrows indicate the direction of transcription. SEQ ID NOS 94 and 95 are shown in this Figure.

FIG. 14.2 shows screening of viral crude stocks by Western blot analysis. Confluent CV-1 cells were infected with 1 plaque forming unit of the respective virus and cultured for 48 hours. Total cellular proteins were separated on a 12% polyacrylamide gel and analyzed by Western blot analysis. The protein samples of vgagl.l, vgagl.2 vgag2. 1, vgag2.2 and vgag7.1 were loaded in duplicate. The positive control, VVKI, is a gag/pol gene containing vaccinia recombinant described by Karacostas et al. (1989). WR-WT is the Western Reserve wild-type strain. HIV-IMN/H9 are total cellular proteins of HIV-lMN-infected H9 cells. CV-1 non are uninfected CV-1 cells. The arrow at the right side indicates the p55 gag precursor protein.

FIG. 14.3 shows Southern blot analyses of HIV-1 gag-expressing viruses hybridized to the gag gene probe. The marker (m) consisted of phage lambda HindIII and phage phi X HaeIII fragments (the fragment sizes are shown kilobase pairs on the right side). WR-WT is the Western Reserve wild-type strain to which the probe does not hybridize. Total DNA extracted from non-infected CV-1 cells (CV-1 DNA) served as a negative control. Positive hybridization controls were HindIII (H) and Asp718 (A) fragments of the plasmid psep-gag.

FIG. 14.4 shows Southern blot analyses of HIV-1 gag-expressing viruses hybridized to the Not region probe. For abbreviations, see the legend of FIG. 14.3.

FIG. 14.5 shows a comparison of the gag protein expression on CV-1 an Vero cells. Confluent CV-1 or Vero cells were infected with 1 plaque forming unit of the respective viruses and grown for 72 hours. Total cellular proteins were analyzed as described in the legend of FIG. 14.2. The arrow at the right side points to the p55 gag precursor protein.

FIG. 15.1 shows construction of the plasmid pSep-gagpolIIIB. Arrows around plasmids indicate the direction of transcription of the respective gene cassettes. The numbers near the restriction endonuclease cleavage site indicate the positions of the sites in the respective plasmids. SEQ ID NOS 94 and 95 are shown in this Figure.

FIG. 15.2 shows screening of viral crude stocks by Western blot analysis. Confluent CV-1 cells were infected with 3 plaque forming units of the respective virus and grown for 48 hours. Total cellular proteins were separated on a 12% polyacrylamide gel and analyzed by Western blot analysis. The protein samples of vgagpol 7, vgagpol 9 and vgagpol 10 were loaded in duplicate. VVKI is a gag-pol gene containing the vaccinia recombinant described by Karakostas et al. (1989). WR-WT is the Western Reserve wild-type strain. HIV-I/H9 are total cellular proteins of HIV-1-infected H9 cells. The arrows at the right side point to p55 gag and pl60 gag-pol precursor proteins.

FIG. 15.3 shows Southern blot analyses of HIV-1 gag-pol expressing viruses hybridized to the gag-pol gene probe. The size markers consisted of the Asp7l8 (ml) and HindIII (m2) fragments of the plasmid pSep-gagpolIIIB (the numbers on the right side are the fragment sizes in kilobase pairs). WR-WT is the Western Reserve wild-type strain to which the probe does not hybridize.

FIG. 16.1 shows maps of the PstI fragments of the fowlpox virus strain HPI.441, the strain f-TK2a and of both possible orientations of the chimeric viruses f-aMN (‘a’- and ‘b’orientation). FPV-tk=fowlpoxvirus thymidine kinase gene; 3'-orf=downstream open reading frame; VV-tk= vaccinia thymidine kinase gene; lacZ=*E. coli* β-galactosidase; gpt=*E. coli* xanthine guanine phosphoribosyl transferase, The arrows indicate the direction of transcription.

FIG. 16.2 shows Western blot analysis of total chicken embryo fibroblast (CEF) proteins infected with different fowlpox viruses. The f-aMN chimeric viruses were three times plaque purified. The gpl6OMN standard was purified from vaccinia virus-infected Vero cells. HP1.441 is the attenuated fowlpox virus strain from which f-TK2a was derived. CEF mock are total cellular proteins of a mock infection of chicken embryo fibroblasts.

FIG. 16.3 shows Western blot analysis of total proteins from CV-1 and Vero cells infected with the fowlpox virus f-aMN. The gpl6OMN standard was purified from vaccinia virus-infected Vero cells. ‘Vero mock’ are total cellular proteins of a mock infection of Vero cells. The samples were applied in duplicate.

FIG. 16.4 shows Southern blot analyses of HIV-1 gpl6OMN-expressing fowlpox viruses hybridized to the gpl6O gene probe. The size markers consisted of the HindIII fragments of the plasmid pSep-ST2 (pSep-ST2 H) (numbers on the right side are the sizes in kilobase pairs). The wild-type strains HP1.441 and f-TK2a do not hybridize with the probe.

DETAILED DESCRIPTION OF THE INVENTION

Figure 21:
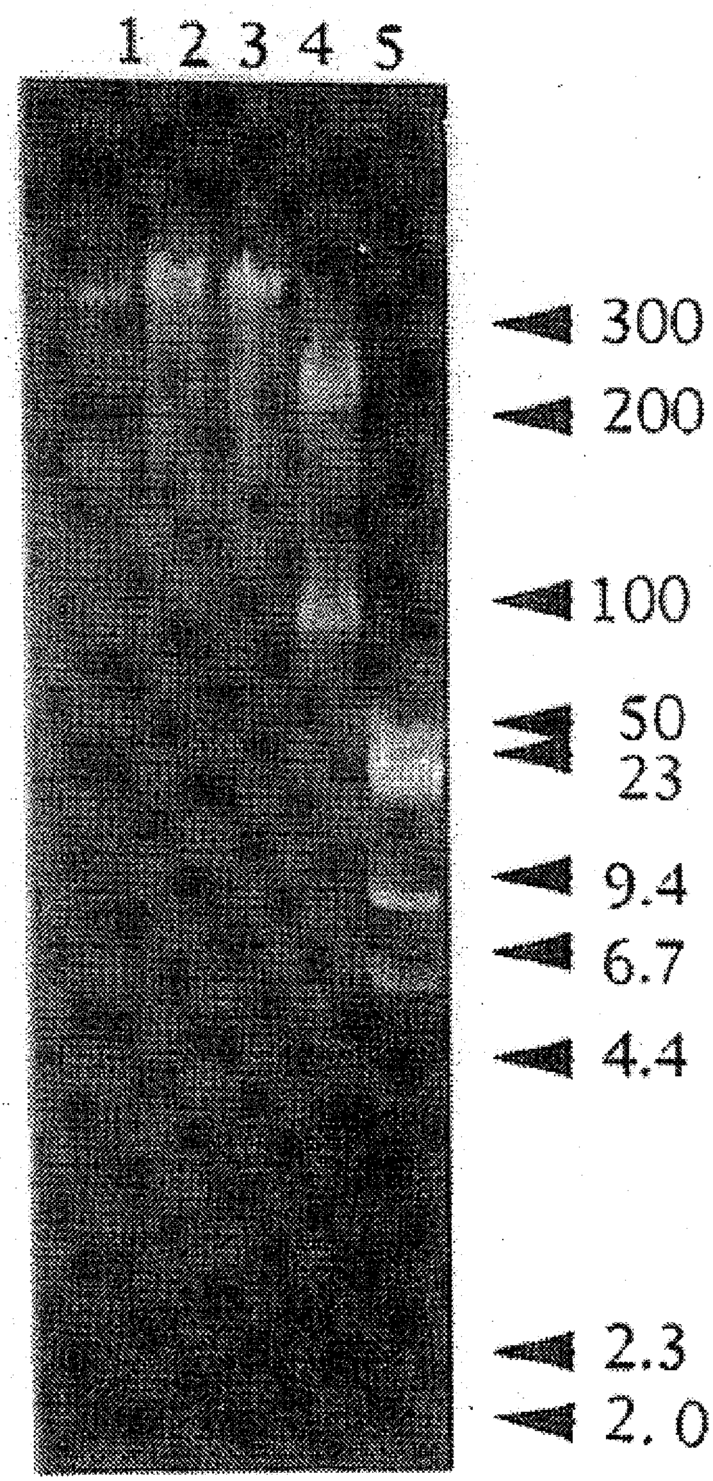

The present invention represents the first construction of a modified genome of a eukaryotic cytoplasmic DNA virus, as exemplified by a poxvirus, completely outside the confines of a living cell. This construction was accomplished using an isolated viral genomic DNA that was cleaved by a sequence-specific endonuclease and then religated with foreign DNA. The resulting modified DNA was then packaged into infectious poxvirus virions by transfection into a host cell infected with another poxvirus that served as a helper virus.

The present invention enables diverse strategies for vector development from eukaryotic cytoplasmic DNA viruses which have been applied previously to other DNA viruses to solve various genetic engineering problems. For instance, this direct cloning approach offers the possibility of cloning genes directly in cytoplasmic DNA viruses, such as poxviruses, that cannot be cloned in bacterial systems, either because they are too large for bacterial vectors or are toxic to bacteria or are unstable in bacteria. Direct molecular cloning allows greater precision over construction of engineered viral genomes and under optimum conditions can increase the speed of cloning as well as produce a variety of constructs in a single ligation reaction, having multiple inserts in various orientations, which permits rapid screening for arrangements affording optimal expression of a foreign gene.

As used in the present context, "eukaryotic cytoplasmic DNA virus" includes iridoviruses and poxviruses. "Iridovirus" includes any virus that is classified as a member of the family Iridoviridae, as exemplified by the African swine fever virus as well as certain amphibian and insect viruses. "Poxvirus" includes any member of the family Poxviridae, including the subfamililes Chordopoxviridae (vertebrate poxviruses) and Entomopoxviridae (insect poxviruses). See, for example, B. Moss in *VIROLOGY*, ed. Fields et al., Raven Press (1990) p. 2080. The chordopoxviruses comprise, inter alia, the following genera from which particular examples are discussed herein, as indicated in parentheses: Orthopoxvirus (vaccinia); Avipoxvirus (fowlpox); Capripoxvirus (sheeppox) Leporipoxvirus (rabbit (Shope) fibroma, myxoma); and Suipoxvirus (swinepox). The entomopoxviruses comprise three genera designated A, B and C.

According to one aspect of the present invention, a method is provided for producing a modified eukaryotic cytoplasmic DNA virus by direct molecular cloning of a modified cytoplasmic DNA virus genome. This method comprises a step of modifying under extracellular conditions a purified DNA molecule comprising a first cytoplasmic DNA virus genome to produce a modified DNA molecule comprising a modified cytoplasmic DNA virus genome.

A purified DNA molecule suitable for modification according to the present method is prepared, for example, by isolation of genomic DNA from virus particles, according to standard methods for isolation of genomic DNA from eukaryotic cytoplasmic DNA viruses. See, for instance, Example 1, hereinbelow. Alternatively, some or all of the purified DNA molecule may be prepared by molecular cloning or chemical synthesis.

Modifying a purified DNA molecule comprising a virus genome within the scope of the present invention includes making any heritable change in the DNA sequence of that genome. Such changes include, for example, inserting a DNA sequence into that genome, deleting a DNA sequence from that genome, or substitution of a DNA sequence in that genome with a different DNA sequence. The DNA sequence that is inserted, deleted or substituted is comprised of a single DNA base pair or more than one DNA base pair.

According to this aspect of the invention, the step of modifying a DNA molecule comprising a first DNA virus genome is performed with any technique that is suitable for extracellularly modifying the sequence of a DNA molecule. For instance, modifying a DNA molecule according to the present invention comprehends modifying the purified DNA molecule with a physical mutagen, such as ultraviolet light, or with a chemical mutagen. Numerous methods of extracellular mutagenesis of purified DNA molecules are well known in the field of genetic engineering.

In another embodiment, the step of modifying the DNA molecule comprises joining together DNA segments to form the modified DNA molecule which comprises the modified viral genome. According to one aspect of this embodiment, some or all of the DNA segments joined together to form the modified DNA molecule are produced by cleaving the DNA molecule comprising the first virus genome with a nuclease, preferably a sequence-specific endonuclease. Alternatively, some or all of the DNA segments joined together to form the modified DNA molecule may be produced by chemical synthesis using well known methods.

In some embodiments, the step of joining together DNA segments to produce the modified DNA molecule comprises an extracellular step of ligating those DNA segments together using a ligase, such as a bacterial or bacteriophage ligase, according to widely known recombinant DNA methods. optionally, this DNA modification step also comprises treating ends of DNA segments cleaved from the DNA molecule comprising the first virus genome with a phosphatase, for instance, calf intestine phosphatase. This enzyme removes phosphate moieties and thereby prevents religation of one DNA segment produced by cleaving the DNA molecule with another such segment.

In an alternative approach to joining the DNA segments, some or all of the DNA segments are joined by extracellular annealing of cohesive ends that are sufficiently long to enable transfection of the modified DNA molecule into a host cell where ligation of the annealed DNA segments occurs.

In another embodiment of this method, the step of modifying the DNA molecule comprising the first virus genome includes a step of joining at least some DNA segments resulting from cleaving a genomic DNA molecule of the first virus together with an additional DNA segment to produce the modified DNA molecule. In a preferred embodiment of this aspect of the invention, this step comprises cleaving a genomic viral DNA molecule with a sequence-specific endonuclease at a unique cleavage site in the first virus genome, thereby producing two DNA "arms" of the genomic virus DNA. The two arms are then ligated together with a foreign DNA comprising a sequence of interest.

A DNA sequence of interest as used herein to describe the sequence of a foreign DNA segment that is ligated with virus DNA arms comprises, in the first instance, a DNA sequence that is not naturally-occurring in a genome of a eukaryotic cytoplasmic DNA virus. Alternatively, a DNA sequence of interest comprises a sequence comprised of a sequence that is naturally-occurring in a genome of a eukaryotic cytoplasmic DNA virus as well as a sequence that is not naturally-occurring in such a genome. Furthermore, a sequence of interest may comprise only sequences that are naturally-occurring in a eukaryotic cytoplasmic DNA virus, where such a sequence is inserted into a location in the genome of that cytoplasmic DNA virus different from the location where that sequence naturally occurs. Moreover, insertion of a naturally-occurring viral sequence of interest from one DNA virus into another, or from one part of a single viral genome into another part of that genome, will necessarily create a sequence that is "not naturally-occurring in the genome of a cytoplasmic DNA virus" according to the present invention, at the junction of the viral genome and the inserted viral sequence of interest.

The foreign DNA segment that is ligated to the two arms of genomic virus DNA comprises ends that are compatible for ligation with the ends of the viral DNA arms. The compatible ends may be complementary cohesive ends or blunt ends. The ligation step in this particular method produces a modified DNA molecule comprising the first virus genome with the DNA sequence of the foreign DNA inserted into the first virus genome at the unique cleavage site.

This embodiment of a method in which a DNA sequence is inserted into the genome of the first virus is exemplified herein by, inter alia, a method for inserting a gene expression cassette into a vaccinia virus genome at a unique cleavage site for the bacterial restriction endonuclease NotI or SmaI, as described in Examples 1 and 3, respectively. This embodiment is also exemplified by insertion of a gene cassette into the genome of a recombinant fowlpox virus vector, at a unique NotI site within the sequence of a bacterial gene within the recombinant fowlpox virus genome, as described in Example 2.

Inserting a foreign DNA into a unique site in a eukaryotic cytoplasmic DNA virus genome according to the present invention is useful for the purpose of expressing a desired protein, particularly a human protein. For instance, Example 5 describes insertion of genes for plasminogen, prothrombin and human immunodeficiency virus glycoprotein 160 (HIV gp160) into a unique cleavage site of a vaccinia virus vector and the use of the resulting modified vaccinia viruses for production of these proteins. The foreign proteins may be produced in cell cultures, for preparing purified proteins, or directly in human or animal hosts, for immunizing the host with a vaccine comprising a modified virus according to the present invention.

In certain embodiments, the step of modifying a virus genome by inserting a DNA sequence comprises introducing or eliminating a marker gene function for distinguishing the modified virus genome from the first virus genome. In one such embodiment, a DNA sequence inserted into the first virus genome comprises a selective marker gene and the step of recovering the infectious modified poxvirus virions produced by the first host cell comprises a step of infecting a second host cell with those infectious virions under conditions that select for a poxvirus genome expressing the selective marker gene. In a preferred embodiment of this aspect of the invention, expression of the selective marker gene in the second host cell confers on the second host cell resistance to a cytotoxic drug. This drug is present during infection of the second host cell at a level sufficient to select for a poxvirus genome expressing the selective marker gene. In this case the drug selects for a modified virus genome having the inserted selective marker gene and selects against any genome lacking that marker gene.

Insertion of a DNA sequence comprising a selective marker gene for distinguishing the modified virus genome from the first virus genome is particularly useful when a genomic DNA molecule of the first virus has been cleaved at a unique cleavage site and, therefore, the resulting viral DNA arms are likely to religate without insertion of the desired DNA sequence. This approach is exemplified by a method for inserting a gene for the enzyme xanthine-guanine-phosphoribosyl-transferase of *Escherichia coli* (hereinafter, the "gpt" gene) into, inter alia, a vaccinia virus genome or a fowlpox virus genome at a unique NotI site, as described in Examples 1 and 2, respectively.

A method for eliminating a marker gene function from the first virus genome to distinguish the modified viral genome from the first genome is exemplified in Example 2. This method relates to insertion of a foreign DNA sequence into a fowlpox virus genome into a NotI site residing in an *E. coli* lacZ gene coding for β-galactosidase. As described in Example 2 (avipox), insertion of a DNA sequence into this site disrupts the lacZ coding sequence and thereby prevents production of β-galactosidase. Expression of this enzyme produces a "blue plaque" phenotype for a virus carrying the lacZ gene. Accordingly, a modified viral genome carrying an insertion of a DNA sequence in this site exhibits a white plaque phenotype that distinguishes the modified virus from the first virus. In other embodiments of methods according to this invention, a functioning *E. coli* lacz gene is transferred into the vector with another gene of interest to serve as a marker for modified viruses containing the desired insert.

In still other embodiments of the method of this invention, the step of modifying a DNA molecule comprises introducing a new cleavage site for a sequence-specific endonuclease into the first virus genome. One example of this embodiment comprises inserting into a existing unique site in a first poxvirus genome a foreign DNA comprised of a synthetic DNA "linker", as described in Example 6. This linker comprises a "multiple cloning site" comprised of several closely adjacent cleavage sites that are useful for insertion of foreign DNA into the modified poxvirus genome. Advantageously, the cleavage sites in the multiple cloning site are not present in the first viral genome and, therefore, are unique in the modified viral genome.

More particularly, the step of modifying a DNA molecule comprising a first viral genome also includes inserting a DNA sequence between a first and a second cleavage site for a sequence-specific endonuclease. In one such embodiment, the first viral genome comprises a multiple cloning site comprised of cleavage sites that are unique in the first viral genome. According to this method, cleaving a DNA molecule comprising a first viral genome at two such unique sites in the multiple cloning site produces two viral DNA arms having cohesive ends that are not compatible for ligation with each other. The intervening DNA segment between the two unique cleavage sites in the multiple cloning site is removed from the cleaved viral DNA arms, for example, by ethanol precipitation of these arms, as described for inserting a human prothrombin gene into a modified poxvirus vector in Example 5.

Inserting a DNA segment into a viral genome between two unique cleavage sites is useful for "forced" cloning of DNA inserts having cohesive ends compatible for ligation with each of the vector arms. In other words, this method involving cleavage of viral DNA at two sites is useful for increasing the yield of viral genomes resulting from ligation of viral DNA arms compared to arms prepared by cleavage of viral DNA at a single site, because the arms of this method do not have ends compatible for ligation. This forced cloning method also directs orientation of the DNA inserted within the modified viral genome because only one viral DNA arm is compatible for ligation to each end of the inserted DNA.

The forced cloning method of the present invention is demonstrated, for example, by insertion of a gene expression cassette comprised of a human prothrombin gene into a multiple cloning site of a vaccinia virus vector, as described in Example 5.

In a preferred embodiment, the intervening DNA segment between two unique cleavage sites in the first viral genome is not essential for replication of the first viral genome and, therefore, neither deleting this sequence nor replacing it with another DNA segment prevents replication of the resulting modified genome. Alternatively, the intervening DNA segment is replaced by a DNA segment comprising that portion of the intervening sequence that is essential for viral replication linked to an additional DNA sequence that is to be inserted into the first viral genome.

In another aspect of the present method, the step of modifying the first viral genome comprises eliminating an undesirable cleavage site for a sequence-specific endonuclease. Modifications of this type can be made repeatedly, if necessary, for example, to delete redundant cleavage sites for the same nuclease, thereby ultimately producing a modified viral genome having a unique cleavage site for a particular nuclease.

Methods that are particularly suitable for eliminating a cleavage site from a viral genome are known in the art. These include various general site-specific mutagenesis methods. One particular method for eliminating an endonuclease cleavage site from a viral genome involves extracellular treatment of genomic viral DNA to select for mutant genomic DNA molecules that are resistant to cleavage by the pertinent endonuclease.

Another method for eliminating a cleavage site from a viral genome is by ligating a cleaved viral DNA molecule with a DNA segment, for instance, a synthetic DNA segment, comprising an end compatible for ligation with the cleaved viral DNA but lacking a portion of the recognition sequence for the nuclease that cleaved the viral DNA. In this method, the cleavage site for the sequence-specific endonuclease that cleaves the viral DNA comprises a nuclease recognition sequence that extends beyond the sequences encompassed in the cohesive ends into the sequences immediately adjacent to the cohesive ends. The synthetic insert comprises cohesive ends compatible for ligation with the viral DNA arms cleaved at a single site. However, the sequence immediately adjacent to one cohesive end of the synthetic insert differs from the recognition sequence that is required for cleavage by the enzyme that cleaved the viral DNA. Therefore, ligation of this end of the synthetic DNA segment with a viral arm does not reconstitute a functional cleavage site for the nuclease that cleaved the viral DNA. This method for eliminating a cleavage site from a viral genome is exemplified in Example 4 by insertion of a synthetic DNA segment comprising a multiple cloning site into a unique cleavage site of a viral genome.

To prevent inactivation of a viral genome as a result of modification, it is evident that the modification of a viral genome according to the present method must be made in a region of the viral genome that is not essential for virus multiplication in cell culture under the conditions employed for propagation of the resulting modified virus. DNA virus genomic regions comprising sequences that are nonessential for multiplication in cell culture and otherwise suitable for modification according to the present methods include sequences between genes (i.e., intergenic regions) and sequences of genes that are not required for multiplication of the modified viral genome.

A nonessential site suitable for modifying a selected genome of a eukaryotic cytoplasmic DNA virus according to the present invention may be identified by making a desired modification and determining whether such modification interferes with replication of that genome under the desired infection conditions. More in particular, restriction enzyme cleavage sites in a viral genome, including unique sites in that genome, are identified, for instance, by digestion of genomic DNA and analysis of the resulting fragments, using procedures widely known in the art. The genome may be disrupted by trial insertion of a short synthetic DNA segment into a selected target cleavage site by the direct cloning method of the present invention. Recovery of a virus comprised of the trial insert at the selected target site provides a direct indication that the target site is in a nonessential region of that genome. Alternatively, if no useful cleavage site exists at a particular genomic target location, such a site may be introduced using either direct molecular cloning or conventional genome construction based on marker rescue techniques. In this case, successful recovery of a virus comprised of the inserted cleavage site at the target location directly indicates that the target location is in a nonessential region suitable for modification according to the present invention.

Certain nonessential genomic regions suitable for practicing the present invention with poxviruses have been described. See, for instance, Goebel et al., *Virology* 179: 247–266 (1990), Table 1, the disclosure of which is hereby incorporated herein by reference.

In further embodiments of the method, at least a portion of the DNA sequence which is inserted into the first viral genome is under transcriptional control of a promoter. In certain embodiments, this promoter is located in the DNA sequence that is inserted into the first viral genome and, therefore, controls transcription of that portion of the inserted DNA sequence downstream from the promoter. This approach is exemplified by insertion into a poxviral genome of a gene cassette comprising a promoter functionally linked to an open reading frame, as described in Examples 1 through 5.

In another preferred embodiment, the promoter controlling transcription of the DNA sequence that is inserted into the first viral genome is located in the modified viral genome upstream of the inserted DNA sequence. This approach is illustrated by insertion of a cDNA encoding the human von Willebrand factor protein into a multiple cloning site that is functionally linked to an upstream promoter in a vaccinia virus vector, as described in Example 7.

In certain embodiments, the promoter controlling the inserted DNA sequence is recognized by an RNA polymerase encoded by the modified viral genome. Alternatively, this promoter might be recognized only by an RNA polymerase encoded by another genome, for example, another viral or cellular genome. For example, this RNA polymerase might be a bacteriophage T7 polymerase that is encoded by another cytoplasmic DNA virus genome or by the genome of a modified host cell. The T7 polymerase and promoter have been used, for instance, in recombinant poxviruses to enhance expression of an inserted DNA sequence. See, for example, Fuerst et al., *J. Mol. Biol.* 205:333–348 (1989). Provision of the T7 RNA polymerase on a separate genome is used to prevent expression of a DNA sequence inserted into the modified poxvirus genome except when the separate genome is present.

In still other embodiments, the promoter controlling the insert is suitable for initiation of transcription by a cytoplasmic DNA virus RNA polymerase. In some embodiments, the promoter comprises a modification of a DNA sequence of a naturally-occurring viral promoter. One such embodiment is exemplified by use of a "synthetic" vaccinia virus promoter, such as the "S3A" (bases 21–107 of SEQ ID NO:13) and "S4" (bases 21–114 of SEQ ID NO:14) promoters described, inter alia, in Examples 5 and 6.

The eukaryotic cytoplasmic DNA virus genomic construction method of the present invention further comprises a step of introducing the modified DNA molecule comprising the modified viral genome into a first host cell which packages the modified DNA molecule into infectious modified cytoplasmic DNA virus virions. The modified DNA molecule is introduced into the first host cell by a method suitable for transfection of that first host cell with a DNA molecule, for instance, by methods known in the art for transfection of other DNA's into comparable host cells. For example, in a preferred embodiment, the modified DNA is introduced into the first host cell using the calcium phosphate precipitation technique of Graham and van der Eb, *Virology* 52:456–467 (1973).

In a preferred embodiment, this method for producing a modified eukaryotic cytoplasmic DNA virus further comprises a step of infecting the first host cell with a second cytoplasmic DNA virus comprising a second cytoplasmic DNA virus genome which is expressed to package the modified DNA molecule into infectious modified cytoplasmic DNA virus virions. In the method comprising infection of the first host cell with a second virus, introducing the recombinant DNA molecule into the first host cell is carried out advantageously about one hour after infecting the first host cell with the second virus.

In another embodiment of this method, the necessary packaging functions in the first host cell are supplied by a genetic element other than a complete genome of a second virus, such as a plasmid or other expression vector suitable for transforming the first host cell and expressing the required helper virus functions. Use of a nonviral genetic element to provide helper functions enables production of genetically stable helper cells that do not produce infectious helper virus. Use of such a helper cell as a first host cell for packaging of a modified DNA molecule advantageously produces only virions comprised of that modified DNA.

In the method comprising infection of the first host cell with a second virus, the second virus is selected so that expression of the second viral genome in the first host cell packages the modified DNA molecule into infectious virions comprised of the modified viral genome. Pursuant to the present invention, it is feasible to effect intracellular packaging of a modified DNA comprising a eukaryotic cytoplasmic DNA virus genome by transfection into cells infected with a closely related virus. For instance, DNA of a first poxvirus genus is packaged by a host cell infected with a second poxvirus of the same poxvirus subfamily, whether from the same or a different genus.

In certain embodiments, expression of the second viral genome in the first host cell produces infectious virions comprised of the second viral genome as well as of the modified viral genome. This situation obtains, for instance, in the case of homolgous packaging of a first poxvirus DNA from one genus by a second poxvirus of the same genus. Here, although the transfected DNA theoretically could be packaged directly, i.e., without transcription of the transfected genome, homologous packaging of the transfected DNA molecule probably involves transcription and replication of both the transfected DNA and the DNA of the helper virus. This situation is illustrated, inter alia, with homologous packaging of poxvirus DNA in Examples 1 and 2.

However, in other embodiments expression of the second viral genome in the first host cell does not produce infectious virions comprised of the second viral genome. In cases involving heterologous packaging, for instance, passive packaging alone cannot produce viable virus particles from the transfected DNA. In such a case it is advantageous to select a second (helper) virus which provides an RNA polymerase that recognizes the transfected DNA as a template and thereby serves to initiate transcription and, ultimately, replication of the transfected DNA. This case is exemplified by the reactivation of a modified genome of an orthopoxvirus (vaccinia) vector by an avipox (fowlpox) helper virus in a mammalian first host cell in which the avipox virus is unable to produce infectious virions comprised of the avipoxvirus genome, as described in Example 3.

The use of a heterologous virus to package the modified DNA molecule, such as the use of fowlpox or ectromelia (mouse pox) virus as a helper for vaccinia virus constructs, advantageously minimizes recombination events between the helper virus genome and the transfected genome which take place when homologous sequences of closely related viruses are present in one cell. See Fenner and Comben (1958); Fenner (1959).

In certain embodiments of the method for using a helper virus for DNA packaging, the step of recovering the infectious virions comprised of the modified viral genome comprises a step of infecting a second host cell with infectious virions produced by the first host cell. Advantageously, the second host cell is infected under conditions such that expression of the second viral genome in the second host cell does not produce infectious virions comprised of the second virus genome. In other words, the second host cell is infected under conditions that select for replication of the modified virus and against the helper virus. This method is exemplified by a method in which the modified genome is a modified vaccinia virus genome, the second genome is a fowlpox virus genome, and the second host cell is a mammalian cell. In this method, the modified virus is plaque purified in cultures of the mammalian host cell in which fowlpox virus does not produce infectious virions, as described in Example 3.

In another embodiment in which the second host cell is infected under conditions that select for the modified virus, the modified viral genome comprises a functional host range gene required to produce infectious virions in the second host cell. The second viral genome lacks this functional host range gene. This embodiment is illustrated by a method in which the modified viral genome is a modified vaccinia virus genome comprising a functional host range gene required to produce infectious vaccinia virus in a human (MRC 5) cell which is used as the second host cell, as described in Example 8.

In yet another embodiment involving selection for modified virus in a second host cell, the modified viral genome comprises a selective marker gene which the second viral genome lacks, and the step of infecting the second host cell is carried out under conditions that select for a viral genome expressing the selective marker gene. For example, expression of the selective marker gene in the second host cell may confer on that cell resistance to a cytotoxic drug. The drug is provided during infection of the second host cell at a level sufficient to select for a viral genome expressing the selective marker gene. This approach is exemplified by a method for inserting a gene for the E. coli gpt gene into a vaccinia virus genome, as in Example 1, or a fowlpox virus genome, as in Example 2, using in each case a homologous helper virus lacking the selective marker gene.

In still another embodiment involving selection for a modified virus in a second host cell, the modified viral genome comprises a deletion of a selective marker gene that is present in the second viral genome. Here, the step of infecting the second host cell is carried out under conditions that select against a viral genome expressing that selective marker gene. For example, expression of a poxvirus thymidine kinase (tk) gene in the second host cell (i.e., a thymidine kinase-negative host cell) renders the second (helper) virus sensitive to the metabolic inhibitor, 5-bromo-deoxyuridine. Example 4 describes the use of these inhibitors during infection of a second host cell to select for a vaccinia virus vector (vdTK) in which the tk gene is deleted and replaced by a multiple cloning site.

Another aspect of the present invention relates to a eukaryotic cytoplasmic DNA virus comprised of a modified viral genome. A modified genome of a cytoplasmic DNA virus within the scope of the present invention comprises distinct component DNA sequences which are distinguishable from each other, for example, by routine nucleic acid hybridization or DNA sequencing methods.

In certain embodiments, for instance, the modified viral genome comprises a first genome of a first eukaryotic cytoplasmic DNA virus. This first genome is comprised of a cleavage site for a sequence-specific endonuclease that is a unique site in the first genome. In this embodiment, the sequences of the modified genome that comprises the first viral genome are homologous to a genome of a naturally-occurring eukaryotic cytoplasmic DNA virus. Further, the sequences of this first virus are interrupted by a DNA sequence of interest as defined hereinabove.

To determine whether this sequence is inserted into a unique cleavage site in the first viral genome, as required for this embodiment of a modified viral genome, the sequences immediately flanking the insert are compared with sequences of cleavage sites for sequence-specific endonucleases.

In one form of this embodiment in which a DNA sequence is inserted into a unique cleavage site in the first viral genome, the inserted sequence in the first viral genome is flanked by two identical intact cleavage sites for a sequence-specific endonuclease and these two sites are the only sites for this nuclease in the complete modified genome. Each of these two sites is comprised of combined portions of cleaved sites from the first viral genome and the inserted DNA sequence.

More particularly, each strand of a double-stranded DNA comprised of a cleavage site for a sequence-specific endonuclease may be considered to comprise a complete cleavage site sequence ($S_LS_R$) consisting of a left cleavage site sequence ($S_L$) and a right cleavage site sequence ($S_R$) separated by the monophosphate linkage that is disrupted by cleavage with the appropriate nuclease. In certain forms of this embodiment, insertion of a DNA sequence into a unique restriction site reproduces two complete sites flanking the insert.

In other forms of this embodiment, however, insertion of the DNA sequence into a unique cleavage site does not recreate the original cleavage site at each end of the inserted DNA sequence. See, for instance, the method for elimination of a cleavage site described in Example 6. Thus, the inserted DNA may be flanked at one end (e.g., the left end) by a complete cleavage site ($S_LS_R$) while the right end terminates in a sequence that differs from $S_L$ directly linked to an $S_R$ sequence in the first viral genome. More generally, in any modified viral genome of this invention, the DNA sequence inserted into a unique site in a first viral genome will be flanked by two the matching parts ($S_L$ and $S_R$) of a cleaved site which does not occur in the modified viral genome outside of the inserted DNA.

In other embodiments, the modified viral genome is comprised of a DNA sequence that is inserted between two unique sites in the first viral genome. In this case, if the first viral genome is a naturally-occurring genome of a eukaryotic cytoplasmic DNA virus, the insert will be encompassed by viral sequences separated from the foreign DNA sequence at least by recognizable SL and SR portions of the two different original cleavage sites.

In additional embodiments, the modified viral genome comprises a unique cleavage site located in a DNA sequence that is not naturally-occurring in a genome of a eukaryotic cytoplasmic DNA virus. In this case, this foreign DNA is not separated from the natural viral DNA sequences by recognizable $S_L$ and $S_R$ portions of cleavage sites. In certain forms of this embodiment, the first foreign DNA sequence is interrupted by a second foreign DNA sequence inserted into a unique cleavage site in the first sequence or between two such sites in the first sequence. In these embodiments the second foreign DNA is separated from the first foreign DNA sequences by recognizable $S_L$ and $S_R$ portions of sequence-specific endonuclease cleavage sites. In this case, all sequences surrounding this second foreign DNA sequence comprise the genome of the first virus according to this invention.

Preferred embodiments of modified eukaryotic cytoplasmic DNA viruses of this invention include a first major embodiment in which the modified viral genome comprises (I) a first genome of a first eukaryotic cytoplasmic DNA virus that is comprised of a cleavage site for a sequence-specific endonuclease. This site is a unique site in the first viral genome. The modified viral genome of this embodiment also comprises (II) a first DNA sequence of interest. This DNA sequence is inserted into the unique site in the first cytoplasmic DNA virus genome.

In one variation of this first embodiment of a modified eukaryotic cytoplasmic DNA virus, the first viral genome comprised of the unique site is a naturally-occurring viral genome. This variation is exemplified herein by a modified poxvirus genome comprised of a naturally-occurring vaccinia virus genome which has unique cleavage sites for the bacterial restriction endonucleases NotI and SmaI, as described in Examples 1 and 3. In this embodiment, the first DNA sequence of interest, which is inserted into the unique site, is exemplified by an *E. coli* gpt gene driven by a naturally-occurring vaccinia virus promoter inserted into the NotI site (Example 1) or into the SmaI site (Example 3) of a vaccinia virus genome.

In a second form of this first embodiment of a modified virus, the first viral genome comprised of the unique site also comprises a second DNA sequence not naturally-occurring in a viral genome. Furthermore, this second DNA sequence includes the unique site for insertion of the first DNA sequence. This variation is exemplified herein by a modified fowlpox virus genome comprising a DNA sequence encoding an *Escherichia coli* β-galactosidase gene, as described in Example 2. This bacterial gene includes a cleavage site for the bacterial restriction endonuclease NotI that is unique in the modified fowlpox virus genome and, therefore, is particularly convenient for insertion of foreign DNA sequences.

In another variation of this first embodiment of a modified virus, at least a portion of the first DNA sequence that is inserted into the unique site is under transcriptional control of a promoter. In some instances, the promoter is located in the first DNA sequence that is inserted into the first viral genome. This holds, for instance, when the inserted DNA comprises a gene cassette including a promoter and a functionally linked gene, as described, inter alia, in Examples 1 and 2.

In a second embodiment of a modified cytoplasmic DNA virus of this invention, the modified viral genome comprises (I) a first viral genome comprised of a first and a second cleavage site for a sequence-specific endonuclease where each of these sites is unique in the first virus genome. In one preferred variation of this embodiment, the first viral genome comprises a multiple cloning site comprised of several unique cleavage sites.

In this second embodiment, the modified viral genome also comprises (II) a first DNA sequence not naturally-occurring in a genome of a eukaryotic cytoplasmic DNA virus, and this first DNA sequence is inserted into the first viral genome between the first and second unique cleavage sites.

In a third embodiment of a modified cytoplasmic DNA virus of this invention, the modified viral genome comprises (I) a first viral genome comprised of a first DNA sequence not naturally-occurring in a genome of a eukaryotic cytoplasmic DNA virus. This first DNA sequence is comprised of a cleavage site for a sequence-specific endonuclease that is a unique site in the modified viral genome. The modified viral genome of this embodiment further comprises (II) a promoter located such that a DNA sequence inserted into the unique site is under transcriptional control of the promoter. This first DNA sequence does not have a translation start codon between the promoter and the unique site used for insertion of a DNA sequence. This embodiment is exemplified by the vaccinia virus vector (vS4) described in Example 6, which has a "synthetic" poxvirus promoter located such that this promoter controls transcription of a DNA sequence inserted into a multiple cloning site designed for insertion of open reading frames.

Another aspect of the present invention relates to a DNA molecule comprising a modified viral genome of a modified eukaryotic cytoplasmic DNA virus of this invention. In a preferred embodiment, this DNA molecule is prepared by extraction of genomic DNA molecules from virions of a modified eukaryotic cytoplasmic DNA virus of this invention, or from cells infected with a modified virus of this invention. Methods suitable for extracting modified viral genomic DNA's from virions are known in the art. In addition, suitable methods for preparing DNA of eukaryotic cytoplasmic DNA viruses are described herein in Example 1.

Still another aspect of the present invention relates to genomic DNA arms of a eukaryotic cytoplasmic DNA virus of this invention. These genomic DNA arms are useful for direct molecular cloning of viral genomes comprising foreign DNA's. More particularly, this aspect of the invention relates to two DNA molecules, the left and right genomic arms of a modified viral genome of a eukaryotic cytoplasmic DNA virus. In the practice of the direct cloning method of this invention, described above, either one or both of these arms may consist entirely of a DNA sequence that is naturally-occurring in a cytoplasmic DNA virus. But the novel DNA molecule of the present aspect of this invention is a modified arm of a viral genome, in other words, a DNA molecule comprising one end of a modified viral genome of a eukaryotic cytoplasmic DNA virus. This end of the modified viral genome comprises a DNA sequence of interest which distinguishes this DNA molecule from genomic arms consisting of only a sequence that is naturally-occurring in a cytoplasmic DNA virus. In addition, the modified viral genome from which the novel arm derives is comprised of a unique cleavage site for a sequence-specific endonuclease. Furthermore, this DNA molecule has a terminus that is homologous to a product of cleaving the unique site in the modified viral genome with the sequence-specific endonuclease.

In a preferred embodiment, this DNA molecule comprising a genomic arm is produced by cleavage of genomic DNA of a modified virus at a unique site for a sequence-specific endonuclease. Alternatively, this DNA molecule may be produced by modifying another DNA molecule to produce a terminus that is homologous to a terminus produced by cleaving a unique site in a modified viral genome. For instance, a DNA molecule according to this aspect of the invention may be produced from an arm of a naturally-occurring genomic viral DNA. The required DNA molecule may be produced from such a naturally-occurring viral arm, for example, by ligation to a synthetic "adaptor" DNA segment comprised of a cohesive end derived from cleavage site that is not present in the first viral genome. In this instance the end of the first viral genome and the ligated adaptor together comprise one end of a modified viral genome. Accordingly, this particular DNA molecule is not produced by cleavage of a modified viral genomic DNA, but it does comprise a terminus that is homologous to a terminus that is produced by cleaving a unique site in a modified viral genome.

In another embodiment of a modified viral DNA arm of the present invention, the DNA sequence not naturally-occurring in a genome of a eukaryotic cytoplasmic DNA virus is comprised of the cleavage site for a sequence-specific endonuclease that is unique in the modified viral genome. This cleavage site further comprises a left cleavage site sequence ($S_L$) for the left genomic arm, or the right cleavage site sequence ($S_R$) for the right genomic DNA arm, occurring complete cleavage site sequence ($S_LS_R$) being unique in the modified viral genome. This embodiment is exemplified, inter alia, by DNA arms produced from a fowlpox virus vector by the bacterial restriction endonuclease NotI, as described in Example 2, or by arms of a vaccinia virus vector (vS4) cleaved at any of several unique sites of an inserted multiple cloning site, as described in Example 6.

Yet another aspect of the present invention relates to a kit for direct molecular cloning of a modified viral genome of a eukaryotic cytoplasmic DNA virus. This kit comprises (I) purified DNA molecules of this invention. These DNA molecules comprise either genomic viral DNA arms of this invention or a complete, intact modified viral genome of this invention, or both. The viral DNA arms are useful for direct ligation to foreign DNA segments to be cloned, while the intact viral DNA's are useful for cloning after cleavage, for instance, with a sequence-specific endonuclease at a site that is unique in the modified viral genome.

The kit further comprises (II) a DNA ligase and (III) solutions of a buffer and other reagents suitable for ligation of DNA segments together to produce a modified DNA molecule comprising said modified viral genome. A suitable buffer and reagents for ligation are described, for instance, in Example 1.

In one embodiment, this kit further comprises a plasmid comprised of a gene expression cassette flanked by sites for cleavage with a sequence-specific endonuclease. When cleaved by the appropriate sequence-specific endonuclease, the sites flanking the cassette produce ends that are compatible for insertion of this cassette into a unique cleavage site of the modified viral genome that is encoded by the DNA molecule.

In another embodiment, the cloning kit further comprises a first host cell and a second (helper) virus suitable for packaging the modified viral genome into infectious virions.

Yet another aspect of the present invention relates to plasmids which are particularly suited to serve as intermediates in the construction of modified cytoplasmic DNA virus vectors of this invention.

According to one embodiment of this aspect, there is provided a plasmid comprising a DNA segment having at each end the same cleavage site for a sequence-specific endonuclease. This site is also a unique site in a first cytoplasmic DNA virus genome according to the present invention. This DNA segment comprises a multiple cloning site comprised of several closely adjacent sequence-specific endonuclease cleavage sites that are unique in the plasmid and, therefore, useful for insertion of foreign DNA segments into the plasmid.

This plasmid is useful for insertion of genes into a unique cleavage site of the DNA segment for subsequent transfer of that segment into a unique cleavage site of a cytoplasmic DNA virus using the direct molecular cloning method of this invention. This plasmid is exemplified by the plasmid pN2 (see Example 1, FIG. 1.3) which has a DNA segment comprising a multiple cloning site flanked by NotI sites and containing the following additional bacterial restriction enzyme cleavage sites in the stated order: XbaI, SpeI, BamHI, SmaI, PstI, EcoRI, EcoRV, HindIII and ClaI.

Another plasmid of the present invention comprises a DNA segment having at each end a cleavage site that is a unique site in a cytoplasmic DNA virus. The DNA segment of this plasmid also comprises several restriction enzyme cleavage sites that are unique in the plasmid. This DNA segment further comprises a selective marker gene (e.g., an *E. coli* gpt gene) under transcriptional control of a cytoplasmic DNA virus promoter (e.g., the vaccinia virus P7.5 promoter). This plasmid is exemplified by two plasmids designated pN2-gpta and pN2-gptb which contain a DNA segment flanked by NotI sites and comprising an E. coli gpt gene under transcriptional control of a vaccinia virus P7.5 promoter. This plasmid was created by insertion of the promoter-gene cassette into the SmaI site of the plasmid pN2, as described in FIG. 1.3.

In a further modification of the above plasmid, the DNA segment further comprises a second poxvirus promoter operatively linked to a DNA sequence comprising a restriction endonuclease cleavage site. This plasmid, as exemplified by the plasmid pN2gpt-S3A (FIG. 4.6) can be used to insert open reading frames lacking their own initiation codon for transfer into a vaccinia virus vector. Similarly, the plasmid pN2gpt-S4 (FIG. 4.6) can be used to insert complete open reading frames including an AUG translation start codon.

In another embodiment, this plasmid further comprises a DNA sequence encoding human plasminogen, wherein the DNA sequence is operatively linked to the poxvirus promoter and start codon. This plasmid is exemplified by plasmid pN2gpt-GPg, encoding human glu-plasminogen, and by plasmid pN2gpt-LPg, encoding lys-plasminogen, in which the coding region for amino acids 1–77 of human plasminogen is deleted (FIGS. 5.2 and 5.3).

In a related form, this plasmid further comprises a DNA sequence encoding HIV-1 gp160, wherein the DNA sequence is operatively linked to the poxvirus promoter and start codon. This is exemplified by plasmid pN2gpt-gp160, having the gp160 gene controlled by the synthetic vaccinia virus promoter S4 (FIG. 5.4).

Another plasmid of the present invention comprises a segment of a cytoplasmic DNA virus genome in which the viral tk gene is located. In this plasmid, the coding region of the tk gene has been modified (deleted) to prevent expression of active tk enzyme. This plasmid is useful as an intermediate in construction of a cytoplasmic DNA virus vector having a defective tk gene, using conventional methods of marker rescue, as described for the vaccinia virus tk gene, using plasmid pHindJ-3. In a related embodiment, a plasmid comprising a modified tk gene region of a cytoplasmic DNA virus further comprises a multiple cloning site comprised of several closely adjacent sequence-specific endonuclease cleavage sites that are unique in the plasmid. Furthermore, each of these sites is absent in a cytoplasmic DNA virus into which the modified tk gene region is to be inserted. Therefore, after insertion of the modified tk gene region comprising these unique sites into that viral genome, these sites are useful for insertion of foreign DNA segments into the cytoplasmic DNA virus genome carrying the modified tk gene region, according to the direct cloning method of the present invention.

This plasmid comprising a modified tk gene region containing a multiple cloning site is exemplified by plasmid pHindJ-3 in which the modified vaccinia virus tk gene region of plasmid pHindJ-2 has inserted a multiple cloning site with the unique sites NotI, SmaI, ApaI and RsrII, flanked by SfiI sites (FIG. 4.2). To further facilitate forced cloning in a vaccinia virus vector, each of the two SfiI sites is also made unique in the vector by exploiting the variable nature of the SfiI recognition sequence, as detailed in Example 4.

In still another embodiment, a plasmid comprises a sequence-specific endonuclease cleavage site that is unique in the genome of that virus. Such plasmids are particularly suitable for construction of gene expressions cassettes for transfer into a vector having the aforementioned unique site. The plasmid pA0 exemplifies the basic plasmid that contains a master cloning site comprised of the unique sites of the master cloning site of the vdTK vaccinia virus vector (FIG. 4.3). The related plasmids pA1 and pA2 were designed for insertion of DNA segments, for instance, synthetic or natural promoter fragments and were constructed by inserting into the XhoI site of pA0 a linker comprising a second multiple cloning site of frequently cutting enzymes that do not cleave pA0. Both plasmids have the same structure except for the orientation of the second multiple cloning site (FIG. 4.3).

In yet another embodiment, a plasmid comprises a poxvirus promoter operatively linked to a translational start codon, wherein this start codon is immediately followed by a second restriction endonuclease cleavage site suitably arranged to permit translation of an open reading frame inserted into the second restriction endonuclease cleavage site. This plasmid is exemplified by plasmids pA1-S1 and pA2-S1 (comprising SEQ ID NO:10) which provide the strong synthetic poxvirus promoter S1 (bases 21–194 of SEQ ID NO:9), including a translational start codon, followed by a single EcoRI site suitable for insertion of open reading frames that do not have an associated start codon (FIGS. 4.4A and 4.4B). Plasmids pA1-S2 and pA2-S2 are similar to pA1-S1 and pA2-S1 but have a different poxvirus promoter, S2 (FIGS. 4.5A and 4.5B, bases 21–73 of SEQ ID NO:11).

In a related embodiment, the plasmid above further comprises a DNA sequence encoding human prothrombin, wherein said DNA sequence is operatively linked to said poxvirus promoter and said start codon. This plasmid is exemplified by the plasmid pA1S1-PT (FIG. 5.1) in which a modified prothrombin cDNA is inserted into the single EcoRI site of the plasmid pA1-S1.

Another plasmid of the present invention comprises a modified EcoRI K fragment of vaccinia virus DNA from which the K1L host range gene is deleted. The helper virus vdhr lacking both the K1L and C7L host range genes is constructed from the C7L-negative strain WR-6/2 by marker rescue with a modified EcoRI K fragment from which the K1L host range gene is deleted. See FIG. 8.1. This modified EcoRI K fragment comprises a selective marker gene (the *E. coli* gpt gene) to facilitate selection for recombinant WR-6/2 genomes comprising the modified EcoRI K fragment using intracellular marker rescue as described by Sam and Dumbell (1981). The exemplifying plasmid is designated pEcoK-dhr (FIG. 8.1).

In a further step pEcoK-dhr is linearized with NotI and ligated with a 1.1 kb P7.5-gpt gene cassette derived from plasmid pN2-gpta (Example 4) by NotI digestion. The resulting plasmid pdhr-gpt (FIG. 8.1) is used in marker rescue experiments to generate the helper virus vdhr according to the marker rescue method of Sam and Dumbell (1981).

The present invention is further described below with regard to the following illustrative examples. Certain constructs are illustrated with tables detailing their characteristics. In those tables, the following abbreviations are used:

CDS=coding sequence rc=reverse complementary sequence rcCDS=reverse complementary coding sequence; arabic numbers are positions of nucleotides ATG=translational start codon EMBL ID=Identifier in EMBL DATABANK

EXAMPLE 1

Direct molecular cloning of foreign DNA comprising a selective marker gene (the gpt gene of *E. coli*) into a unique (NotI) cleavage site in the genome of an orthopoxvirus (vaccinia)

This example demonstrates direct molecular cloning of a gene expression cassette into a poxvirus genome, according to the present invention, by intracellular packaging of genetically engineered poxvirus DNA. In addition, this example illustrates use of a genetic selection procedure for efficient recovery of modified vaccinia viruses containing an inserted selective marker gene. The experimental results also reveal that recombination frequently occurs between the DNA to be packaged and that of the infecting helper virus during packaging when the helper virus DNA is homologous with the DNA to be packaged.

More particularly, a first direct molecular cloning experiment described below shows that a marker gene (gpt-gene) cassette can be inserted as a NotI restriction fragment in NotI-cleaved vaccinia virus DNA and subsequently packaged in vaccinia virus-infected mammalian cells. One of nine plaques examined comprised virus having the predicted structure for a single insert of the gpt-gene in the "a" orientation (see FIG. 1.11). The structure of this clone (designated vp7) was stable during large scale replication in the absence of the selection agent.

In a second series of cloning experiments, seven of twelve clones examined had the expected structure. In this series, however, four small plaques (E1–E4) of slowly replicating viruses were included, although preferably these are not normally selected in the practice of the present invention. Recombinants having multiple inserts of the selective marker gene were also obtained under selective conditions. The stability of these multiple inserts was not examined in the absence of the selective agent which is known to stabilize certain otherwise unstable structures. See Falkner and Moss, *J. Virol.* 64:3108–3111 (1990).

The relatively low yield of predicted structures is not expected given the known precision of genetic engineering methods for site-specific cleavage and ligation of DNA molecules. However, the particular sequence selected for insertion in this model system, the gpt-gene cassette, comprised vaccinia virus DNA sequences of the P7.5 promoter which are homologous to two endogenous promoters in the vaccinia vector which drive two vaccinia virus 7.5-kD polypeptide genes located within the inverted terminal repetitions of the vaccinia genome. See Venkatesan et al., *Cell* 25:805–813 (1981). This P7.5 promoter has been used to construct vaccinia virus recombinants by conventional intracellular recombination and can be stably integrated into the vaccinia thymidine kinase gene. Mackett and Smith (1986). Occasionally, however, submolar amounts of DNA fragments appear during analyses of conventional recombinants, which may result from secondary recombination events. Where a P7.5 promoter is inserted near the endogenous P7.5 promoters (i.e., within several kilobases), only recombinants that have an inverted repeat structure are stable, and this observation has been exploited to develop a deletion procedure based on insertion of a tandemly repeated P7.5 promoter segment. Spehner et al., *J. Virol.* 64:527–533 (1990).

In the present case of insertion of the gpt-gene cassette into the NotI site of vaccinia virus, the distance between the P7.5 promoters of the left inverted terminal repetition and that of the inserted cassette is about 30 kb, probably close enough to cause destabilizing secondary recombination events. In fact, only the structures of a few slowly replicating, unstable clones had an insert in the "b" orientation which would produce a tandem repeat arrangement of the inserted and endogenous promoters. Thus, the rare occurrence of this structure can be explained most likely by the closeness of the locations of the P7.5 promoters of the gpt-gene cassette and the endogenous P7.5 promoters and the known instability of tandemly repeated copies of the P7.5 promoter.

In contrast, the virus vp7 and several other isolates (A1, A4, C1 and C2) had inserts in the "a" orientation and were stable. The structural analysis of one isolate, C4, was consistent with a head-to-tail double insert.

The titers of packaged gpt-gene positive viruses in the second series of cloning experiments (five different samples) were approximately $1\times10^5$ pfu per $8\times10^6$ cells, while in the first experiment a titer of $1–2\times10^2$ pfu was obtained from the same number of cells. The titer of modified viruses will be influenced by several factors, including ligation and packaging efficiencies, reaction and culture conditions in the cloning procedure, and by the amount of care taken to avoid shearing of the high molecular vector DNA during handling. Titers of about $10^5$ plaque forming units (pfu) per $8\times10^6$ cells are generally expected under the standard conditions described hereinbelow.

While the present example shows that the unique intergenic NotI site of vaccinia virus can be used for insertion of foreign DNA, it also illustrates the need to consider whether a proposed insert may contain viral sequences of a type and orientation that are known or likely to cause instability of modified viruses. Inserts lacking homology with viral sequences near the insertion site (e.g., within 30 kb) are to be preferred for stability. Accordingly, inserts comprising only short synthetic promoter sequences that are recognized by the transcription system of the vector are preferred to those containing large segments of viral DNA including natural promoters of the viral vector. See, for instance, the S1 promoter in Example 4, below.

The following materials and methods were used throughout this and all subsequent examples, except where otherwise specified.

Purification of orthopox virus and DNA: Vaccinia virus (wildtype Western Reserve (WR) strain; American Type Culture Collection No. VR 119) was purified by two successive sucrose gradients according to Mackett et al. in *DNA CLONING: A PRACTICAL APPROACH*, ed. D. Glover, IRL Press (1985) p. 191–211. Viral DNA was prepared by the proteinase K-SDS procedure according to Gross-Bellard et al., *Eur. J. Biochem.* 36:32–38 (1973).

Engineering of isolated poxvirus DNA: Viral DNA (typically 2 to 5 μg) was cleaved with appropriate amounts of one or more sequence-specific endonucleases (for example, the bacterial restriction endonuclease NotI), optionally treated with calf intestine alkaline phosphatase (Boehringer, Inc.), and purified by phenol extraction and ethanol precipitation, according to routine recombinant DNA methods. The resulting viral DNA arms were ligated with a five to fifty-fold molar excess of the DNA fragment to be inserted, having ends compatible for ligation with the viral arms. An aliquot of the ligation reaction was analyzed by field inversion gel electrophoresis.

More particularly, in the second series of experiments (A–E) described below, 2 μg of NotI-digested vaccinia DNA that was not treated with phosphatase were ligated with 200–600 ng of gpt-gene cassette insert in a volume of 30 μl with 5–15 units of T4 ligase for 48 h at 12° C., as summarized in Table 1.

In vivo packaging in mammalian cells: $8\times10^6$ African Green monkey (CV-1) cells were infected with helper virus (either vaccinia WR wildtype or WR6/2 virus, or other viruses as indicated) at 0.2 pfu/cell for 2 h. For the initial demonstration of packaging with intact DNA isolated from virions, 20 μg of viral (vPgD) DNA were used. For packaging of extracellularly engineered genomes, 1 μg of DNA purified from a ligation reaction were used. DNA's were transfected into cells by the calcium phosphate precipitation technique. Graham and van der Eb (1973). The cells were incubated for 15 min at room temperature and then nine ml of medium (DMEM, 10% fetal calf serum, glutamine and antibiotics) per one ml precipitate were added to the cells. After four hours the medium was changed and further incubated for two days.

Crude virus stocks were prepared according to standard procedures. Mackett et al., 1985. Plaque assays and selection conditions for the *E. coli* gpt gene are known in the art. See Falkner and Moss, *J. Virol.* 62:1849–1854 (1988); Boyle and Coupar, *Gene* 65:123–128 (1988).

Field inversion gel electrophoresis (FIGE). Viral DNA was separated on a 1% agarose gel in Tris/Acetate/EDTA buffer (40 mM Tris/20 mM glacial acetic acid/2 mM EDTA, pH 8.0) with a microcomputer controlled power supply (Consort Model E790). To separate the whole range of fragments, four programs were run successively, as follows: program 1–5 h at 7 V/cm forward pulse (F) 6 sec, reverse pulse (R) 3 sec, pause 1 sec; program 2–5 h at 7 V/cm, F 4 sec, R 2 sec, pause 1 sec; program 3–5 h at 7 V/cm, F 2 sec, R 1 sec, pause 1 sec; and program 4–5 to 10 h at 7 V/cm, F 8 sec, R 4 sec, pause 1 sec.

Construction of plasmid pN2: The plasmid Bluescript II SK$^-$ (Stratagene, Inc.) was digested with HindII and ligated to NotI linkers (Pharmacia, Inc.). The resulting plasmid, pN2, has a multiple cloning site flanked by NotI sites.

More particularly, the multiple cloning site of pN2 consists of the following sites in the stated order: NotI, XbaI, SpeI, BamHI, SmaI, PstI, EcoRI, EcoRV, HindIII, ClaI and NotI. The inserted NotI linker sequence of pN2 and twenty bases of the 5' and 3' flanking regions of pBluescript II SK- (Stratagene, Inc. La Jolla, USA) are shown in SEQ ID NO:1. The insert sequence starts at position 21 and ends at position 28. The first "T" residue at the 5'-end corresponds to position number 2266, the last "G" residue at the 3'-end to position number 2313 of the plasmid pN2.

Construction of plasmids pN2-gpta and pN2-gptb: The 1.1 kb HpaI-DraI fragment (containing the P7.5 promoter-gpt gene cassette) was isolated from the plasmid pTKgpt-F1s and inserted into the SmaI site of the plasmid pN2 (FIG. 1.3). Falkner and Moss, 1988. The two resulting plasmids are orientational isomers and were designated pN2-gpta and pN2-gptb. The vaccinia virus P7.5 promoter-*E. coli* gpt-gene cassette and twenty bases of the 5'-and 3'-flanking regions of pN2 are shown for pN2-gpta in SEQ ID NO:2. The insert starts at position 21 and ends at position 1113. The A-residue of the translational initiation codon of the gpt gene corresponds to position 519. The T-residue of the translational stop codon of the gpt gene corresponds to position number 975. (The first "C" residue at the 5'-end corresponds to the position number 2227, the last "T" residue at the 3'-end to position number 3359 of the plasmid pN2-gpta).

The reverse complementary form of the vaccinia virus P7.5 promoter-*E. coli* gpt gene cassette and twenty bases of the 5'- and 3'-flanking regions of pN2 are shown for pN2-gptb in SEQ ID NO:3. The insert starts at position 21 and ends at position 1113. The T-residue of the (reverse complement of the) translational initiation codon CAT corresponds to position 615. The A-residue of the (reverse complement of the) translational stop codon of the gpt gene corresponds to the position number 159.

Other standard techniques of recombinant DNA analysis (Southern blot analysis, PAGE, nick translation, for example) were performed as described. See Sambrook et al., *MOLECULAR CLONING*, Cold Spring Harbor Laboratory Press (1989).

Packaging of naked viral DNA: To establish conditions needed for packaging of naked poxvirus DNA by a helper virus, intact DNA isolated from virions of an exemplary recombinant vaccinia virus (vPgD) was transfected into monkey (CV-1) cells infected with a helper virus (vaccinia WR wildtype). The selected recombinant virus has several readily assayable phenotypic markers, Thus, the vPgD genome has incorporated into the viral tk locus a gene for a drug resistance marker (a gene for the enzyme xanthine-guanine-phosphoribosyl-transferase of *Escherichia coli*, i.e., the "gpt" gene) and a gene for a conveniently detected marker protein (human plasminogen). This virus was originally constructed from the vaccinia virus strain WR 6/2, described by Moss et al., *J. Virol.* 40:387–95 (1960), which has a deletion of about 9 kb and, consequently, does not express the viral major secreted 35K protein gene, as described by Kotwal et al., *Nature* 335:176–178 (1988). The expected phenotype of the packaged virus, therefore, includes: tk-negative (i.e., replication in the presence of bromodeoxy-uridine), gpt-positive (i.e., replication in the presence of mycophenolic acid and xanthine), positive for the expression of the human plasminogen gene and negative for the expression of the secreted 35K protein.

Eight gpt-positive plaques from the above packaging experiment were analyzed. All were tk-negative, and, as shown in FIG. 1.1, all expressed plasminogen. Six of these isolates (lanes 5, 6, 7, 11, 12 and 14) did not express the 35K secreted vaccinia protein and thus showed all the characteristics of the transfected genomic DNA. Two of the plaques also expressed the 35K protein marker (lanes 4 and 13) and therefore were recombinants between the helper wild-type virus (lanes 8 and 15) and the input viral genomes.

This experiment established that naked poxvirus DNA extracted from virions is packaged when transfected into helper virus-infected cells under the tested conditions. Therefore, these conditions were employed for transfection of genomic poxvirus DNA that had been modified by direct molecular cloning, as outlined in FIG. 1.2.

Packaging of extracellularly engineered poxvirus DNA: The genome of vaccinia virus contains a single cleavage site for the NotI sequence-specific endonuclease in the region known as the HindIII F fragment. Inspection of the sequence around this site, identified by Goebel et al. (1990), revealed that it is located in an intergenic region that is unlikely to be essential for viral replication. A marker gene expression cassette was constructed in two plasmids (pN2-gpta and pN2-gptb; FIG. 1.3) by insertion of the *E. coli* gpt gene in each of the two possible orientations. The gpt gene was controlled by the promoter of the vaccinia virus gene coding for the 7.5 kDa protein described in Cochran et al., *J. Virol.* 54:30–37 (1985) (labeled P1 in FIG. 1.2 and P7.5 in FIG. 1.3). The entire marker gene cassette resided on a single 1.1 kb NotI fragment of these plasmids. This restriction fragment from pN2-gpta was ligated with NotI digested WR wildtype DNA and transfected into cells that had been infected with helper virus (WR).

In a first cloning experiment, Southern blot analyses of the genomic structures of phenotypically gpt-positive progeny plaques was carried out. The viral isolates were plaque-purified three times and amplified under gpt-selection. The HindIII-digested DNA fragments of cells (CV-1) infected with the different viruses were separated on a 1% agarose gel by a combination of normal electrophoresis and field inversion gel electrophoresis. The gel was then blotted and hybridized with $^{32}$P-labelled vaccinia WR DNA and a labelled probe containing gpt sequences. The results confirmed that all phenotypically marker-positive clones contained the 1.1 kb gpt insert.

FIG. 1.4 shows blots of HindIII DNA fragments from cells infected with the nine virus isolates (lanes 4–12); plaques 2.1.1 to 7.1.1 and 10.1.1 to 12.1.1). The expected 0.8 kb HindIII fragment that contains the gpt sequences can be observed. In lanes 2 and 3, where HindIII-digested wild-type virus DNA (100 and 50 ng, respectively) were loaded, no cross-hybridization to viral sequences was visible.

In the next experiment, total DNA's of CV-1 cell cultures infected with the nine different plaques were digested with NotI. The Southern blot analysis of the separated fragments is shown in FIG. 1.5. Unexpectedly, two bands were visible in most virus isolates, the predicted 1.1 kb insert and a second, larger fragment. Only plaque number 7.1.1 (lane 8) showed the expected single 1.1 kb band. While the hybridization signal of the larger fragment is equally strong in all examined DNA's, the intensity of the 1.1 kb band varied from DNA to DNA, indicating that the 1.1 kb insert may be present in different molar amounts in different genomes. The wildtype virus control (lane 2) did not hybridize to the gpt-gene probe.

The same blot was also hybridized with a vaccinia virus DNA probe. Three fragments are expected, of about 145 kb, 45 kb and 1.1 kb. The blot patterns obtained included the expected bands but also showed an additional band at about 5 kb. Only plaque 7.1.1 did not have the unexpected 5 kb band.

The orientation of the DNA insert in selected engineered vaccinia genomes was also investigated by Southern blot analysis. As shown in FIG. 1.2, the insert in viral DNA's may be in either the "a" or "b" orientations which are distinguishable by digestion of the DNA's with appropriate restriction enzymes. Following preliminary analyses, isolate 7.1.1 was designated clone vp7, appeared to have the genomic structure of the expected modified virus and therefore was expanded and purified. The DNA of this clone was compared with that of wildtype virus by digestion with several restriction enzymes and separation on an agarose gel by field inversion gel electrophoresis (FIG. 1.6). In a NotI digest of vp7 stained with ethidium bromide (lane 2), only the 145 kb and 45 kb bands contained sufficient DNA mass to be visible, since the band for the 1.1 kb insert was estimated to contain only about 3 ng DNA. However, hybridization with a gpt-specific probe revealed a weak band at 1.1 kb (FIG. 1.7, lane 2). In digests with HindIII, the expected bands at 1.4 and 0.8 kb were observed. As predicted, the 0.8 kb band hybridized with the gpt-gene probe (FIGS. 1.6 and 1.7, lanes 4). In double digests with NotI and HindIII, the expected 0.8 kb fragment was also observed (FIGS. 1.6 and 1.7, lanes 6).

In digests of vp7 DNA with PstI, a predicted 4.1 kb fragment containing gpt sequences was observed (FIGS. 1.6 and 1.7, lanes 8; the 4.1 kb ethidium bromide-stained band in FIG. 1.6 is actually a doublet of 4.1 kb fragments, one of which contains the gpt insert). Upon cleavage with both PstI and NotI, the gpt gene cassette was released as a 1.1 kb fragment (FIGS. 1.6 and 1.7, lanes 10).

The patterns of digests obtained with these and other restriction nucleases, including SalI (FIGS. 1.6 and 1.7, lanes 12), are consistent with the interpretation that vp7 is a stable modified virus that has the gpt-gene integrated into the NotI site of the vaccinia virus genome in the "a" orientation (see FIG. 1.11).

A second series of cloning experiments were done under slightly modified conditions (see Table 1 and methods, above). Five different ligation reactions (A–E) were set up containing constant amounts of NotI-cleaved vaccinia vector DNA and increasing amounts of insert DNA. Packaging was done under standard conditions in vaccinia virus-infected CV-1 cells. The titers of gpt-positive vaccinia viruses in all cases were about $1\times10^5$ pfu per $8\times10^6$ cells. The plaque population in all cloning experiments was heterogeneous in size: about half had a normal size while the other half were smaller than normal.

TABLE 1

| Effect of ratio of insert to vector DNA on yield of modified viruses | | | | | |
|---|---|---|---|---|---|
| Experiment | A | B | C | D | E |
| NotI-cleaved | 2 | 2 | 2 | 2 | 2 |
| vector DNA ($\mu$g) | 0.2 | 0.2 | 0.4 | 0.4 | 0.6 |
| gpt-gene insert ($\mu$g) | | | | | |
| insert molar excess | 17 | 17 | 34 | 34 | 51 |
| T4 ligase (units) | 5 | 15 | 5 | 15 | 15 |
| gpt-positive virus ($10^5$) (pfu/8 × $10^6$ cells) | 1.12 | 0.88 | 0.96 | 0.96 | 1.16 |

Twelve gpt-positive plaques were isolated, four each in three series designated series A, C and E, comprising 8 normal-sized (large) plaques (A1-4 and C1-4) and 4 small plaques (E1-4). Each of these plaques was analyzed by infecting CV-1 cells in gpt-selective medium, isolating total cell DNA's and digesting them with restriction nucleases, separating the fragments by FIGE and blotting the onto a nitrocellulose membrane.

In FIG. 1.8, the NotI-digested DNA samples hybridized with the vaccinia virus DNA probe are shown (A1-4, lanes 1–4; C1-4, lanes 5–8; E1-4, lanes 9–12). Due to overloading of the gel, the bands smeared somewhat but the essential features are clearly visible. The 145 kb and the 45 kb bands provided the main signal. A weak band at about 5 kb of unknown origin can be seen in some of the samples. The 1.1 kb band, comprising the P7.5-promoter-gpt gene cassette, makes up only 0.6% of the viral genome and contains only 300 bp of hybridizing sequence (i.e., the P7.5 promoter). Therefore, this band was not expected to give a detectable hybridization signal under the conditions used. In a longer exposure of the blot, when the larger bands are heavily overexposed, the 1.1 kb bands did become visible.

As to the nature of the small plaque phenotype, small plaques E1, E3 and E4 produced only weak hybridization signals (FIG. 1.8, lanes 9–12) indicating that the virus in these plaques had not replicated as extensively as those in normal-sized plaques (lanes 1-8), while isolate E2 failed to produce a detectable amount of DNA (lane 10).

The samples shown in FIG. 1.8 were also hybridized with the gpt gene probe (FIG. 1.9). The expected single hybridization signal was obtained with plaques A1, A4, C1, C2, C4, E3 and E4 (FIG. 1.9, lanes 1, 4, 5, 6, 8, 11 and 12). The plaque A2 (lane 2) had the gpt gene integrated into the 45 kb band. (The weak signal in the 145 kb band may be due to contamination with a second minor species or to secondary recombination events.) The plaque A3 (lane 3) has gpt gene sequences integrated into the 145 kb and 45 kb bands, while the plaque C3 (lane 7) has an integration of those sequences into the 145 kb band and into the NotI site. The plaques A2, A3 and C3 are probably recombinants that arose by illegitimate intracellular recombination of homologous sequences present in the model gene cassette insert and in the inverted repetitions of the viral DNA.

As with the vaccinia virus DNA probe, the small plaques E1–E4 produced only weak hybridization signals (FIG. 1.9, lanes 9–12) indicating that the virus in these plaques had not replicated as extensively as those in normal-sized plaques. The wildtype virus DNA and uninfected CV-1 cell DNA did not hybridize with the gpt gene probe (FIG. 1.9, lanes 13 and 15).

The orientation and copy number of the gpt gene inserts were determined by digesting the samples shown in FIG. 1.9 with PstI and Southern blot analysis. The expected sizes of new PstI fragments resulting from insertion of the gpt gene are shown in FIG. 1.11. Hybridization with the gpt gene probe revealed that the patterns of plaques A1, A4, C1 and C2 (FIG. 1.10 lanes 1, 4, 5 and 6) comprised a single PstI fragment of 4.1 kb as expected for a single insert in the "a" orientation (FIG. 1.11). For plaque El, a weak hybridization signal from a 21 kb band, which was observed only in long exposures of the blot, was consistent with the "b" orientation of the gpt gene insert.

The structures of the viral DNA's from plaques C4 and E3 (FIG. 1.10, lanes 8 and 11) were consistent with double tandem inserts in the "b" orientation. In this case hybridizing fragments of 21 kb and 1.1 kb are expected (FIG. 1.11). The structure of the virus in plaque E4, comprising two fragments of 4.1 kb and 1.1 kb, is consistent with a tandem insertion of two gpt genes in the "a" orientation. The DNA from plaques A2, A3 and C3 exhibited more complex patterns indicative of insertions at multiple sites which were not further analyzed.

In summary, in the second cloning experiment five of eight normal-sized plaques had genomic structures expected for insertion of a single gpt gene cassette into the unique NotI site of the vaccinia virus genome. The slower growing small-sized plaques exhibited unstable structures which were lost during subsequent plaque purification steps.

EXAMPLE 2

Direct molecular cloning of a selective marker gene (*E. coli* gpt) into a unique (NotI) cleavage site of a modified avipoxvirus genome (fowlpox virus clone f-TK2a)

This example illustrates the general applicability of direct molecular cloning of modified cytoplasmic DNA virus genomes by illustrating an application to modified avipoxvirus genomes that are engineered in vitro and packaged in vivo. Avipoxviruses have the largest genomes of the poxvirus family. The genome of fowlpox virus (FPV) is about 300 kb in size, and heretofore FPV recombinants expressing foreign genes have been constructed only by marker rescue techniques. See, for example, Boyle and Coupar, *Virus Res.* 120:343–356 (1988); Taylor et al., *Vaccine* 5:497–503 (1988).

The present example illustrates production of a modified fowlpox virus by direct molecular cloning of a gene expression cassette consisting of a poxvirus promoter driving the *E. coli* gpt gene into a unique NotI site in the genome of a recombinant fowlpox virus, f-TK2a. This NotI site is located in a lacZ gene which was previously inserted into this recombinant by intracellular recombination. Engineered DNA is packaged in primary chicken embryo fibroblasts infected with the HP2 helper fowlpox virus which replicates more slowly than the f-TK2a recombinant. Selection for gpt-positive plaques leads to isolation of engineered fowlpox viruses. Since the lacZ marker gene is inactivated by an insertion at the NotI site, the progeny virus are distinguished from vector virus lacking an insert, by a colorless phenotype in the blue plaque assay for lacZ gene expression.

Purification of fowlpox virus and DNA: The fowlpox virus (FPV) strain HP1 and the attenuated strain HP1.441 (passage number 441 of HP1) were obtained from A. Mayr, Munich. Mayr and Malicki, *Zentralblatt f. Veterinärmedizin*, Reihe B, 13:1–12 (1966). The fowlpox virus strain HP2 was derived from HP1.441 by plaque purification. Primary chicken embryo fibroblasts (CEF) were prepared as described in European Patent Application No. 0 338 807. The cells were grown in tissue culture medium 199 (TCM 199; Gibco BRL) supplemented with 5% fetal calf serum, glutamine and antibiotics. Fowlpox virus was purified by two successive sucrose gradients according to Joklik, W. K., *Virology* 18:9–18 (1962). Viral DNA was prepared by the proteinase K/SDS procedure according to Gross-Bellard et al., *Eur. J. Biochem.* 36:32–38 (1973).

Construction of a fowlpox virus vector (f-TK2a) having a unique (NotI) cleavage site in an inserted DNA segment: The vaccinia virus tk-gene, together with the *E. coli* lacZ gene was inserted into the intergenic region between the tk-gene and the 3'-orf of fowlpox virus. The plasmids pTKm-VVtka and pTKm-VVtkb were constructed by cloning the functional vaccinia virus tk-gene into the intermediate plasmid pTKm-sP11. Upon intracellular recombination of pTKm-VVtka and pTKm-VVtkb with wildtype fowlpox virus DNA two novel FPV vectors, termed f-TK2a and f-TK2b, respectively, were created. Each vector contains two functional tk-genes, the endogenous FPV gene and the inserted vaccinia virus tk-gene, in addition to the inserted lacZ gene, any of which can be used as a non-essential site for insertion of foreign DNA. In particular, the NotI site in the lacZ gene is a unique cleavage site in the f-TK2a and b vectors and, therefore, is advantageous for direct molecular cloning of foreign DNA into these vectors. Complete details of the construction of the fowlpox virus vectors f-TK2a and f-TK2b are disclosed in U.S. Ser. No. 07/935,313 entitled "Recombinant Fowlpoxvirus" by Dorner et al., which claims priority of an equivalent European application filed concurrently with this application, the entire disclosure of which is hereby incorporated herein by reference.

In vivo packaging in avian cells: $8\times10^6$ CEF cells are infected with 0.2 pfu/cell of helper virus (HP2) for 2 h. For packaging engineered FPV genomes, 1 $\mu$g of purified ligation reaction product is used. Cells are transfected with DNA's by the calcium phosphate precipitation technique and incubated for 15 min at room temperature. Graham and van der Eb (1973). Nine ml medium (TCM 199, 10% fetal calf serum, glutamine and antibiotics) per one ml precipitate are added to the cells. After four hours the medium is changed and further incubated for two days. Crude virus stocks are prepared according to standard procedures. Mackett et al. (1985). Plaque assays and gpt-selection are conducted as described by Scheiflinger et al. (1991).

Direct molecular cloning into a unique NotI cleavage site of a fowlpox virus genome: The recombinant FPV strain f-TK2a is suitable as a vector for directly cloning a gene cassette, for instance a model gpt gene cassette as described herein, into a unique NotI cleavage site. Scheiflinger et al. (1991). This NotI site of the vector is in the coding region of a lacZ gene, which serves as a color screening marker that is inactivated upon gene insertion. Thus, lacZ-positive viruses form blue plaques in the presence of the chromogenic substrate X-Gal, while viruses with inserts in this NotI site show a white plaque phenotype. The genome of the f-TK2a vector also has incorporated the vaccinia virus tk gene that also serves as an alternate gene insertion region. Both the lacZ and tk genes were inserted into the fowlpox virus genome in the intergenic region between the fowlpox tk gene and the 3'-open reading frame, by conventional methods. Scheiflinger et al. (1991).

Patterns of DNA cleavage by NotI were established for the genomic DNA's of FPV viruses HP1.441 and the vector strain f-TK2a (FIG. 2.1). HP1.441 was derived from a virulent FPV strain through attenuation by serial passage in chicken embryo fibroblasts. HP1.441 is the 441st passage of HP1 and is used as a vaccine strain against fowlpox and is well adapted for rapid replication in cell culture. Mayr and Malicki (1966).

DNA from HP1.441 was analyzed as a reference for the FPV vector strain f-TK2a which is a derivative of HP1.441. The restriction analysis of the HP1.441 DNA (FIG. 2.1, lanes 1 and 2) showed that this strain has no NotI sites. Cleavage of vector f-TK2a DNA with NotI resulted in two large fragments of about 100 and 200 kb (FIG. 2.1, lane 4).

Direct molecular construction of a fowlpox virus expressing the gpt gene: A model gene expression cassette comprising the *E. coli* gpt gene was constructed in the plasmid pN2-gpta which contains the gpt gene driven by an early/late poxvirus promoter flanked by NotI sites (FIG. 1.3).

For cloning into the vector f-TK2a, the gpt gene cassette is excised from its plasmid and ligated with NotI cleaved genomic DNA of f-TK2a as outlined in FIG. 2.2. Ligated DNA is transfected into fowlpox helper virus-infected CEF cells. gpt-positive plaques that remain white under an overlay containing X-Gal are further analyzed by Southern blot analysis after infection of chicken embryo fibroblasts. Total cell DNA is isolated and the separated NotI fragments are subjected to Southern blot analysis with $^{32}$P-labelled DNA's of the helper fowlpox (HP2) and gpt gene sequences, as described in Example 1. gpt-positive viruses containing the gpt gene on the 1.1 kb NotI fragment indicating that correct ligation has occurred in the cloning step.

Production of modified viruses with both insert orientations in one construction step: The present example also illustrates how viruses having a single copy of the inserted gene cassette in either orientation, as well as viruses containing multiple copies of the inserted gene, can be recovered from a single direct molecular cloning step. The orientation of the DNA insert in selected engineered fowlpox genomes is determined by Southern blot analysis of DNA's cleaved with appropriate restriction enzymes. As shown in FIG. 2.2, the DNA inserted into a viral DNA may be in either the "a" or "b" orientations. For preliminary analyses of insert number and orientation with the present model gene cassette, for instance, total DNA of cells infected with selected plaques is digested with the restriction endonuclease ClaI and NotI and separated on a 0.8% agarose gel. The blot is hybridized with a gpt gene probe and a fowlpox virus probe.

In the NotI-digested DNA samples of recombinant viruses, the gpt cassette is excised as a 1.1 kb fragment. Cleavage with ClaI of DNA's having an insert in the a or b orientation also results in different characteristic fragments hybridizing with a gpt gene probe, as determined from the structures presented in FIG. 2.2.

EXAMPLE 3

Heterologous packaging of engineered orthopox (vaccinia) virus genomic DNA by an avipox (fowlpox) helper virus and subsequent selection for recombinants in host cells of a species in which the helper virus cannot replicate Heterologous packaging of poxvirus DNA, for instance, packaging of an orthopoxvirus DNA by an avipox virus, has not been reported. However, the present example demonstrates that in vivo packaging of extracellularly engineered vaccinia virus DNA can be achieved by fowlpox virus in chicken embryo fibroblasts. The use of a vector virus having a different host range from that of the helper virus provides a simple and efficient procedure for purifying an engineered virus in one plaque assay step. Thus, in the present example, the recombinant orthopoxvirus was recovered by plaque assay on mammalian (CV-1) cells which do not support full replication of the avipox helper virus. Inclusion of a dominant selective marker in the DNA inserted into the vector advantageously facilitates the use of selective plaque assay conditions for elimination of viruses comprising vector DNA lacking the desired insert.

Another advantage of the heterologous packaging approach is the reduced potential for recombination between vector and helper viruses. For example, orthopox and avipox viruses belong to different genera, have different morphologies and replication facilities, and share only minimal sequence homology as demonstrated by a lack of cross-hybridization under standard hybridization conditions. Therefore, homologous recombination of the genomes of avipox and orthopox viruses is exceedingly unlikely and use of these two viruses can practically eliminate undesirable recombination events that frequently occur between homologous sequences of closely related viruses. Fenner and Comben, *Virology* 5:530–548 (1958); Fenner, *Virology* 8:99–507 (1959). An alternative approach for preventing vector-helper recombination during packaging is to use recombination deficient virus strains or host cells.

In this example, a model expression cassette comprising a marker gene (the *E. coli* gpt gene driven by a poxvirus promoter) was inserted extracellularly into a unique SmaI site of vaccinia virus DNA. The use of this restriction enzyme to cleave the viral DNA produces blunt ends which advantageously may be ligated to blunt-ended DNA inserts prepared by any other nuclease that produces blunt ends, or, for example by using a polymerase or exonuclease to create blunt ends from an insert having single-stranded ends.

For packaging, the engineered genomic DNA was transfected into fowlpox virus-infected host cells in which both vaccinia and fowlpox viruses can replicate (chicken embryo fibroblasts). Since the host range of the fowlpox helper virus is restricted to avian cells, vaccinia virus clones were selected by plaque-purification of progeny from the transfected cells on mammalian host cells (African Green Monkey Kidney CV-1 cells). Simultaneous selection for gpt gene expression was used to isolation of only modified vaccinia viruses. In contrast to the conventional method of producing poxvirus recombinants where in one intracellular genetic cross usually only one copy of a foreign gene can be inserted in a single orientation, in the present example, both possible orientations of a single insert, as well as double insertions of the model gene cassette were identified as products of a single extracellular genomic modification reaction.

The experimental results in the present example show that the packaging efficiency of ligated vaccinia virus DNA's by fowlpox helper virus was low compared to packaging of intact vaccinia virus DNA with fowlpox virus, which produces yields in the range of $5\times10^3$ to $1\times10^4$ pfu per $6\times10^6$ chicken embryo fibroblasts after three days of replication. In one packaging experiment (producing plaques designated the "F12" series, infra) the yield of packaged modified virus was $9\times10^2$ pfu, and in a second experiment (producing the "F13" series), $5\times10^2$ pfu, per $6\times10^6$ chicken cells. One source of this relatively low packaging frequency in these experiments is the lack of dephosphorylation treatment of the vector DNA arms which, therefore, were able to relegate efficiently without any insert. Such treatment was omitted because dephosphorylation of blunt-ended DNA fragments is usually inefficient. This problem can be overcome by construction of host virus strains having multiple cleavage sites with "sticky" ends that enable directional ("forced") cloning, thereby making the insertion of foreign DNA fragments much more efficient.

Another factor influencing the packaging efficiency is interference at the cellular level between the helper and the packaged virus. Under standard packaging conditions, within three days of incubation the helper virus (fowlpox) usually replicates to titers of about $1\times10^8$ pfu per $6\times10^6$ chicken embryo fibroblasts. The large excess of fowlpox virus compared to packaged vaccinia virus creates conditions that produce negative interference phenomena and inhibits replication of the packaged virus.

This interference is minimized by using mammalian cells for packaging in combination with fowlpox helper virus as described in Example 7. In that case, the host cells do not support full replication of the helper fowlpox virus. Although, no testing of ligated vaccinia virus DNA for packaging efficiency by fowlpox virus has been made in a mammalian host cell, a packaging yield of $2\times10^6$ pfu per $8\times10^6$ mammalian (CV-1) cells was obtained with uncleaved vaccinia virus DNA.

In each viral recombinant generated by intracellular recombination with a given insertion plasmid an insert has one orientation depending on the polarity of the homologous flanking regions in that plasmid. Due to transcriptional interference phenomena, for instance, expression levels for genes inserted into a poxvirus vector depend on the orientation of the foreign gene relative to the viral genome. Ink and Pickup (1989). Therefore, it is desirable to obtain in one reaction step modified viruses having either possible orientation. One of the advantages of the procedure in this example is that both possible orientations of the inserted DNA are obtained in one ligation reaction, allowing immediate screening for variants having the highest expression level. The preferred orientation of the cassette of this example in the selected SmaI insertion site of vaccinia virus is the "b" orientation, as evidenced by the fact that the majority of modified viruses had this genomic structure. In this cassette the P7.5 promoter controlling the foreign gene is in the inverted repeat orientation relative to the endogenous 7.5 kDa polypeptide gene. As discussed in Example 1, the endogenous 7.5 kDa polypeptide genes are located in the inverted terminal repetitions of the vaccinia genome. The distance of the P7.5 promoter of the gpt gene and the P7.5 promoter in the left terminal repetition is about 20 kb. The "a" orientation should therefore be less stable and less frequently obtained, in accordance with the observation that this orientation was found only twice. However, the viral isolates F13.4 (orientation a) and vF12.5 (orientation b) were propagated to large scale with gpt-selection and were found to have stable predicted structures. The stability of the various structures comprising multiple inserts without selection remains to be determined.

The ligations contained several-fold excess of insert over the vector, thereby favoring insertion of multiple copies of the cassette as observed. However, it is unclear why in this example double insertions were more frequent than in Example 1. Due to internal recombination events only certain configurations of multiple inserts are expected to be stable. Further studies to evaluate stability of viruses with multiple inserts and the optimal ratio of vector to insert for stability and expression level which depends on copy number can all be conducted as necessary for each construct, according to the teachings of this application.

Purification of virus and DNA: The viruses and methods of Examples 1 and 2 were used.

Engineering of viral DNA: Viral DNA purified from virions was cleaved with SmaI and purified by one phenol extraction and three chloroform extractions. In the first experiment below, 2 $\mu$g of cleaved virus DNA were ligated with 400 ng (34 fold molar excess) of the insert fragment (the 1.1 kb HpaI-DraI fragment excised from plasmid pTKgpt-Fls) in a volume of 30 $\mu$l for 40 h with 15 units of T4 ligase (Boehringer, Inc.). The second ligation experiment was done under the same conditions except that a seventeen-fold molar excess of the 1.1 kb SmaI insert and 5 units of ligase were used.

In vivo heterologous packaging in avian cells: Chicken embryo fibroblasts ($6\times10^6$) infected with the helper virus (0.5 pfu/cell of HP1.441) and incubated for 2 h. Two $\mu$g of ligated DNA was transfected into the infected cells and treated further as described for the homologous packaging procedure in Example 1. The initial plaque assay was done in CV-1 cells as described in Example 1.

Demonstration of packaging of modified vaccinia virus DNA by fowlpox helper virus: The design of this experiment is shown in FIG. 3.1. Vaccinia virus genomic DNA was prepared from sucrose gradient purified virions, cut with the restriction endonuclease SmaI, and ligated with the blunt-ended foreign gene cassette. Ligated DNA was transfected into fowlpox virus-infected chicken embryo fibroblasts for packaging. Progeny virus was identified by plaque assay on mammalian (CV-1) cells which do not support complete replication of fowlpox virus to produce infectious virions.

In more detail, first, the HpaI-DraI fragment bearing the model gene cassette (containing the gpt gene driven by the vaccinia virus P7.5 promoter) was excised from the plasmid pTKgpt-F1s and ligated directly into the unique SmaI site of vaccinia wildtype virus (WR strain). Falkner and Moss (1988). The gpt gene was selected to permit positive selection of modified viruses. Boyle and Coupar (1988); Falkner and Moss (1988). The single SmaI site in vaccinia virus DNA is located in the open reading frame A51R in the HindIII A fragment of the genome. The A51R gene is non-essential for viral replication in cell culture. Goebel et al. (1990).

Ligated material was transfected into chicken embryo fibroblasts infected with fowlpox helper virus. After three days the cells were harvested and a crude virus stock was prepared. Packaged vaccinia virus was identified by plaque assay on an African Green monkey kidney cell line (CV-1) in medium that selects for cells infected with a virus carrying the gpt gene. This selection scheme prevents viruses containing self-ligated wildtype vaccinia virus DNA from forming plaques while allowing modified viruses containing an inserted model gpt gene cassette to do so.

The packaging frequency was low in initial experiments. The titer of gpt-positive vaccinia virus in the crude stock prepared from $6\times10^6$ chicken embryo fibroblasts was in the range of $1\times10^2$ to $1\times10^3$ pfu.

Thirteen gpt-positive plaques were amplified under gpt-selection in CV-1 cells. Total DNA of infected cells was isolated, digested with HindIII, separated on a 0.7% agarose gel and further processed for analysis by Southern blot analysis with a gpt gene probe. As shown in FIG. 3.2, several viruses having blot patterns predicted for different modified genomic structures were obtained.

In lanes 2, 4, 11 and 13 (corresponding to plaques #F12.3, F12.5, F13.3 and F13.5) a single hybridizing fragment of about 45 kb is visible, that is expected when one copy of the gene cassette is inserted into the viral genome in the "b" orientation into the viral genome (see FIG. 3.3). An expected novel fragment of 5.2 kb is also present in all cases, and also appears when the same DNA's are tested as in FIG. 3.2 using a vaccinia virus probe.

Two viruses having patterns consistent with the "a" orientation were obtained in lanes 7 and 12 (corresponding to plaques #F12.8 and F13.4), where a single gpt-hybridizing fragment of about 5.7 kb is expected. The 5.7 kb fragment in lane 7 is more visible in longer exposures of the autoradiograph. The pattern seen in lane 5 (plaque F12.6) may represent a single insert in the "a" orientation, but the expected 5.7 kb band is somewhat larger for unknown reasons.

The pattern of three viral isolates is consistent with a tandem insertion in the "a" orientation (lanes 1, 6 and 10, corresponding to plaques #F12.2, F12.7 and F13.2). In these cases two gpt-positive hybridizing fragments, of 5.7 and 1.1 kb, are expected (see also FIG. 3.3). Fragments of 5.7 and 1.1 kb were also observed in equimolar amounts with the viral DNA in a blot hybridized with a vaccinia virus probe.

The genome of the isolate in lane 3 (plaque F12.4) probably contains a tandem duplicate insert in the "b" orientation. In this case two fragments, of 45 kb and 1.1 kb, are expected to hybridize with the gpt-gene.

The viral DNA in lane 9 (plaque F13.1) may comprise a head-to-head double insertion. In this case a 45 kb and a 5.7 kb fragment hybridizing with a gpt-gene probe are expected. However, in addition such a DNA should contain a novel 0.6 kb fragment that hybridizes with a vaccinia DNA probe, and, in fact, this fragment was detected on a blot hybridized with a vaccinia probe. Nevertheless, the expected 5.7 kb fragment was somewhat smaller than predicted and produced a hybridization signal that was weaker than expected. Therefore, confirmation of the structure of this recombinant requires more detailed analysis.

Further analysis revealed that the viruses F12.7 and F12.3, interpreted above as having double insertions with tandem 'a' structures, and the virus F12.4, interpreted above as having double insertions with tandem 'b' structures, actually have multiple tandem inserts in the 'a' or 'b' orientations, respectively. The Southern blot analysis of FIG. 3.2 does not distinguish between double tandem and multiple tandem inserts.

EXAMPLE 4

Construction of an orthopoxvirus (vaccinia) vector (vdTK) with a directional master cloning site and plasmids with compatible expression cassettes This example demonstrates application of the methods of the present invention to create novel poxvirus cloning vectors by direct molecular modification and cloning of existing poxvirus genomes. In particular, this example describes a vaccinia virus vector (vdTK) which allows directional insertion (i.e., "forced cloning") of foreign genes into a short "multiple cloning site" segment comprised of several different endonuclease cleavage sites each of which is unique in the vector genome. Forced cloning eliminates the need for selection or screening procedures to distinguish the desired recombinants from vector virus lacking an insert because incompatibility of DNA ends cleaved by different nucleases prevents religation of the vector arms without a foreign insert. Consequently, the forced cloning approach is the most efficient way to insert a foreign gene into a viral vector.

The directional vector vdTK is created by inserting a multiple cloning site (comprised of unique NotI, SmaI, ApaI and RsrII sites) in place of the tk gene of vaccinia virus (see FIG. 4.1A). This nonessential locus is the site most frequently used for insertion of foreign genes into vaccinia virus, mainly because positive selection for tk-negative viruses is available. Thus, when ligated vdTK vector DNA is packaged by a tk-positive helper virus, the vector virus may be positively selected from the excess of helper virus. Further, insertion of foreign DNA into the vaccinia virus tk-locus by conventional methods generally results in stable recombinants.

The multiple cloning site of the new vdTK vector is comprised of NotI and SmaI cleavage sites which are unique in the vector. Prior to insertion of the multiple cloning site, NotI and SmaI cleavage sites preexisting in the wildtype vaccinia virus (WR strain) are deleted by direct molecular modifications according to the present invention. Viruses having the desired modifications are detected by screening techniques based on the polymerase chain reaction (PCR) method for amplification of specific nucleic acid sequences. This example also describes a set of plasmids which facilitate expression of DNA's encoding complete or partial open reading frames in the vdTK vaccinia vector. The present invention comprehends insertion of open reading frames directly into a poxvirus expression vector having all appropriate regulatory elements suitably placed for expression of the inserted open reading frame. However, the instant vdTK vector is not equipped with such regulatory sequences for expression of an inserted open reading frame that lacks its own transcription and translation signals. Accordingly, the plasmids of this example provide convenient gene expression cassettes for routine linkage of open reading frames to poxvirus promoters and, optionally, to a translation start codon. An open reading frame and associated regulatory sequences are then efficiently transferred into the vdTK vector master cloning site by forced cloning. Modified viruses having the insert in either orientation can be obtained by using one of two plasmids having the expression cassette in the desired orientation within its master cloning site. The gene expression cassettes of the plasmids exemplified here have two nested sets of restriction enzyme cleavage sites to facilitate cloning of open reading frames into the vdTK vector. The cassettes have a master cloning site comprised of the same unique sites as the master cloning site of the vdTK vector. In addition, in the middle of this master cloning site the cassettes contain a variety of sites for frequently cutting enzymes that are useful for insertion of open reading frames into the cassettes. Thus, DNA's inserted into a cassette by means of the frequent cutter sites are flanked on either side by several different unique sites which are suitable for forced cloning of the cassette into the master cloning site of the vdTK vector.

This example also describes gene expression cassettes suitable for insertion into a single unique site in the vaccinia virus vector vdTK. To overcome the reduced cloning efficiency of using a single enzyme for cleaving the vector DNA, the expression cassettes of these plasmids include the *E. coli* gpt gene as a selective marker.

The vdTK vaccinia vector system is preferentially used in conjunction with the heterologous packaging procedure described in Examples 3 and 7. The plasmids containing the gpt marker can also be used with homologous helper virus lacking the gpt marker. Examples of constructs for expression of polypeptides using the vdTK vector and related plasmid system are presented hereinbelow in Example 5.

In addition to the above advantages, the expression cassette plasmids of this invention also provide a means of overcoming a general problem of incompatibility between the ends of cleaved poxvirus vector DNA's and many insert DNA's, as a convenient alternative to the common use of synthetic adaptor DNA segments. Thus, isolation of DNA fragments encoding open reading frames usually is facilitated by use of restriction endonucleases having recognition sequences which are short and, consequently, randomly occur at high frequencies in all natural DNA sequences. On the other hand, such frequently cutting enzymes generally are not suitable for efficient direct cloning into genomes as large as those of poxviruses, for instance, because such enzymes cleave large DNA's into many fragments. Religation of these fragments would occur in random order, producing few intact viral genomes. Therefore, insertion sites in a vaccinia vector preferably are cleavage sites of infrequently cutting restriction endonucleases which are unlikely to be used for isolation of open reading frame fragments or insert DNA's in general. The present plasmids overcome this general incompatibility by allowing efficient insertion of fragments from frequent cutters into the plasmid followed by efficient transfer into the vaccinia vector using infrequently cutting enzymes.

Deletion of the unique NotI cleavage site from wildtype vaccinia (WR) virus: The unique NotI site of vaccinia virus may be eliminated by insertion into this site of a "NotI deletion adaptor" segment having cohesive ends compatible for ligation with NotI-cleaved DNA but lacking sequences required for recognition by the NotI endonuclease. Thus, the sequences formed by the ligated cohesive ends of the NotI-cleaved viral DNA and viral DNA and adaptor are not cleavable by NotI. This adaptor also contains several selected restriction endonuclease cleavage sites for directed insertion of DNA fragments.

More particularly, one $\mu$g of vaccinia virus WR wild type DNA is cut with NotI and ligated with one $\mu$g of the double-stranded NotI-deletion adaptor. The adaptor consists of two partially complementary strands: odN1 (SEQ ID NO:16) and odN2 (SEQ ID NO:23). The central part of the adaptor contains the restriction endonuclease cleavage sites StuI, DraI, SspI and EcoRV. Annealed adaptor oligonucleotides are used for the ligation reaction. The ligated material is transfected into fowlpox virus-infected chicken embryo fibroblasts and packaged as described in Example 3.

An alternative procedure for deleting the single NotI site of vaccinia virus (WR strain) is outlined in FIG. 4.1B. In the first step, vaccinia virus DNA is cut with SacI, the SacI "I" fragment is isolated from low melting point agarose and cloned into the SacI site of a suitable plasmid, such as pTZ19R (obtainable from Pharmacia, Inc.). The resulting plasmid, pTZ-SacI, is cut with NotI, treated with Klenow polymerase to fill in the sticky ends and religated. The ligated material is transfected into *E. coli* cells (HB101). The colonies are isolated according to standard cloning procedures. The resulting plasmid, pTZ-SacIdN has the NotI site deleted and is used in a reverse gpt-selection experiment as described by Isaacs et al., *Virology* 178:626–630 (1990), modified as follows.

CV-1 cells ($8\times10^6$) are infected with 0.2 pfu of the viral isolate vp7, a vaccinia virus that has integrated into the single NotI site a gpt gene cassette (see Example 1). Subsequently, a calcium-phosphate precipitate containing 20 $\mu$g of DNA from the modified SacI fragment prepared from the plasmid pTZ-SacIdN is transfected into the cells. The cells are further treated as described in the packaging procedure in Example 1. Crude virus stocks are used to infect mouse STO cells (obtained from the American Type Culture Collection, Rockville, MD; ATCC# CRL 1503) in the presence of 6-thioguanine (6-TG). This is a negative selection procedure that requires the loss of the gpt gene for a virus to replicate and, therefore, leads in the present case to integration of the modified SacI "I" fragment and, thereby, deletion of the gpt gene. See Isaacs et al. (1990). All plaques growing in the presence of 6-TG should lack the gpt gene and contain a modified SacI I fragment. The estimated yield is in the range of 0.1–0.2% of the total plaques (i.e., the normal frequency of recombinants in this type of marker rescue experiment). Since the selection procedure is extremely efficient identification of the correct structures is not expected to require examination of large numbers of clones. See Isaacs et al. (1990) However, whether the first procedure above or this alternative procedure is used to delete the single NotI of vaccinia virus, the following screening procedure may be used to identify the desired construct.

Identification by PCR-screening of virus (vdN) having the NotI site deleted: Vaccinia virus clones having the NotI site deleted may be identified by analysis of plaques growing in a cell line (CV-1) that does not support the growth of the fowlpox helper virus. The DNA's of viruses in individual plaques are analyzed by a PCR-based screening method, as follows.

The first primer for the PCR reaction is the oligonucleotide odn1, (SEQ ID NO:16), and the second primer was odN3 (SEQ ID NO:24). The sequence of second primer is located in the vaccinia virus genome about 770 bp downstream of the first primer sequence. The template is total DNA from $1\times10^6$ CV-1 cells infected with half the virus of a single plaque. DNA is prepared by standard techniques and about 50 ng is used for the PCR reaction. The PCR reactions are carried out according to standard techniques using commercially available PCR kits. Positive PCR reactions produce a DNA fragment of about 770 bp. Such a virus having the NotI site deleted is designated "$vd^{N}$".

Deletion of the unique SmaI restriction site from vaccinia virus vdN: The WR strain of vaccinia virus contains a single SmaI site in an open reading frame (A51R) which is not essential for virus replication in cell cultures. Goebel et al. (1990). Although this site may be used for foreign gene insertion, in the present example, however, this site is deleted in favor of creating a more versatile vaccinia virus vector by introducing a new unique SmaI site as part of a multiple cloning site cassette.

Accordingly, vdN virus DNA (1 μg) is cut with SmaI and ligated with an excess of a hexamer linker having the recognition sequence for the restriction nuclease HindIII (odS1, 5'-AAGCTT-3'). Insertion of this linker into the vaccinia virus SmaI cleavage site results in destruction of the SmaI recognition sequence and the introduction of a new HindIII recognition sequence. The ligated material is packaged by transfection into cva cells that have been infected with fowlpox virus, as described in Example 7.

Alternatively, the single SmaI site of vaccinia virus (WR strain) is deleted according to the procedure outlined in FIG. 4.1C, by modifying a cloned fragment of vaccinia virus DNA instead of directly modifying the complete vaccinia virus DNA. In a first step, vaccinia virus DNA is cut with SalI, the SalI F-fragment is isolated from low melting point agarose and cloned into the SalI site of a suitable plasmid, such as pTZ9R (obtainable from Pharmacia, Inc.). The resulting plasmid, pTZ-SalF, has two SmaI sites, one in a multiple cloning site and the other in the vaccinia sequences (FIG. 4.1C). pTZ-SalF is partially digested with SmaI and I-SceI linkers are added, as follows: first strand, I-SceI linker 1 (SEQ ID NO:25) and its complementary strand, I-SceI linker 2 (SEQ ID NO:26). The correct plasmid having the SmaI site deleted from the vaccinia sequences is identified by cleavage with SmaI and I-SceI. The final plasmid, pTZ-SalFdS, is used to introduce the SmaI deletion into a vaccinia virus genome using the reverse gpt gene selection experiment as described for deletion of the NotI site, except that preferred virus to be modified is the isolate F12.5, a virus that has integrated into the single SmaI site a gpt gene cassette (see Example 3).

The resulting insertion of a site for endonuclease I-SceI advantageous for direct molecular cloning because this enzyme, isolated from yeast, recognizes an 18mer site and, therefore, cuts random DNA sequences extremely infrequently. For instance, I-SceI cuts the yeast genome only once. Thierry et al., *Nucleic Acids Res.* 19:189–190 (1991). I-SceI is commercially available from Boehringer, Inc. Advantageously, an I-SceI site is introduced into a vector having no preexisting sites for that enzyme, thereby creating a new vector with a single site that can be used for gene insertions. Whether a vaccinia virus DNA or other vector DNA contains a site for I-SceI cleavage can be determined by routine restriction analyses of the vector DNA.

Where this alternative procedure for deletion of the SmaI site from vaccinia virus DNA is used, the order of steps for constructing the vector vdTK is as follows: deletion of the SmaI site resulting in virus vdS (see above); deletion of the NotI site by insertion of the NotI gpt gene cassette (see Example 1) into the single NotI site of vdS by cloning and packaging, resulting in the virus vdSNgpt and reverse gpt-selection as described above, using vdSNgpt and pTZ-SacIdN as substrates for the marker rescue experiment; and deletion of the tk gene as outlined in below in the present example.

An alternative procedure by which the vector vdTK actually was constructed is as follows. The SmaI site of vaccinia wild-type virus was deleted, creating the intermediate virus vdS. In a second experiment the NotI site was deleted from vaccinia wild-type virus creating the intermediate virus vdN. The virus vdSN was obtained by co-infection using both viruses of CV-1 cells and PCR screening of the recombinant virus (that was created by a simple genetic cross-over event). The viability of the different intermediates was determined by titrations.

Table 2 at section A shows the results after individual isolates from the vdN cloning experiment were plaque purified five times (to insure that wildtype virus-free clones were obtained) and then amplified. After titration, crude virus stocks of the first amplification, together with wild-type control (WR-WT), were used to infect CV-1 cells at 0.1 pfu/cell. These cells were harvested after 48 h and used to prepare crude stocks which were re-titered. These results are shown in Table 2 at section B. Isolates vdN/A1 #6.1111 and vdN/A1 #10.1111 were designated as clones vdN#6 and vdN#10, respectively, and used for large scale virus preparations.

Table 3 at section A shows the results after single isolates of the vdS cloning experiment were plaque purified five times and then amplified and titered. Crude stocks of the first amplification, together with wild-type control (WR-WT), were used to infect CV-1 cells at 0.1 pfu/cell. The cells were harvested after 48 hours and the resulting crude stocks were re-titered. These results are shown in FIG. 4.2 at section B. The isolates vdS# 7.11 were designated as clones vdS#2 and vdS#7, respectively, and used for large scale virus preparations. In each case, the virus isolate showing the best growth characteristics was selected to be amplified and grown to large scale.

TABLE 2

Viability Studies of the Viral Intermediate vdN

| | | |
|---|---|---|
| A) Titer after first amplification of six viral vdN-isolates (pfu/ml crude stock): | | |
| vdN/A1# | 2.1111 | $1.0 \times 10^7$ pfu/ml |
| vdN/A1# | 4.1111 | $1.3 \times 10^8$ pfu/ml |
| vdN/A1# | 6.1111 | $9.0 \times 10^7$ pfu/ml |
| vdN/A1# | 8.1111 | $8.0 \times 10^7$ pfu/ml |
| vdN/A1# | 10.1111 | $4.0 \times 10^7$ pfu/ml |
| vdN/A1# | 12.1111 | $1.1 \times 10^8$ pfu/ml |
| B) Titer after second amplification: | | |
| vdN/A1# | 2.1111 | $3.6 \times 10^8$ pfu/ml |
| vdN/A1# | 4.1111 | $2.5 \times 10^8$ pfu/ml |
| vdN/A1# | 6.1111 | $5.9 \times 10^8$ pfu/ml |
| vdN/A1# | 8.1111 | $4.2 \times 10^8$ pfu/ml |
| vdN/A1# | 10.1111 | $4.3 \times 10^8$ pfu/ml |
| vdN/A1# | 12.1111 | $2.2 \times 10^8$ pfu/ml |
| WR-WT | | $5.4 \times 10^8$ pfu/ml |

TABLE 3

Viability Studies of the Viral Intermediates vdS

| | | |
|---|---|---|
| A) Titer after first amplification of five viral vdS-isolates (pfu/ml crude stock) | | |
| vdS# | 2.11 | $4.1 \times 10^7$ pfu/ml |
| vdS# | 3.11 | $6.5 \times 10^7$ pfu/ml |
| vdS# | 4.11 | $8.0 \times 10^7$ pfu/ml |
| vdS# | 5.11 | $2.7 \times 10^7$ pfu/ml |
| vdS# | 7.11 | $4.7 \times 10^7$ pfu/ml |
| B) Titer after second amplification | | |
| vdS# | 2.11 | $1.6 \times 10^8$ pfu/ml |
| vdS# | 3.11 | $1.4 \times 10^8$ pfu/ml |
| vdS# | 4.11 | $8.0 \times 10^7$ pfu/ml |
| vdS# | 5.11 | $1.3 \times 10^8$ pfu/ml |
| vds# | 7.11 | $1.7 \times 10^8$ pfu/ml |
| WR-WT | | $2.8 \times 10^8$ pfu/ml |

Identification by PCR-screening of virus (vdSN) having the SmaI site deleted: Clones of the vdSN vaccinia virus having the SmaI site deleted are identified by PCR screening as follows. The first primer for the PCR reaction is the oligonucleotide odS2 (SEQ ID NO:27) and the second primer is the oligonucleotide odS3 (SEQ ID NO:28). The sequence of oligonucleotide odS2 is located in the vaccinia genome about 340 bp upstream of the SmaI site, while that of oligonucleotide odS3 is located about 340 bp downstream of this site. The template is total DNA of CV-1 cells infected with a virus plaque as described above for vdN identification. The PCR-amplified band of about 680 bp is tested for susceptibility to SmaI, with resistance to SmaI cleavage indicating insertion of the HindIII or I-SceI linker, while wildtype control DNA is cut into two pieces of about 340 bp. A vaccinia virus having the desired insertion of a linker in the SmaI site is designated vdSN.

Deletion of the coding region of the thymidine kinase gene from vaccinia virus vdSN: From vaccinia virus vdSN, a novel vector strain (designated vdTK) is developed by replacing the tk gene, which is located in a genetically stable region of the vaccinia genome, with a segment comprised of several unique restriction endonuclease cleavage sites (FIG. 4.1A).

The tk coding sequence is first deleted from a plasmid (pHindJ-1) comprising a segment of the vaccinia genome (the HindIII J segment) in which the tk gene is located (see FIG. 4.2). In place of the tk-gene, a multiple cloning site with the unique sites NotI, SmaI, ApaI and RsrII, flanked by SfiI sites is then inserted. Finally, the modified virus segment is transferred into the vaccinia virus genome vdSN which was then designated vdTK (FIG. 4.1A). To further facilitate forced cloning, each of the two SfiI sites also may be made unique in the vector by exploiting the variable nature of the SfiI recognition sequence (GGCCNNNNNGGCC, SEQ ID NO:85). The sequences of two SfiI sites are as follows: SfiI(1), GGCCGGCTAGGCC (SEQ ID NO:29) and SfiI(2), GGCCATATAGGCC (SEQ ID NO:30). This plasmid containing the final modification of the tk gene (pHindJ-3) is constructed from precursor plasmid pHindJ-1 by loop-out mutagenesis, and deletion of the tk gene is confirmed by sequence analysis.

Construction of precursor plasmid pHindJ-1: Vaccinia wildtype virus DNA was cut with HindIII and the resulting fragments were separated on a 0.8% low melting point agarose gel. The HindIII J fragment was excised under UV-light and prepared according to standard techniques. The fragment was inserted into the single HindIII site of the plasmid pTZ19R (Pharmacia, Inc.) resulting in pHindJ-1.

Construction of plasmid pHindJ-2: Plasmid pHindJ-1 is transfected into *E. coli* strain NM522 and single-stranded DNA is prepared by superinfection with the helper phage M13K07 according to the protocol supplied by Pharmacia. The single-stranded DNA serves as the template for site directed mutagenesis with the primer odTK1 (SEQ ID NO:31). This primer is complementary to the promoter region and the region around the translational stop codon of the tk-gene. In its central part it contains the unique restriction sites BamHI, HpaI, NruI and EcoRI. The mutagenesis procedure is carried out with a mutagenesis kit provided by Amersham, Inc., according to the manual provided by the supplier.

For construction of pHindJ-2, the tk-gene sequence has been described in Weir and Moss, *J. Virol.* 46:530–537 (1983). The tk-gene sequence is accessible in the EMBL Data Library under the identifier (ID) PVHINLJ. The sequence of the vector part (pTZ19R) of the plasmid is available from Pharmacia, Inc. The sequence around the deleted vaccinia virus tk gene in the plasmid pHindJ-2 is shown in SEQ ID NO:4. The 5' region of the tk gene (bases #1–19 in the present listing; bases #4543–#4561 in ID PVHINLJ) is followed by the unique restriction sites BamHI, HpaI, NruI and EcoRI and the 3' region of the tk gene (bases #44–#67 present listing; bases #5119–#5142 in ID PVHINLJ). Bases #4562 to 5118 in ID PVHINLJ, which contain part of the tk promoter and the tk gene coding region, are deleted in pHindJ-2.

Construction of the plasmid pHindJ-3: Plasmid pHindJ-2 is digested with BamHI and EcoRI and a double-stranded linker containing the unique restriction sites NotI, SmaI, RsrII and ApaI, flanked by SfiI sites is inserted. The linker consists of oligonucleotides P-J(1) (SEQ ID NO:32) and P-J(2) (SEQ ID NO:33).

The modified sequence of pHindJ-3 is shown in SEQ ID NO:5. The inserted multiple cloning site corresponds to oligonucleotide P-J(1). The inserted sequence starts at position 21 and ends at position 99. The flanking sequences are the same as described in pHindJ-2, supra.

To insert the tk-deletion into vaccinia virus, plasmid pHindJ-3 is digested with HindIII and a shortened HindIII J fragment having a tk-gene deletion is used for a marker rescue experiment. Sam and Dumbell (1981). Viruses having the tk gene deleted are isolated by tk negative selection and identified by subsequent PCR screening.

More particularly, the modified HindIII fragment present in pHindJ-3 is excised with HindIII and isolated with a low melting point agarose gel. The marker rescue is performed essentially as described by Sam and Dumbell (1981) with the following modifications. $5\times10^6$ CV-1 cells are infected with 0.2 pfu per cell of vaccinia virus vdSN. After one hour of incubation, one ml of a calcium-phosphate precipitate containing 1 $\mu$g of the modified HindIII J fragment is transfected into the infected cells. After two days growth a crude virus stock is prepared as described in Example 1 and titrated on human 143B tk-negative cells in the presence of bromodeoxy-uridine (BrdU) as described by Mackett et al. (1982). tk-negative plaques may be further analyzed by PCR screening.

Identification of the thymidine kinase deletion virus (vdTK) by PCR-screening: The first primer for the PCR reaction is oligonucleotide odTK2 (SEQ ID NO:34), the sequence of which is located about 300 bp upstream of the tk gene. The second primer, odTK3 (SEQ ID NO:35), is located about 220 bp downstream of the stop codon of the tk gene. The template is total DNA of CV-1 cells infected with a virus plaque, as described for vdN screening. The amplification product resulting from virus having the tk gene deletion is about 520 bp, while the wildtype control produces a fragment of about 1.1 kb.

Construction of plasmids comprising gene expression cassettes for transfer to the vdTK vector: The plasmid pA0 is the basic plasmid that contains a master cloning site comprised of the unique sites of the master cloning site of the vdTK vaccinia virus vector. Plasmid pA0 was constructed by replacing the multiple cloning site of a commercially available plasmid with a segment comprised of the unique sites of the vdTK vector and an XhoI site, as illustrated in FIG. 4.3.

More in particular, to delete the multiple cloning site of the pBluescript II SK- phagemid (Stratagene), the plasmid was digested with SacI and Asp718. The large vector fragment was ligated with an adaptor consisting of the annealed oligonucleotides P-A(0.1) (SEQ ID NO:36) and P-A(0.2) (SEQ ID NO:37).

The multiple cloning site of pA0 (corresponding to the oligonucleotide P-A(0.1)) and twenty bases of the 5'- and 3'-flanking regions of pEluescriptII SK- are shown in SEQ ID NO:6. The insert starts at position 21 and ends at position 95. (The first "A" residue at the 5'-end corresponds to position number 2187, the last "G" residue at the 3'-end corresponds to position number 2301 of the plasmid pA0).

Construction of the plasmids pA1 and pA2: The plasmids pA1 and pA2 (compriisng SEQ ID NO:8) were designed for insertion of DNA segments, e.g., synthetic or natural promoter fragments. They were constructed by inserting into the Xhol site of pA0 a linker comprising a second multiple cloning site of frequently cutting enzymes that do not cleave pA0. Both plasmids have the same structure except for the orientation of the second multiple cloning site (FIG. 4.3).

The pA0 plasmid was digested with XhoI and ligated with an adaptor consisting of the annealed oligonucleotides P-A (1.1) and P-A(1.2). Plasmids of both possible orientations of the adaptor were isolated and designated pA1 and pA2.

The multiple cloning site of pA1 (corresponding to the oligonucleotide P-A(1.1)) and twenty bases of the 5'- and 3'-flanking regions of pA0 are shown in SEQ ID NO:7. The insert starts at position 21 and ends at position 83. (The first "C" residue at the 5'-end corresponds to position number 2222, the last "C" residue at the 3'-end corresponds to position number 2324 of the plasmid pA1).

The multiple cloning site of pA2 (corresponding to the oligonucleotide P-A(1.2)) and twenty bases of the 5' and 3'-ends of pA2 are shown in SEQ ID NO:10. The insert starts at position 21 and ends at position 195. (The first "C" residue at the 5'-end corresponds to position number 2252, the last "G" residue at the 3'-end corresponds to position number 2466 of the plasmid pA2-S1).

Construction of plasmids pA1-S1 and pA2-S1: Plasmids pA1-S1 and pA2-S1 provide the strong synthetic poxvirus promoter S1 (bases 21–194 of SEQ ID NO:9), including a translational start codon, followed by a single EcoRI site suitable for insertion of open reading frames that do not have an associated start codon. Promoter S1 is a modified version of a strong poxvirus late promoter designated P2.

Plasmids pA1-S1 and pA2-S1 are obtained by inserting a first double-stranded promoter fragment into the NdeI and BamHI site of pA1 or pA2, respectively, by forced cloning (FIG. 4.4A) In particular, vector pA1 is digested with NdeI and BamHI and ligated with an adaptor consisting of the annealed oligonucleotides P-P2m1.1 and P-P2m1.2. The resulting plasmid is designated pA1-S1.

The synthetic promoter sequence of pA1-S1 (corresponding to the oligonucleotide P-P2m1.1) and twenty bases of the 5'- and 3'-flanking regions of pA1 are shown in SEQ ID NO:9. The insert starts at position 21 and ends at position 193. (The first "C" residue at the 5'end corresponds to position number 2228, the last "G" residue at the 3'end corresponds to position number 2440 of the plasmid pA1-S1).

The vector pA2 was digested with NdeI and BamHI and ligated with an adaptor consisting of annealed oligonucleotides P-P2m1.1 and P-P2m1.2, as for pA1-S1, above. The resulting plasmid is designated pA2-S1.

The synthetic promoter sequence of pA2-S1 (corresponding to the oligonucleotide P-P2m1.2) and twenty bases of the 5'- and 3'-flanking regions of pA2 are shown in SEQ ID NO:10. The insert starts at position 21 and ends at position 195. (The first "C" residue at the 5'end corresponds to position number 2252, the last "G" residue at the 3'end corresponds to position number 2466 of the plasmid pA2-S1).

Construction of plasmids pA1-S2 and pA2-S2: The plasmids pA1-S2 and pA2-S2 contain the strong synthetic promoter S2 (bases 21–73 of SEQ ID NO:11), a modified version of a strong late synthetic poxvirus promoter described by Davison and Moss, *J. Mol. Biol.* 210:771–784 (1989). These plasmids do not provide a translational start codon with the promoter and, therefore, are suited for insertion of complete open reading frames that include a start codon. The promoters have different orientations with respect to the vdTK master cloning site in these two plasmids.

Plasmids pA1-S2 and pA2-S2 are obtained by forced cloning of a second double-stranded promoter fragment into the HpaI and EcoRI sites of pA1 and pA2, respectively (FIG. 4.5A). More particularly, plasmid pAl is digested with the enzymes HpaI and EcoRI, and ligated with a synthetic linker sequence consisting of annealed oligonucleotides P-artP(5) and P-artP(6). The resulting plasmid is designated pA1-S2.

The synthetic promoter sequence of pA1-S2 (corresponding to the oligonucleotide P-artP(5) and twenty bases of the 5'- and 3'-flanking regions of pA1 are shown in SEQ ID NO:11. The insert sequence starts at position 21 and ends at position 68. (The first "T" residue at the 5'-end corresponds to position number 2240, the last "A" residue at the 3'-end corresponds to position number 2327 of the plasmid pA1-S2).

Similarly, the plasmid pA2 is digested with the enzymes HpaI and EcoRI, and ligated with the annealed oligonucleotides P-artP(5) and P-artP(6) as for pA1-S2. The resulting plasmid is designated pA2-S2. The synthetic promoter sequence of pA2-S2 (corresponding to the oligonucleotide P-artP(6) and twenty bases of the 5'- and 3'-flanking regions of pA2 are shown in SEQ ID NO:12. The insert starts at position 21 and ends at position 72. (The first "T" residue at the 5'-end corresponds to position number 2263, the last "A" residue at the 3'-end corresponds to position number 2354 of the plasmid pA2-S2).

After insertion of an open reading frame into any of the plasmids pA1-S1, pA2-S1, pA1-S2 or pA2-S2, the entire expression cassette can be excised and inserted by forced cloning into corresponding sites in the virus vector vdTK. The cassette can be inserted into the virus genome in either orientation depending on the cloning plasmid used.

Construction of plasmids comprising expression cassettes with a selective marker (pN2gpt-S3A and pN2gpt-S4): Besides plasmids designed for forced cloning, described hereinabove, two additional plasmids were constructed for transferring genes into one unique (NotI) site in a poxvirus vector with the help of the *E. coli* gpt selectable marker gene. They also provide two additional poxvirus promoters besides the S1 and S2 promoters described hereinabove.

The plasmid pN2gpt-S3A (FIG. 4.7) can be used to insert open reading frames lacking their own initiation codon. The genes to be transferred into vaccinia virus (the gpt marker and the open reading frame) can be excised either with NotI alone or with two enzymes, for example, NotI and SmaI (or RsrII or ApaI). The excised fragment is then inserted into the corresponding site(s) of the virus vector vdTK.

The plasmid pN2gpt-S4 (FIG. 4.7) can be used to insert complete open reading frames including an AUG translation start codon. The cassettes consisting of the gpt marker gene and the open reading frame can be excised as described for pN2gpt-S3A. The promoters S3A (bases 21–107 of SEQ ID NO:13) and S4 (bases 21–114 of SEQ ID NO:14) are modified versions of strong poxvirus late promoters.

These plasmids were constructed by first making plasmids pN2-gpta and pN2-gptb (FIG. 4.6) which contain an *E. coli* gpt gene driven by the vaccinia virus P7.5 promoter, flanked by several unique restriction sites including NotI (FIG. 1.3). Insertion of the S3A or S4 promoter-fragment into the unique PstI and ClaI sites in pN2-gptb resulted in the plasmids pN2gpt-S3A and pN2gpt-S4.

Construction of plasmids pN2-gpta and pN2-gptb: See Example 1 and FIG. 4.6.

Construction of plasmid pN2gpt-S3A: The parental plasmid pN2-gptb was digested with PstI and ClaI and ligated with a synthetic linker sequence consisting of the oligonucleotides P-artP(7) and P-artP(8) (SEQ ID NO:40). The resulting plasmid was designated pN2gpt-S3A.

The synthetic promoter sequence of pN2gpt-S3A (corresponding to the oligonucleotide P-artP(7)) and twenty bases of the 5'- and 3'-flanking regions of pN2-gptb are shown for pN2gpt-S3A in SEQ ID NO:13. The inserted DNA sequence starts at position 21 and ends at position 107. (The first T-residue at the 5'-end corresponds to position number 3328, the last A-residue at the 3'-end to position number 3454 of the plasmid pN2gpt-S3A).

Construction of plasmid pN2gpt-S4: The plasmid pN2-gptb was digested with PstI and ClaI and ligated with an adaptor sequence consisting of the oligonucleotides P-artP (9) and P-artP(10) (SEQ ID NO:41). The resulting plasmid was designated pN2gpt-S4.

The synthetic promoter sequence of pN2gpt-S4 (corresponding to the oligonucleotide P-artP(9)) and twenty bases of the 5'- and 3'-flanking regions of pN2-gptb are shown for pN2gpt-S4 in SEQ ID NO:14. The inserted DNA sequence starts at position 21 and ends at position 114. (The first "T" residue at the 5'-end corresponds to base #3328, the last "A" residue at the 3'-end to position base #3461 of the plasmid pN2gpt-S4).

EXAMPLE 5

Expression of polypeptides in a vaccinia virus vector (vdTK) by direct molecular insertion of gene expression cassettes This example demonstrates the facility with which cloned genes can be inserted into a vaccinia virus vector (vdTK) of the present invention for rapid creation of poxvirus expression constructs using direct molecular insertion of gene expression cassettes described in Example 4. Here, use of the vdTK vector-cassette system to make constructs for expressing several particular model polypeptides is described, including human blood proteins (prothrombin and variants of plasminogen) and a human virus antigen (HIV gp160).

Construction of a modified vaccinia virus (vPTI) expressing human prothrombin: Human prothrombin (PT) serves as a model for foreign protein expression in a vaccinia virus vector of the present invention. A cDNA encoding prothrombin has been shown previously to be expressible by a conventionally constructed recombinant vaccinia virus, as disclosed in PCT Application PCT/EP91/00139 by Falkner et al. ("the Falkner application"), the entire disclosure of which is hereby incorporated herein by reference.

A modified prothrombin cDNA is excised as a 2.0 kb EcoRI fragment from the plasmid pTKgpt-PTHBb, and inserted into the single EcoRI site of the plasmid pA1-S1 (Example 4, FIG. 4.4A) resulting in the plasmid pA1S1-PT (FIG. 5.1). In the expression cassette of this plasmid, the prothrombin cDNA is driven by the synthetic poxvirus promoter S1 which also provides a translation initiation codon.

The sequence of human prothrombin has been published by Degen et al., *Biochemistry* 22:2087–2097 (1983). This sequence is accessible in the EMBO Data Library under the Identifier (ID) HSTHR1. The sequence in ID HSTHR1 is not complete; it lacks the first 19 bp of the prothrombin coding region. The present inventors have sequenced the missing part of the cDNA in ID HSTHR1 and present this hereinbelow.

Due to the many modifications and base changes, the full sequence of the present human prothrombin cDNA clone including the S1 promoter and 20 bases of plasmid flanking sequences is shown in SEQ ID NO:15.

By the engineering steps outlined in the Falkner application, the cDNA was modified as follows: two additional codons (bases #22–27) were introduced resulting in the incorporation of two new amino acids; the 3'-untranslated sequence was removed by introduction of an EcoRI site: bases #1963–1965 (#1920–1922 ID HSTHR1) were changed from TGG to GAA by site directed mutagenesis.

One base pair change was found in the present PT-cDNA, that results in a novel NcoI site: base #525 (#482 in ID HSTHR1) is changed from C to A. This is a silent mutation because the CCC codon (Pro) is changed to CCA (Pro) which results in a new NcoI site. (The first base of SEQ ID NO:15 from pA1S1-PT corresponds to base #2394 and the last base to #4381 of the full sequence of plasmid pA1S1-PT).

For transfer into the vaccinia virus vector vdTK, the cassette is excised from the plasmid pA1S1-PT with NotI and RsrII endonucleases and isolated after separation on a low melting point agarose gel. The virus vector vdTK DNA is cleaved with NotI and RsrII, extracted with phenol and precipitated with ethanol. The small NotI-RsrII connecting fragment of the multiple cloning site of the vector DNA is lost during the ethanol precipitation step. The vaccinia vector arms are ligated with a twenty-fold molar excess of cassette. Packaging of ligated vaccinia virus DNA with fowlpox helper virus in chicken cells is described in Example 3. Packaged viruses from plaques produced by infection of in CV-1 cells are plaque purified again and small crude stocks are prepared. The virus isolates may be further analyzed by Southern blot analysis and expression analysis as described in the Falkner application. A viral isolate having the correct genomic structure for insertion of the prothrombin cDNA is designated vPT1. A similar recombinant vaccinia virus produced by marker rescue induced prothrombin expression in Vero cells at levels of activity of about 50–60 mU/ml of cell culture supernatant. See the Falkner application.

Construction of a vaccinia virus (vGPg1) expressing human glu-plasminogen: The native form of plasminogen (Pg) has an amino terminus starting with the amino acid glutamic acid (glu) and is therefore called glu-plasminogen (glu-Pg). A partially processed form of plasminogen that lacks the first 77 amino terminal amino acids (the activation peptide) is called lys-plasminogen (lys-Pg). The affinity of lys-Pg for its substrate fibrin is much higher than that of glu-Pg. In addition, recombinant lys-Pg is considerably more stable than glu-Pg in supernatants of cell cultures infected with a (conventional) vaccinia recombinant carrying the glu-Pg gene.

The complete human plasminogen cDNA (including its translational start and stop codons) was excised from a plasmid (phPlas-6) as a BalI-SmaI fragment. The sequence of human plasminogen has been published by Forsgren et al., *FEBS Letters* 213:254–260 (1987), and is accessible in the EMBO Data Library (GenBank) under the Identifier (ID) HSPMGR. Therefore sequences of this plasmid have not been included in the instant Sequence Listing because this plasmid is not a unique source of the plasminogen DNA sequence. However, the coding region of the present plasminogen sequence differs from the published sequence in at least one nucleotide: the "A" residue at position #112 (ID HSPMGR) is a "G" residue in the instant DNA, resulting in an amino acid substitution (Lys→Glu).

The plasminogen cDNA was inserted into the HpaI site of the plasmid pN2gpt-S4 (Example 4, FIG. 4.6), which was selected for constructing a gene expression cassette with a selectable marker because the plasminogen cDNA contains two ApaI sites and one RsrII site and therefore does not allow the use of the expression cassettes designed for forced cloning. The resulting plasmid was designated pN2gpt-GPg (FIG. 5.2).

The joining region of the S4 promoter including the initiation codon of plasminogen (base #32 this listing; base #55 in ID HSPMGR) is shown for pN2gpt-GPg in SEQ ID NO:17. The coding region of glu-plasminogen was omitted in the sequence listing. The sequence continues with the stop codon (base #35 this listing; base #2485 in ID HSPMGR) and 25 bases of the 3'-untranslated plasminogen sequence. This sequence is followed by 29 bases of the multiple cloning site of phPlas6 and by 20 bases of the multiple cloning site of plasmid pN2gpt-S4.

To transfer the glu-plasminogen gene cassette into a vaccinia virus genome, the NotI fragment of pN2gpt-GPg containing the two genes and their promoters (the P7.5 promoter controlling the gpt-selection marker, and the S4-promoter controlling the glu-plasminogen gene) is isolated from a low melting point agarose gel and purified. This cassette is ligated with arms of vaccinia virus vdTK DNA cut with NotI. Packaging and plaque purification are described in Example 3. A virus having the correct structure for the inserted plasminogen-gene cassette is designated vN2gpt-GPg. This virus is used for expression of plasminogen in CV-1 cells as described for an analogous vaccinia virus constructed by marker rescue techniques. Secreted glu-Pg in cell culture supernatants was detected at a level of about 1.5 $\mu g/10^6$ cells after 24 hours of infection with a conventionally constructed vaccinia virus under standard conditions for cultivation of vaccinia virus vectors for expression of foreign proteins in cell culture. The glu-plasminogen in the cell culture supernatant was detectable only in the presence of a protease inhibitor (50 $\mu g$/ml of aprotinin).

Construction of a vaccinia virus (vLPg1) expressing human lys-plasminogen: A sequence encoding lys-plasminogen was prepared by deletion of the 231 bp coding region for the first 77 amino acids (Glu1 to Lys77) of plasminogen from the complete plasminogen cDNA as shown in FIG. 5.3. This sequence was inserted into the gene expression cassette of a plasmid (pN2gpt-S4) having a selectable marker gene (*E. coli* gpt), resulting in the plasmid designated pN2gpt-LPg (FIG. 5.3).

In this plasmid, the pre-sequence (coding for the signal peptide that mediates secretion) is directly fused with the first nucleotide of lysine residue 78 in plasminogen. The novel signal peptide cleavage site created by the fusion is similar to many known signal cleavage sites. See, for instance, von Heinje, *Eur. J. Biochem.* 133:17–21 (1983).

In addition, an NcoI site was introduced at the site of the initiation codon of the Pg cDNA to facilitate cloning into the single NcoI site of the plasmid pN2gpt-S4 and to achieve the optimal context of the promoter and the Pg-coding region. To facilitate excision of Pg cDNA with NcoI, one of two internal NcoI sites (NcoI (2); FIG. 5.3) was deleted from the Pg cDNA, as follows.

The plasmid phPlas6 was transferred into *E. coli* strain NM522 and single-stranded DNA was prepared by superinfection with the helper phage M13K07. The first round of mutagenesis was done with two oligonucleotides, oNco1 and oNco2, using the single-stranded phPlas6 DNA as a template with a commercially available mutagenesis kit (Amersham, Inc.). The oligonucleotide Nco1 converts two A-residues upstream of the plasminogen start codon into two C-residues, resulting in an NcoI site around the start codon without changing the coding region of the plasminogen pre-sequence. The oligonucleotide oNco2 converts a T into a C residue within the internal NcoI site (NcoI(2)) of the Pg cDNA, producing a silent mutation that inactivates this NcoI site.

The coding region for amino acids 1–77 of plasminogen was deleted by second loop-out mutagenesis step using 42-base oligonucleotide oNco3. All mutations were confirmed by sequencing and restriction analysis.

The plasmid having the three mutations, phLplas, was linearized with SmaI and partially digested with NcoI. The 2.2 kb NcoI-SmaI fragment was isolated and inserted into plasmid pN2gpt-S4 that had been cut with NcoI and SmaI. The resulting plasmid was designated pN2gpt-LPg.

Due to the many modifications of the plasminogen cDNA in pN2gpt-LPg, the full sequence of the NcoI-SmaI fragment of pLplas including 20 bases of the S4 promoter and 20 bases of the downstream plasmid region of pN2gpt-S4 is shown in SEQ ID NO:18. The plasminogen cDNA sequence was modified as follows. The former two A-residues at positions #19 and #20 (bases #53 and 54 in ID HSPMGR) were changed into two C-residues, resulting in an NcoI site; base #21 this listing (#55 in ID HSPMGR) is the A-residue of the plasminogen start codon; base #2220 (base #2485 in ID HSPMGR) is the T-residue of the stop codon; base #111 in ID HSPMGR (base #77 this listing) was joined with base #343 in ID HSPMGR (base #78 this listing) resulting in the deletion of the sequence coding for the "activation peptide"; the T-residue #926 (base #1191 in ID HSPMGR) was changed into a C residue (conservative exchange) resulting in the disappearance of an internal NcoI site.

To transfer the lys-plasminogen gene cassette into a vaccinia virus genome, the NotI fragment of pN2gpt-LPg containing the gene expression cassette comprised of two promoter-gene combinations (the P7.5 promoter-gpt gene and the S4 promoter-lys-plasminogen gene) is ligated with NotI cleaved vaccinia virus vdTK vector DNA and packaged as described in Example 7. An isolate having the proper structure for the inserted gene cassette, designated vN2gpt-LPg, is used for expression of lys-plasminogen in CV-1 cells under conditions used previously for a conventionally constructed recombinant under standard conditions for cultivation of vaccinia virus expression vectors for production of proteins in cell culture. Secreted lys-Pg in cell culture supernatants was detected at a level of about 1.0–2.0 $\mu g/10^6$ cells after 24 hours of infection with the conventional recombinant. The lys-plasminogen in the cell culture supernatant was stable without addition of a protease inhibitor.

Construction of a vaccinia virus (vgp160-1) for expressing human immunodeficiency virus glycoprotein 160 (HIV gp160): The complete open reading frame of HIV gp160 is obtained on a 2.5 kb EcoRV fragment containing excised from replicative form (RF) DNA of an M13 phage mPEenv. Fuerst et al., *Mol. Cell. Biol.* 7:2538–2544 (1987). This fragment is inserted into the plasmid pN2gpt-S4 as outlined in FIG. 5.4. In the resulting plasmid, pN2gpt-gp160, the gp160 gene is controlled by the synthetic vaccinia virus promoter S4.

The sequence of HIV gp160 has been published by Ratner et al., *Nature* 313:277–284 (1985). The sequence of clone BH8 is accessible in the EMBO Data Library (GenBank) under the Identifier (ID) HIVH3BH8. Therefore, the gp160 sequence is not included in SEQ ID NO:19, but the joining region of the S4 promoter and an EcoRV HIV-gp160 fragment including the initiation codon of gp160 gene (base #28 this listing; base 226 in ID HIVH3BH8) is shown. The EcoRV HIV-gp160 fragment stems from the M13 phage (replicative form) mPEenv described by Fuerst et al., *Mol. Cell. Biol.* 7:2538–2544 (1987). The sequence continues with the stop codon (base #31 this listing; base #2779 in ID HIVH3BH8) and one half of the downstream EcoRV site. This sequence is followed by 20 bases of the multiple cloning site of plasmid pN2gpt-S4. The first base (T) of this listing corresponds to base #3368, the last base (G), to #5973 in the sequence of pN2gpt-gp160.

To transfer the HIV gp160 gene-expression cassette into a vaccinia virus genome, the NotI fragment containing both gene-promoter combinations (the P7.5 promoter-gpt selection marker and the S4 promoter-gp160 gene) is ligated with NotI-cleaved DNA of the vaccinia virus vector vdTK and packaged as described in Example 7. An isolate having the correct structure of insertion of the cassette, designated vN2gpt-gp160, is used for expression of gp160 in African green monkey (Vero) cells under conditions used previously for a conventionally constructed recombinant. Barrett et al., *AIDS RESEARCH AND HUMAN RETROVIRUSES* 6:159–171 (1989).

Construction of a vaccinia virus vector providing for screening for modified viruses carrying insertions by coinsertion of a lacZ gene: To demonstrate the screening for insertion by coinsertion of an *E. coli* lacZ gene in combination with the direct cloning approach, the plasmid pTZgpt-S3AlacZ provides a useful model construct (FIG. 5.5). The plasmid pTZ19R (Pharmacia, Inc.) was cut with PvuII, and the large 2.5 kb vector fragment was prepared and ligated with NotI linkers (Boehringer, Inc.). The resulting plasmid, pTZ-N, has a deletion of the multiple cloning site that is located within the sequences of the alpha complementation peptide in the pT219R plasmid. Therefore, possible recombination events between the lacZ gene to be inserted into PTZ-N and the sequences of the alpha complementation peptide are excluded.

To construct a gene expression cassette for direct molecular cloning, the 1.2 kb NotI fragment, containing the gpt gene cassette and the S3A promoter, is excised from pN2gpt-S3A (Example 4) and inserted into pTZ-N resulting in the plasmid pTZgpt-S3A. The 3.0 kb EcoRI lacZ fragment, excised from plasmid pTKgpt-F1sβ described by Falkner and Moss (1988), is inserted into the single EcoRI site of pTZgpt-S3A. The resulting plasmid designated pTZgpt-S3AlacZ.

The 4.4 kb NotI fragment of this plasmid, consisting of the two marker genes (*E. coli* gpt and lacZ), is ligated with NotI cleaved DNA of the virus vdTK (Example 4). The ligation and packaging conditions are described in Example 3. The estimated yield of modified viruses in the case of gpt-selection is described in Example 3.

An additional vaccinia virus vector was constructed as follows. The plasmids pTZS4-lacZa and pTZS4-lacZb provided useful model constructs (FIG. 5.6). Plasmid PTZ-N was constructed as above. The gene expression cassette, the 1.2 kb NotI fragment containing the gpt-gene cassette and the S4 promoter was excised from pN2gpt-S4 (Example 4) and inserted into PTZ-N resulting in the plasmid pTZgpt-S4. A 3.3 kb SmaI-StuI lacZ fragment was excised from plasmid placZN*, which was constructed by digesting the plasmid pFP-Zsart (European Patent Application No. 91 114 300.-6, Recombinant Fowlpox Virus) with NotI and ligating pFP-Zsart with the oligonucleotide P-NotI$^-$ (5'-GGCCAT-3'). This 3.3 kb SmaI-StuI lacZ fragment was inserted into the single SmaI site of pTZgpt-S4. The resulting plasmids were designated pTZS4-lacZa and pTZS4-lacZb. The 4.5 kb NotI fragment of this plasmid was ligated with the NotI cleaved DNA of the virus vdTK and packaged as described above.

The combination of lacZ and gpt-selection in a single cloning step offers no advantage because all gpt-positive plaques will contain the lacZ gene. However, for the construction of viruses having insertions in different sites, a second screening procedure is desirable. The marker of first choice is the gpt marker, but lacZ screening offers an alternative method for detection of inserts, for instance, when the target viral genome already contains a copy of a selectable marker such as the *E. coli* gpt gene.

For such screening, two ml of 1/10, 1/100 and 1/1000 dilutions of crude virus stocks prepared after packaging (see Example 3) is plated on 30 large (diameter of 8.5 cm) petri dishes (10 petri dishes per dilution). The blue plaque assay is done according to standard procedures. Chakrabarti et al., *Mol. Cell. Biol.* 5:3403–3409 (1985).

EXAMPLE 6

Construction of a vaccinia virus vector (vS4) with a directional master cloning site under transcriptional control of a strong late vaccinia virus promoter The present example describes a vaccinia virus cloning vector (vS4) that is designed for direct molecular insertion of a complete open reading frame into a master cloning site that is functionally linked to a vaccinia virus promoter. Accordingly, use of this vector according to methods of the present invention enables insertion of genes directly into a poxvirus vector without separate construction of an insertion plasmid, as required in conventional construction of recombinant poxviruses by intracellular recombination. This vector also obviates the need for separate construction of a gene expression cassette for transfer into a vaccinia virus vector by direct molecular insertion, as described hereinabove.

The master cloning site of vector S4 is located in the genetically stable central region of the vaccinia virus genome and is comprised of several cleavage sites that are unique in the vector, thus permitting directional insertion. The S4 promoter immediately upstream of the master cloning site is a strong synthetic variant of a late vaccinia virus promoter. This expression vector is suitable for direct cloning and expression of large open reading frames which include a translation start codon, as illustrated here by a cDNA encoding a human blood protein, the von Willebrand factor (vWF).

Construction of the vaccinia virus vector vS4: An adaptor containing the synthetic vaccinia virus promoter S4 is inserted into the vaccinia virus vector vdTK (Example 4, FIGS. 4.1A–C) at the unique NotI site (FIG. 6.1). Insertion of the selected adaptor oligonucleotides inactivates the upstream NotI site while the downstream NotI site remains functional as a unique cloning site.

More particularly, DNA (1 μg) of the vector vdTK (Example 4, FIGS. 4.1A–C) is cleaved with NotI and ligated with (0.5 μg) annealed oligonucleotides P-artP(11) (SEQ ID NO:38) and P-artP(12) (SEQ ID NO:39). The ligation mix is packaged and plaques are identified as described in Example 3. Plaques are subjected to PCR screening as described (Example 4, Identification of the virus vdTK by PCR screening). An isolate having the insert in the correct orientation is designated vS4.

Insertion of the von Willebrand factor cDNA into vS4: Plasmid pvWF contains the complete von Willebrand factor cDNA flanked by NotI sites. The sequence of human vWF has been published by Bonthron, D. et al., *Nucl. Acids Res.* 14:7125–7128 (1986). The sequence is accessible in the EMBO Data Library under the Identifier (ID) HSVWFR1. SEQ ID NO:20 shows the junction in the virus genome of vvWF of the viral S4 promoter and the 5'-untranslated region of the present vWF cDNA in the plasmid pvWF up to the translational start codon (base #249 in this listing; base #100 in ID HSVWFR1). The coding region of vWF was omitted in the instant sequence listing. The sequence continues with the stop codon (base #252; base #8539 in ID HSVWFR1) and the 3'-untranslated sequence up to the NotI site (base #304) and twenty bases of overlap with the 3'-region of the viral genome of vvWF.

The vWF CDNA fragment is released with NotI, isolated and ligated with vS4 vector DNA that has been cleaved with NotI and treated with phosphatase, as illustrated in FIG. 6.2.

One μg of ligated DNA is packaged as described in Example 7. Plaques are picked and analyzed by PCR screening. The first primer for the PCR reaction is oligonucleotide odTK2 which is located about 300 bp upstream of the tk-gene; the reverse primer ovWF1 is located in the vWF gene about 50 bp downstream of the initiation codon. PCR amplification occurs only when the vWF insert is in the correct orientation relative to the S4 promoter in the vector. PCR-positive plaques are identified and analyzed further. Alternatively, if the yield of desired modified virus is low, on the order of 0.1 to 0.01%, then they may be identified by in situ plaque hybridization methods adapted from those known in the art. See, for instance, Villareal and Berg, *Science* 196:183–185 (1977).

A virus clone having the cDNA insert by PCR or hybridization and further showing the expected restriction pattern with PvuII is designated vvWF. Such vectors may be tested for expression of von Willebrand factor as described for other human proteins in Example 5, modified as appropriate according to genetic engineering principles well known by one skilled in this art.

EXAMPLE 7

Heterologous packaging of orthopox (vaccinia) virus genomic DNA by an avipox (fowlpox) helper virus and simultaneous selection for modified virus in host cells of a species in which the helper virus cannot replicate Example 3 describes packaging of modified vaccinia virus DNA with fowlpox helper virus in avian cells and subsequent isolation of progeny virus plaques in mammalian (CV-1) cells in which the avipox helper virus cannot replicate. The present example illustrates packaging of vaccinia virus DNA by fowlpox directly in CV-1 cells, thereby permitting simultaneous packaging and host range selection for packaged virus. Besides eliminating helper virus from the initial stock of progeny, this procedure circumvents the tedious requirement for producing primary cultures of chicken embryo fibroblasts for each packaging experiment. Instead, continuous. mammalian cell lines that are commonly used for vaccinia virus replication also can be used for packaging vaccinia virus with fowlpox helper virus.

It is known that fowlpox virus (FPV) replicates completely only in avian cells; no viable progeny virus is obtained from infected mammalian cells. The precise point in the life cycle of FPV at which replication is aborted in mammalian cells is not known. However, FPV is known to produce viral proteins in mammalian cells and even to induce protective immunity in mammals when used as a live vaccine. Taylor et al., *Vaccine* 6:497–503 (1988). Nevertheless, FPV has not been shown previously to have a capacity for packaging heterologous poxvirus genomic DNA, particularly directly engineered vaccinia virus DNA.

In an initial experiment, CV-1 cells ($5\times10^6$) were infected with one pfu/cell of fowlpox virus (strain HP1.441) and incubated for one hour. Subsequently, a calcium-phosphate precipitate (one ml containing one μg of vaccinia virus wildtype DNA) was transfected into the infected cells. After 15 min at room temperature, 10 ml of medium (DMEM, 10% fetal calf serum) were added. The cells were incubated for four hours, and the medium was changed. The cells were then incubated for six days, and a crude virus stock was prepared. The progeny virus were titered on CV-1 cells. Typical vaccinia plaques were visible after two days.

The dependence of packaging efficiency on the amount of genomic viral DNA was determined over a range of DNA amounts from 0.1 to 10 μg per 5×10$^6$ CV-1 cells. See FIG. 7.1. Amounts of DNA in excess of 1 μg (e.g., 10 μg) produced a coarse calcium-phosphate precipitate that reduced the efficiency of transfection in terms of pfu/μg of input DNA. FIG. 7.1.

The dependence of the packaged vaccinia virus yield on the incubation time for packaging was analyzed using a constant amount of vaccinia virus wildtype DNA (1 μg) and a constant amount of FPV helper virus (1 pfu/cell) under the conditions described above for the initial experiment in this example except that the medium added 15 minutes after transfection was changed after four hours, and the cells were then incubated for an additional 1 to 5 days before preparing a crude virus stock (total volume of 2 ml). Virus stock from control cells infected with FPV only and incubated for 5 days produced no visible plaques. This experiment was repeated three times and a typical outcome is shown in Table 4, below.

TABLE 4

Effect of incubation time on yield of vaccinia virus from DNA packaging by fowlpox helper virus in mammalian (CV-1) cells.

| Incubation Time (hours) | Titer (pfu/ml) |
|---|---|
| 24 | $1.0 \times 10^2$ |
| 48 | $4.6 \times 10^4$ |
| 72 | $5.0 \times 10^5$ |
| 96 | $5.6 \times 10^6$ |
| 120 | $2.1 \times 10^7$ |

The titer of packaged vaccinia virus, detected by plaque assay on mammalian (CV-1) cells, rose continually from about 10$^2$ pfu/ml at 24 hours to about 2×10$^7$ after 120 hours. Incubation times in the range of 48 to 72 hours produced convenient levels of packaged vaccinia virus (between 10$^4$ and 10$^6$ pfu/ml) and, therefore, are suitable for routine packaging of vaccinia virus DNA by fowlpox virus in mammalian cells.

Vaccinia DNA can be packaged in mammalian cells abortively infected with fowlpox virus. It was shown previously that fowlpox virus can also infect mammalian cells, but the viral life cycle is not completed in these non-typic host cells. Depending on the cell type, viral growth stops either in the early or in the late stage and viable fowlpox virus is not formed. Taylor et al. (1988). These findings prompted an investigation into packaging vaccinia DNA in a continuous mammalian cell line. Confluent monolayers of CV-1 cells were infected with 0.05 pfu per cell of the FPV strain HP1.441 and then transfected with a ligation mixture consisting of NotI-cleaved vaccinia virus DNA and a gpt gene cassette having NotI flanking sites. More particularly, vaccinia DNA (1 μg) was digested with NotI and ligated with indicated amounts of insert DNA (P7.5 gpt gene cassette). The unique NotI site in vaccinia virus is located in an intergenic region in the HindIII F fragment. Goebel et al., *Virology* 179:247 (1990). After incubation for three days the cells were harvested and the crude virus stock was titered on CV-1 cells in the presence (+MPA) and in the absence (−MPA) of gpt-selective medium. The outcome is summarized in Table 5.

TABLE 5

Titers after abortive packaging

| expt. # | insert (ng) | titers (pfu × 10$^{-2}$/6 × 10$^6$ cells) −MPA* | +MPA | chimeras (%) |
|---|---|---|---|---|
| 1. | 200 | 17.2 | 1.6 | 9.3 |
| 2. | 200 | 42.5 | 5.1 | 12.3 |
| 3. | 400 | 64.0 | 3.8 | 5.9 |
| 4. | 400 | 26.8 | 3.8 | 14.2 |
| 5. | | 210.0 | | |

*MPA, mycophenolic acid.

The most important result was that fowlpox virus could package the modified vaccinia DNA in a cell type that prevents its own growth. Moreover, the yield of chimeric plaques was in the range of 5–10%. This compares favorably with the classical in vivo recombination technique, in which usually about 0.1% of the total plaques are recombinants. Ligation of the vector arms alone (Table 5, experiment #5) resulted in a higher titer compared to ligation experiments 1–4 with insert, probably due to lack of contaminants present in the agarose-purified insert molecules.

Some of the isolated viruses were plaque-purified and further characterized. They showed the typical HindIII restriction patterns of vaccinia virus and, in addition, foreign gene bands characteristic for the two possible orientations of the single insert. With insertion into the NotI site, no viruses with multiple inserts were observed.

Heterologous packaged chimeric vaccinia viruses do not cross hybridize with fowlpox virus. In order to study the effects of heterologous packing by FPV on the structure of chimeric vaccinia viruses, DNAs of isolates F13.4, F12.5, F13.2, F13.2 and F12.4, together with those of four purified isolates from the NotI cloning experiment and the fowlpox virus controls, were digested with HindIII, and the resulting fragments were separated by electrophoresis and analyzed by Southern hybridization with a fowlpox virus probe prepared from sucrose gradient-purified virions. No cross hybridization of the vaccinia viruses with FPV DNA was observed.

EXAMPLE 8

Homologous packaging of engineered vaccinia virus genomic DNA by a vaccinia virus host range mutant (vdhr) that is unable to replicate in a human cell line The present example illustrates construction and utilization of a helper poxvirus comprised of deletions that limit its host range, particularly the ability to replicate in certain human cell lines. Therefore, modified vaccinia virus free of helper virus can be prepared by packaging of vector DNA with this mutant helper virus and isolating clones of the engineered virus by infecting appropriate human cells.

This mutant helper virus is derived from host range mutants of vaccinia virus which are unable to replicate in a variety of human cells and which display altered cytopathic effects on many other cells that are permissive for infection by wildtype vaccinia virus. See, for example, Drillien et al., *Virology* 111:488–499 (1981). In particular, the genome of this helper virus comprises mutations of two host range genes which together prevent it from replicating in human (MRC 5) cells in which only vaccinia virus genomes having at least one intact host range gene can replicate.

Construction of the host range mutant vaccinia virus vdhr: The genomic location and DNA sequence of one vaccinia virus gene required for replication in human cells has been described by Gillard et al., *Proc. Natl. Acad. Sci. USA* 83:5573–5577 (1986). Recently, this gene has been designated KiL. Goebel et al. (1990). A second vaccinia virus host range gene has been mapped. Perkus et al., *J. Virology* 63:3829–2836 (1990). This second gene, designated C7L by Goebel et al. (1990), lies in a region encompassing parts of the HindIII C and HindIII N fragments. This region is deleted in the vaccinia virus WR6/2 strain. Moss et al., *J. Virol.* 40:387–395 (1981). Strain WR-6/2 therefore lacks the C7L host range gene.

The helper virus vdhr lacking both the K1L and C7L host range genes is constructed from the C7L-negative strain WR-6/2 by marker rescue with a modified EcoRI K fragment from which the K1L host range gene is deleted. See FIG. 8.1. This modified EcoRI K fragment comprises a selective marker gene (the *E. coli* gpt gene) to facilitate selection for modified WR-6/2 genomes comprising the modified EcoRI K fragment using intracellular marker rescue. Sam and Dumbell (1981). A conditional lethal mutant which lacks the ability to grow on human cell lines has also been described. Perkus et al. (1989).

More particularly, the 5.2 kb EcoRI K fragment of vaccinia virus wildtype DNA is subcloned into the plasmid pFP-tk18i. The resulting plasmid is designated pFP-EcoK1. The vaccinia virus host range gene K1L, see Gillard et al. (1986), is deleted and simultaneously a unique NotI site is introduced by loopout mutagenesis using the oligonucleotide P-hr(3) (SEQ ID NO:42). The resulting plasmid is designated pEcoK-dhr.

The plasmid pFP-tk18i was constructed by modification of the plasmid pFP-tk-10.4. See Falkner et al. application, Example 3 at 8. Plasmid pFP-tk10.4 was digested with NcoI and ligated with an adaptor consisting of annealed nucleotides P-NcoI(1) and P-NcoI (2), resulting in the introduction of a multiple cloning site into the single NcoI site of the FPV tk-gene with the restriction endonuclease cleavage sites EcoRI, NotI and The sequence of vaccinia virus has been published by Goebel et al., *Virology* 179:247–266 (1990). It is accessible in the EMBO Data Library (GenBank) under the Accession Number M35027. The sequence of the vaccinia virus host range gene K1L has been published by Gillard et al., *Proc. Natl. Acad. Sci. USA* 83:5573–5577 (1986), and is accessible in the EMBO Data Library (GenBank) under the Identifier (ID) PXVACMHC. Therefore, the coding sequence of the K1L gene is not included in SEQ ID NO:21. In pEcoK-dhr the K1L gene is deleted and replaced by a NotI site. The joining region between the PXVACMHC sequence and the NotI site insert is shown (bases #1–20 of this listing correspond to bases #72–91 in ID PXVACMHC). The coding region of K1L was deleted and replaced by a NotI site followed by two G residues (bases #21–30 in the sequence listing). The sequence continues with 20 bp flanking region (bases #31–50 this listing; bases #944–963 in ID PXVACMHC).

In a further step pEcoK-dhr is linearized with NotI and ligated with a 1.1 kb P7.5-gpt gene cassette derived from plasmid pN2-gpta (Example 4) by NotI digestion. The resulting plasmid pdhr-gpt is used generate the helper virus vdhr.

The NotI cassette (comprising the P7.5 promoter-gpt gene cassette) inserted into pEcoK-dhr and twenty bases of the 5' and 3' flanking regions are shown for pdhr-gpt in SEQ ID NO:22. The flanking region (bases #1–20 this listing) correspond to bases #72–91 in ID PXVACMHC (see SEQ ID NO:21 for pEcoK-dhr). The inserted DNA sequence starts at position 21 (the first "G" of a NotI site) and ends at position 1189 (the last "C" residue of a NotI site). The A-residue of the translational initiation codon of the gpt gene corresponds to position #548. The T-residue of the translational stop codon of the gpt gene corresponds to position number #1004. The sequence continues with 20 bases of flanking region (bases #1192–1209 this listing; bases #944–961 in ID PXVACMHC). The two "G" residues #1190 and 1191 in this listing, correspond to position 29 and 30 of pEcoK-dhr.

To transfer the Eco K fragment into vaccinia virus, the plasmid is transfected into primary chicken embryo fibroblasts cells infected with the vaccinia virus deletion mutant WR-6/2. Modified viruses are selected as gpt-positive (using mycophenolic acid). A gpt-positive is plaque-purified three times in CEF cells and designated vdhr.

Characterization of the vdhr helper virus: The structure of gpt-positive vaccinia virus vdhr is analyzed by Southern blot analysis and host range tests. The vdhr virus is capable of forming plaques on chicken embryo fibroblasts and two monkey cell lines (BSC40 and Vero) but is defective for replication in the human cell line MRC-5.

Packaging of engineered vaccinia virus DNA using the host range mutant vdhr as a helper virus: A construct for expression of a cDNA encoding human prothrombin demonstrates the utility of this approach. The product from a ligation mixture described in Example 5, FIG. 5.1, is transfected into chicken embryo fibroblasts infected with vdhr as a helper virus. After 2 days the cells are harvested and a crude virus stock is prepared. Packaged virus is assayed for plaque formation on human (MRC 5) cells in which the desired vaccinia virus replicates but the mutant vdhr helper virus does not.

After three days the cells are stained with neutral red and plaques are selected for further analysis by Southern blot. Modified vaccinia virus clones having the desired structure are identified. Viruses which have undergone recombination with the highly homologous helper virus are also expected.

EXAMPLE 9

Construction of novel chimeric vaccinia viruses encoding HIV gp160 (vP2-gp160$_{MN}$A, vP2-gp160$_{MN}$B and vselP-gp160$_{MN}$) and expression of recombinant gp160$_{MN}$ in Vero cells The present example illustrates construction by direct molecular cloning of a vaccinia virus recombinant for large scale production of gp160 of the HIV-1$_{MN}$ isolate. Production of the gp160 of the HIV-1$_{IIIB}$ isolate described by Ratner et al., *Nature* 313:277–284 (1985), using a conventionally constructed vaccinia virus expression vector, has been described by Barrett et al., *AIDS Res. Human Retroviruses* 5:159–171 (1989). The HIV-1$_{IIIB}$ isolate, however, is a rare HIV variant. Efforts at developing vaccines based on HIV envelope proteins should include more representative HIV-1 isolates such as the MN-isolate. Gurgo et al., *Virology* 164:531–536 (1988); Carrow et al., *Aids Res. Human Retroviruses* 7:831–839 (1991). Accordingly, the present vaccinia virus vectors were constructed via direct molecular cloning to express the gp160 protein of the HIV$_{MN}$ isolate.

Construction of the plasmid pP2-gp160$_{MN}$ and of the chimeric viruses vP2-gpt160$_{MN}$A and vP2-gp160$_{MN}$B: The strategy of inserting the gp160-gene into vaccinia virus involved (i) modifying the gp160-gene by removing the large 5'-untranslated region (5'-UTR) and introducing a suitable cloning site upstream of the start codon, (ii) cloning the modified gp160-gene downstream of the strong late fowlpox virus P2-promoter (European Patent Application No. 91 114 300.-6, Aug. 26, 1991) and (iii) inserting a blunt-ended fragment consisting of the P2-gp160 and P7.5-gpt gene cassettes into the single restriction endonuclease cleavage sites of appropriate viral host strains, e.g. into the SmaI site of the host vaccinia strain vdTK (Example 4), the SmaI or the NotI sites of the vaccinia strain WR 6/2 of Moss et al., *J. Virol.* 40:387 (1981), or the vaccinia wild-type strain WR.

For these purposes, a new SmaI site was introduced into the plasmid pN2gpt-S4 (Example 4), resulting in the plasmid pS2gpt-S4 (FIG. 9.1, SEQ ID NO:62). Subsequently the S4-promoter was exchanged by the P2-promoter resulting in the plasmid pS2gpt-P2 (SEQ ID NO:63). This plasmid allows the cloning of complete open reading frame (orf's) but can also be used to clone incomplete orfs lacking their own start codon; the start codon is provided, for instance, when cloning into the single NcoI site (CCATGG) of this plasmid. Construction of the plasmids and viruses is described in further detail below. For the modification of the gp160-gene, a PCR-generated proximal fragment was exchanged leading to a gp160-gene cassette with a minimal 5'-UTR. This cassette is present in the final construct, the plasmid pP2-gp160$_{MN}$ (FIG. 9.1, SEQ ID NO:69). Additional characteristics of the plasmid are shown in table 6 below.

TABLE 6 pP2qp160mn (SEQ ID NO:69)

| Location | Description |
|---|---|
| 1–3529 | pS2gpt-P2 sequences |
| 2396–2851 | rcCDS of *E. coli* gpt gene |
| 2851 | T of rc initiation codon TAC of the gpt gene |
| 2395 | A of the rc stop codon of TTA |
| 3081–3323 | rc of vaccinia P7.5 promoter |
| 3358–3526 | P2 promoter sequence according to EP application Avipox “intergenic region”. |
| 3534–6001 | CDS of the HIV-1 strain MN gp160 sequence (EMBL ID REHIVMNC) |
| 3534 | A of the initiation codon ATG of the gp160MN |
| 6102 | T of the stop codon TAA of the gp160MN |
| 6173–6926 | pS2gpt-P2 sequences |

The plasmids were constructed as follows:

pS2gpt-S4: The plasmid pN2gpt-S4 (Example 4) was digested with XbaI and ligated with a SmaI-adaptor (SEQ ID NO:43: 5'-CTAGCCCGGG-3') inactivating the XbaI and creating a SmaI site. The resulting plasmid was designated pS2gpt-S4 (SEQ ID NO:62).

Additional characteristics of this plasmid are shown in the table 7 below.

TABLE 7 pS2gpt-S4 (SEQ ID NO:62)

| Location | Description |
|---|---|
| 1–2226 | pN2gpt-S4 sequences of SEQ ID NO:14. Position 1 corresponds to the first nucleotide G ‘5-TGGCACTTT TCGGGGAAAT-3' (bases 2–20 of SEQ ID NO:62). |
| 2227–2236 | SmaI-adaptor 5'-CTAGCCCGGG-3' (SEQ ID NO:43). |
| 2396–2851 | rcCDS of *E. coli* gpt gene |
| 2851 | T of rc initiation codon TAC of the gpt gene |
| 2395 | A of the rc stop codon of TTA |
| 3081–3323 | rc of vaccinia P7.5 promoter |
| 3358–3451 | S4-promoter of SEQ. ID#14 (oligonucleotide P-artP (9) see p. 120) |
| 2237–4145 | pN2gpt-S4 sequences of SEQ. ID No. 14 |

pS2gpt-P2: The S4-promoter segment of plasmid pS2gpt-S4 was removed by cleavage with PstI and HpaI and replaced with a 172 bp PstI-HpaI P2-promoter segment. This promoter segment was generated by PCR with the plasmid pTZgpt-P2a (Falkner et al., European Patent Application No. 91 114 300.-6, Aug. 26, 1991) as the template and the oligonucleotides P-P2 5'(1) and P-P2 3'(1) as the primers. The PCR-product was cut with PstI and HpaI and ligated the PstI and HpaI-cut large fragment of pS2gpt-S4. The sequence of P-P2 5'(1) (SEQ ID NO:44) is: 5'-GTACGTACGG CTGCAGTTGT TAGAGCTTGG TATAGCGGAC AACTAAG-3'; the sequence of P-P2 3'(1) (SEQ ID NO:45) is: 5'-TCTGACTGAC GTTAACGATT TATAGGCTAT AAAAAATAGT ATTTTCTACT-3'. The correct sequence of the PCR fragment was confirmed by sequencing of the final plasmid, designated pS2gptP2 (SEQ ID NO:63). The sequence primers used were P-SM(2) (SEQ ID NO:46), 5'-GTC TTG AGT ATT GGT ATT AC-3' and P-SM(3) (SEQ ID NO:47), 5'-CGA AAC TAT CAA AAC GCT TTA TG-3'. Additional characteristics of the plasmid pS2gpt-P2 are shown in table 8 below.

TABLE 8 pS2gpt-P2 (SEQ ID NO:63)

| Location | Description |
|---|---|
| 1–3357 | ps2gpt-S4 sequences |
| 2396–2851 | rcCDS of *E. coli* gpt gene |
| 2851 | T of rc initiation codon TAC of the gpt gene |
| 2395 | A of the rc stop codon of TTA |
| 3081–3323 | rc of vaccinia P7.5 promoter |
| 3358–3526 | P2 promoter sequence according to EP application Avipox “intergenic region”. |
| 3527–4277 | pS2gpt-S4 sequences |

pMNevn2: The plasmid pMNenvl was provided by R. Gallo (National Cancer Institute, Bethesda, Md.). It contains the gp160-gene of the HIV MN-strain cloned as a 3.1 kb EcoRI-PvuII fragment in the vector pSP72 (Promega, Inc.). The 0.6kb EcoRI-Asp718 fragment of pMNenvl was replaced with a 0.13 kb EcoRI-Asp718 fragment, removing large parts of the 5'-untranslated region of the gp160-gene. This 0.13 kb fragment was generated by PCR using the plasmid pMNenvl as the template and the oligonucleotides P-MN(1) and P-MN(2) as the primers. The forward primer P-MN(1) introduced, in addition, a StuI site 1 bp upstream of the start codon. The sequence of P-MN(1) (SEQ ID NO:48) is 5'-AGCTAGCTGA ATTCAGGCCT CATGAGAGTG AAGGGGATCA GGAGGAATTA TCA-3'; the sequence of P-MN(2) (SEQ ID NO:49) is 5'-CATCTGATGC ACAAAATAGA GTGGTGGTTG-3'. The resulting plasmid was designated pMNenv2. To exclude mutations the PCR generated fragment in this plasmid was sequenced with the primers P-Seq (2) (SEQ ID NO:50) 5'-CTG TGG GTA CAC AGG CTT GTG TGG CCC-3' and P-Seq(3) (SEQ ID NO:51) 5'-CAA TTT TTC TGT AGC ACT ACA GAT C-3'.

pP2-gp160MN: The 2.7 kb StuI-PvuII fragment, containing the MN gp160-gene, isolated from the plasmid pMNenv2 was inserted into the HpaI site of pS2gpt-P2 resulting in the plasmid pP2-gp160MN (SEQ ID NO:69).

The chimeric viruses vP2-gp160$_{MN}$A and vP2-gp160$_{MN}$B were constructed as follows. The SmaI-fragment consisting of the P2-gpl60 and P7.5-gpt-gene cassettes was inserted by direct molecular cloning into the single SmaI site of the host vaccinia strain vdTK (Example 4) resulting in the chimeric viruses vP2-gp160$_{MN}$A and vP2-gp160$_{MN}$B (FIG. 9.2). In particular, the vaccinia virus vdTK of Example 4 was cut at its single SmaI site and ligated with the 4.0 kb SmaI fragment that contains the P7.5-gpt-gene and the P2-gp160 gene cassettes. Correspondingly, the vaccinia strain WR6/2 was cut at its single SmaI (NotI) site and ligated with the 4.0 kb SmaI (NotI) fragment that contains the P7.5-gpt gene and the P2-gp160 gene cassettes. The cloning procedures were carried out as described in Example 1. In the virus vP2-gp160$_{MN}$A, the gp160 gene is transcribed in the same direction as the genes clustered around the viral thymidine kinase gene; in the virus vP2-gp160$_{MN}$B, the gp160 gene is transcribed in the reverse direction. Since gene position effects can influence expression levels in vaccinia constructs, the SmaI (NotI)-fragment consisting of the P2-gp160 and P7.5-gpt gene cassettes was also inserted into the SmaI (NotI) site of the WR 6/2 strain. The in vivo packaging was done as described in Example 3.

Structure of the chimeric viruses. To confirm the theoretical structures of the chimeric viruses (FIG. 9.3), Southern blot analyses are carried out. DNA's of the purified viruses are cleaved with PstI and resulting fragments are separated on an agarose gel, transferred to a nitrocellulose membrane and hybridized to a vaccinia thymidine kinase (tk) gene and a gp160-gene probe. With the tk gene probe, in the case of vP2-gp160$_{MN}$A, the predicted 6.9 and the 14.3 kb fragments are visible, and for vP2-gp160$_{MN}$B, the predicted 8.7 and 12.5 kb fragments are visible. With the gp160 probe (pMNenv1), the predicted 14.3 kb of vP2-gp160$_{MN}$A and 8.7 kb fragment of vP2-gp160$_{MN}$B are visible, confirming the integration of the foreign gene cassettes in two different orientations.

Expression studies with the chimeric viruses vP2-gp160$_{MN}$A and vP2-gp160$_{MN}$B. Vero cells are chosen for expression studies. Growth of cells, infection with the chimeric viruses and purification of the recombinant gp160 protein are carried out as described by Barrett et al., supra.

Western blot analysis of gp160: The Western blot analysis are done essentially as described by Towbin et al., *Proc. Natl. Acad. Sci. USA* 83:6672–6676 (1979). The first antibody is a mouse monoclonal anti-HIV gp120 antibody (Du Pont, Inc. #NEA9305) used at a 1:500 dilution. The second antibody is a goat-anti-mouse IgG (H+L) coupled with alkaline phosphatase (BioRad, Inc., #170-6520) used at a 1:1000 dilution. The reagents (BCIP and NBT) and staining protocols are from Promega, Inc.

Construction of the plasmid pselP-gp160MN and of the chimeric virus vselP-gp160$_{MN}$. The synthetic early/late promoter selP (SEQ ID NO:70) which is one of the strongest known vaccinia virus promoters, was used in this example to express the gp160-gene of the HIV-1 MN strain. See European Patent Application No. 91 114 300.-6. First, the plasmid pselP-gpt-L2 was constructed (FIG. 9.4). This plasmid includes the selP-promoter followed by a multiple cloning site for the insertion of foreign genes, as either complete or incomplete open reading frames, and translational stop codons in all reading frames followed by the vaccinia virus early transcription stop signal, TTTTTNT. Rohrmann et al., *Cell* 46:1029–1035 (1986). The P7.5 qpt gene cassette is located adjacent to the promoter and serves as a dominant selection marker. Falkner et al., *J. Virol.* 62:1849–1854 (1988). The selP-promoter/marker gene cassettes are flanked by restriction endonuclease cleavage sites that are unique in the vaccinia virus genome (SfiI, NotI, RsrII) and can also be excised as blunt ended fragments (for instance, by cleavage with HpaI and SnaBI). To be able to insert the gp160 gene into pselP-gpt-L2, an NcoI site was introduced around the translational start codon. This mutation results in the substitution of the amino acid arginine (AGA) with alanine (GCC). This mutation in the second amino acid of the signal peptide is not likely to interfere with efficient expression of the gp160-gene. The cloning procedure and the sequence around the wildtype and the modified gp160-gene is outlined in FIG. 9.5A. FIG. 9.5B shows sequences around translational start codons of wild-type (SEQ ID NO:73) and modified gp160 genes (SEQ ID NO:75). To introduce the mutation into the gp160-gene, a PCR-generated proximal fragment was exchanged. The construction of the plasmids is described in more detail below.

pL2: For the construction of pL2, the 0.6 kb XbaI-ClaI fragment of the plasmid pTM3, see Moss et al., *Nature* 348:91 (1990), was substituted by an XbaI-ClaI adaptor fragment consisting of the annealed oligonucleotides o-542 (SEQ ID NO:52) 5'-CGA TTA CGT AGT TAA CGC GGC CGC GGC CTA GCC GGC CAT AAA AAT-3' and o-544 (SEQ ID NO:53) 5'-CTA GAT TTT TAT GGC CGG CTA GGC CGC GGC CGC GTT AAC TAC GTA AT-3'. The intermediate plasmid resulting from this cloning step was called pL1. The 0.84 kb AatII-SphI fragment (parts of noncoding gpt-sequences) were substituted by the AatII-SphI adaptor fragment consisting of the annealed oligonucleotides o-541 (SEQ ID NO:54: 5'-CTT TTT CTG CGG CCG CGG ATA TGG CCC GGT CCG GTT AAC TAC GTA GAC GT-3') and o-543 (SEQ ID NO:55: 5'-CTA CGT AGT TAA CCG GAC CGG GCC ATA TAG GCC GCG GCC GCA GAAAAA GCATG-3'). The resulting plasmid was called pL2.

pTZ-L2: The XbaI-SphI fragment (consisting of the T7-promoter-EMC-T7-terminator segment, the multiple cloning site and the P7.5-gpt gene cassette) was treated with Klenow-polymerase and inserted between the PvuII sites of the plasmid pTZ19R (Pharmacia, Inc.). The resulting plasmid was called pTZ-L2 (SEQ ID NO:64). Additional features of this plasmid are shown in table 9 below.

TABLE 9 pTZ-L2 (SEQ ID NO:64)

| Location | Description |
|---|---|
| 1–55 | pTZ19R sequences (Pharmacia) |
| 56–108 | Linker I in rc orientation (5TNT, NotI, SfiI, RsrII, HpaI, SnaBI, AatII |
| 110–860 | *E. coli* gpt sequences in rc orientation. The gpt open reading frame starts with a rc TAC start codon at position 860 and ends with a rc ATT stop codon at pos 403 |
| 861–1338 | Vaccinia Virus p7.5 promoter sequences in rc orientation |
| 1339–1344 | HpaI site between bacteriophage T7 terminator and Vaccinia Virus p7.5 promoter |
| 1345–1488 | Bacteriophage T7 terminator sequences in rc orientation. See Dunn & Studier, J. Mol. Biol. |

TABLE 9-continued pTZ-L2 (SEQ ID NO:64)

| Location | Description |
|---|---|
| | 166: 477–535 (1983) |
| 1489–1558 | Multiple cloning site in rc orientation (SalI, translation stop codons for all three open reading frames, StuI, XhoI, PstI, BamHI, SpeI, SaoI, SmaI, EcoRI, NcoI) |
| 1559–2131 | sequences from the Encephalomyocarditis Virus (EMC-Virus) 5'untranslated region ( ) in rc orientation |
| 2132–2187 | Bacteriophage T7 promoter sequences in rc orientation ( ) |
| 2190–2242 | Linker II in rc orientation (SnaBI, HpaI, NotI, SfiI, 5TNT) |
| 2243–4701 | pTZ19R sequences (Pharmacia) |

PTZselP-L2 and pselP-gpt-L2: The 0.6 kb ClaI-NcoI fragment (the T7-promoter-EMC-sequence) was replaced with a synthetic promoter fragment consisting of the annealed oligonucleotides o-selPI (SEQ ID NO:56: 5'-CGA TAA AAA TTG AAA TTT TAT TTT TTT TTT TTG GAA TAT AAA TAA GGC CTC-3'; 51 mer) and o-selPII (SEQ ID NO:57: 5'-CAT GGA GGC CTT ATT TAT ATT CCA AAA AAA AAA AAT AAA ATT TCA ATT TTT AT 3'). The resulting intermediate plasmid pTZselP-L2 still contains the T7-terminator and a HpaI site, that were removed in the following cloning step thereby inserting a vaccinia early transcription stop signal and reducing the size of the P7.5 promoter fragment from 0.28 to 0.18 kb. The 239bp SalI-NdeI fragment was substituted by the SalI-NdeI adaptor consisting of the annealed oligonucleotides o-830 (SEQ ID NO:58: 5'-TCG ACT TTT TAT CA-3') and o-857 (SEQ ID NO:59: 5'-TAT GAT AAA AAC-3'). The resulting plasmid was called pselP-gpt-L2 (SEQ ID NO:65). Additional features of this construct are shown in table 10 below.

TABLE 10 pselP-gpt-L2 (SEQ ID NO:65)

| Location | Description |
|---|---|
| 1–55 | pTZ19R sequences (Pharmacia) |
| 56–108 | Linker I in rc orientation (5TNT, NotI, SfiI, RsrII, HpaI, SnaBI, AatII) |
| 110–860 | *E. coli gpt sequences in rc orientation. The gpt* open reading frame starts with a rc TAC start codon at position 860 and ends with a rc ATT stop codon at position 403 |
| 861–1245 | Vaccinia Virus p7.5 promoter sequences in rc orientation starting with the p7.5 internal NdeI site at position 1241 |
| 1246–1258 | Vaccinia Virus early transcription stop signal in rc orientation flanked by a NdeI site (position 1245) and a SalI site (position 1253) |
| 1259–1322 | Multiple cloning site in rc orientation (SalI, translation stop codons for all three reading frames, StuI, XhoI, PstI, BamHI, SpeI, SacI, SmaI, EcoRI, NcoI) |
| 1323–1374 | Vaccinia Virus synthetic early late promoter in rc orientation flanked by a NcoI site at position 1317 and a ClaI site at position 1370 |
| 1375–1414 | Linker II in rc orientation (SnaBI, HpaI, NotI, SfiI, 5TNT) |
| 1415–3878 | pTZ19R Sequences (Pharmacia) |

pselP-gp160MN: The 3.1 kb env gene containing the EcoRI-PvuII fragment of pMNenvI was inserted into the EcoRI and StuI cut plasmid pselP-gpt-L2 resulting in the intermediate plasmid pselP-gpl60.1. The 0.8 kb NcoI-NsiI fragment of pselP-gp160 was substituted by a PCR-generated 0.31 kb NcoI-NsiI fragment resulting in the final plasmid pselP-gp160$_{MN}$ (SEQ ID NO:66). Additional features of this plasmid are shown in table 11 below.

TABLE 11 pselP-gp160MN (SEQ ID NO:66)

| Location | Description |
|---|---|
| 1–55 | pTZ19R sequences (Pharmacia) |
| 56–108 | Linker I in rc orientation (5TNT, SfiI, RsrII, HpaI, SnaBI, AatII) |
| 110–860 | *E. coli* gpt sequences in rc orientation. The gpt open reading frame starts at position 860 with a rc TAC start codon and ends at position 403 with a rc ATT stop codon |
| 861–1245 | Vaccinia Virus p7.5 promoter sequences in rc orientation starting with the p7.5 internal NdeI site at position 1241 |
| 1246–1258 | Vaccinia Virus early transcription stop signal in rc orientation (position 1245–1252) flanked by a NdeI site at position 1241 and a SalI site at position 1253. |
| 1259–3916 | HIV-1 MN env gene in rc orientation. The ORF starts at position 3916 with a rc TAC start codon and ends at position 1348 with a rc ATT stop codon |
| 3917–3970 | Vaccinia Virus synthetic early late promoter in rc orientation flanked by a NcoI site (position 3913) and a ClaI site (position 3966) |
| 3971–4015 | Linker II in rc orientation (SnaBI, HpaI, NotI, SfiI, 5TNT) |
| 4016–6474 | pTZ19R sequences (Pharmacia) |

The primers used for the PCR reaction were o-NcoI (40mer) SEQ ID NO:60: 5'-GAG CAG AAG ACA GTG GCC ATG GCC GTG AAG GGG ATC AGG A-3', and o-NsiI (30mer) SEQ ID NO:61: 5'-CAT AAA CTG ATT ATA TCC TCA TGC ATC TGT-3'. For further cloning the PCR product was cleaved with NcoI and NsiI.

Chimeric viruses vselP-gp160$_{MN}$A vselP-gp160$_{MN}$B: The HpaI-fragment consisting of the selP-gp160 and P7.5gpt gene cassettes is inserted by direct molecular cloning (FIG. 9.6) into the single SmaI site of the vaccinia strain WR6/2which is a highly attenuated vaccinia virus strain. Moss et al., *J. Virol.* 40:387–395 (1981); Buller et al., *Nature* 317:813–815 (1985). The vaccinia virus strain WR6/2 is cut at its single SmaI site and ligated with the 4.0 kb HpaI fragment that contains the P7.5-gpt gene and the selP-gp160-gene cassettes. The cloning procedures are carried out as described in Example 1.

The resulting chimeric viruses, vselP-gp160$_{MN}$A and vselP-gp160$_{MN}$B, are purified and further characterized. In the virus vselP-gp160$_{MN}$A, the gp160 gene is transcribed in the same direction (left to right) as the genes clustered around the insertion site [the A51R open reading frame. Goebel et al., *Virology* 179:247–266 (1990). In the virus vselP-gp160$_{MN}$B, the gp160-gene is transcribed in the reverse direction. The in vivo packaging is done as described in Example 3.

Structure of the chimeric viruses: To confirm the theoretical structures of the chimeric viruses (FIG. 9.7), Southern blot analyses are carried out. The DNA of the purified viruses was cleaved with SalI and fragments are separated on an agarose gel, transferred to a nitrocellulose membrane and hybridized to vaccinia SalF-fragment probe (pTZ-SalF) and a gp160 gene probe (pMNenv1). With the SalF-fragment probe, for vselP-gp160$_{MN}$A the predicted 6.8 and 10.7 kb fragments are visible; and for vselP-gp160$_{MN}$B, the predicted 3.5 and 13.7 fragments are visible. With the gp160 probe, the same fragments are seen, but the 10.7 kb fragment in vselP-gp160$^{MN}$A and the 3.5 kb fragment in vselP-gp160$_{MN}$B give less intense signals, because only about 400 bp of each total fragment is homologous to the probe.

Since direct cloning also results in integration of tandem multimer structures, the DNA of the viruses is also digested with XbaI which does not cut the inserted DNA. The XbaI wild-type fragment is 447bp in size. Integration of one copy of the 3.8 kb sized insert results in a fragment of 4.3 kb. In multimeric structures the size of the 4.3 kb fragment increases in increments of 3.8 kb.

Expression studies with the chimeric viruses vselP-gp160$_{MN}$A and vselP-gp160$_{MN}$B: Vero cells are used for expression studies. Growth of cells, infections with the chimeric viruses and purification of the recombinant gp160 protein are carried out as described by Barrett et al., supra.

EXAMPLE 10

Construction of novel chimeric vaccinia viruses encoding human protein S (vProtS) and expression of recombinant protein S This example illustrates the construction of recombinant protein S expressed by chimeric vaccinia virus. Human protein S is a 70 kDa glycoprotein involved in the regulation of blood coagulation. DiScipio et al., *Biochemistry,* 18:890–904 (1979). The cDNA and the genomic DNA of Protein S have been cloned and characterized. Lundwall et al., *Proc. Natl. Acad. Sci. USA* 83:6716 (1986); Hoskins et al., *Proc. Natl. Acad. Sci. USA* 84:349 (1987); Edenbrandt et al., *Biochemistry,* 29:7861 (1990); Schmidel et al., *Biochemistry* 29:7845 (1990)

Human protein S, normally synthesized as a 70 kDa protein in liver and endothelial cells, see DiScipio et al., supra, has been expressed in permanent cell lines derived from human 293 and hamster AV12-664 cells (adenovirus transformed cell lines) at levels of up to 7 μg/$10^6$ cells/day, see Grinnell et al., *Blood* 76:2546 (1990), or in mouse C127 cell/papilloma virus system at similar expression levels, see Malm et al., *Eur. J. Biochem.* 187:737 (1990). The protein derived from the latter cells was larger than plasma-derived protein S probably due to aberrant glycosylation.

The present expression of protein S uses a double gene cassette consisting of the complementary DNA for the human blood factor protein S and the gpt gene, each controlled by a vaccinia promoter. This was cloned into the unique NotI site and packaged in fowlpox helper virus-infected mammalian cells. Human protein S was expressed in infected Vero cells in levels of 4–6 μg per $10^6$ cells.

For the cell screening, for optimal protein S expression by the chimeric vaccinia virus, five different host cell lines were used, WI 38 (human embryonal lung fibroblast), CV-1 and Vero (monkey kidney cells), Chang liver and SK Hep1. Protein S was indistinguishable from plasma-derived protein S by several criteria: the recombinant material derived from the infected cells of this cell line showed the same electrophoretic migration patterns and the same chromatographic elution profiles as plasma-derived protein S. This indicates that the correct post-translational modification of this complex glycoprotein has occurred. The methods are described in detail below.

Construction of the plasmid pN2-gptaProtS. Single-stranded DNA prepared from the plasmid pBluescript-ProtS, comprising the cDNA coding for human protein S (provided by R. T. A. McGillivray) was used to mutagenize the region around the translational start codon of the protein S coding region into an NcoI site (CCATGG). The mutagenic primer, oProtS1 (SEQ ID NO:68), has the sequence 5'-ACC CAG GAC CGC CAT GGC GAA GCG CGC-3'; the mutagenesis was carried out as described in the mutagenesis protocol (Amersham, Inc.). The signal peptide is mutated, with the second amino acid changed from Arg to Ala (FIG. 10.1B and SEQ ID NOS. 78 and 80) This introduces the NcoI site required for further cloning and brings the ATG start codon into an optimal context for translation. This may improve the secretion of protein S.

The protein S cDNA was subsequently excised as an NcoI-NotI fragment and inserted into the vaccinia insertion plasmid pTKgpt-selP (Falkner et al., supra) a plasmid providing a strong synthetic vaccinia promoter. The promoter-protein S gene cassette was then excised as a BglII-NotI fragment and inserted into the plasmid pN2-gpta (Example 1) resulting in pN2-gptaProtS (see FIG. 10.1A; SEQ ID NO:67). Additional features of this construct are shown in table 12 below.

TABLE 12 pN2-gptaProtS (SEQ ID NO:67)

| Location | Description |
|---|---|
| 1–2217 | Bluescript II SK- sequences (Stratagene) |
| 2218–2225 | NotI site 1 |
| 2226–4938 | ProtS sequences in rc orientation. The open reading frame starts at position 4938 with a rc TAC start codon and ends at position 2910 with a rc ATT stop codon |
| 4939–4992 | Vaccinia Virus synthetic early late promoter in rc orientation flanked by a NcoI site (position 4935) and a fused BglII/BamHI site (position 4987–4992). The NcoI site harbors the Prot S rc start codon TAC |
| 4993–5493 | Vaccinia Virus p7.5 promoter sequences |
| 5494–6127 | *E. coli* gpt sequences. The ORF starts at position 5494 with ATG start codon and ends at position 5950 with a TAA stop codon. |
| 6228–6235 | NotI site 2 |
| 6236–6811 | Bluescript II SK- sequences (Stratagene) |

In this plasmid, the gpt-gene controlled by the vaccinia virus P7.5 promoter and the protein S cDNA, is transcribed divergently and flanked by NotI sites.

Insertion of the cDNA for human protein S into the single NotI site of vaccinia virus to form vProtS. The NotI-fragment consisting of the gpt gene and protein S gene cassettes was ligated with the vaccinia vector arms and transfected into FPV infected mammalian CV-1 cells. Only packaged vaccinia virus multiplied under these conditions. More particularly, vaccinia wild-type DNA of the WR strain (1 μg) was cut with NotI, the enzyme was heat-inactivated for 30 min at 65° C. The vector was ligated overnight with 1 μg of the 3.8 kb gpt/Protein S gene cassette (excised as a NotI fragment out of the plasmid pN2gpta-ProtS) in 30 μl using 15 units of T4 DNA ligase.

The crude virus stocks prepared after five days of incubation were titrated in the presence and in the absence of mycophenolic acid (MPA). This procedure distinguished chimeric from back-ligated wild-type virus. With MPA $4\times10^4$ and without the drug $6\times10^5$ pfu/$10^6$ host cells were obtained. About 6–7% of the viral plaques were chimeric viruses. Ten of the gpt-positive isolates were plaque-purified twice, grown to small crude stocks and were used to infect CV-1 cells. Total DNA was prepared, cut with the restriction enzymes SacI and NotI and subjected to Southern blot analysis (FIGS. 10.2A–C). The SacI digest, hybridized with the cloned SacI-I fragment (plasmid pTZ-SacI; Example 4), allowed the determination of the orientation of the inserted DNA because SacI cuts the inserts asymmetrically. In all ten isolates the inserts were in the ‘a’-orientation (fragments of 6.3 and 4.6 kb; see FIGS. 10.2A and 10.2C), indicating that this configuration is strongly preferred. The NotI fragments were hybridized with the protein S probe. In this case the 3.8 kb NotI gene cassette was released (FIG. 10.2B).

Expression of human protein S by a chimeric vaccinia virus. Crude stocks were grown from gpt-positive chimeric viruses and used for infection of various mammalian cell lines. Monolayers of $5\times10^6$ cells were infected with 0.1 pfu/cell in the presence of serum free medium (DMEM) supplemented with 50 $\mu$g/ml vitamin K and incubated for 72 hours. Supernatants were collected and protein S antigen was determined using an ELISA test kit from Boehringer Mannheim, FRG (Kit Nr. 1360264). Amounts of protein S synthesized are given in Table 13 in milli-units (1 U corresponds to 25 $\mu$g of protein S).

Alternatively, 10 $\mu$l of supernatant from Vero cells were analyzed in a Western Blot analysis using 50 ng of human plasma-derived protein S as a standard and a mouse polyclonal serum specific for “hu Prot S” (Axell) (FIG. 10.3). Blots were stained using an alkaline phosphatase conjugated goat anti-mouse polyclonal serum (Dakopatts) and NBT/BCIP as a substrate.

Purification of recombinant protein S from cell culture supernatants was performed as described by Grinnell et al. (1990).

TABLE 13

| Cell line | ATCC# | mU huProtS per $10^6$ cells |
|---|---|---|
| SK Hepl | (HTB52) | 750 |
| Vero | (CCL 81) | 127 |
| Chang Liver | (CCL 13) | 135 |
| CV-1 | (CCL 70) | 450 |
| WI 38 | (CCL 75) | 440 |

EXAMPLE 11

Construction of novel chimeric vaccinia viruses encoding human factor IX and expression of recombinant factor IX A double gene cassette consisting of the complementary DNA for the human blood factor IX and the gpt gene, each controlled by a vaccinia promoter, was cloned into the unique NotI site of the vaccinia virus WR genome and packaged in fowlpox helper virus-infected mammalian cells. Human factor IX was expressed in several cell types.

Human clotting factor IX is a 56 kDa glycoprotein involved in the regulation of blood coagulation. This clotting factor undergoes complex post-translational modifications: vitamin K dependent carboxylation of the first 12 glutamic residues, glycosylation, 3-hydroxylation of an aspartic acid and amino terminal protein processing. Davie, E. W., “The Blood Coagulation Factors: Their cDNAs, Genes and Expression”, *HEMOSTATIS AND THROMBOSIS*, Colman et al., eds., J. B. Lippincott Co. (1987). Hemophilia B, an X chromosome-linked bleeding disorder, is caused by mutation of factor IX. Patients with hemophilia are currently treated by substitution with plasma-derived factor IX.

The cDNA and the genomic DNA of factor IX (“FIX”) have been cloned and characterized and FIX has been expressed in permanent cell lines. Busby et al., *Nature* 316:271 (1985); Kaufman et al., *J. Biol. Chem.* 261:9622 (1986); Balland et al., *Eur. J. Biochem.* 172:565 (1922); Lin et al., *J. Biol. Chem.* 265:144 (1990). Expression of factor IX in vaccinia recombinants has also been described. de la Salle, et al., *Nature* 316:268 (1985).

Construction of plasmids—pN2gpta-FIX: The FIX cDNA (kindly provided by R. T. A. MacGillivray) was cut from pBluescript-FIX with EcoRI and ligated with the EcoRI linearized plasmid pTM3. Moss et al., *Nature* 348:91 (1990) Single strand DNA was isolated from a recombinant plasmid which contained the FIX insert in the correct orientation and a NcoI site (CCATGG) was introduced around the FIX ATG start codon by oligonucleotide mediated site directed mutagenesis using oligonucleotide oFIX.1 (SEQ ID NO:71: 5'-TCA TGT TCA CGS GCT CCA TGG CCG CGG CCG CAC C-3') and a commercial mutagenesis kit (Amersham, Inc.; kit No. PPN 1523). Vector and FIX NcoI sites were fused, insert DNA was isolated by NcoI and NotI digestion and ligated with the NcoI/NotI cut vector pTKgpt-selP. Falkner et al., supra The promoter/FIX cassette was cut out from this plasmid with BglII and NotI and ligated with the BamHI/NotI linearized vector pN2-gpta (Example 1). From this construct a NotI cassette containing the FIX cDNA (under the control of the selP promoter) and the gpt gene (under the control of the vaccinia P7.5 promoter) was isolated and used for in vitro molecular cloning and packaging as described in Example 10. Additional characteristics of this plasmid are shown in table 14 below.

TABLE 14 pN2gpta-FIX (SEQ ID NO:72)

| Location | Description |
|---|---|
| 1–2217 | Bluescript II SK-sequences (Stratagene) |
| 2218–2225 | NotI site 1 |
| 2226–3659 | FIX sequence in rc orientation. The open reading frame starts at position 3659 with a rc TAC start codon and ends at position 2276 with a rc ATT stop codon |
| 3660–3713 | Vaccinia Virus synthetic early late promoter in rc orientation flanked by a NcoI site (position 3656 and fused BglII/BalII site (position 3708–3713). The NcoI site harbors the FIX rc start codon TAC |
| 3714–4214 | Vaccinia Virus p7.5 promoter sequences |
| 4215–4848 | *E. coli* gpt sequences. The ORF starts at position 4215 with an ATG start codon and ends at position 4671 with a TAA stop codon. |
| 4849–4856 | NotI site 2 |
| 4857–5532 | Bluescript II SK-sequences (Stratagene) |

Insertion of the cDNA for human Factor IX into the single NotI site of vaccinia virus. Prior to insertion of the factor IX cDNA into vaccinia virus, this cDNA was inserted into the plasmid pN2-gpta resulting in the plasmid pN2gpta-FIX (FIG. 11.1A, SEQ ID NO:72). To obtain the optimal sequence context between the synthetic vaccinia promoter and the factor IX coding region, the 5' untranslated region of factor IX was deleted by introduction of a novel NcoI site at the start codon of factor IX and fusion of this NcoI site with the NcoI site provided by the promoter. This mutation resulted in a mutated signal peptide (FIG. 11.1B, SEQ ID NOS 81–84).

In the wildtype factor IX the second amino acid of the signal peptide is a glutamine residue while in pN2gpta-FIX the second amino acid is a glutamic acid residue.

The NotI fragment consisting of the gpt-gene and factor IX gene cassettes was ligated with the vaccinia vector arms and transfected into FPV infected mammalian CV-1 cells. Only packaged vaccinia virus multiplied under these conditions. The crude virus stocks prepared after five days of incubation were titrated in the presence and in the absence of mycophenolic acid (MPA). This procedure distinguished chimeric from back ligated wild-type virus. With MPA $5\times10^4$ and without the drug $5\times10^6$ pfu/$10^6$ host cells were obtained. In this example, about 1% of the viral plaques were chimeric viruses. Ten of the gpt-positive isolates were plaque-purified twice, grown to small crude stocks and were used to infect CV-1 cells. Total DNA was prepared from eight cell cultures infected with the respective viral isolates, digested with the restriction enzymes SfuI, Ndel and NotI and subjected to Southern blot analysis.

The SfuI digest, hybridized with the factor IX probe, allowed the determination of the orientation of the inserted DNA because SfuI cuts the inserts asymmetrically. In all eight isolates the inserts were in the 'a'-orientation (fragments of 6.3 and 4.6 kb; see FIG. 11.2A), indicating that this configuration is strongly preferred. The NdeI (NotI) fragments were also hybridized with the factor IX probe. In this case a fragment of 6.6 kb (the 3.8 kb NotI gene cassette) was released, proving the predicted structure.

Expression Of Human Factor IX. Crude stocks were grown from eight single plaque isolates and used for infection of various mammalian cell lines. $5\times10^6$ cells in a 10 cm petri dish were infected with a moi of 0.1 pfu/cell in the presence of serum free medium (DMEM) and 50 μg/ml vitamin K. Infected cells were incubated for 72 hours until cells started to detach from the bottom of the petri dish. Supernatants were collected, cell fragments were removed by centrifugation and FIX amounts were determined using an ELISA test kit from Boehringer Mannheim, FRG (Kit Nr. 1360299). Amounts of FIX antigen and of factor IX activities are given in Table 15.

Alternatively, 10 μl of supernatant from Vero cells were analyzed in a Western Blot analysis using 50 ng of human plasma derived huFIX as a standard and a mouse polyclonal serum specific for huFIX (Axell). Blots were stained using an alkaline phosphatase conjugated goat anti-mouse polyclonal serum (Dakopatts) and NBT/BCIP as a substrate. As shown in FIG. 11.3, the recombinant material migrated as a broad band similar to the plasma-derived factor IX standard. Clotting assays of the partially purified Vero cell derived factor IX showed that about 50% of the material was active factor IX. The virus isolate #5, designated VFIX#5, was grown to large scale and used for further experiments.

As in the case of the protein S chimeric viruses (Example 10), the factor IX expressing chimeras had inserts in one preferred orientation.

The protein of transcription of the gene of interest (factor IX and protein S) was from right to left, i.e., the same direction as the genes clustered around the NotI site. It seems therefore, that strongly transcribed units have to be aligned in the preferred transcriptional direction when cloned into the NotI cluster. Viruses with this configuration of the insert are strongly preferred and show the best growth characteristics. The direction of transcription of the second gene cassette, the P7.5 gpt gene, was from the left to right. The P7.5 promoter segment is therefore in an inverted repeat configuration relative to the nearby endogenous gene coding for the 7.5 kDa protein, i.e. the expected stable configuration is preferred. Since no chimeras with the reverse orientation were found, the 'b'-orientation is probably unstable. Insertion of the above mentioned gene cassettes in the 'b'-orientation by in vivo recombination would have failed, leading to the misinterpretation that the NotI intergenic region is essential for viral growth. This situation illustrates one of the advantages of the direct cloning approach: only 'allowed' are structures are formed.

By insertion of simple small gene cassettes, both orientations and multimers were obtained (Example 1) while insertion of complex gene cassettes (divergently transcribed double gene cassettes with homologies to internal genes such as the P7.5 promoter segment) preferred structures were formed.

The cell screening for optimal factor IX expression showed that infection of CV-1 and SK Hep1 cells resulted in the highest antigen levels. The material from CV-1 cells had the highest clotting activities (table 15), indicating that this cell line possesses effective post-translational modification systems. Factor IX has been expressed previously in the conventional vaccinia expression system using the P7.5 promoter and HepG2 and BHK cells (de la Salle et al., 1985). Cell lines with better growth characteristics, like Vero and CV-1 cells, have been shown to produce higher levels of expression with the instant viruses, due to improved promoters and methods. In addition, deletion of the 5'-untranslated region of the factor IX cDNA and the modification of the signal peptide seems to have positive effects on secretion and expression levels.

TABLE 15

Factor IX Expression in Different Cell Lines

| cell line | ATCC# | antigen | activity (mU/$10^6$ cells)* | ratio % |
|---|---|---|---|---|
| SK Hepl | (HTB52) | 810 | 183 | 22.5 |
| Vero | (CCL81) | 500 | 282 | 56.4 |
| Chang Liver | (CCL13) | 190 | 100 | 52.6 |
| CV-1 | (CCL70) | 850 | 1290 | 51.8 |
| RK13 | (CCL37) | 300 | 460 | 53.3 |

*1 unit corresponds to 5 μg FIX per ml human plasma

EXAMPLE 12

Construction of the chimeric fowlpox virus f-envIIIB and expression of recombinant HIVIIIB envelope proteins in chicken embryo fibroblasts The large scale production of gp160 in a vaccinia virus-Vero cell expression system has been described recently. Barrett et al. (1989). Since vaccinia virus is still pathogenic to many vertebrates including mammals and fowlpox virus is host restricted to avian species we have developed an avipox based expression system. See U.S. Ser. No. 07/734, 741 and CIP thereof. Chimeric fowlpox viruses have now been constructed by direct molecular cloning to express the envelope gene of the HIV-1 IIIB isolate. Ratner et al. (1985). In this recombinant virus the env gene is controlled by a strong synthetic late promoter. For the production of envelope glycoproteins, the chimeric fowlpox virus is used to infect chicken embryo aggregate cell cultures. Mundt et al., PCT/WO91/09937.

Construction and structure of the chimeric fowlpox virus f-envIIIB. For construction of f-envIIIB (FIG. 12.1) a double gene cassette consisting of the P7.5-promoter/gpt gene and the S4-promoter/gp160 gene were excised as a NotI-fragment out of the plasmid pN2gpt-gp160 (Example 5). This cassette was ligated with NotI-cleaved genomic DNA of the fowlpox virus f-TK2a (Example 2) and chimeric virus was isolated as described in Materials and Methods. Total DNA from chicken embryo fibroblasts infected with twelve different plaques was digested with SspI and further analyzed by Southern blot analysis and hybridization with an isolated gp160 fragment as a probe (FIG. 12.2A). The predicted fragments of 3.7, 1.0 and 0.8 kb were found in 11 cases indicating that the gp160 gene had been integrated in the 'b'-orientation (FIG. 12.2B). One viral isolate, f-LF2e, did not hybridize to the gp160 probe.

The fact that one preferred orientation of the insert exists, points to the possibility that the 'b'-orientation virus has growth advantages over the 'a'-orientation, the 'a'-orientation may even be unstable. Letting the viral vector choose the best orientation may be considered as an advantage of the direct cloning approach.

Expression studies with the chimeric virus f-envIIIB. Expression studies were done in chicken embryo fibroblasts (CEF). Confluent monolayers of CEFs were infected with 0.1 pfu per cell of the different viral crude stocks, grown for five days. Total cellular proteins were separated on 10% polyacrylamide gels, transferred onto nitrocellulose membranes and further processed as described in Materials and Methods. A Western blot analysis showing the expression of gp160, gp120 and gp41 is shown in FIGS. 12.3 and 12.4. All viral isolates, except f-LF2e, induced expression of the env glycoproteins. The virus f-LF2e was also negative in the Southern blot analysis and therefore does not carry the gp160 gene sequences.

Construction of f-envIIIB. Two micrograms of DNA of host virus vector f-Tk2a (Example 2) were cut with NotI and ligated with 500 nanograms of the gene cassette consisting of the P7.5-promoter/gpt gene and the S4-promoter/gp160 gene. The ligation was carried out in a volume of 20 $\mu$l and 5U of ligase for four days at 12° C. The ligation mixture was transfected into $6\times10^6$ CEFs infected with 0.5 pfu per cell of HP2, a fowlpox isolate obtained by plaque-purification of HP1.441. After an incubation period of five days a crude stock was prepared (final volume 1 ml) which was amplified. The crude stock was titrated on CEFs in six-well plates and grown for 5 days under gpt-selection (25 $\mu$g/ml mycophenolic acid, 125 ug xanthine). Cells on which the minimal dilution resulted in a visible cytopathic effect, were harvested and amplified twice according the same protocol. The crude stock obtained from the second amplification from the second amplification was titered on CEFs in the presence of gpt-selection and 12 single plaques (f-LF2a-1) were picked.

Western blot analysis of gp160. The Western blot analysis were done essentially as described by Towbin et al., supra. For gp160/gp120 detection, the first antibody was a mouse monoclonal anti-HIV gp120 antibody (Du Pont, Inc. # NEA9305 used at a 1:500 dilution. For the gp41 detection the human anti-HIV-gp41 3D6 Mab (provided by H. Katinger, Universitat fur Bodenkultur, Inst. fur Angewandte Mikrobiologie) was used at a 1:500 dilution. The second antibody was a goat-anti-mouse IgG (H+L) coupled with alkaline phosphate (BioRad, Inc. #170–6520) used at a 1:1000 dilution. The reagents (BCIP and NBT) and staining protocols are from Promega, Inc.

EXAMPLE 13

Construction of the chimeric vaccinia virus vRMN6b1 and expression of recombinant gp160MN in Vero cells In Example 9, the construction of chimeras expressing gpl6O, under the control of the fowlpox virus (FPV) P2 promoter, described in EPA 91.114.300.6, is set forth. This promoter is a strong late promoter. Since it is desirable not only to use the vaccinia gpl6OMN constructs for production purposes, but also as live vaccines, new constructs that express gp16OMN early and late in the viral live cycle were made. The FPV P2 promoter was synthetically modified such that an early transcription promoting sequence was inserted downstream of the late promoter region. This hybrid promoter was designated "Sep." The HIV gp16OMN sequence was cloned downstream of this promoter.

Unexpectedly high expression levels of gp16OMN were obtained with these specific constructs. The Sep-controlled gp16OMN is expressed at similar or higher levels as in the T7-double infection system. Fuerst et al. (1987). The T7-double infection system has a major drawback, however, requiring two different viruses to express a single antigen. The virus vRMN6b1 is used to produce gp16OMN and supplants the need for the gpl60/T7-double infection system.

Construction of the plasmid pSep-ST2 and of the chimeric virus vRMN6b1: The plasmid pSep-ST2 contains the HIV-1 gp16OMN sequences controlled by the strong semi-synthetic poxvirus promoter Sep and a selection cassette consisting of the P7.5 promoter gpt-gene. Falkner and Moss (1988). This plasmid was assembled from two plasmids, obtained from Dr. M. Reitz (NCI, Bethesda, Md.), designated pMNenvl and pMN-ST2, and with the plasmid pSep (l). FIG. 13.1. The construction of the plasmid psep(l) and the structure of the Sep promoter is outlined in FIG. 13.2 (SEQ ID NOS 87–89). The "late" region of this promoter is based on the 'P2'-promoter described in U.S. Ser. No. 07/935,313, which was provided with an "early" component by ligation with specific oligonucleotides. FIG. 13.2.

To construct the virus vRMN6b1, the double gene cassette, excised as a NotI fragment out of the plasmid pSep-ST2 and consisting of the P7.5-gpt selection marker and the Sep regulated gp16OMN gene, was inserted directly into the NotI site of the WR-WT strain.

Six gpt-positive viruses were plaque purified six times and screened for expression of the env protein by Western blot analysis. Three of them did not express gp16OMN (the viruses vRMNI.1, vRMN2.11, vRMN3.1) while the other three isolates (vRMN4.11, vRMN6b1, vRMN8.11) showed a strong signal in the 160 kDa size range (FIG. 13.5). The virus vRMN6b1 was finally chosen on the basis of its high expression level for further characterization.

Structure of the chimeric virus vRMN6b1: Direct molecular cloning of inserts into a unique viral restriction site can result in different genomic structures. Scheiflinger et al. (1992). The most common ones are the orientational isomers of the insert. Interestingly the insert of all six gpt-positive viruses had the 'b'-orientation, i.e., the direction of transcription of the Sep-gpl6O cassette is from right to left (from the central part to the left terminus). To confirm the theoretical structure of the chimeric virus vRMN6b1 Southern blot analyses were carried out (FIGS. 13.3 and 13.4). The DNA's of the purified viruses vRMN6b1 and WR-WT (control) were cleaved with several restriction enzymes, separated on an agarose gel, transferred to a nitrocellulose membrane and hybridized to a gpl6O gene probe (FIG. 13.3). An identical blot was hybridized with a probe obtained by PCR amplification of the region around the NotI site ("the Not-region probe") of the wild-type virus generated with the primers P-N(l) and P-N(2) (FIG. 13.4).

Using the gpl6O gene probe pMNenv1 and the Not-region probe, the predicted fragments were visible. Some of the smaller fragments were only visible after longer exposure times (not shown). The predicted sizes of the different fragments are summarized in Table 16. As expected the WR-WT virus did not hybridize with the gpl6O probe.

The chimeric virus vRMN6b1 induces very high levels of gp160: To estimate gpl6O expression levels with a known, efficient system, the T7 bacteriophage polymerase/vaccinia hybrid system was used to generate a comparative Western blot analysis for the expression of gpl6O induced by vRMN6b1. Fuerst et al. (1987); Barrett et al. (1989). Confluent monolayers of cells were infected with 0.1 pfu's of the respective viruses and, after 48 hours, total proteins were analyzed. The highest levels were obtained with vRMN6b1 in CV-1 cells. FIG. 13.6, lane vRMN6b1 CV-I'. Interestingly, expression levels in Vero cells were similar to those obtained in the vaccinia virus phage T7 polymerase hybrid system. FIG. 13.6. This blot shows that a strong, early/late promoter can be optimized for very high expression levels of gpl6O. With vRMN6b1 as a vehicle only one virus is required for the production of gpl6O, as compared to two viruses with the T7 hybrid system, thereby reducing effort and cost of production of gpl6O.

Methods: The plasmids pMNenvl and pMN-ST2 were provided by M. Reitz (NCI, Bethesda, Md.). The construction of the plasmid pMNenv2 is described above. Briefly, a 2.65 kb StuI/PvuII fragment derived from the plasmid pMNenv2, containing the HIV 1-MN env gene, was ligated with the SnaBI- linearized plasmid pSep(l). The construction of psep(l) is described in the legend of FIG. 13.2. The resulting plasmid, containing the insert in the proper orientation with respect to the "Sep-promoter" was designated pSep-gpl6Omn. In order to repair a point mutation located within the gpl6O-orf, a 1.9 kb NsiI/SalI fragment of pSep-gpl6Omn was replaced by an equivalent fragment derived from the plasmid pMN-ST2. The resulting plasmid was designated pSep-ST2.

The semi-synthetic poxvirus promoter Sep was constructed by combination of the late fowlpoxvirus promoter P2 with a synthetic early promoter sequence. Briefly, the HpaI/NcoI digested vector pS2gpt-P2 (see U.S. Ser. No. 07/914,738) was ligated with the annealed oligonucleotides P-Sep(3) and P-Sep(4). The sequence of the oligonucleotides was P-Sep(3) (SEQ ID NO:90) 5':CTCGTAAAAA TTGAAAAACT ATTCTAATTT ATTGCACGGT CGCGA-3'; and P-Sep(4) (SEQ ID NO:91): 5'-CATGGTACGT ACCGTGCAAT AAATTAGAAT AGTTTTTCAA TTTTTACGAG-3'. The resulting plasmid was designated pSep(l).

The viruses were digested with the restriction enzymes SalI, HindIII, PstI, NotI, XbaI and HpaI. The fragments were hybridized to the $^{32}$P-labeled gpl6O probe pMNenv1. The marker (m) consisted of phage lambda HindIII fragments and of phage phi X HaeIII fragments. The marker size is indicated in kilobasepairs.

The viruses were digested with the restriction enzymes SalI, HindIII, PstI, NotI, XbaI and HpaI. The fragments were hybridized to a $^{32}$P-labeled PCR probe (generated with the primers P-N(l) (SEQ ID NO:92), 5'-GCTCCCGCAG GTACCGATGC AAATGGCCAC-3', and P-N(2) (SEQ ID NO:93), 5'-GGGGAGAGAT CGAAAGTGAA TTTGACATAGC-3', and the a template consisting of WR-WT virus. The marker (m) consisted of phage lambda HindIII fragments and of phage phi X HaeIII fragments; the marker size is indicated in kilobasepairs.

The Western blot analysis were done essentially as described by Towbin et al. (1979). The first antibody was the human monoclonal anti-HIV-gp41 antibody 3D6 used at a 1:500 dilution. Grunow et al. (1988). The second antibody was a goat anti-human IgG coupled with alkaline phosphatase (BioRad, Inc. #172–1004) used at a 1:1000 dilution. The reagents (BCIP and NBT) and staining protocols are from Promega, Inc.

TABLE 16

Sizes of genomic restriction endonuclease fragments of the viruses vRMN6bl and WR-WT theoretically hybridizing to the gpl60 and the Not-region probes (fragment sizes are given in kilo basepairs, kb).

| | vRMN6b1 | | WR-WT | |
|---|---|---|---|---|
| enzyme | gpl60 pr. | Not-region pr. | gp160 pr. | Not-region pr. |
| SalI | 26.6 + 0.75 | 26.6 + 0.75 | — | 23.3 |
| HindIII | 12.8 + 1.3 + 1.2 | 12.8 + 2.3 | — | 13.5 |
| PstI | 5.9 | 20.9 + 5.9 | — | 22.8 |
| Notl | 4.0 | 145 + 45 | — | 145 + 45 |
| XbaI | 5.7 | 5.7 | — | 1.6 |
| Hpal | 5.2 | 5.2 | — | 1.1 |

EXAMPLE 14

Construction of the chimeric vaccinia virus vgag (1) and expression of recombinant HIV gag protein Human immunodeficiency virus type 1 (HIV-1) contains an RNA genome that encodes gag, pol, and env proteins, as well as additional regulatory proteins. Ratner et al. (1985); Sanchez-Pescador et al. (1985). The primary gag translation product is a 55 kDa precursor, Pr55gag, that is normally processed into the major core proteins p24, p17, and p15 by proteolysis. p15 is, in turn, cleaved into p7 and p6. Veronese et al. (1988). A myristic acid residue is present at the N-terminus of both p17 and the gag precursor. Veronese et al. (1988); Mervis et al. (1988). By analogy to other retroviruses, the myristic acid likely is required for transport of viral proteins to the plasma membrane. Rein et al. (1986). HIV gag and gag/pol proteins have been expressed in several expression systems, such as yeast, vaccinia system and baculovirus. Kramer et al. (1986); Walker et al. (1987); Flexner et al. (1988); Gowda et al. (1989); Karacostas et al. (1989); Shioda and Shibuta (1990); Hu et al. (1990); Madison et al. (1987); Gheysen et al. (1989). Expression of the gag precursor (Prs55gag) alone, without the HIV protease, leads to the formation of virus-like particles. Gheysen et al. (1989). They are likely candidates for vaccine preparations either for subunit vaccines or as components of live vaccines.

In this example, the efficient expression of the gag precursor controlled by the early late promoter Sep in a chimeric virus is described. The virus may be used for the production of HIV-1 gag protein. The chimeric virus has some unique properties such as delayed onset of cytopathic effects in Vero cells and an attenuated phenotype. The latter makes the chimeric virus especially useful as a safe and efficient vector for the production of gag proteins and gag pseudoparticles for vaccine and diagnostic use.

Construction of the plasmid pSep-gag and of the chimeric viruses vgag(1) and vgag(2): The HIV gag sequence was derived from the plasmid pMN-ST2 provided by M. Reitz (NCI, Bethesda, Md.). It was subcloned from pMN-ST2 into pBluescript IISK-, shown in FIG. 14.1, and designated pgagMN(S/H). To shorten the 5'-untranslated region of the gag sequence and to subsequently introduce an NcoI site at the gag translation initiation codon, the 150 bp ClaI-SacI fragment of pgagMN(S/H) was replaced by a fragment annealed from the synthetic oligonucleotides P-gag(1) (SEQ ID NO:94) and P-gag(2) (SEQ ID NO:95). The gag ORF was inserted into pSep(l), resulting in psep-gag, from which the Sep-gag and P7.5-gpt genes can be excised as a 3.1 kb NotI fragment.

Chimeric viruses were constructed as described above. Three original isolates (#1, #2 and #7) were further plaque-purified six times by gpt-selection and screened for Pr55gag expression. FIG. 14.2. The viruses vgagl.l, and vgagl.2, e.g., vgag2.1 and 2.2, respectively were derived from the same initial plaques. All plaque isolates expressed a strong band in the 55 kDa region (p55). FIG. 14.2. The blot shows in addition, a similar virus designated VVKI and described by Karacostas et al. (1989), which was kindly provided by B. Moss, NIH, Bethesda, Md. This virus has a P7.5 promoter-gag/pol precurser gene cassette incorporated into the viral tk locus. Since infection was effected under the same conditions in the same cell line, a direct comparison of the Sep-gag and the P7.5-gag (VVKI) is possible. The Sep-gag constructs express at least fiveto ten-fold higher levels.

Structure of the chimeric viruses: To confirm the theoretical structures of the chimeric viruses, Southern blot analyses were carried out. Total DNA's from CV-1 cells infected with the respective viruses were prepared, digested with HindIII and subjected to a Southern blot analysis with a gag gene probe pgag(2) see FIG. 14.1) and the Not-region probe (see Example 13). With the gag gene probe, three fragments of 12.8, 0.8 and 0.6 kb were expected for an insertion in the 'b'-orientation (direction of transcription of the Sep promoter is from right to left). As shown in FIG. 14.3, all isolates examined had 'b'-orientation inserts. With the Not-region probe, two fragments of 12.8 and 2.3 kb were expected and found. FIG. 14.4. As hybridization controls, the HindIII (H) and Asp718 (A) fragments of plasmid psep-gag were included in the Southern blot analysis. FIGS. 14.3 and 14.4.

Interestingly, only the 'b'-orientation was detected (as in the case of the Sep-gpl6O constructs of Example 13), indicating that the strong Sep promoter must have the same orientation as the adjacent gene cluster. These findings highlight again the advantages of the direct cloning method. Insertion of this construct with a conventional insertion vector, directing the insert in a specific orientation, probably would have failed if the wrong direction of orientation was chosen.

Further expression studies with the chimeric viruses vgag (l) and vgag(2): Based on the characterization steps described above, the virus vgag(l), derived from vgagl.2 after one more plaque purification step, and the virus vgag (2), derived from a second round of screening for high-expression isolates, were grown to high titers. With these two viruses and the virus VVKI, a comparison of the gag-specific expression levels on CV-1 and Vero cells was performed. FIG. 14.5.

The viruses vgag(1) and vgag(2) show about the same levels of expression in both cell lines. Their expression levels are much higher, however, than in the control construct VVKI. FIG. 14.5. Interestingly, the gag precursor expressed by the virus vgag(l) is more intensely processed as compared to the virus vgag(2).

Materials and Methods: Construction of the plasmids. The HIV-1 MN gag open reading frame was prepared as a 1.8 kb SacI/HincII fragment from the plasmid pMN-ST2, provided by Dr. M. Reitz, NCI, Bethesda, Md., and inserted into the SacI/HincII digested vector pbluescript SK- (Stratagene). The resulting plasmid was designated pgagMN(S/H). The 5'-end of pgagMN(S/H) was modified by digestion with ClaI and SacI and insertion of the annealed oligonucleotides P-gag(1) (SEQ ID NO:94): 5'-ACC ATG GGT GCG AGA GCG TCG GTA TTA AGC GGG GGA GAA TTA GAT-3'; and P-gag(2) (SEQ ID NO:95): 5'-CGA TCT AAT TCT CCC CCG CTT AAT ACC GAC GCT CTC GCA CCC ATG GTA GC T-3'. This plasmid was designated pgag2. A 1.7 kb NcoI/HincII fragment of pgag2 was inserted into the NcoI/StuI digested plasmid pSep(l), thereby creating the vector psep-gag. For the construction of chimeric viruses, the 3.1 kb Not fragment encompassing the Sep-promoter/gag-gene/P7.5-promoter-gpt gene cassette was used. Construction of the chimeric viruses was carried out as described above.

Western blot analysis gag-protein: Western blot analyses were performed essentially as described by Towbin et al. (1979). The first antibody was a sheep anti-p24 antibody (Accurate Chemical & Scientific Corporation; Westbury, N.Y., #BOK-D7320) used at a 1:500 dilution. The second antibody was a donkey anti-sheep IgG, coupled with alkaline phosphatase (obtained from Serotec, Inc.) used at a 1:1000 dilution. The reagents (BCIP and NBT) and staining protocols were from Promega, Inc.

EXAMPLE 15

Construction of the chimeric vaccinia virus vgagpol and expression of recombinant HIV-1 gag-pol gene products including pseudoparticles Human immunodeficiency virus type I (HIV-1) contains an RNA genome that encodes gag, pol, and env proteins, as well as additional regulatory proteins. The primary gag translation product is a 55-kDa precursor, p55 gag, that is processed into the major core proteins p24, pl7, and pl5 by proteolysis. The pol open reading frame encodes the protease, reverse transcriptase, and integrase. For a review, see Levy, J. A., *Microbiol. Rev.* 57:183–289 (1993).

Expression of the products of the pol gene requires a relatively inefficient ribosomal frame shifting event within the gag gene that leads to the formation of small amounts of the putative gag-pol precursor which is a protein of about 160 kDa. Jacks et al. (1988). The predominant intracellular polypeptides produced in CV-1 cells infected with a vaccinia virus carrying the gag-pol gene were p55, p41, p24 and p17. Reverse transcriptase activity was detected in cellular supernatants and could be concentrated by centrifugation indicating that pseudoparticles had formed. Karakostas et al. (1989).

Vaccines employing inactivated HIV-1 particles are considered a viable approach in vaccine development. Since they are derived from infectious HIV they pose many risks, e.g., during manufacture, incomplete virus inactivation and the existence of infectious residual HIV-1 genomic RNA. HIV-1 pseudoparticles are structurally very similar to normal HIV particles and are efficient immunogens. There have been many reports on the expression of HIV-1 pseudoparticles. See, for example, Gheysen et al. (1988); Hu et al. (1990); Karacostas et al. (1989). The problem of the low level of antigen expression, however, remains unsolved.

We have now expressed HIV-1 gag-pol genes under the control of the strong early/late hybrid poxvirus promoter Sep and obtained very high expression levels of the gag-pol gene products. A direct comparison with the vaccinia recombinant vVKI of Karakostas et al. (1989) showed that the Sep-gag-pol constructs obtained by direct molecular cloning into the viral NotI site show an estimated ten-fold higher expression level and, therefore, are better candidates for the expression of HIV-1 gag-pol gene products including pseudoparticles.

Construction of the plasmid pSep-gagpolIIIB and of the chimeric viruses vgagpol 7, vgagpol9 and vgagpol10: The HIV gag-pol sequences were derived from the plasmid pHB10 provided by R. Gallo, NCI Bethesda, Md. They were subcloned from pHB10 into pBluescript IISK and called pgagpol 1. FIG. 15.1. To shorten the 5'-untranslated region of the gag-pol sequence and to subsequently introduce an NcoI site around the gag translation codon, the small ClaI-SacI fragment of pgagpol 1 was replaced by a fragment annealed from oligonucleotides P-gag(1) (SEQ ID NO:94) and P-gag(2) (SEQ ID NO:95) (see Example 14) resulting in pgagpol(2). The optimized gag-pol ORF was finally inserted into psep(l), resulting in pSep-gagpolIIIB, from which the Sep-gagpol and P7.5-gpt genes can be excised as a NotI fragment.

Chimeric viruses were constructed as described (in Materials and Methods). Three isolates were further plaque-purified six times by gpt-selection and screened for gag-pol expression by Western blot analysis. FIG. 15.2. The viruses vgagpol 7, vgagpol 9 and vgagpol 10 express a strong band in the 55 kDa region and a weak one in the 160 kDa region. FIG. 15.2. The blot shows, in addition, the expression level of a similar virus, VVKI, described by Karakostas et al. (1989), which was kindly provided by B. Moss, NIH, Bethesda, Md. This virus has incorporated a P7.5 promoter-gag-pol gene cassette into the viral tk locus. It expresses about ten-fold lower levels than the vgagpol viruses described above.

Structure of the chimeric viruses: To confirm the structures of the chimeric viruses, Southern blot analyses were carried out. FIG. 15.3. Total DNA's from CV-1 cells infected with the respective viruses were prepared, digested with HindIII, subjected to the Southern blot procedure and hybridized to a gag-pol gene probe (see FIG. 15.1) and the Not-region probe (see Example 13). With the gag-pol gene probe, the expected fragments of about 5.0, 0.9 and 0.6 kb were found, indicating that all three had the 'a'-orientation (direction of transcription of the Sep promoter from left to right). The Asp718 and HindIII fragments of the plasmid pSep-gagpolIIIB were used as size markers. FIG. 15.3-ml, pSep-gagpolIIIB (HindIII); m2, pSep-gagpolIIIB (Asp7l8). The structure of the viruses also was confirmed with the Not-region probe (data not shown).

Further expression studies with the chimeric viruses vgag (1) 1.3 and vgag(2): Based on the screening and characterization steps described above, the virus vgagpol 7 was grown to high titer. Expression levels in CV-1 and Vero cells of the gag-pol gene products were confirmed. In addition, cellular supernatants were analysed. High levels of reverse transcriptase activity and of the gag-pol gene products were detectable.

Materials and Methods: Construction of the plasmids. The intermediate plasmid pgag/pol(l) was constructed by insertion of a 4.76 kb SacI/StuI fragment derived from the plasmid pBHIO in the SacI/HincII-cleaved vector pBluescript II SK- (Stratagene). Ratner et al. (1986); obtained from R. Gallo. The 5'-end of the gag gene was modified by removal of a 149 bp SacI/ClaI fragment and insertion of the annealed oligonucleotides P-gag(1) (SEQ ID NO: 94): 5'-ACCATGGGTG CGAGAGCGTC GGTATTAAGC GGGGGAGAAT TAGAT-3'; and P-gag(2) (SEQ ID NO:95): 5'-CGATCTAATT CTCCCCCGCT TAATAC-CGAC GCTCTCGCAC CCATGGTAGC T-3'. The resulting plasmid was designated pgag/pol(2). A 4.4 kb gag-pol gene NcoI/NdeI fragment of pgag/pol (2) was treated with Klenow Polymerase and inserted into the SnaBI linearised vector pSep(l). The gag-pol gene cassette of the resulting plasmid pSep-gag/polIIIB was used for the construction of the chimeric virus vgag/pol.

Construction of the chimeric viruses: The cloning and in vivo packaging procedures were carried out as described in Examples 9 and 3, respectively.

Western Blot Analysis of gag and pol proteins: The Western Blot analyses were done essentially as described by Towbin et al. (1979). For analysis of the gag-proteins, the first antibody was a sheep anti-p24 antibody (Accurate Chemical & Scientific Corporation, Westbury, N.Y., #BOK-D7320) used at a 1:500 dilution. The second antibody was a donkey anti-sheep IgG coupled with alkaline phosphatase (obtained from Serotec, Inc.) used at a 1:1000 dilution. For analysis of the pol proteins, the first antibody was a monoclonal, mouse anti-reverse transcriptase (HIV-$1_{IIIB}$) antibody (ABT, #9002, BIO-TRADE) used at a 1:1000 dilution (protein content 1 ng/ul). The second antibody was a goat antimouse IgG (H+L) alkaline phosphatase conjugate (BIO-RAD #170-6520). The reagents (BCIP and NBT) and staining protocols were from Promega, Inc.

Formation of Pseudoparticles

The virus vgagpolIIIB#9 was used to produce HIV-1 pseudoparticles in CV-1 or Vero cells. The pseudoparticles present in the cellular supernants of infected cells were isolated by centrifugation techniques. CV-1 (or Vero) cells were infected with 0.01 pfu per cell and incubated for 3–4 days until the cytopathic effect was complete. The cellular supernants clarified at 1000 g for 5 min were subsequently purified by two sucrose-gradient centrifugations as described by Karacostas et al., *Proc. Natl. Acad. Sci. USA* 86:8964 (1989).

For the Western blot analysis the pellets were resuspended in SDS-containing lysis buffer. A similar banding pattern as shown in FIG. 15.2 could be observed in the Western blot analysis indicating that the sedimenting material contained the expected antigenic composition.

For the vaccination studies, the pelleted pseudoparticles were resuspended in PBS and treated with formalin to inactivate residual vaccinia infectivity. The pseudoparticles generated both humoral and cell mediated immune response in mice and rabbits and may therefore be useful immunogens in the prophylaxis and immunotherapy of AIDS.

EXAMPLE 16

Construction of the chimeric fowlpox virus f-aMN and expression of recombinant HIV gp160MN in chicken cells In Example 12, the construction of fowlpox virus (FPV) chimeras expressing gpl6O controlled by a synthetic late promoter are discussed. Since it is desirable not only to use the FPV gpl6O MN constructs for production purposes, but also as live vaccines for priming the immune response in humans, new constructs that express gpl6O early and late in the viral life cycle were made. The hybrid promoter Sep (see Example 13) was used for these new constructs.

Construction of the chimeric viruses of the f-aMN series: To construct the viruses of the f-aMN series, the double gene cassette consisting of the P7.5-gpt selection marker and the Sep-gpl6O gene was excised as a NotI fragment out of the plasmid pSep-ST2 and inserted directly into the unique NotI site of the fowlpox virus strain f-TK2a. Since direct cloning usually results in the appearance of two orientations of the insert, a schematic outline of the structures surrounding the insertion sites for the two possible orientations is shown in FIG. 16.1. The construction of the plasmid pSep-ST2 has been described in Example 13 and is shown in FIG. 13.1. This plasmid contains the HIV-1 gpl6OMN sequences controlled by the strong, semi-synthetic fowlpox virus promoter Sep and a selection cassette consisting of the P7.5 promoter gpt gene. Falkner and Moss (1988).

Twelve gpt positive viruses were plaque purified three times and screened for expression of the env protein by Western blotting. FIG. 16.2. For this purpose, confluent monolayers of CEF's were infected with one plaque forming unit of the respective fowlpox virus and harvested after four days. Total cellular proteins were separated on a 7.5% polyacrylamide gel, transferred to a nitrocellulose filter and further processed according to a standard Western blotting protocol. See Materials and Methods. All of chimeric viruses expressed the HIV-1 gpl6O product. FIG. 16.2. The viruses f-aMN4#3 and f-aMN6#20 were finally chosen on the basis of their high expression levels for large scale purification and further characterization.

Fowlpox virus, although incapable of forming progeny virus in mammalian cells, does induce expression of foreign genes. Taylor et al. (1988). To estimate expression levels in mammalian cells, Vero and CV-1 cells were infected with f-aMN, grown for 48 and 72 hours and analyzed by Western blot analysis. FIG. 16.3. Taking into account that Western blotting is a relatively insensitive method, these experiments show that, in spite of infecting a non-avian host, relatively high levels of gpl6O were observed. Expression in CV-1 cells was slightly higher than in Vero cells. Up to now, expression of foreign genes induced by FPV in mammalian cells could only be demonstrated by highly sensitive methods such as immunoprecipitations and immunofluorescence, underscoring the unexpected nature of the high efficiency seen with the new Sep-Promoter-gpl6O constructs. See Taylor et al. (1988).

Structure of the chimeric viruses: To confirm structures of the chimeric viruses, Southern blot analyses were carried out. The total DNA of CEF's infected with the respective viruses was cleaved with PstI, separated on an agarose gel, transferred to a nitrocellulose membrane and hybridized to the gpl6O gene probe pMNenvl. With this probe, in case of the 'a'-orientation, a 28.2 kb fragment is expected which became visible in all isolates examined. See FIGS. 16.1 and 16.4. For unknown reasons this cloning step resulted in a preferred orientation, the 'a'-orientation. In the 'b'-orientation a PstI fragment of 3.O kb was expected. FIG. 16.1. The correct insertion of the gpl6O sequences into fowlpox virus was demonstrated by this analysis.

The viruses f-aMN4#3 and f-aMN6#20 were chosen for large scale purification and further characterization. They were shown to be free of the parental virus f-TK2a. Immunization studies with the virus f-aMN4#3 in chickens (Example 17), mice and rabbits are carried out.

Construction of the chimeric viruses: Viruses were constructed essentially described in Example 3. Western blot analysis of gpl6O were performed as described in Example 13.

EXAMPLE 17

Immunization studies with f-aMN

The chimeric fowlpoxvirus f-aMN, which is derived from the highly attenuated FPV vaccine strain HP1.441 of Mayr and Malicki (1966), expresses HIV-1 gpl6OMN. Seroconversion experiments with 12 week-old SPF-chickens (Charles River, WIGA) were conducted to determine the immunizing properties of this virus strain. From the literature, it is known that FPV induces a weak humoral but a strong cell-mediated immunity. Mayr and Malicki (1966). This particular seroconversion experiment was designed to examine the priming effects of the live virus f-aMN. Doses ranging from $10^5$ pfu to $10^7$ pfu per animal were used for immunization.

The experimental design of the immunization study is outlined in Table 17. Doses ranging from $10^5$ pfu to $10^7$ pfu per animal were used for immunization. A second immunization was given after 3 weeks. A booster immunization of 50 ug per animal subunit gpl6OMN was given after another 3 weeks. Antibody development against gpl6O was analyzed by Western blotting and ELISA.

Preparation of the virus vaccine: The virus f-aMN was grown on chicken embryo fibroblasts and purified as described in U.S. Ser. No. 07/882,768, hereby incorporated by reference.

'Surf' Western blot analysis: Total cellular proteins of HIV-1-infected H9 cells were separated on a preparative polyacrylamide gel and blotted onto a nitrocellulose filter. Individual wells of a SURF-blot apparatus (Idea Scientific Co., Minneapolis, Minn.) were filled with different dilutions of the respective serum sample and incubated for 1 hour. Further incubations were performed as described in Example 13.

TABLE 17

| Vaccination schedule (12 week old chickens) | | |
|---|---|---|
| 1. f-aMN: | sucrose purified viruses*, band, aliquots diluted in PBS to the respective titers (original titer: $1.2 \times 10^9$) | |
| 2. HPI.441: | (control) sucrose-purified viruses, band; aliquots diluted in PBS to the respective titer (original titer: $5 \times 10^9$) | |
| day 0: | a) | bleed #1, 1 ml per animal; pool blood |
| | b) | injection of chickens (i.v. in wing vein) with 0.5 ml of the respective virus dilution |
| (group A) | 5 chicks with $10^5$ pfu per animal of f-aMN | |
| (group B) | 5 chicks with $10^6$ pfu per animal of f-aMN | |
| (group C) | 5 chicks with $10^7$ pfu per animal of f-aMN | |
| (group D) | 5 chicks with $10^7$ pfu per animal of HP1.441 | |
| day 21: | a) | bleed #2 (1 ml per animal; pool blood) |
| | b) | boost (same schedule as day 0) |
| day 35: | a) | bleed #3 (i ml per animal; pool blood) |
| | b) | boost with purified 50 ug gpl6OMN |
| day 50: | a) | bleed #4 (total blood; end of experiment). |

*- vaccine stocks are provided as frozen aliquots (−80° C.) of an appropriate size in PBS; vaccine stocks are vortexed prior to use.

The chicken sera of each group was pooled and examined in three different ELISA assays: a gp160MN-strain specific ELISA, a gp160IIIB-strain specific ELISA and a whole-virus ELISA. Table 18 outlines the results of the immunization experiments.

TABLE 18

Elisa - Titer of pooled chicken sera after vaccination

| Group | Virus | Infection log 10 Titer (pfu) | Day 0, 1. Infection with Fowlpox, Elisa GP160 MN | GP160 IIIB | HIV-1 IIIB | Day 21, 2. Infection with Fowlpox (Booster), Elisa GP160 MN | GP160 IIIB | HIV-1 IIIB | Day 35, Immunization with 50 μg GP160 MN, Elisa GP160 MN | GP160 IIIB | HIV-1 IIIB | Day 50, End of Experiment, Elisa GP160 MN | GP160 IIIB | HIV-1 IIIB |
|---|---|---|---|---|---|---|---|---|---|---|---|---|---|---|
| A | f-aMN | 5.0 | < | < | < | < | < | < | < | < | < | 2560 | 1230 | 640 |
| B | f-aMN | 6.0 | < | < | < | < | < | < | < | < | < | 1280 | 1280 | 1280 |
| C | f-aMN | 7.0 | < | < | < | < | < | < | 160 | < | < | 5120 | 5120 | 2560 |
| D | HP1.441 (Control) | 7.0 | < | < | < | < | < | < | < | < | < | < | < | < |

As expected from the literature, the capacity of a vaccine strain to induce a humoral immune response of a fowlpox virus, in this case of a recombinant fowlpox virus, is low. Only the highest dose ($10^7$ pfu per animal, given twice) resulted in a weak titer of 1:160 in the gp160MN-specific ELISA. Boosting with 50 μg of purified gp160MN, however, resulted in a dose-dependent increase of the titers reaching maximum titers of 1:5120. Even after priming with HP1.441 wild-type virus, no seroconversion was obtained after a single dose of the gp160 subunit vaccine (Table 18), confirming the capacity of the f-aMN virus to efficiently prime humoral immune reactions. Interestingly though, these antibodies cross-reacted with the HIV-1 IIIB strain.

In order to examine the capacity of the vaccine strains to prime humoral immune response in a non-avian species, rabbits were selected for study. The vaccination scheme was similar to the chicken experiment and is shown in Table 19. The animals were vaccinated twice with the live vector and then boosted with the gp160 subunit. Higher doses of the virus were used for immunization, because fowlpox does not replicate in rabbits. The results of the immunizations are shown in Table 20. Seroconversions (1:320) without boosting with gp160 subunit were achieved only with the highest dose of $10^8$ pfu per animal. With the $10^8$ dose, a strong ELISA titer (1:2560) developed after a single boost with gp160MN subunit in the MN-strain specific ELISA, and a somewhat lower titer in the gp160IIIB ELISA. With the lower dose of $10^7$, seroconversion could be demonstrated only after boosting with gp160 subunit reaching titers of 1:160. With the control virus as priming agent, no antibodies were demonstrated even after boosting with the gp160 subunit.

These results demonstrate the use of f-aMN as a priming vehicle in animal systems such as chickens, in which fowlpox virus normally replicates, and in rabbits, in which FPV does not replicate. Rabbits have long been used as models to evaluate human vaccines. The experiments with this non-avian species therefore strongly suggest that other non-avian warm-blooded animals, e.g., the human, can be primed efficiently with the f-aMN virus.

TABLE 19

Vaccination schedule (10 week old rabbits)

The vaccine stocks were provided as frozen aliquots (−80° C.) of an appropriate size in PBS; vaccine stocks were vortexed prior to use.

1. f-aMN Sucrose purified (banded) virus, aliquots diluted in PBS to the respective titers (original titer: $1.2 \times 10^9$ pfu/ml)
2. HP1.441 (control) sucrose-purified (banded) virus; aliquots diluted in PBS to the respective titer (original titer: $5 \times 10^9$ pfu/ml)

day 0:

a) bleed #1, 1 ml per animal; pool blood
b) injection of rabbits (i.v. in ear vein) with 0.5 ml of the respective virus dilution 3 rabbits with $10^6$ pfu per animal of f-aMN (Group Z)
3 rabbits with $10^7$ pfu per animal of f-aMN (Group Y)
3 rabbits with $10^8$ pfu per animal of f-aMN (Group X)
3 rabbits with $10^8$ pfu per animal of HP1-441 (Group W)

day 21:

a) bleed #2 (1 ml per animal; pool blood)
b) boost (same schedule as day 0)

day 35:

a) bleed #3 (1 ml per animal; pool blood)
b) boost with purified 50 μg gp160MN day 50:

a) bleed #4 (total blood; end of experiment)

In order to reproduce and extend the animal priming studies, chickens and rabbits were immunized according to the vaccination schedules shown in Tables 21 and 23.

The immunizations of the chickens were carried out in a manner similar to that shown in Table 17, with the following modifications. An additional group of chickens (group E), the 'PBS control', was included and a second immunization with gp160-subunit vaccine was given at day 50. An additional set of titers were also determined after day 79. In these experiments the HIV-1 MN strain-specific ELISA was used to measure the immune response.

The results of the chicken experiments confirm the high priming efficiency of the f-MN virus (Table 22). Two immunizations with the gp160 subunit vaccine alone (groups D and E, Table 22) resulted in a low titer of 1:100 after a long period of time. Two priming doses of the live vaccine, followed by a booster injection of the gp160 subunit vaccine, even at the low titer of $10^5$, resulted in the high titer of 1:10,000 (groups A–C, Table 22). A titer of this magnitude could not be obtained in any animal tested so far by conventional immunization procedures with the subunit gp160 vaccine.

The immunizations of the rabbits were carried out essentially as shown in Table 19, with the following modifications (See Table 23). In addition to the intravenous (i.v.) route, intramuscular (i.m.) and subcutaneous (s.c.) injections were given. Additional groups of rabbits (groups V, Q, L), the 'PBS controls', were included and second immunizations with gp160-subunit vaccine were given at day 50. Finally, the dosage of the live vaccine was reduced (Table 23). The HIV-1 MN-strain specific ELISA only was used to measure the immune response.

At the low dosage, for i.v. injections of the rabbits (first i.v. injection $10^4$ pfu and second i.v. injection $10^6$ pfu), no specific priming effect was achieved by day 50 as compared to the controls (Table 24, group Z). With the next dosage combination, first i.v. injection $10^5$ pfu and second i.v. injection $10^7$ pfu (group Y, Table 24), the maximal titer of 1:10,000 was achieved by day 50. The dosage (first i.v. injection $10^6$ pfu and second i.v. injection $10^8$ pfu; group X) did not improve the titers significantly. Without priming with live virus, a rise in ELISA titers was observed only after the second booster injection with the gpl60 subunit (Table 24, group W) at day 79.

The intramuscular injections also confirmed the priming potential of the f-aMN chimeric fowlpox virus. To achieve optimal titers, the dosage scheme first i.m. injection $10^6$ pfu and second i.m. injection $10^8$ pfu, was found to be optimal (Table 24, group S). The subcutaneous route also resulted in a measurable priming effect (Table 24).

gp160MN strain and IIIB strain specific ELISAS: Microtiter plates were coated with purified gp160IIIB or gp160MN at a concentration of 5 μg/ml. After overnight incubation at 4° C., the plates were washed five times with PBS containing 0.05% Tween-20. Serum samples were serially diluted in PBS containing 0.5% Tween and 1% serum proteins, beginning with a 1:80 dilution. One hundred microliters of each sample were transferred to the coated plates. After an incubation of 1 hour at 37° C., the plates were washed five times with PBS-Tween solution and incubated for another hour with 100 μl horseradish peroxidase-conjugated anti-IgG per well. After washing five times with PBS-Tween, 100 μl of O-phenylenediamine dihydrochlorate was added to each well. The color reaction was stopped by the addition of 5M $H_2SO_4$ and the absorbance was measured at 495 nm with a microplate spectrophotometer.

Whole Virus ELISA: The pooled sera were tested for whole HIV-1 virus with the whole virus kit of Behring Enzygnost® as recommended by the manufacturer.

TABLE 20

Elisa - Titer of pooled rabbit sera after vaccination

| | Infection | | Day: 0 1. Infection with Fowlpox | | | Day: 21 2. Infection with Fowlpox (Booster) | | | Day: 35 Immunization with 50 μg GP160 MN | | | Day: 50 End of Experiment | | |
|---|---|---|---|---|---|---|---|---|---|---|---|---|---|---|
| | | log 10 | Elisa | | | Elisa | | | Elisa | | | Elisa | | |
| | | Titer | GP160 | | HIV-1 | GP160 | | HIV-1 | GP160 | | HIV-1 | GP160 | | HIV-1 |
| Group | Virus | (pfu) | MN | IIIB | IIIB | MN | IIIB | IIIB | MN | IIIB | IIIB | MN | IIIB | IIIB |
| X | f-aMN #311 | 8.0 | < | < | < | < | < | < | 320 | 320 | < | 2560 | 1280 | 160 |
| Y | f-aMN #311 | 7.0 | < | < | < | < | < | < | < | < | < | 160 | 160 | < |
| Z | f-aMN #311 | 6.0 | < | < | < | < | < | < | < | < | < | < | < | < |
| W | HP1.441 (Control) | 8.0 | < | < | < | < | < | < | < | < | < | < | < | < |

TABLE 21

Vaccination Schedule of Chickens
Each group consisted of six chickens; the f-MN vaccine (first immunization and booster 1) were given intravenous (iv) into the wing vein; boosters 2 and 3 consisted of 50 ug gp160 MN in 0.5 ml solution and alum as an adjuvant; intramuscular injections (im) were given at two sites into the left and right thighs;

| group | first immunization and booster 1 |
|---|---|
| group A iv | per animal 0.5 ml $10^5$ pfu f-aMN |
| group B iv | per animal 0.5 ml $10^6$ pfu f-aMN |
| group C iv | per animal 0.5 ml $10^7$ pfu f-aMN |
| group D iv (wildtype) | per animal 0.5 ml $10^7$ HP1.441 |
| group E iv | per animal 0.5 ml PBSA |
| **time schedule for vaccinations and blood samples** | |
| day −7 | pre-vaccination blood sample |
| day 0 | first immunization |
| day 21 | Booster 1 and blood sample |
| day 35 | Booster 2 and blood sample |
| day 50 | Booster 3 and blood sample |
| day 79 | blood sample |

TABLE 22

Elisa Titers of Pooled Chicken Sera After Vaccination

| Group | Virus | Infection log 10 titer (pfu) Day 0 | Infection log 10 titer (pfu) Day 21 | GP 160 MN - Elisa-Titer Day 0 (1. Infection with Fowlpox) (i.v.) | 21 Booster 1 (2. Infection with Fowlpox) (i.v.) | 35 Booster 2 (Immunisation with 50 μg GP 160 MN/MCC) | 50 Booster 3 (Immunisation with 50 μg GP 160 MN/MCC) | 79 End of Experiment |
|---|---|---|---|---|---|---|---|---|
| A | f-aMN | 5.0 | 5.0 | < | < | < | 10000 | 10000 |
| B | f-aMN | 6.0 | 5.0 | < | < | < | 10000 | 10000 |
| C | f-aMN | 7.0 | 7.0 | < | < | 100 | 10000 | 10000 |
| D | HP1.441 (Control) | 7.0 | 7.0 | < | < | < | < | 100 |
| E | PBS (Control) | — | — | < | < | < | < | 100 |

< = <1:100

TABLE 23

Vaccination Schedule of 10 Week Old Rabbits
Boosters 2 and 3 consisted of 50 μg gp160 MN in 0.5 ml solution and alum as an adjuvant; intravenous injections (iv) were given into the ear vein; intramuscular injections (im) were given at two sites into the left and right thighs; subcutaneous injections (sc): same site as im injections

| Group | First Immunization | Booster 1 |
|---|---|---|
| Group Z iv | 0.5 ml $10^4$ pfu f-aMN | 0.5 ml $10^6$ pfu f-aMN |
| Group Y iv | 0.5 ml $10^5$ pfu f-aMN | 0.5 ml $10^7$ pfu f-aMN |
| Group X iv | 0.5 ml $10^6$ pfu f-aMN | 0.5 ml $10^8$ pfu f-aMN |
| Group W iv | 0.5 ml $10^6$ HP1.441 | 0.5 ml $10^6$ HP1.441 |
| Group V iv | 0.5 ml PBS | 0.5 ml PBS |
| Group U im | 0.5 ml $10^4$ pfu f-aMN | 0.5 ml $10^6$ pfu f-aMN |
| Group T im | 0.5 ml $10^4$ pfu f-aMN | 0.5 ml $10^7$ pfu f-aMN |
| Group S im | 0.5 ml $10^6$ pfu f-aMN | 0.5 ml $10^8$ pfu f-aMN |
| Group R im | 0.5 ml $10^6$ pfu f-aMN | 0.5 ml $10^8$ pfu HP1.441 |

TABLE 23-continued

| Group | First Immunization | Booster 1 |
|---|---|---|
| Group Q im | 0.5 ml PBS | 0.5 ml PBS |
| Group P sc | 0.5 ml $10^4$ pfu f-aMN | 0.5 ml $10^6$ pfu f-aMN |
| Group O sc | 0.5 ml $10^5$ pfu f-aMN | 0.5 ml $10^7$ pfu f-aMN |
| Group N sc | 0.5 ml $10^6$ pfu f-aMN | 0.5 ml $10^8$ pfu f-aMN |
| Group M sc | 0.5 ml $10^6$ HP1.441 | 0.5 ml $10^8$ HP1.441 |
| Group L sc | 0.5 ml PBS | 0.5 ml PBS |

Time Schedule for vaccinations and Blood Samples

| Day | Event |
|---|---|
| Day 7 | Pre vaccination blood sample |
| Day 0 | First immunization |
| Day 21 | Booster 1 and blood sample |
| Day 35 | Booster 2 and blood sample |
| Day 50 | Booster 3 and blood sample |
| Day 79 | Blood sample |

TABLE 24

Elisa Titers of Pooled Rabbits Sera After Vaccination

| Group | Virus | Infection log 10 titer (pfu) Day 0 | Infection log 10 titer (pfu) Day 21 | Application | GP 160 MN - Elisa-Titer Day 0 (1. Infection with Fowlpox) (i.v.) | 21 Booster 1 (2. Infection with Fowlpox) (i.v.) | 35 Booster 2 (Immunisation with 50 μg GP 160 MN/MCC) (i.m.) | 50 Booster 3 (Immunisation with 50 μg GP 160 MN/MCC) (i.m.) | 79 End of Experiment |
|---|---|---|---|---|---|---|---|---|---|
| Z | f-aMN | 4.0 | 6.0 | i.v. | < | < | < | < | 10000 |
| Y | f-aMN | 5.0 | 7.0 | i.v. | < | < | < | 10000 | 10000 |
| X | f-aMN | 6.0 | 8.0 | i.v. | < | < | 100 | 10000 | 10000 |
| W | HP1.441 (Control) | 6.0 | 8.0 | i.v. | < | < | < | < | 1000 |
| V | PBS (Control) | — | — | i.v. | < | < | < | < | 1000 |
| U | f-aMN | 4.0 | 6.0 | i.m. | < | < | < | 100 | 1000 |
| T | f-aMN | 5.0 | 7.0 | i.m. | < | < | < | 100 | 1000 |
| S | f-aMN | 6.0 | 8.0 | i.m. | < | < | < | 100 | 10000 |
| R | HP1.441 (Control) | 6.0 | 8.0 | i.m. | < | < | < | 100 | 1000 |
| Q | PBS (Control) | — | — | i.m. | < | < | < | < | 1000 |

TABLE 24-continued

Elisa Titers of Pooled Rabbits Sera After Vaccination

| Group | Virus | Infection log 10 titer (pfu) Day 0 | Day 21 | Application | GP 160 MN - Elisa-Titer Day 0 (1. Infection with Fowlpox) (i.v.) | 21 Booster 1 (2. Infection with Fowlpox) (i.v.) | 35 Booster 2 (Immunisation with 50 μg GP 160 MN/MCC) (i.m.) | 50 Booster 3 (Immunisation with 50 μg GP 160 MN/MCC) (i.m.) | 79 End of Experiment |
|---|---|---|---|---|---|---|---|---|---|
| P | f-aMN | 4.0 | 6.0 | s.c. | < | < | < | 100 | 1000 |
| O | f-aMN | 5.0 | 7.0 | s.c. | < | < | < | 100 | 1000 |
| N | f-aMN | 6.0 | 8.0 | s.c. | < | < | < | 100 | 1000 |
| M | HP1.441 (Control) | 6.0 | 8.0 | s.c. | < | < | < | < | 1000 |
| L | PBS (Control) | — | — | s.c. | < | < | < | < | 1000 |

What is claimed is:

1. A method for producing a protein employing a modified vaccinia viral expression system comprising the following steps:

(a) providing a modified vaccinia virus containing a heterologous insert encoding a protein, wherein said insert was molecularly cloned directly into the viral genome into a unique restriction endonuclease cleavage site;

(b) infecting a vertebrate cell culture with the modified vaccinia virus from step (a);

(c) culturing the infected cells under conditions resulting in expression of the protein; and, (d) isolating the protein produced by the infected cells.

2. The method according to claim 1, wherein the protein is selected from the group consisting of HIV gp160, HIV Gag, and HIV Gag-Pol.

3. The method according to claim 1, wherein the protein is selected from the group consisting of prothrombin, Factor IX, Protein S, von Willebrand Factor, lys-plasminogen, and glu-plasminogen.

4. The method according to claim 1, wherein the restriction endonuclease is selected from the group consisting of NotI, SmaI, ApaI, and RsrII.

5. A method for producing a protein employing a modified fowlpox viral expression system comprising the following steps:

(a) providing a modified fowlpox virus containing a heterologous insert encoding a protein, wherein said insert was molecularly cloned directly into the viral genome into a unique restriction endonuclease cleavage site recognized by a restriction endonuclease selected from the group consisting of NotI, SmaI, ApaI, and RsrII;

(b) infecting a vertebrate cell culture with the modified vaccinia virus from step (a);

(c) culturing the infected cells under conditions resulting in expression of the protein; and, (d) isolating the protein produced by the infected cells.

6. The method according to claim 5, wherein the protein is selected from the group consisting of HIV gp160, HIV Gag, and HIV Gag-Pol.

7. The method according to claim 5, wherein the protein is selected from the group consisting of prothrombin, Factor IX, Protein S, von Willebrand Factor, lys-plasminogen, and glu-plasminogen.

8. A method for producing a protein employing a modified vaccinia viral expression system comprising the following steps:

(a) infecting cells with a modified vaccinia virus containing a heterologous insert encoding a protein, wherein said insert was molecularly cloned directly into the viral genome into a unique restriction endonuclease cleavage site;

(b) culturing the infected cells from step (a) under conditions resulting in expression of the protein.

9. The method according to claim 8, further comprising isolating the protein produced by the infected cells of step (b).

10. The method according to claim 8, wherein the protein is selected from the group consisting of HIV gp160, HIV Gag, and HIV Gag-Pol.

11. The method according to claim 8, wherein the protein is a human blood protein.

12. The method according to claim 11, wherein the human blood protein is selected from the group consisting of prothrombin, Factor IX, Protein S, von Willebrand Factor, lys-plasminogen, and glu-plasminogen.

13. A method for producing a protein employing a modified fowlpox viral expression system comprising the following steps:

(a) infecting cells with a modified fowlpox virus containing a heterologous insert encoding a protein, wherein said insert was molecularly cloned directly into the viral genome into a unique restriction endonuclease cleavage site recognized by a restriction endonuclease selected from the group consisting of NotI, SmaI, ApaI, and RsrII; and, (b) culturing the infected cells from step (a) under conditions resulting in expression of the protein.

14. The method according to claim 13, further comprising isolating the protein produced by the infected cells of step (b).

15. The method according to claim 13, wherein the protein is selected from the group consisting of HIV gp160, HIV Gag, and HIV Gag-Pol.

16. The method according to claim 13, wherein the protein is a human blood protein.

17. The method according to claim 16, wherein the human blood protein is selected from the group consisting of prothrombin, Factor IX, Protein S, von Willebrand Factor, lys-plasminogen, and glu-plasminogen.

* * * * *